US012699094B2

(12) United States Patent
Diehl et al.

(10) Patent No.: US 12,699,094 B2
(45) Date of Patent: Aug. 4, 2026

(54) FLUORESCENT BIOSENSOR FOR ACETYL COENZYME A

(71) Applicant: UNIVERSITY OF UTAH RESEARCH FOUNDATION, Salt Lake City, UT (US)

(72) Inventors: Katharine L. Diehl, Salt Lake City, UT (US); Joseph J. Smith, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 468 days.

(21) Appl. No.: 18/448,632

(22) Filed: Aug. 11, 2023

(65) Prior Publication Data

US 2025/0052755 A1 Feb. 13, 2025

(51) Int. Cl.
*G01N 33/573* (2006.01)
*C07K 14/00* (2006.01)

(52) U.S. Cl.
CPC ....... *G01N 33/5735* (2013.01); *C07K 14/001* (2013.01); *C07K 2319/60* (2013.01)

(58) Field of Classification Search
CPC ................................................ C07K 2319/01
See application file for complete search history.

(56) References Cited

U.S. PATENT DOCUMENTS

2016/0153023 A1  6/2016  Goodman et al.

OTHER PUBLICATIONS

Monteiro DCF, Patel V, Bartlett CP, Nozaki S, Grant TD, Gowdy JA, et al. The structure of the PanD/PanZ protein complex reveals negative feedback regulation of pantothenate biosynthesis by coenzyme A. Chem Biol. Apr. 23, 2015;22(4):492-503. (Year: 2015).*
Huttanus HM, Senger RS. A synthetic biosensor to detect peroxisomal acetyl-CoA concentration for compartmentalized metabolic engineering. PeerJ. Sep. 8, 2020;8:e9805. doi: 10.7717/peerj.9805. PMID: 33194349; PMCID: PMC7485502. (Year: 2020).*
Lieberman WK, Brown ZA, Kantner DS, Jing Y, et al.. Chemoproteomics Yields a Selective Molecular Host for Acetyl-CoA. J Am Chem Soc. Aug. 2, 2023;145(30):16899-16905. doi: 10.1021/jacs.3c05489. Epub Jul. 24, 2023. PMID: 37486078; PM (Year: 2023).*
Lin W, Mehta S, Zhang J. Genetically encoded fluorescent biosensors illuminate kinase signaling in cancer. J Biol Chem. Oct. 4, 2019;294(40):14814-14822. doi: 10.1074/jbc.REV119.006177. Epub Aug. 21, 2019. PMID: 31434714; PMCID: PMC6779441. (Year: 2019).*
BCC Reasearch. Life Science Tools and Reagents: Global Markets Report Overview. Version dated May 19, 2022. Available online at https://web.archive.org/web/20220519080456/https://www.bccresearch.com/market-research/biotechnology/life-science-tools-reagents-markets-report.html (5 pages).
ABCAM. Acetyl COA Assay Kit (ab87546). Version dated Jun. 25, 2022. Available online at https://web.archive.org/web/20220701000000*/https://www.abcam.com/acetyl-coa-assay-kit-ab87546.html (5 pages).
Cambronne, X. A., et al. "Biosensor reveals multiple sources for mitochondrial NAD+." Science 352.6292 (2016): 1474-1477.
Greenwald, E. C., et al. "Genetically encoded fluorescent biosensors illuminate the spatiotemporal regulation of signaling networks." Chemical reviews 118.24 (2018): 11707-11794.
Kamphorst, J. J., et al. Quantitative analysis of acetyl-CoA production in hypoxic cancer cells reveals substantial contribution from acetate. Cancer Metab. 2, 23 (2014) (8 pages).
Kyte, J. et al. "A Simple Method for Displaying the Hydropathic Character of a Protein." J. Mol. Biol 157 (1982): 105-132.
Monteiro, D. C. F. et al. Formation of a heterooctameric complex between aspartate a-decarboxylase and its cognate activating factor, PanZ, is CoA-dependent. Biochem. Biophys. Res. Commun. 426, 350-355 (2012).
Monteiro, D. C. F. et al. The structure of the PanD/PanZ protein complex reveals negative feedback regulation of pantothenate biosynthesis by coenzyme A. Chem. Biol. 22, 492-503 (2015).
Pietrocola, F., et al. Acetyl Coenzyme A: A Central Metabolite and Second Messenger. Cell Metab. 21, 805-821 (2015).
Ryu, K. W., et al. "Metabolic regulation of transcription through compartmentalized NAD+ biosynthesis." Science 360.6389 (2018): eaan5780.
Shi, L. et al. Acetyl-CoA and the Regulation of Metabolism: Mechanisms and Consequences. Curr. Opin. Cell Biol. 33, 125-131 (2015) (11 pages).
Trefely, S. et al. Quantitative subcellular acyl-CoA analysis reveals distinct nuclear metabolism and isoleucine-dependent histone propionylation. Mol. Cell 82, 447-462.e6 (2022).
Zhang, S. et al. Metabolic engineering for efficient supply of acetyl-CoA from different carbon sources in *Escherichia coli*. Microb. Cell Factories 18, 130 (2019).

* cited by examiner

*Primary Examiner* — Daniel E Kolker
*Assistant Examiner* — Pricila Hauk Teodoro
(74) *Attorney, Agent, or Firm* — Michael Best & Friedrich LLP

(57) ABSTRACT

Disclosed herein are a polypeptide biosensor and compositions comprising the polypeptide biosensor that detects acetyl coenzyme A (acetyl-CoA). The polypeptide comprises an acetyl-CoA binding protein and a fluorescent protein. Further described herein are methods of using the biosensor to detect acetyl-CoA and expression vectors comprising the biosensor.

28 Claims, 34 Drawing Sheets

Specification includes a Sequence Listing.

Ac-CoA $K_D$ = 1.7 μM +/- 0.2

FIG. 1C

| Ac-CoA binding to PanZ-CFP (RU 2070) | | | | | |
|---|---|---|---|---|---|
| $K_D$ (μM) | | | Kinetic Fit | | |
| | Rmax | $K_D$ | $k_{on}$ ($M^{-1} \bullet S^{-1}$) | $k_{off}$ ($s^{-1}$) | $t_{1/2}$ (ln2/k) |
| Replicate 1 | 20 | 1.98 | 1.69E+04 | 0.0335 | 20.69 |
| Replicate 2 | 19 | 1.86 | 1.90E+04 | 0.0355 | 19.53 |
| Replicate 3 | 22 | 1.95 | 2.37E+04 | 0.0462 | 15.00 |
| Replicate 1 | 32 | 2.03 | 3.05E+04 | 0.0619 | 11.20 |
| Replicate 2 | 32 | 0.857 | 8.62E+04 | 0.0739 | 9.38 |
| Average | | 1.74 | 3.53E+04 | 0.0502 | 15.16 |
| Standard Error | | 0.20 | 1.16E+04 | 0.0070 | 1.99 |

FIG. 1D

| CoA binding to PanZ-CFP (RU 2070) | | | | | |
|---|---|---|---|---|---|
| $K_D$ (μM) | | | Kinetic Fit | | |
| | Rmax | $K_D$ | $k_{on}$ ($M^{-1} \bullet S^{-1}$) | $k_{off}$ ($s^{-1}$) | $t_{1/2}$ (ln2/k) |
| Replicate 1 | 13 | 15.2 | 1.16E+04 | 0.176 | 3.94 |
| Replicate 2 | 9.1 | 8.6 | 1.48E+04 | 0.127 | 5.46 |
| Replicate 1 | 30 | 18 | 1.19E+04 | 0.217 | 3.19 |
| Replicate 2 | 25 | 10 | 2.14E+04 | 0.213 | 3.25 |
| Average | | 12.95 | 1.49E+04 | 0.183 | 3.961 |
| Standard Error | | 1.91 | 1.97E+03 | 0.018 | 0.456 | cyto PancAce                    cyto cpGFP nuc PancAce                    nuc cpGFP mito PancAce                    mito cpGFP

FLUORESCENT BIOSENSOR FOR ACETYL COENZYME A

STATEMENT REGARDING FEDERALLY SPONSORED RESEARCH

This invention was made with government support under grant R35 GM143080 awarded by the National Institutes of Health. The government has certain rights in the invention.

REFERENCE TO AN ELECTRONIC SEQUENCE LISTING

This application was filed with a Sequence Listing XML in ST.26 XML format in accordance with 37 C.F.R. § 1.821. The Sequence Listing XML file submitted in the USPTO Patent Center, "026389-0021-US01_sequence_list-ing_XML_30 Jan. 2026.xml," was created on Jan. 30, 2026, contains 89 sequences, has a file size of 135 kilobytes (138,684 bytes), and is incorporated by reference in its entirety into the specification.

FIELD

This disclosure relates to a polypeptide biosensor and compositions comprising the polypeptide biosensor that detects acetyl coenzyme A (acetyl-CoA). The polypeptide comprises an acetyl-CoA binding protein and a fluorescent protein. The disclosure further relates to methods of using the biosensor to detect acetyl-CoA and expression vectors comprising the biosensor.

INTRODUCTION

Acetyl-coenzyme A (acetyl-CoA) is a core metabolite that serves central metabolic, catabolic, and signaling functions. Current methods to quantify acetyl-CoA from cells include enzyme-coupled assays such as PicoProbe™ Acetyl-CoA assay (BioVision, Milpitas, CA) and mass spectrometry. Due to the relatively low abundance and stability of acetyl-CoA and other short-chain acyl-CoAs, indirect methods of acetyl-CoA detection are commonly employed. However, these methods are inherently destructive and require frac-tionation to obtain subcellular resolution. Fluorescent bio-sensors have been developed for cellular metabolites to enable real time imaging of, for example, ATP, NAD$^+$, and glucose in live cells. However, no such biosensor exists for acetyl-CoA.

Thus, there is a need for a biosensor that detects acetyl-CoA.

SUMMARY

In an aspect, the disclosure relates to a recombinant acetyl-coenzyme A (acetyl-CoA) biosensor polypeptide that may comprise an acetyl-CoA binding protein having an amino acid sequence at least 95% identical to SEQ ID NO: 1, wherein the acetyl-CoA binding protein may be divided into: a first acetyl-CoA binding protein fragment comprising an N-terminal portion of the acetyl-CoA binding protein; and a second acetyl-CoA binding protein fragment compris-ing a C-terminal portion of the acetyl-CoA binding protein, wherein the first and second acetyl-CoA binding protein fragments collectively may include all of the amino acids of the acetyl-CoA binding protein; and a fluorescent protein may be inserted between the first and second acetyl-CoA binding protein fragments and attached to a C-terminus of the first acetyl-CoA binding protein fragment and an N-ter-minus of the second acetyl-CoA binding protein fragment; and wherein: (i) the C-terminus may be an arginine at position 69 of SEQ ID NO: 1 (Arg69) and the N-terminus may be a glutamic acid at position 70 of SEQ ID NO: 1 (Glu70); (ii) the C-terminus may be a tryptophan at position 23 of SEQ ID NO: 1 (Trp23) and the N-terminus may be a proline at position 24 of SEQ ID NO: 1 (Pro24); (iii) the C-terminus may be a valine at position 71 of SEQ ID NO: 1 (Val71) and the N-terminus may be a threonine at position 72 of SEQ ID NO: 1 (Thr72); (iv) the C-terminus may be an aspartic acid at position 99 of SEQ ID NO: 1 (Asp99) and the N-terminus may be an alanine at position 100 of SEQ ID NO: 1 (Ala100); (v) the C-terminus may be an aspartic acid at 104 of SEQ ID NO: 1 (Asp104) and the N-terminus may be an arginine at position 105 of SEQ ID NO: 1 (Arg105); or (vi) the C-terminus may be a glycine at position 116 of SEQ ID NO: 1 (Gly116) and the N-terminus may be a phenylalanine at position 117 of SEQ ID NO: 1 (Phe117); and wherein the recombinant acetyl-CoA biosensor poly-peptide may selectively bind acetyl-CoA, and the binding of acetyl-CoA may induce a change in the fluorescence of the fluorescent protein. In an embodiment, the fluorescent pro-tein may be a circularly permuted GFP (cpGFP), a circularly permuted yellow fluorescent protein (cpYFP), or a circularly permuted blue fluorescent protein (cpBFP). In some embodiments, the cpGFP may comprise an amino acid sequence of SEQ ID NO: 2, the cpYFP may comprise an amino acid sequence of SEQ ID NO: 3, and the cpBFP may comprise an amino acid sequence of SEQ ID NO: 4. In some embodiments, the acetyl-CoA binding protein may comprise an amino acid sequence at least 99% identical to SEQ ID NO: 1. In some embodiments, the acetyl-CoA binding protein may comprise the amino acid sequence of SEQ ID NO: 1. In some embodiments, the fluorescent protein may be either directly attached to the C-terminus of the first acetyl-CoA binding protein fragment or may be attached by a first amino acid linker that is from 1 to 3 amino acids in length; and the fluorescent protein may be either directly attached to the N-terminus of the second acetyl-CoA binding protein fragment or may be attached by a second linker that is from 1 to 3 amino acids in length. In some embodiments, the first and second amino acid linkers may be each independently selected from the group consisting of a Gly, Gly-Ala, Ala-Ser, and Gly-Ala-Ser. In some embodiments, (i) the first linker may be Gly-Ala and the second linker may be Gly-Ala; (ii) the first linker may be Ala-Ser and the second linker may be Ala-Ser; (iii) the first linker may be Gly-Ala-Ser and the second linker may be Gly; (iv) the C-terminus and N-terminus are directly attached to the fluorescent protein; (v) the C-terminus may be directly attached to the fluorescent protein and the second linker may be Gly-Ala-Ser; (vi) the first linker may be Gly-Ala-Ser and the N-ter-minus may be directly attached to the fluorescent protein; (vii) the first linker may be Gly-Ala and the N-terminus may be directly attached to the fluorescent protein; or (viii) the first linker may be Gly and the second linker may be Gly-Ala-Ser. In some embodiments, the recombinant acetyl-CoA biosensor polypeptide may further comprise one or more of a histidine tag, a TEV cleavage site, a FLAG® tag, a human influenza hemagglutinin (HA) tag, a nuclear export signal, a nuclear localization signal, a cytoplasmic localiza-tion signal, and a mitochondrial localization signal at the N-terminal portion of the acetyl-CoA binding protein. In some embodiments, (i) the recombinant acetyl-CoA biosen-sor polypeptide may comprise the amino acid sequence of SEQ ID NO: 5; (ii) the recombinant acetyl-CoA biosensor polypeptide may comprise the amino acid sequence of SEQ ID NO: 6; (iii) the recombinant acetyl-CoA biosensor polypeptide may comprise the amino acid sequence of SEQ ID NO: 7; (iv) the recombinant acetyl-CoA biosensor polypeptide may comprise the amino acid sequence of SEQ ID NO: 8; (v) the recombinant acetyl-CoA biosensor polypeptide may comprise the amino acid sequence of SEQ ID NO: 9; (vi) the recombinant acetyl-CoA biosensor polypeptide may comprise the amino acid sequence of SEQ ID NO: 10; (vii) the recombinant acetyl-CoA biosensor polypeptide may comprise the amino acid sequence of SEQ ID NO: 11; (viii) the recombinant acetyl-CoA biosensor polypeptide may comprise the amino acid sequence of SEQ ID NO: 12; (ix) the recombinant acetyl-CoA biosensor polypeptide may comprise the amino acid sequence of SEQ ID NO: 13; (x) the recombinant acetyl-CoA biosensor polypeptide may comprise the amino acid sequence of SEQ ID NO: 14; (xi) the recombinant acetyl-CoA biosensor polypeptide may comprise the amino acid sequence of SEQ ID NO: 15; (xii) the recombinant acetyl-CoA biosensor polypeptide may comprise the amino acid sequence of SEQ ID NO: 16; (xiii) the recombinant acetyl-CoA biosensor polypeptide may comprise the amino acid sequence of SEQ ID NO: 17; (xiv) the recombinant acetyl-CoA biosensor polypeptide may comprise the amino acid sequence of SEQ ID NO: 18; or (xv) the recombinant acetyl-CoA biosensor polypeptide may comprise the amino acid sequence of SEQ ID NO: 19. In some embodiments, the recombinant acetyl-CoA biosensor polypeptide may comprise the amino acid of SEQ ID NO: 5.

In a further aspect, the disclosure relates to an expression vector comprising: a nucleic acid that encodes the recombinant acetyl-CoA biosensor polypeptide as descried herein; and a promoter operably linked to the nucleic acid. In an embodiment, the expression vector may be a lentiviral vector, an adeno-associated virus (AAV) vector, or a cytomegalovirus (CMV) vector.

Another aspect of the disclosure provides a method of detecting acetyl-CoA in a sample that may comprise contacting the sample with the recombinant acetyl-CoA biosensor polypeptide as described herein; exciting the recombinant acetyl-CoA biosensor polypeptide in the sample at an excitation wavelength; measuring a fluorescence intensity of the recombinant acetyl-CoA biosensor polypeptide in the sample at an emission wavelength; and comparing the fluorescence intensity to a standard curve, wherein the fluorescence intensity correlates with a concentration of acetyl-CoA in the sample. In an embodiment, the excitation wavelength may be from about 460 nm to about 490 nm. In some embodiments, the excitation wavelength may be 485 nm. In some embodiments, the emission wavelength may be from about 513 nm to about 540 nm. In some embodiments, the emission wavelength may be 514 nm. In some embodiments, the pH of the sample may be maintained at a pH of 6.5-8.0.

Another aspect of the disclosure provides a method of monitoring acetyl-CoA activity in a cell, comprising: providing a cell with the recombinant acetyl-CoA biosensor polypeptide of any one of clauses 1-11; exciting the recombinant acetyl-CoA biosensor polypeptide in the cell at a first excitation wavelength between about 400 nm and about 430 nm while measuring a first fluorescence intensity at an emission wavelength between about 513 nm and about 540 nm; exciting the recombinant acetyl-CoA biosensor polypeptide in the cell at a second excitation wavelength between about 460 nm and about 490 nm while measuring a second fluorescence intensity at the emission wavelength; and normalizing the second fluorescence intensity based on the first fluorescence intensity. In some embodiments, normalizing may comprise dividing the second fluorescence intensity by the first fluorescence intensity. In some embodiments, the method may further comprise treating the cell with an acetyl-CoA precursor or nutrient affecting the function of the cell and comparing the normalized fluorescence intensity of the cell to the normalized fluorescence intensity of a control cell. In some embodiments, one or more of a nuclear export signal, a nuclear localization signal, a cytoplasmic localization signal, and a mitochondrial localization signal may be attached to an N-terminus of the recombinant acetyl-CoA biosensor polypeptide. In some embodiments, the method may further comprise determining where acetyl-CoA is localized in the cell. In some embodiments, the first excitation wavelength may be 405 nm. In some embodiments, the second excitation wavelength may be 485 nm. In some embodiments, the emission wavelength may be 514 nm. In some embodiments, the providing step may comprise transforming the cell with a plasmid comprising a polynucleotide that encodes the recombinant acetyl-CoA biosensor polypeptide.

The disclosure provides for other aspects and embodiments that will be apparent in light of the following detailed description and accompanying figures.

BRIEF DESCRIPTION OF THE DRAWINGS

FIG. 1C is a table of kinetic data for acetyl-CoA binding to a PanZ-CFP fusion protein obtained from the SPR experiments like those depicted in FIG. 1A. FIG. 1D is a table of kinetic data for acetyl-CoA binding to a PanZ-CFP fusion protein obtained from the SPR experiments like those depicted in FIG. 1B. This data shows that PanZ has selectivity for binding to acetyl-CoA over the structurally very similar CoA molecule, suggesting that it would have sufficient selectivity to be the basis for a useful biosensor in cells where both molecules exist.

FIG. 25A, FIG. 25B, and FIG. 25C are bar graphs showing the normalized sensor signal from live Hela cells that express the sensor in the nucleus (FIG. 25A), cytoplasm (FIG. 25B), or mitochondrion (FIG. 25C). Different enzymes that produce or consume acetyl-CoA in different compartments in the cell are being knocked-down. The cells were transfected with siRNAs targeting the proteins indicated on the X-axis of the graph. The cells were imaged by confocal fluorescence microscopy ($\lambda_{ex}$=405 nm, 485 nm; $\lambda_{em}$=514 nm) at 48 hours post-transfection. To obtain the normalized signal, the signal from PancAce was normalized by dividing $F_{488}/F_{405}$, then $F_{Pan}/F_{GFP}$, then normalizing to the signal from cells that were transfected with non-targeting siRNA for the same time interval ("$F_0$"): $(F_1-F_0)/F_0$. n=5-6. *p<0.05, **p<0.005. These data show that compartmentalized acetyl-CoA level changes depend on the specific enzyme targeted.

DETAILED DESCRIPTION

Figure 1A:
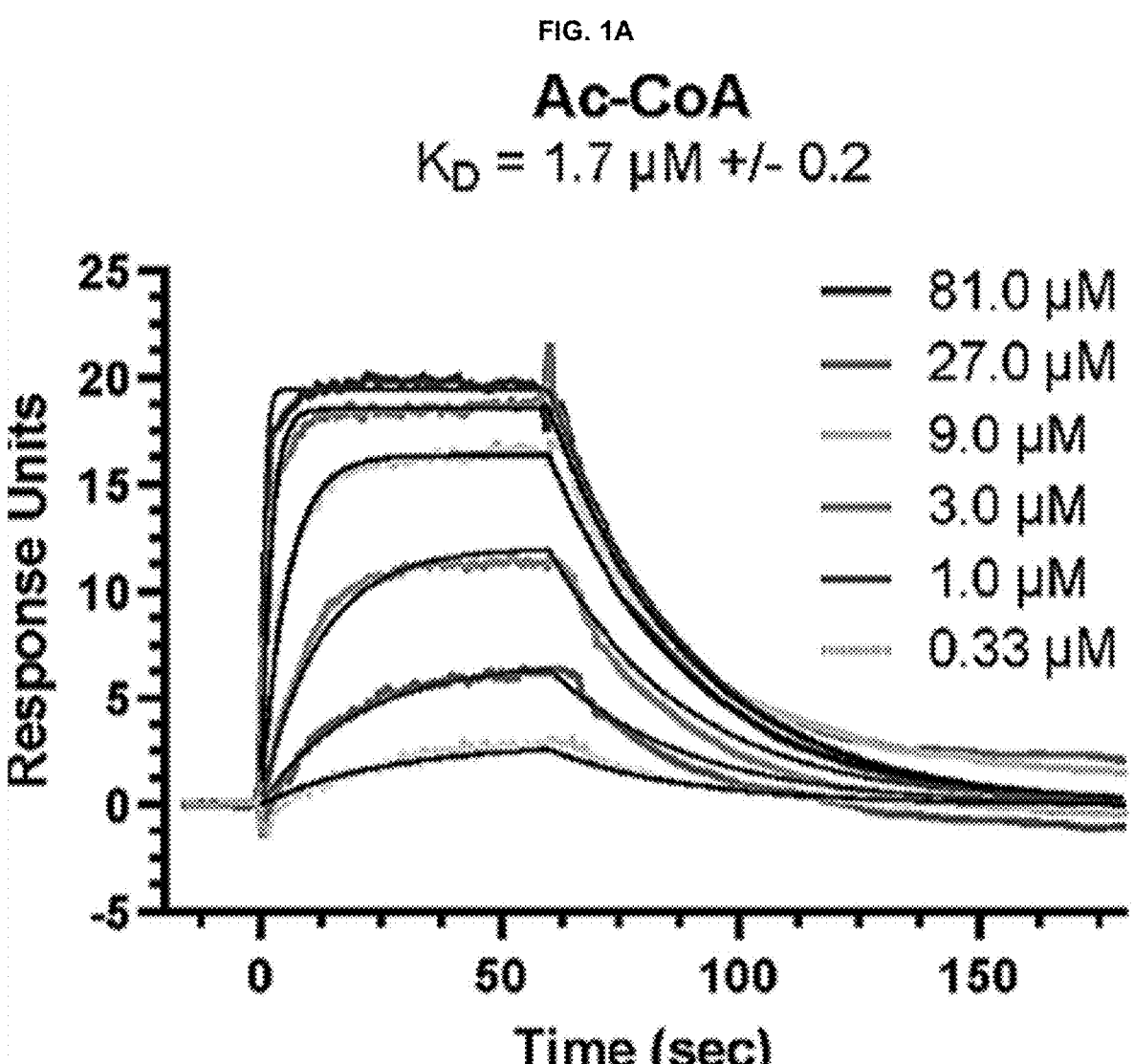
FIG. 1A is a graph showing a representative plot of surface plasmon resonance (SPR) data for acetyl coenzyme A (acetyl-CoA) binding to a PanZ-CFP fusion protein. The dissociation constants ("$K_D$") are shown in the figure.
Figure 1B:
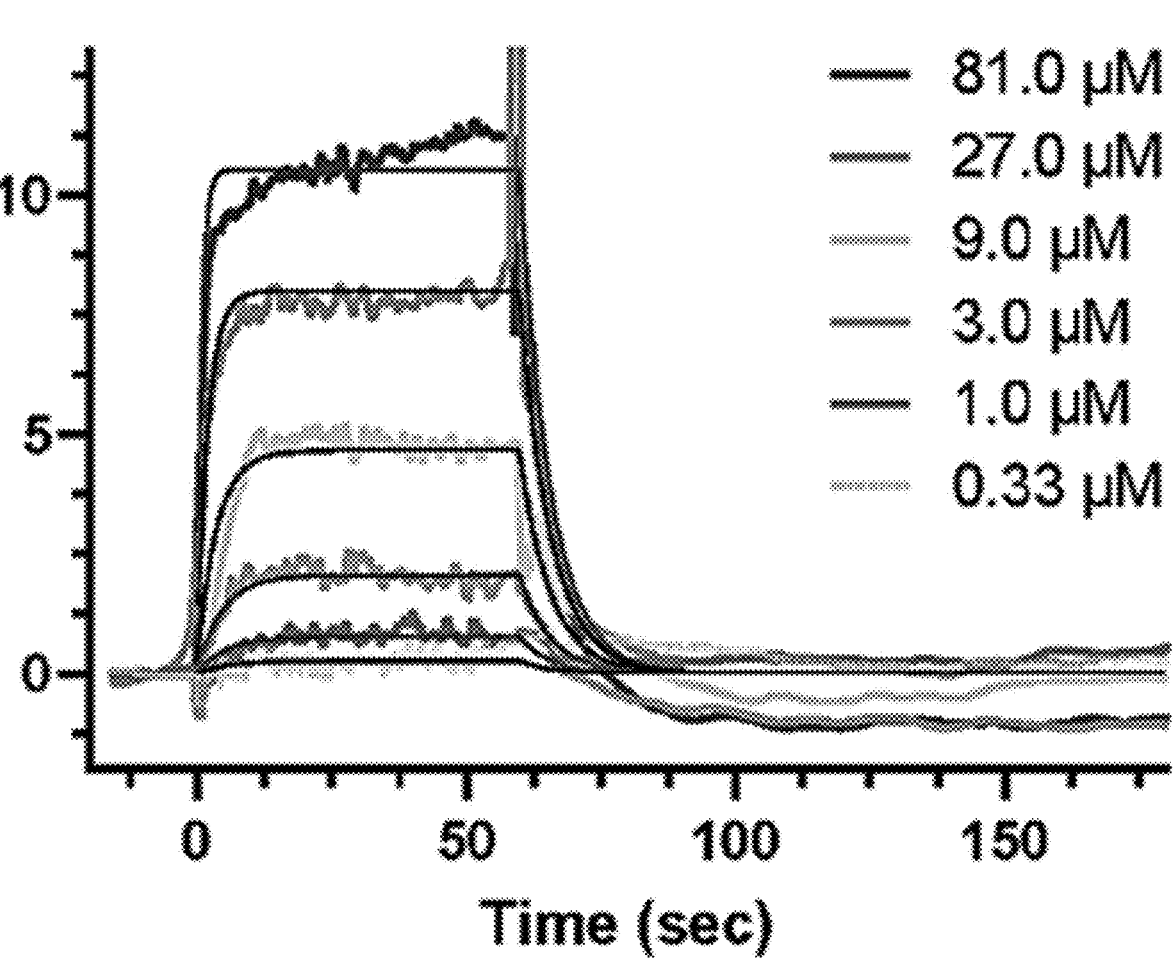
FIG. 1B is a graph showing a representative plot of surface plasmon resonance (SPR) data for coenzyme A (CoA) binding to a PanZ-CFP fusion protein. The dissociation constants ("$K_D$") are shown in the figure.

Described herein are recombinant polypeptide biosensors that can be used to detect and/or quantify acetyl coenzyme A (acetyl-CoA). The recombinant polypeptide biosensors comprise an acetyl-CoA binding protein that is divided into first and second acetyl-CoA binding protein fragments and a fluorescent protein inserted between the first and second Acetyl-CoA binding protein fragments. Further described herein are methods of using the biosensor to detect and/or quantify acetyl-CoA and expression vectors comprising nucleic acids that encode the recombinant polypeptide biosensors.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" or "approximately" as used herein as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, preferably within 5-fold, and more preferably within 2-fold, of a value.

"Acetyl-CoA" or "acetyl COA" are abbreviations of acetyl coenzyme A. Acetyl-CoA has a number of physiological roles and is a component of cellular respiration that adds acetyl groups to biochemical reactions. These reactions are used in metabolizing proteins, carbohydrates, and lipids that provide energy sources in the forms of adenosine triphosphate (ATP), lactic acid, and ketone bodies. Acetyl-CoA also plays an important regulatory role in intracellular mechanisms and it is essential for energy production when fasting or starving.

"Acetyl-CoA biosensor," "recombinant acetyl-CoA biosensor," "biosensor," or "sensor" are used interchangeably herein and refer to any of the recombinant acetyl-CoA biosensor polypeptides described herein. "ACoABP-X fusion protein" refers to a recombinant acetyl-CoA biosensor polypeptide where an acetyl-CoA binding protein ("ACoABP") is divided into first and second acetyl-CoA binding protein fragments and a fluorescent protein ("X") is inserted between the first and second acetyl-CoA binding protein fragments. For example, PanZ-cpGFP refers to a recombinant acetyl-CoA biosensor, as described herein, where the acetyl-CoA binding protein is "PanZ", the PanZ is divided into first and second acetyl-CoA binding protein fragments and the circularly permuted green fluorescent protein ("cpGFP") is inserted between the first and second acetyl-CoA binding protein fragments of the PanZ. "ACoABP (N #₁)-N₀₋₃-X-N₀₋₃-(N #₂) AcCoABP," is also used to refer to a recombinant acetyl-CoA biosensor described herein, where:

(a) "N" generally refers to amino acids;

(b) ACoABP (N #₁) refers to a first acetyl-CoA binding protein fragment comprising an N-terminal portion of an acetyl-CoA binding protein, where (N #₁) is the identity and position of the C-terminal amino acid of the first acetyl-CoA binding protein fragment at the position where the acetyl-CoA binding protein has been divided;

(c) (N #₂) AcCoABP refers to a second acetyl-CoA binding protein fragment comprising a C-terminal portion of the acetyl-CoA binding protein, where (N #₂) is the identity and position of the N-terminal amino acid of the second acetyl-CoA binding protein fragment at the position where the acetyl-CoA binding protein has been divided;

(d) X is a fluorescent protein inserted between the first and second acetyl-CaO binding protein fragments and attached to the C-terminus of the first acetyl-CoA binding protein fragment and the N-terminus of the second acetyl-CoA binding protein fragment; and (e) "No-3" refers to an amino acid linker that is either a direct bond (i.e., No) or includes 1-3 amino acids (i.e., N₁₋₃).

For example, PanZ(R69)-GA-cpGFP-GA-(E70)PanZ refers to a recombinant acetyl-CoA polypeptide where the AcCoA binding protein is PanZ, the acetyl-CoA binding protein has been recombinantly divided between the Arg69 (R69) and glu70 (E70) of PanZ to form a first acetyl-CoA binding protein fragment (i.e., "PanZ(R69)") and a second acetyl-CoA binding protein fragment (i.e., "(E70)PanZ"), a circularly permuted green fluorescent protein (i.e., "cpGFP") has been recombinantly inserted between the first and second acetyl-CoA binding protein fragments. Specifically, in this example, the N-terminal end of the cpGFP is attached to R69 at the C-terminus of the first acetyl-CoA binding protein fragment by a two amino acid linker consisting of an N-terminal glycine and C-terminal alanine ("GA). Similarly, the C-terminal end of the cpGFP is attached to E70 at the N-terminus of the second acetyl-CoA binding protein fragment by a two amino acid linker consisting of an N-terminal glycine and a C-terminal alanine ("GA").

The term "PancAce" is used herein to refer to the recombinant acetyl-CoA biosensor having the amino acid sequence of SEQ ID NO: 5.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Conservative amino acid substitution" as used herein refers to a substitution of an amino acid residue for another amino acid residue having similar biochemical properties. "Conservative" amino acid substitutions are those substitutions that do not substantially affect or decrease an activity of a polypeptide such as an acetyl-CoA binding domain or a fluorescent protein. A polypeptide can include one or more conservative substitutions up to and including 1-10 total conservative substitutions, 1% conservative substitutions, 5% conservative substitutions, 10% conservative substitutions, 15% conservative substitutions, 20% conservative substitutions, 25% conservative substitutions, 30% or more conservative substitutions, or any intervening value. Specific, non-limiting examples of a conservative substitution include the following shown in TABLE 1.

TABLE 1

| Conservative Amino Acid Substitutions | |
|---|---|
| Original Amino Acid | Conservative Substitutions |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

While examples of polypeptide sequences are provided in the amino acid sequences attached to this application, not all variants of polypeptide sequences with all possible combinations of conservative amino acid substitutions encompassed by the disclosure are provided in the sequence listing. This table can be used in combination with the sequence listing to provide explicit examples of polypeptide sequences encompassed by the disclosure.

The terms "control," "reference level," and "reference" are used herein interchangeably. The reference level may be a predetermined value or range, which is employed as a benchmark against which to assess the measured result. "Control group" as used herein refers to a group of control subjects or cells. A control may be a subject or cell without a recombinant acetyl-coenzyme A (acetyl-CoA) biosensor polypeptide as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

"Fluorescent protein" as used herein refers to any protein characterized by a barrel structure that allows the protein to absorb light at one or more absorbance wavelength(s) and fluoresce (i.e., emit light) at one or more emission wavelength(s) in the visible spectrum. Fluorescent proteins may include, but are not limited to, green fluorescent proteins (GFPs), yellow fluorescent proteins (YFPs), blue fluorescent proteins (BFPs), red fluorescent proteins (RFPs) and cyan fluorescent proteins (CFPs), among others. The fluorescent proteins may be modified or derivatized to enhance fluorescence or GFPs. For example, enhanced fluorescent proteins may include amino acid mutations relative to corresponding wild type fluorescent proteins, that enhance the fluorescence of the protein. Numerous enhanced fluorescent proteins have been made and are well characterized in the art including, but not limited to enhanced GFPs (EGFPs), enhanced YFPs (EYFPs), enhanced BFPs (EBFPs), enhanced CFPs (ECFPs), and the like. The fluorescent protein also may be circularly permuted by fusing the original N- and C-termini of a fluorescent protein together, either directly or using a peptide linker, and forming new termini near the chromophore while still retaining a similar 3-dimensional structure as the original fluorescent protein. Circularly permuted fluorescent proteins also are well known in the art and include, but are not limited to, circularly permuted GFPs (cpGFPs), circularly permuted YFPs (cpYFPs), circularly permuted BFPs (cpBFPs), circularly permuted CFPs (cpCFPs) and circularly permuted RFPs (cpRFPs), among others.

"Fusion protein" as used herein refers to a chimeric protein created through the joining of two or more genes that originally coded for separate proteins. The translation of the fusion gene results in a single polypeptide with functional properties derived from each of the original proteins. A fusion protein may also be a recombinant protein.

"Genetic construct" as used herein refers to DNA or RNA molecules that comprise a polynucleotide that encodes a protein. The coding sequence includes initiation and termination signals operably linked to regulatory elements including a promoter and polyadenylation signal capable of directing expression in cells or cells of a subject to whom the nucleic acid molecule is administered. As used herein, the term "expressible form" refers to gene constructs that contain the necessary regulatory elements operable linked to a coding sequence that encodes a protein such that when present in a cell or subject, the coding sequence will be expressed.

The term "heterologous" as used herein refers to nucleic acid comprising two or more subsequences that are not found in the same relationship to each other in nature. For instance, a nucleic acid that is recombinantly produced typically has two or more sequences from unrelated genes synthetically arranged to make a new functional nucleic acid, for example, a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. Similarly, a heterologous protein indicates that the protein comprises two or more subsequences that are not found in the same relationship to each other in nature (for example, a "fusion protein," where the two subsequences are encoded by a single nucleic acid sequence).

"Identical" or "identity" as used herein in the context of two or more polynucleotide or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Label" or "tag" as used interchangeably herein refer to any substance capable of aiding a machine, detector, sensor, device, column, or enhanced or unenhanced human eye from differentiating a labeled nucleotide, polynucleotide, polypeptide, or composition from an unlabeled nucleotide, polynucleotide, polypeptide, or composition. Labels may be used for any of a number of purposes and one skilled in the art will understand how to match the proper label with the proper purpose. Examples of uses of labels include purification of biomolecules, identification of biomolecules, detection of the presence of biomolecules, detection of protein folding, and localization of biomolecules within a cell, tissue, or organism. Examples of labels include but are not limited to: radioactive isotopes (such as carbon-14 or $^{14}C$) or chelates thereof; dyes (fluorescent or nonfluorescent), stains, enzymes, nonradioactive metals, magnets, protein tags, any antibody epitope, any specific example of any of these; any combination between any of these, or any label now known or yet to be disclosed. A label may be covalently attached to a biomolecule or bound through hydrogen bonding, Van Der Waals, or other forces. A label may be covalently or otherwise bound to the N-terminus, the C-terminus, or any amino acid of a polypeptide, or the 5' end, the 3' end or any nucleic acid residue in the case of a polynucleotide.

An example of a label is a protein tag. A protein tag comprises a sequence of one or more amino acids that may be used as a label as discussed above, particularly for use in protein purification. In some examples, the protein tag is covalently bound to the polypeptide. It may be covalently bound to the N-terminal amino acid of a polypeptide, the C-terminal amino acid of a polypeptide, or any other amino acid of the polypeptide. The protein tag may be encoded by a polynucleotide sequence that is immediately 5' of a nucleic acid sequence coding for the polypeptide such that the protein tag is in the same reading frame as the nucleic acid sequence encoding the polypeptide. Protein tags may be used for all of the same purposes as labels listed above and are well known in the art. Examples of protein tags include chitin binding protein (CBP), maltose binding protein (MBP), glutathione-S-transferase (GST), poly-histidine (His), thioredoxin (TRX), FLAG® tag, TEV cleavage site, V5, c-Myc, human influenza hemagglutinin (HA) tag, a nuclear export signal (NES), a nuclear localization signal or nuclear localization sequence (NLS), a cytoplasmic localization signal or cytoplasmic localization sequence (CLS), and a mitochondrial localization signal or mitochondrial localization sequence (MLS), and the like.

A His-tag facilitates purification and binding to on metal matrices, including nickel matrices, including nickel matrices bound to solid substrates such as agarose plates or beads, glass plates or beads, or polystyrene or other plastic plates or beads. Other protein tags include BCCP, calmodulin, Nus, Thioredoxin, Streptavidin, SBP, and Ty, or any other combination of one or more amino acids that can work as a label described above.

"Nucleic acid" or "oligonucleotide" or "polynucleotide" as used herein means at least two nucleotides covalently linked together. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a target sequence under stringent hybridization conditions. Thus, a polynucleotide also encompasses a probe that hybridizes under stringent hybridization conditions. Polynucleotides may be single stranded or double stranded or may contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain. With respect to fusion polypeptides, the terms "operatively linked" and "operably linked" can refer to the fact that each of the components performs the same function in linkage to the other component as it would if it were not so linked.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, fluorescent proteins, and receptors. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, for example, enzymatic domains, extracellular domains, transmembrane domains, pore domains, and cytoplasmic tail domains. "Domains" are portions of a polypeptide that form a compact unit of the polypeptide and are typically 15 to 350 amino acids long. A domain of a polypeptide or protein may be any part of a protein that exhibits a particular defined structure and/or mediates a particular protein function. An example of a domain is the acetyltransferase (GNAT) domain of PanZ (PanD regulatory factor). Exemplary domains include domains with acetyl-CoA binding activity. Typical domains are made up of sections of lesser organization such as stretches of beta-sheet and alpha-helices. "Tertiary structure" refers to the complete three-dimensional structure of a polypeptide monomer. "Quaternary structure" refers to the three-dimensional structure formed by the noncovalent association of independent tertiary units. A "motif" is a portion of a polypeptide sequence and includes at least two amino acids. A motif may be 2 to 20, 2 to 15, or 2 to 10 amino acids in length. A motif may include 3, 4, 5, 6, or 7 sequential amino acids. A domain may be comprised of a series of the same type of motif.

"Promoter" as used herein means a synthetic or naturally derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, human U6 (hU6) promoter, and CMV IE promoter.

The term "recombinant" when used with reference to, for example, a cell, nucleic acid, protein, or vector, indicates that the cell, nucleic acid, protein, or vector has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed, or not expressed at all.

"Sample" or "test sample" as used herein can mean any sample in which the presence and/or level of a target is to be detected or determined or any sample comprising a recombinant acetyl-CoA biosensor polypeptide or component thereof as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" as used herein refers to any vertebrate or invertebrate, including, but not limited to, a mammal that wants or is in need of the herein described compositions or methods and bacteria cells. The subject may be a human or a non-human. The subject may be a cell. The subject may be a bacterial cell such as, but not limited to, *Escherichia coli* (*E. coli*). The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamsters, guinea pig, cat, dog, rat, and mouse. The mammal can be a primate such as a human. The mammal can be a non-human primate such as, for example, monkey, cynomolgus monkey, rhesus monkey, chimpanzee, gorilla, orangutan, and gibbon. The subject may be of any age or stage of development, such as, for example, an adult, an adolescent, or an infant. The subject may be male. The subject may be female. In some embodiments, the subject has a specific genetic marker. The subject may be undergoing other forms of treatment.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides, respectively.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. Representative examples of "biological activity" include the ability to bind acetyl-CoA and emit a fluorescent signal upon binding acetyl-CoA. Variant can mean a functional fragment thereof. Variant can also mean multiple copies of a polypeptide. The multiple copies can be in tandem or separated by a linker. A conservative substitution of an amino acid, for example, replacing an amino acid with a different amino acid of similar properties (for example, hydrophilicity, degree and distribution of charged regions) is recognized in the art as typically involving a minor change. These minor changes may be identified, in part, by considering the hydropathic index of amino acids, as understood in the art (Kyte et al., J. Mol. Biol. 1982, 157, 105-132). The hydropathic index of an amino acid is based on a consideration of its hydrophobicity and charge. It is known in the art that amino acids of similar hydropathic indexes may be substituted and still retain protein function. In one aspect, amino acids having hydropathic indexes of +2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome, or yeast artificial chromosome. A vector may be a DNA or RNA vector. A vector may be a self-replicating extrachromosomal vector, and preferably, is a DNA plasmid. For example, the vector may encode a recombinant acetyl-CoA biosensor polypeptide.

Recombinant Acetyl-Coenzyme A Biosensor Polypeptides

Provided herein are recombinant acetyl-coenzyme A (acetyl-CoA) biosensor polypeptides that can detect free acetyl-CoA in solution, as well as in a cell. The recombinant acetyl-CoA biosensor polypeptide may include an acetyl-CoA binding protein and a fluorescent protein. The recombinant acetyl-CoA biosensor polypeptide may selectively bind acetyl-CoA. This binding causes a specific conformational change in the biosensor and results in a change in fluorescence emission. The binding of acetyl-CoA may induce a change in the fluorescence of the fluorescent protein. This change in fluorescence allows for detection of acetyl-CoA. The acetyl-CoA binding protein may have an amino acid sequence at least 40%, at least 45%, at least 50%, at least 55%, at least 60%, at least 65%, at least 70%, at least 75%, at least 80%, at least 85%, at least 90%, at least 95%, or at least 99% identical to SEQ ID NO: 1. In some embodiments, the acetyl-CoA binding protein may have an amino acid sequence of SEQ ID NO: 1. The acetyl-CoA binding protein may be derived from *Escherichia coli* (*E. coli*), such as the acetyl-CoA binding protein PanZ, which may also be referred to as "PanM" in the art. The acetyl-CoA binding protein may also be derived from enterobacterial species including *Shigella, Salmonella, Klebsiella,* and *Yersinia*. As discussed above, the acetyl-CoA binding protein may be divided into a first acetyl-CoA binding protein fragment including an N-terminal portion of the acetyl-CoA binding protein, and a second acetyl-CoA binding protein fragment including a C-terminal portion of the acetyl-CoA binding protein. The first acetyl-CoA binding protein fragment and the second acetyl-CoA binding protein fragment collectively may include all of the amino acids of the acetyl-CoA binding protein. The first acetyl-CoA binding protein fragment comprises the amino acids at or near the N-terminal portion of the acetyl-CoA binding protein and is attached to the N-terminal end of the fluorescent protein, while the second acetyl-CoA binding fragment comprises the amino acids at or near the C-terminal portion of the acetyl-CoA binding protein and is attached to the C-terminal end of the fluorescent protein.

The fluorescent protein may include any protein characterized by a barrel structure that allows the protein to absorb light at one or more absorbance wavelength(s) and fluoresce (i.e., emit light) at one or more emission wavelength(s) in the visible spectrum. As discussed in more detail above, fluorescent proteins may include, but are not limited to, GFPs, YFPs, BFPs, RFPs, CFPs, EGFPs, EYFPs, EBFPs, ECFPs, cpGFPs, cpYFPs, cpBFPs, cpCFPs, and cpRFPs, among others. In some embodiments, the fluorescent protein may be a cpGFP, a cpYFP, or a cpBFP. In some embodiments, the cpGFP may have an amino acid sequence of SEQ ID NO: 2, the cpYFP may have an amino acid sequence of SEQ ID NO: 3, and the cpBFP may have an amino acid sequence of SEQ ID NO: 4.

The fluorescent protein is inserted between the first acetyl-CoA binding protein fragment and the second acetyl-CoA binding protein fragment. Specifically, the fluorescent protein is attached to a C-terminus of the first acetyl-CoA binding protein fragment and an N-terminus of the second acetyl-CoA binding protein fragment. In some embodiments, the C-terminus of the first acetyl-CoA binding protein fragment may be an arginine at position 69 (Arg69) of the acetyl-CoA binding protein and the N-terminus of the second acetyl-CoA binding protein fragment may be a glutamic acid at position 70 (Glu70) of the acetyl-CoA binding protein. In some embodiments, the C-terminus of the first acetyl-CoA binding protein fragment may be a tryptophan at position 23 (Trp23) of the acetyl-CoA binding protein and the N-terminus of the second acetyl-CoA binding protein fragment may be a proline at position 24 (Pro24) of the acetyl-CoA binding protein. In some embodiments, the C-terminus of the first acetyl-CoA binding protein fragment may be a valine at position 71 (Val71) of the acetyl-CoA binding protein and the N-terminus of the second acetyl-CoA binding protein fragment may be a threonine at position 72 (Thr72) of the acetyl-CoA binding protein. In some embodiments, the C-terminus of the first acetyl-CoA binding protein fragment may be an aspartic acid at position 99 (Asp99) of the acetyl-CoA binding protein and the N-terminus of the second acetyl-CoA binding protein fragment may be an alanine at position 100 (Ala100) of the acetyl-CoA binding protein. In some embodiments, the C-terminus of the first acetyl-CoA binding protein fragment may be an aspartic acid at 104 (Asp104) of the acetyl-CoA binding protein and the N-terminus of the second acetyl-CoA binding protein fragment may be an arginine at position 105 (Arg105) of the acetyl-CoA binding protein. In some embodiments, the C-terminus of the first acetyl-CoA binding protein fragment may be a glycine at position 116 (Gly116) of the acetyl-CoA binding protein and the N-terminus of the second acetyl-CoA binding protein fragment may be a phenylalanine at position 117 (Phe117) of the acetyl-CoA binding protein.

In some embodiments, the N-terminus of the fluorescent protein may be directly attached to the C-terminus of the first acetyl-CoA binding protein fragment (i.e., by a peptide bond). In other embodiments, the N-terminus of the fluorescent protein may be attached to the C-terminus the first acetyl-CoA binding protein fragment by a first amino acid linker (which also may be referred to as a peptide linker) that is from 1-3 amino acids in length. In some embodiments, the first amino acid linker may be selected from the group consisting of a Gly linker, a Gly-Ala linker, an Ala-Ser linker, and a Gly-Ala-Ser linker.

In some embodiments, the C-terminus of the fluorescent protein may be directly attached to the N-terminus of the second acetyl-CoA binding protein fragment (i.e., by a peptide bond). In other embodiments, the C-terminus of the fluorescent protein may be attached to the N-terminus the second acetyl-CoA binding protein fragment by a second peptide linker that is from 1-3 amino acids in length. In some embodiments, the second amino acid linker may be selected from the group consisting of a Gly linker, a Gly-Ala linker, an Ala-Ser linker, and a Gly-Ala-Ser linker.

In some embodiments, the first amino acid linker may be Gly-Ala and the second amino acid linker may be Gly-Ala. In some embodiments, the first amino acid linker may be Ala-Ser and the second amino acid linker may be Ala-Ser. In some embodiments, the first amino acid linker may be Gly-Ala-Ser and the second amino acid linker may be Gly. In some embodiments, the C-terminus of the first acetyl-CoA binding protein fragment may be directly attached to the N-terminus of the fluorescent protein and the N-terminus of the second acetyl-CoA binding protein fragment may be directly attached to the C-terminus of the fluorescent protein. In some embodiments, the C-terminus of the first acetyl-CoA binding protein fragment may be directly attached to the N-terminus of the fluorescent protein and the second amino acid linker may be Gly-Ala-Ser. In some embodiments, the first amino acid linker may be Gly-Ala-Ser and the N-terminus of the second acetyl-CoA binding protein fragment may be directly attached to the fluorescent protein. In some embodiments, the first linker may be Gly-Ala and the N-terminus of the second acetyl-CoA binding protein fragment may be directly attached to C-terminus of the fluorescent protein. In some embodiments, the first linker may be Gly and the second linker may be Gly-Ala-Ser.

In some embodiments, the recombinant acetyl-CoA biosensor polypeptide may have the amino acid sequence of SEQ ID NO: 5. In some embodiments, the recombinant acetyl-CoA biosensor polypeptide may have the amino acid sequence of SEQ ID NO: 6. In some embodiments, the recombinant acetyl-CoA biosensor polypeptide may have the amino acid sequence of SEQ ID NO: 7. In some embodiments, the recombinant acetyl-CoA biosensor polypeptide may have the amino acid sequence of SEQ ID NO: 8. In some embodiments, the recombinant acetyl-CoA biosensor polypeptide may have the amino acid sequence of SEQ ID NO: 9. In some embodiments, the recombinant acetyl-CoA biosensor polypeptide may have the amino acid sequence of SEQ ID NO: 10. In some embodiments, the recombinant acetyl-CoA biosensor polypeptide may have the amino acid sequence of SEQ ID NO: 11. In some embodiments, the recombinant acetyl-CoA biosensor polypeptide may have the amino acid sequence of SEQ ID NO: 12. In some embodiments, the recombinant acetyl-CoA biosensor polypeptide may have the amino acid sequence of SEQ ID NO: 13. In some embodiments, the recombinant acetyl-CoA biosensor polypeptide may have the amino acid sequence of SEQ ID NO: 14. In some embodiments, the recombinant acetyl-CoA biosensor polypeptide may have the amino acid sequence of SEQ ID NO: 15. In some embodiments, the recombinant acetyl-CoA biosensor polypeptide may have the amino acid sequence of SEQ ID NO: 16. In some embodiments, the recombinant acetyl-CoA biosensor polypeptide may have the amino acid sequence of SEQ ID NO: 17. In some embodiments, the recombinant acetyl-CoA biosensor polypeptide may have the amino acid sequence of SEQ ID NO: 18. In some embodiments, the recombinant acetyl-CoA biosensor polypeptide may have the amino acid sequence of SEQ ID NO: 19. A particular embodiment of the present disclosure provides a recombinant acetyl-CoA biosensor polypeptide having the amino acid sequence of SEQ ID NO: 5 and having selectivity for acetyl-CoA.

A recombinant acetyl-CoA biosensor polypeptide described herein may include one or more additional elements such as one or more of tags (e.g., a histidine tag, a tobacco etch virus protease (TEV) cleavage site, a FLAG® tag, a human influenza hemagglutinin (HA) tag), localization sequences (e.g., a nuclear export signal (NES), a nuclear localization signal (NLS), a cytoplasmic localization signal (CLS), and a mitochondrial localization signal (MLS)), labels (e.g., a fluorescent label), modified amino acids, artificial amino acids, and the like. The additional element(s) may be at the N-terminal portion of the acetyl-CoA binding protein and/or the C-terminal portion of the acetyl-CoA binding protein.

The syntheses of the recombinant acetyl-CoA biosensor polypeptides described herein can be carried out by any method known in the art. For example, the recombinant acetyl-CoA biosensor polypeptides described herein may be produced by recombinant methods where the recombinant acetyl-CoA biosensor polypeptide may be produced through recombinant DNA technology. This may involve inserting DNA encoding the recombinant acetyl-CoA biosensor polypeptide into bacterial or mammalian cells, expressing the recombinant acetyl-CoA biosensor polypeptide in the cells, and then purifying the recombinant acetyl-CoA biosensor polypeptide from the cells using methods known in the art.

Genetic Constructs

The recombinant acetyl-CoA biosensor polypeptide may be encoded by or comprised within a genetic construct. The genetic construct, such as a plasmid or expression vector, may comprise a nucleic acid that encodes the recombinant acetyl-CoA biosensor polypeptide. In some embodiments, an expression vector may comprise a nucleic acid that encodes a recombinant acetyl-CoA biosensor polypeptide described herein and a promoter operably linked to the nucleic acid.

Genetic constructs may include polynucleotides such as vectors and plasmids. The vector may be an expression vector or system to produce protein by routine techniques and readily available starting materials including Sambrook et al., Molecular Cloning and Laboratory Manual, Second Ed., Cold Spring Harbor (1989), which is incorporated fully by reference. The construct may be recombinant. The genetic construct may be part of a genome of a recombinant viral vector, including recombinant lentivirus, recombinant adenovirus, and recombinant adenovirus associated virus. The genetic construct may comprise regulatory elements for gene expression of the coding sequences of the nucleic acid. The regulatory elements may be a promoter, an enhancer, an initiation codon, a stop codon, or a polyadenylation signal.

The genetic construct may comprise heterologous nucleic acid encoding the recombinant acetyl-CoA biosensor polypeptide and may further comprise an initiation codon, which may be upstream of the recombinant acetyl-CoA biosensor polypeptide coding sequence, and a stop codon, which may be downstream of the recombinant acetyl-CoA biosensor polypeptide coding sequence. The genetic construct may include more than one stop codon, which may be downstream of the recombinant acetyl-CoA biosensor polypeptide coding sequence. A stop codon may be in-frame with a coding sequence in the recombinant acetyl-CoA biosensor polypeptide. The genetic construct may include one or more stop codons that are out of frame of a coding sequence in the recombinant acetyl-CoA biosensor polypeptide. The initiation and termination codon may be in frame with the recombinant acetyl-CoA biosensor polypeptide coding sequence.

The vector may also comprise a promoter that is operably linked to the recombinant acetyl-CoA biosensor polypeptide coding sequence. The promoter may be a constitutive promoter, an inducible promoter, a repressible promoter, or a regulatable promoter. The promoter may be a ubiquitous promoter. The promoter may be a tissue-specific or organelle-specific promoter. The promoter operably linked to the recombinant acetyl-CoA biosensor polypeptide coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metallothionein.

The genetic construct may also comprise a polyadenylation signal, which may be downstream of the recombinant acetyl-CoA biosensor polypeptide coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal.

Coding sequences in the genetic construct may be optimized for stability and high levels of expression.

The genetic construct may also comprise an enhancer upstream of the recombinant acetyl-CoA biosensor polypeptide coding sequence. The enhancer may be necessary for DNA expression. The enhancer may be a viral enhancer such as one selected from CMV, HA, RSV, or EBV. The genetic construct may also comprise a mammalian origin of replication in order to maintain the vector extrachromosomally and produce multiple copies of the vector in a cell. The genetic construct may also comprise a regulatory sequence, which may be well suited for gene expression in a mammalian or human cell into which the vector is administered. The genetic construct may also comprise a reporter gene, such as green fluorescent protein ("GFP") and/or a selectable marker, such as hygromycin ("Hygro").

The genetic construct may be useful for transfecting, transducing, or transforming cells with a nucleic acid encoding the recombinant acetyl-CoA biosensor polypeptide, wherein the transfected, transduced, or transformed host cell may be cultured and maintained under conditions wherein expression of the recombinant acetyl-CoA biosensor polypeptide takes place. The genetic construct may be transformed, transfected, or transduced into a cell. The genetic construct may be formulated into any suitable type of delivery vehicle including, for example, a viral vector, lentiviral vector, adeno-associated virus (AAV) vector, mRNA electroporation, and lipid-mediated transfection for delivery into a cell. The genetic construct may be part of the genetic material in attenuated live microorganisms or recombinant microbial vectors which live in cells. The genetic construct may be present in the cell as a functioning extrachromosomal molecule.

Further provided herein is a cell transformed, transfected, or transduced with a recombinant acetyl-CoA biosensor polypeptide or component thereof as detailed herein. Suitable cell types are detailed herein. In some embodiments, the cell is a bacterial cell.

Viral Vectors

A genetic construct may be a viral vector. Further provided herein is a viral delivery system. Viral delivery systems may include, for example, lentivirus, retrovirus, adenovirus, cytomegalovirus (CMV), mRNA electroporation, or nanoparticles. In some embodiments, the vector is a lentiviral vector. In some embodiments, the viral vector is an adeno-associated virus (AAV) vector. In some embodiments, the viral vector is a CMV vector.

Lentiviral vectors may be used to deliver the recombinant acetyl-CoA biosensor polypeptide using various construct configurations. AAV vectors may be used to deliver the recombinant acetyl-CoA biosensor polypeptide using various construct configurations. CMV vectors may be used to deliver the recombinant acetyl-CoA biosensor polypeptide using various construct configurations. In some embodiments, the lentiviral vector is a modified lentiviral vector. In some embodiments, the AAV vector is a modified AAV vector. In some embodiments, the CMV vector is a modified CMV vector. The AAV vector or modified AAV vector may be based on one or more of several capsid types, including AAV1, AAV2, AAV5, AAV6, AAV8, and AAV9.

Compositions

Further provided herein are compositions comprising the above-described recombinant acetyl-CoA biosensor polypeptides. In some embodiments, the composition may comprise from about 0.1 µM to about 10 µM, about 0.5 µM to about 10 µM, about 1 µM to about 10 µM, about 1.5 µM to about 10 µM, about 2 µM to about 10 µM, about 2.5 µM to about 10 µM, about 3 µM to about 10 µM, about 3.5 µM to about 10 µM, about 4 µM to about 10 µM, about 4.5 µM to about 10 µM, about 5 µM to about 10 µM, about 5.5 µM to about 10 µM, about 6 µM to about 10 µM, about 6.5 µM to about 10 µM, about 7 µM to about 10 µM, about 7.5 µM to about 10 µM, about 8 µM to about 10 µM, about 8.5 µM to about 10 µM, about 9 µM to about 10 µM, about 9.5 µM to about 10 µM, about 0.1 µM to about 9.5 µM, about 0.1 µM to about 9 µM, about 0.1 µM to about 8.5 µM, about 0.1 µM to about 8 µM, about 0.1 µM to about 7.5 µM, about 0.1 µM to about 7 µM, about 0.1 µM to about 6.5 µM, about 0.1 µM to about 6 µM, about 0.1 µM to about 5.5 µM, about 0.1 µM to about 5 µM, about 0.1 µM to about 4.5 µM, about 0.1 µM to about 4 µM, about 0.1 µM to about 3.5 µM, about 0.1 µM to about 3 µM, about 0.1 µM to about 2.5 µM, about 0.1 µM to about 2 µM, about 0.1 µM to about 1.5 µM, or about 0.1 µM to about 1 µM of the recombinant acetyl-CoA biosensor polypeptide or recombinant DNA encoding the recombinant acetyl-CoA biosensor. In some embodiments, the composition may comprise about 1 µM of the recombinant acetyl-CoA biosensor polypeptide or recombinant DNA encoding the recombinant acetyl-CoA biosensor. The recombinant acetyl-CoA biosensor polypeptides or recombinant DNA encoding the recombinant acetyl-CoA biosensor as detailed herein may be formulated into compositions in accordance with standard techniques well known to those skilled in the art. The compositions can be formulated according to the mode of administration to be used. The compositions may be sterile, pyrogen free, and particulate free. An isotonic formulation may also be used. Generally, additives for isotonicity may include sodium chloride, dextrose, mannitol, sorbitol, and lactose. In some cases, isotonic solutions such as phosphate buffered saline may be preferred. Stabilizers may include gelatin and albumin.

Administration

The recombinant acetyl-CoA biosensor polypeptides disclosed herein or compositions comprising the same may be administered or provided to a cell. The cell may be a bacterial cell. The cell may be in a subject. The recombinant acetyl-CoA biosensor polypeptides disclosed herein or compositions comprising the same may be administered or delivered to an organelle of a cell, such as the nucleus, mitochondria, cytoplasm, and the like. Methods of introducing a peptide into a host cell are known in the art, and any known method can be used to introduce a recombinant acetyl-CoA biosensor polypeptide into a cell. Suitable methods may include, for example, transformation, transduction, transfection, electroporation, direct microinjection, and the like.

The recombinant acetyl-CoA biosensor polypeptides as detailed herein or the compositions comprising the same may be administered to a subject. Such compositions can be administered in dosages and by techniques well known to those skilled in the medical arts taking into consideration such factors as the age, sex, weight, and condition of the particular subject, and the route of administration. The presently disclosed recombinant acetyl-CoA biosensor polypeptides or compositions comprising the same may be administered to a subject by different routes including orally, parenterally, sublingually, transdermally, rectally, transmucosally, topically, intranasal, intravaginal, via inhalation, via buccal administration, intrapleurally, intravenous, intraarterial, intraperitoneal, subcutaneous, intradermally, epidermally, intramuscular, intranasal, intrathecal, intracranial, intraarticular, or combinations thereof. The recombinant acetyl-CoA biosensor polypeptides or compositions comprising the same may be delivered to a subject by several technologies including liposome mediated, nanoparticle facilitated, recombinant vectors such as recombinant lentivirus, recombinant adenovirus, and recombinant adenovirus associated virus. For veterinary use, the recombinant acetyl-CoA biosensor polypeptides or compositions comprising the same may be administered as a suitably acceptable formulation in accordance with normal veterinary practice. The veterinarian may readily determine the dosing regimen and route of administration that is most appropriate for a particular animal. The recombinant acetyl-CoA biosensor polypeptides or compositions comprising the same may be administered by traditional syringes, or other physical methods such as electroporation ("EP"), "hydrodynamic method", or ultrasound.

Upon delivery of the presently disclosed recombinant acetyl-CoA biosensor polypeptides as detailed herein, or the compositions comprising the same, the transfected, transduced, transformed cells may express the recombinant acetyl-CoA biosensor polypeptide.

Cell Types

Any of the delivery methods and/or routes of administration detailed herein can be utilized with a myriad of cell types. Further provided herein is a cell transformed, transfected, or transduced with a recombinant acetyl-CoA biosensor polypeptide as detailed herein. For example, provided herein is a cell comprising an isolated polynucleotide encoding a recombinant acetyl-CoA biosensor polypeptide as detailed herein. In some embodiments, the cell may be a bacterial cell such as, but not limited to, *E. coli, Shigella, Salmonella, Klebsiella*, and *Yersinia*. In some embodiments, the cell may be a yeast such as *Saccharomyces cerevisiae*. In some embodiments, the cell may be an immune cell. Immune cells may include, for example, lymphocytes such as T cells and B cells and natural killer (NK) cells, innate immune cells, adaptive immune cells, NKT cells, IFN-γ producing killer dendritic cells (IKDC), memory T cells (TCMs), and effector T cells (TEs). The cell may be a stem cell such as a human stem cell, an embryonic stem cell, a hematopoietic stem cell, an induced pluripotent stem cell (iPSC), stem cell-derived cell types such as neurons. The cell may be a primary cell such as a neuron, a muscle cell, a kidney cell, and the like. Cells may further include, but are not limited to, immortalized myoblast cells, dermal fibroblasts, bone marrow-derived progenitors, skeletal muscle progenitors, human skeletal myoblasts, CD133+ cells, mesoangioblasts, cardiomyocytes, hepatocytes, chondrocytes, mesenchymal progenitor cells, hematopoietic stem cells, smooth muscle cells, and MyoD- or Pax7-transduced cells. The cell may be a cancer cell. The cell may be a cell from a cell line such as a Human Embryonic Kidney (HEK) 293 cell.

Methods

Methods of Detecting Acetyl-CoA

Provided herein are methods of detecting and/or quantifying acetyl-CoA in a sample. The methods may include contacting a sample with the recombinant acetyl-CoA biosensor polypeptide described herein and exciting the recombinant acetyl-CoA biosensor polypeptide in the sample at an excitation wavelength. The excitation wavelength may be from about 460 nm to about 490 nm. In a particular embodiment, the excitation wavelength may be 485 nm. After excitation of the recombinant acetyl-CoA biosensor polypeptide, the method may include measuring a fluorescence intensity of the recombinant acetyl-CoA biosensor polypeptide in the sample at an emission wavelength. The emission wavelength may be from about 513 nm to about 540 nm. In a particular embodiment, the emission wavelength may be 514 nm. The method may further includes comparing the fluorescence intensity to a standard curve, wherein the fluorescence intensity correlates with a concentration of acetyl-CoA in the sample. The standard curve may be generated by exciting the recombinant acetyl-CoA biosensor polypeptide in one or more control samples at the excitation wavelength and measuring a fluorescence intensity of the recombinant acetyl-CoA biosensor polypeptide in the one or more control samples at the emission wavelength. The standard curve may be based upon (i) one or more control samples comprising the recombinant acetyl-CoA biosensor polypeptide as described herein and without acetyl-CoA and (ii) one or more samples comprising the recombinant acetyl-CoA biosensor polypeptide as described herein and a known concentration (or series of known concentrations) of acetyl-CoA. The pH of the sample may be maintained at a pH of 6.5-8.0.

Methods of Monitoring Acetyl-CoA Activity in a Cell

Provided herein are methods of monitoring acetyl-CoA activity in a cell. The methods may include providing a cell with a recombinant acetyl-CoA biosensor polypeptide described herein and exciting the recombinant acetyl-CoA biosensor polypeptide in the cell at a first excitation wavelength between about 400 nm and about 430 nm while measuring a first fluorescence intensity at an emission wavelength between about 513 nm and about 540 nm. In a particular embodiment, the first excitation wavelength may be 405 nm. In another particular embodiment, the emission wavelength may be 514 nm. The method may further include exciting the recombinant acetyl-CoA biosensor polypeptide in the cell at a second excitation wavelength between about 460 nm and about 490 nm while measuring a second fluorescence intensity at the emission wavelength. In a particular embodiment, the second excitation wavelength may be 485 nm. The second fluorescence intensity may be normalized based on the first fluorescence intensity. Normalizing may include dividing the second fluorescence intensity by the first fluorescence intensity.

The cell may be treated with an acetyl-CoA precursor or nutrient affecting the function of the cell. Then, the normalized fluorescence intensity of the cell may be compared to the normalized fluorescence intensity of a control cell that did not receive the acetyl-CoA precursor or the nutrient. The acetyl-CoA precursor or nutrient may be one or more of glucose, fatty acids (e.g., fatty acyl CoA, octanoate, and palmitate), amino acids (e.g., glutamine, isoleucine, and valine), acyl CoA dehydrogenase, mono- and dicarboxylates (e.g., acetate, lactate, and alpha-ketoglutarate), and ketone bodies (e.g., acetoacetate and 3-beta-hydroxybutyrate).

The method may further comprise determining where the acetyl-CoA is localized in the cell by using a NES, a NLS, a CLS, or a MLS attached to the recombinant acetyl-CoA biosensor polypeptide as described herein.

Kits

Provided herein is a kit, which may be used to detect, quantify, monitor activity of, determine the presence of, and/or determine the location of acetyl-CoA. The kit comprises genetic constructs or a composition comprising the same, as described above, and instructions for using said composition. In some embodiments, the kit may comprise at least one genetic construct comprising a polynucleotide sequence that encodes a recombinant acetyl-CoA biosensor polypeptide described herein, wherein the polynucleotide may, for example, comprise a nucleic acid sequence selected from SEQ ID NOS: 24-38, SEQ ID NOS: 62-76, SEQ ID NO: 83, SEQ ID NO: 85, and SEQ ID NO: 87, a complement thereof, a variant thereof, or a fragment thereof. The kit may comprise at least one recombinant acetyl-CoA biosensor polypeptide comprising, for example, an amino acid sequence selected from SEQ ID NOS: 5-19, SEQ ID NOS: 43-57, SEQ ID NO: 77, SEQ ID NO: 79, and SEQ ID NO: 81, a complement thereof, a variant thereof, or fragment thereof. The kit may further include instructions for using the genetic construct or the recombinant acetyl-CoA biosensor polypeptide.

Instructions included in kits may be affixed to packaging material or may be included as a package insert. While the instructions are typically written on printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

EXAMPLES

The foregoing may be better understood by reference to the following examples, which are presented for purposes of illustration and are not intended to limit the scope of the invention. The present disclosure has multiple aspects and embodiments, illustrated by the appended non-limiting examples.

Example 1

Materials and Methods

Figure 4:
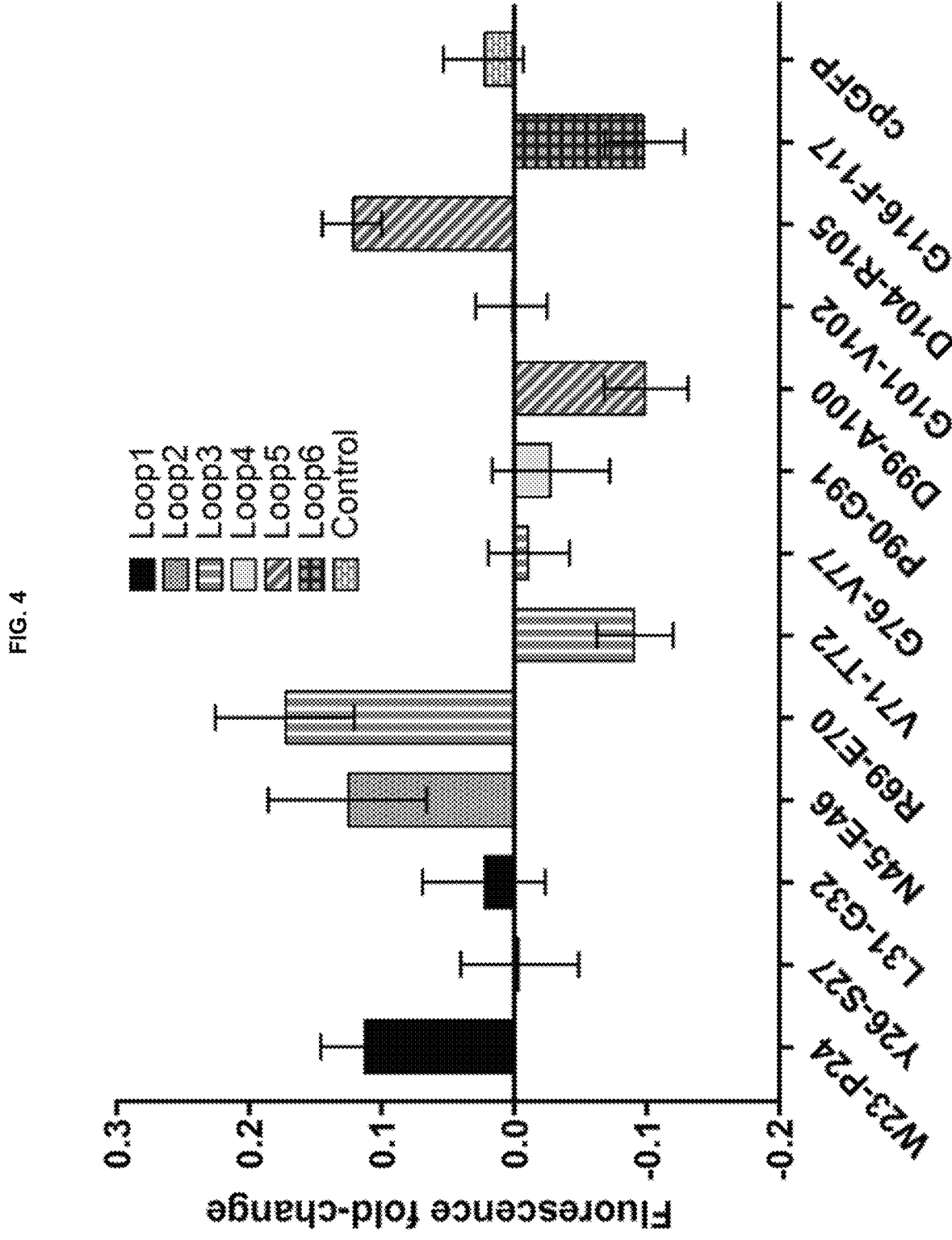
FIG. 4 is a bar graph showing the fluorescence change of the same series of PanZ-cpGFP fusion proteins from FIG. 3 in the presence of 1 mM acetyl-CoA compared to in the absence of acetyl-CoA ($(F_1-F_0)/F_0$). $\lambda_{ex}$=485, $\lambda_{em}$=514 nm, n=3. The location of each cpGFP insertion site listed at the bottom of the graph is labeled according to what loop it corresponds with in FIG. 2. All of these fusions contain an Ala-Ser (AS) linker at each junction, i.e., (Nterm)PanZ-AS-cpGFP-AS-PanZ (Cterm). From this data, it is shown that several of the fusion proteins show a reproducible change in intensity in the presence of acetyl-CoA that is a larger change than for cpGFP alone, which represents the background since cpGFP has no intrinsic acetyl-CoA binding ability. These include tryptophan at position 23 (W23), arginine at position 69 (R69), valine at position 71 (V71), aspartic acid at position 99 (D99), aspartic acid at position 104 (D104), and glycine at position 116 (G116). R69 had the largest magnitude of change, so it was selected to further optimize. Nevertheless, the other foregoing insertion sites can be characterized as acetyl-CoA sensors as well.

Molecular Cloning. All PCR was done with Q5® High-Fidelity DNA Polymerase kit (New England Biolabs (NEB), Ipswich, MA) according to manufacturer's protocols. All primers were ordered from University of Utah Core Labs (Salt Lake City, UT). All plasmids were sequence verified by GENEWIZ®.

cpGFP Insertion Sites Screen. The *E. coli* PanZ gene was purchased from Integrated DNA Technologies (IDT, Coralville, IA) and was subcloned into the pET30A vector using the N-terminal 6× histidine tag followed by a TEV cleavage site (HTSD1.10). The cpGFP gene was Addgene 186790 and subcloned into the pET30A vector using the N-terminal 6× histidine tag followed by a TEV cleavage site (HTSD1.00). cpGFP was inserted into the PanZ gene between the amino acids as shown in FIG. 4, based off of recombinant protein sequence (based off of PanZ sequence), with an AS amino acid linker on the N and C-terminal ends of cpGFP using NEBuilder® HiFi DNA Assembly Master Mix (NEB) (HTSD6.00-6.13).

Linker Length Screen. cpGFP (HTSD1.00) was inserted into 6× histidine tagged PanZ (HTSD1.10) after amino acid R69 with all 16 possible combinations of N- and C-terminal linkers with amino acid sequences GAS, GA, G, no linker using NEBuilder® HiFi DNA Assembly Master Mix (NEB) (HTSD8.00-8.15).

cpGFP Mutation to Other Color Fluorophores. Quick Change Mutagenesis was done to cpGFP (HTSD1.00) to generate point mutants cpYFP (HTSD1.01) and cpBFP (HTSD1.02). NEBuilder® HiFi DNA Assembly Master Mix (NEB) was then used to insert them into 6× histidine tagged PanZ (HTSD1.10) with GA amino acid linkers on the N- and C-terminal of the R69-E70 position. This yielded Banana PANcACe(HTSD8.05Y) and Blueberry PANcACe (HTSD8.05B).

Lentiviral vectors. PancAce and cpGFP were subcloned from the pet30A plasmid into the pLJM1 plasmid (Addgene 19319) using the NEBuilder® Hifi DNA Assembly. The localization tags were subcloned from plasmids (Addgene 186787, 186788, and 186789).

Recombinant Protein Preparation. PanZ, cpGFP, cpYFP, cpBFP, and all sensor construct plasmids were transformed into BL21 Rosetta (DE3) cells for expression. Glycerol stocks of each construct were saved at −80° C. Glycerol stocks were used to inoculate 10 mL LB media with kanamycin. Cultures were grown at 37° C. overnight then used to inoculate 1 L LB with kanamycin. The 1 L cultures were grown at 37° C. to $OD_{600}$=0.6. The temperature was then turned to 18° C. and flasks were induced with 0.5 mM IPTG for 18 hrs. Bacteria were pelleted at 4000 g for 30 minutes. The pellet was then purified or stored at −80° C. until purification. The pellet from 1 L of culture was resuspended in lysis buffer (50 mM Tris pH 7.5, 500 mM NaCl, 10 mM imidazole) then sonicated for 1 minute on, 3 minutes off with duty cycle 50%. Clarified lysates were obtained by spinning lysates at 17000×g for 30 minutes. Clarified lysates were then run over 1 mL of equilibrated Ni-resin and washed with 30 mL wash buffer (50 mM Tris pH 7.5, 50 mM NaCl, 50 mM imidazole). Recombinant proteins were then eluted with 5, 1 mL aliquots of elution buffer (50 mM Tris pH 7.5, 500 mM NaCl, 500 mM imidazole). Aliquots were then pooled, and buffer exchanged in (EMD Millipore, Burlington, MA; 30 kDa MWCO) into storage buffer (50 mM Tris pH 7.5, 150 mM NaCl, 10% glycerol). Proteins were concentrated to ~100 µM then aliquoted and stored at −80° C. until use.

Surface Plasmon Resonance. Acetyl-CoA and CoA binding to PanZ-CFP were analyzed via SPR using a MASS-1 instrument (Bruker Daltonics, Billerica, MA). Independent experiments were performed using freshly prepared PanZ-CFP, Acetyl-CoA, and CoA stocks on two separate days (surfaces 1 & 2). HLC200 µM sensor surfaces (Xantec Bioanalytics, Düsseldorf, Germany) were activated with EDC/NHS, and then 250 nM PanZ-CFP ligand was captured on the sensor "Spot B" at 10 µL/minute at 2020 RU (surface 1) and 2360 RU (surface 2). The surface was then blocked with 1 µM ethanolamine. The experimental running buffer was 50 mM Tris pH 7.5, 150 mM NaCl, 0.05% Tween-20 for surface 1 replicates and 200 mM Tris pH 7.5, 150 mM NaCl, 0.05% Tween-20 for surface 2 replicates. Experiments were performed at room temperature with a flowrate of 30 µL/minute. A three-fold dilution series (81-0.33 µM) with 1 minute association and 2 minutes dissociation was run in multiple replicates (at least two for each analyte on each surface). Data were double blanked by subtracting the blank in-line control surface (Spot A) and buffer reference injections. Kinetic binding data were globally fit to the Langmuir model for 1:1 binding for each replicate of concentration series using the Sierra Analyser software (version 3.4.1, Bruker Daltonics, Billerica, MA). The representative replicate data and fit were exported and then plotted using GraphPad Prism version 9.4.1. The average KD from these fits is reported along with the standard error (five replicates for acetyl-CoA and four for CoA).

Position and Linker Screen. Assays were done in 96 well plates with 100 µL final well volumes. All sensors and control proteins were diluted to 10 µM in protein storage buffer (50 mM Tris pH 7.5, 150 mM NaCl, 10% glycerol). Acetyl-CoA was dissolved in water at a concentration of 10 mM. A 5× assay buffer was used (1 µM Tris pH 7.5, 750 mM NaCl). Wells were set up in triplicate with 60 µL water, 20 µL reaction buffer, and 10 µL sensor. Then either 10 µL of water or 10 µL of acetyl-CoA were added to 1 µM sensor before reading. Plates were read at excitation 485 nm emission 528 nm. Triplicates were averaged and percent difference between no acetyl-CoA and acetyl-CoA wells were calculated.

Acetyl-CoA and CoA Titration and Spectrum Scans. Assays were done in 384 well plates with 30 L final well volume. All sensors and control proteins were diluted to 6 µM in protein storage buffer. Acetyl-CoA and CoA were dissolved in water at a concentration of 60 µM then serial diluted to 30 µM, 15 µM, 6 µM, 3 µM, 0.6 µM, 0.06 µM, and 0.006 µM. Wells were set up in triplicate with 14 µL water, 6 µL assay buffer, and 5 µL sensor. 5 µL of an acetyl-CoA stock or water were added to 1 µM sensor before reading. For Titration curves, plates were read at excitation 485 nm and emission 514 nm. For excitation scans plates were excited from 400 nm to 500 nm at 1 nm increments and emissions were read at 428 nm. For emission scans plates were excited at 485 nm, 427 nm, or 405 nm and emissions were read from 500 nm to 575 nm in 1 nm increments. Triplicates were averaged and plotted for scans and percent difference between no acetyl-CoA and acetyl-CoA wells were calculated for titrations.

pH Titration. Assays were done in 384 well plates with 30 µL final volume. All sensors and control proteins were diluted to 6 µM in protein storage buffer. Acetyl-CoA was dissolved in water at a concentration of 6 mM. Different assay buffers were made, all 1 µM Tris, 750 mM NaCl with pH 6.5, 6.75, 7.0, 7.25, 7.5, 7.75, and 8.0. Wells were set up in triplicate with 14 µL water, 6 µL assay buffer, and 5 µL sensor. 5 µL of acetyl-CoA or water were added to 1 µM sensor before reading. Plates were read at excitation 485 nm and emission 514 nm. Triplicates were averaged and plotted.

Acyl-CoA Screen. Assays were done in 384 well plates with 30 µL final volume. All sensors and control proteins were diluted to 6 µM in protein storage buffer. CoA, acetyl-CoA, propionyl-CoA, butyryl-CoA, malonyl-CoA, and succinyl-CoA were dissolved in water at a concentration of 6 mM. Wells were set up in triplicate with 14 µL water, 6 µL assay buffer, and 5 μL sensor. 5 μL of an acyl-CoA or water were added to 1 μM sensor before reading. Plates were read at excitation 485 nM and emission 514 nm. Triplicates were averaged and percent difference between acyl-CoAs and water were calculated.

Flow Cytometry Starvation. All assays were done with the BD FACSAria™ III Cell Sorter. All sensors and control proteins were expressed in Rosetta (DE3) cells. PanZ was used as a non-fluorescent control, cpGFP was used as a fluorescent control, and PANcACe was the experimental. Cultures were grown in LB with kanamycin overnight at 37° C. then used to induce new cultures. Cells were grown at 37° C. to an $OD_{600}$ of 0.6 then induced with 0.5 mM IPTG and grown overnight at 18° C. The overnight culture was divided into 5, 1 mL aliquots for fed, 15 minutes, 1 hour, 2 hours, and 3 hours starved timepoints. Aliquots were spun down for 5 minutes at 4000×g. Fed, 15 minutes, 1 hour, and 2 hours cells were resuspended in feeding media (i.e., PBS+28 mM glucose) while 3 hours cells were resuspended in starvation media (i.e., PBS). All cultures were put at 37° C. to shake between steps. At 2 hours, 1 hour, and 15 minutes before reading, cells were spun down as before and resuspended in starvation media then returned to shaking. On the flow cytometer cells were read with 405 nm and 485 nm excitations with 514 nm emission.

Flow Cytometry Refeeding. All assays were done with the BD FACSAria™ III Cell Sorter. All sensors and control proteins were expressed in Rosetta (DE3) cells. PanZ was used as a non-fluorescent control, cpGFP was used as a fluorescent control, and PANcACe was the experimental. Cultures were grown in LB with kanamycin overnight at 37° C. then used to induce new cultures. Cells were grown at 37° C. to an $OD_{600}$ of 0.6 then induced with 0.5 mM IPTG and grown overnight at 18° C. The overnight culture was divided into 5, 1 mL aliquots for starved, 15 minutes, 1 hour, 2 hours, and 3 hours refeeding timepoints. Aliquots were spun down for 5 minutes at 4000×g. Cells were resuspended in starvation media for 3 hours before being moved into feeding media for the duration of their time point. Cells waiting to be starved were kept in feeding media. Cells were shaken at 37° C. between steps. On the flow cytometer cells were read with 405 nm and 485 nm excitations with 514 nm emission.

Flow Cytometry Data Analysis. Analysis was done in Flowing Software (Turku Bioscience, Turku, Finland). First a PanZ histogram was used as a negative control to determine how much signal came from non-fluorescent cells. The region with more fluorescence than PanZ was marked as Region 1. For PANcACe and cpGFP the ratio of 485 excitation/405 excitation was calculated on a cell-by-cell basis. This ratio was plotted in a histogram including only cells from region 1. The median of this ratio for each time point was taken. For the starvation assays the percent difference was calculated between each starvation timepoint and the fed control. For the refeeding assay the percent difference was calculated between each refeeding timepoint and the starved control.

Plate Reader Refeeding. All assays were done with the BioTek Synergy™ Plate Reader with injectors. All sensors and control proteins were expressed in Rosetta (DE3) cells. PanZ was used as a non-fluorescent control, cpGFP was used as a fluorescent control, and PANcACe was the experimental. Reads were done with excitation 405 nm and 485 nm and emission at 514 nm. Cultures were grown in LB with kanamycin overnight at 37° C. then used to induce new cultures. Cells were grown at 37° C. to an $OD_{600}$ of 0.6 then induced with 0.5 mM IPTG and grown overnight at 18° C. Cultures were split into 2, 600 μL aliquots and spun at 4000 rpm for 5 minutes.

Glucose Starvation and Refeeding. The supernatant was discarded and pellets were resuspended in 600 μL either starvation buffer (100 mM $NaPO_4$, 2 mM $MgCl_2$, 15 mM $(NH_4)_2SO_4$+0 mM glucose) or refed buffer (100 mM $NaPO_4$, 2 mM $MgCl_2$, 15 mM $(NH_4)_2SO_4$+28 mM glucose). 85 μL was added to 3 wells of a 96 well plate for each sample. Plates were shaken at room temperature for 3 hours. Plates were read for 10 minutes every 30 seconds with 10 seconds of shaking between reads. 15 μL starvation buffer was added to fed cells and 15 μL of refeeding buffer (100 mM $NaPO_4$, 2 mM $MgCl_2$, 15 mM $(NH_4)_2SO_4$+280 mM glucose) was added to starved cells via injectors. Plates were read for 60 minutes every 30 seconds with 10 seconds of shaking between reads.

Acetate Starvation and Refeeding. The supernatant was discarded and pellets were resuspended in 600 μL either starvation buffer (100 mM $NaPO_4$, 2 mM $MgCl_2$, 15 mM $(NH_4)_2SO_4$+0 mM glucose) or fed buffer (100 mM $NaPO_4$, 2 mM $MgCl_2$, 15 mM $(NH_4)_2SO_4$+28 mM glucose). 85 μL was added to 3 wells of a 96 well plate for each sample. Plates were shaken at room temperature for 3 hours. Plates were read for 10 minutes every 30 seconds with 10 seconds of shaking between reads. 15 μL starvation buffer was added to fed cells and 15 μL of refeeding buffer (100 mM $NaPO_4$, 2 mM $MgCl_2$, 15 mM $(NH_4)_2SO_4$+100 μM acetate) was added to starved cells via injectors. Plates were read for 60 minutes every 30 seconds with 10 seconds of shaking between reads.

2-Deoxyglucose Starvation and Refeeding. The supernatant was discarded and pellets were resuspended in 600 μL either starvation buffer (100 mM $NaPO_4$, 2 mM $MgCl_2$, 15 mM $(NH_4)_2SO_4$+28 mM 2-deoxyglucose) or refeeding buffer (100 mM $NaPO_4$, 2 mM $MgCl_2$, 15 mM $(NH_4)_2SO_4$+28 mM glucose). 85 μL was added to 3 wells of a 96 well plate for each sample. Plates were shaken at room temperature for 3 hours. Plates were read for 10 minutes every 30 seconds with 10 seconds of shaking between reads. 15 μL starvation buffer was added to fed cells and 15 μL refeeding buffer was added to starved cells via injectors. Plates were read for 60 minutes every 30 seconds with 10 seconds of shaking between reads.

Human cell handling and preparation of the stable Hela cell lines. The 293T and HeLa cells were maintained in standard DMEM with 4.5 g/L glucose (11995-065, Gibco, Waltham, MA), 10% v/v heat inactivated FBS (10082-147, Gibco, Waltham, MA), and 1% v/v penicillin/streptomycin (15070063, Gibco, Waltham, MA) at 37° C. and 5% $CO_2$. The cells were subcultured by trypsinization (25200-056, Gibco, Waltham, MA).

Lentivirus. 293T cells were used to produce lentivirus from the pLJM1 proviral vector containing the PancAce or cpGFP gene with the corresponding localization tags. For each construct, a 10-cm dish of 293T cells in standard media with 3% v/v FBS was transfected with 4 μg provirus plasmid (pLJM1 with gene of interest), 4 μg HIV gag-pol plasmid (psPAX2), and 0.57 μg VSV-G plasmid (pMD2.G) using 26 μL of X-tremeGENE™ HP (6366244001, Sigma Millipore, St. Louis, MO) in 1 mL of Opti-MEM™ (11058-021, Gibco, Waltham, MA). After 24 h, the cells were recovered into 10 mL of standard media with 3% v/v FBS. After 48 h, the virus-containing media was harvested and replaced with 10 mL of standard media with 3% v/v FBS. After 72 h, the virus-containing media was harvested and combined with the media collected at 48 h. The virus was filtered through 0.45 μm to remove cell debris and was stored unconcentrated in 1 mL aliquots at −80° C. The Hela cells were transduced in 6-well plates with 1 mL of unconcentrated virus+10 μg/mL polybrene (TR-1003-G, Sigma Millipore, St. Louis, MO) per well for 24 h. At 48 hours post-transduction, the cells were subjected to 1 μg/mL puromycin (J67236.XF, ThermoFisher, Waltham, MA) to select for infected cells, and the selection was maintained until all the non-transduced HeLa cells were dead (about 72 h). Low passage frozen stocks were prepared of the six resultant polyclonal HeLa cell lines (PancAce mito, nuc, cyto and cpGFP mito, nuc, cyto) in 10% DMSO-containing standard media. For experiments, cells were thawed and passaged for a maximum of 4-5 weeks as sensor/GFP expression and cell viability tended to be compromised after that period.

Perturbations of the Hela cells. The PancAce/cpGFP-expressing HeLa cells were counted and plated into glass bottom 96-well plates suitable for confocal microscopy (P96-1.5H-N, CellVis). The control condition (Fed or non-targeting siRNA) in each experiment was performed in triplicate wells, and the experimental conditions were performed in singlet wells. Each experiment was performed at least 4 times on entirely different days and plates. Immediately before beginning a microscopy session, the media was changed to serum and phenol red free based media that otherwise matched the contents of the corresponding experimental condition.

Deprivation experiments. DMEM containing no glucose, phenol red, or FBS (A14430-01, Gibco, Waltham, MA) plus 4 mM glutamine (Gibco, Waltham, MA, 25030081) was used as the base deprivation media. For the Fed condition, 4.5 g/L glucose (A24940-01, Gibco, Waltham, MA) and 10% v/v FBS was added to the base media. For the (−) glucose condition, only 10% v/v FBS was added. For the dFBS condition, 4.5 g/L glucose and 10% v/v dFBS (A33820-01, Gibco, Waltham, MA) was added. For the dFBS/(−) glucose condition, only 10% v/v dFBS was added. The cells were placed in these media formulations for approximately 16 h.

Refeeding experiments. The cells were deprived of glucose as described above in DMEM with 4 mM glutamine and 10% FBS but without glucose or phenol red. After 16 h, the media was changed to DMEM with 4 mM glutamine and 4.5 g/L glucose but without phenol red or FBS (to prepare the cells for imaging). Images were collected at the indicated time points.

Branch chain amino acid (BCAA) deprivation. Powdered DMEM without glucose, glutamine, isoleucine, leucine, valine, sodium pyruvate, sodium bicarbonate, or phenol red was used as the basis for these media formulations (US Biological, Salem, MA, D9800-36). This powdered DMEM was reconstituted in water using sodium bicarbonate to adjust the pH and sterile filtered prior to use as described by the manufacturer. The media was supplemented with 4.5 g/L glucose, 4 mM glutamine, 0.8 mM leucine, and 10% FBS to generate the BCAA-deprived media (i.e., no isoleucine or valine). The control media was generated in the same way, but 0.8 mM isoleucine and 0.8 mM valine were also added. Cells were incubated in either the (+)BCAA or (−)BCAA media for 24 h.

siRNA experiments, siRNAs were purchased as SMART-Pool™ from Horizon (Dharmacon, Lafayette, CO). The siRNAs were reconstituted as instructed by the manufacturer in 1× siRNA buffer (Horizon, Waterbeach, United Kingdom) in RNase-free water to a concentration of 20 μM. These stock aliquots were stored at −20° C. Each well of a 96-well plate was transfected with 0.3 μL of Lipofectamine 3000

(L3000001 ThermoFisher, Waltham, MA) and 50 nM siRNA (final concentration) in 300 μL total of Opti-MEM™. After incubation for 5-6 hours, the cells were recovered by changing the media to standard DMEM with 10% FBS and 1% pen/strep. The knockdowns were validated by immunoblot as detailed in the Immunoblotting section below. The siRNAs and antibodies are listed in TABLE 2 and TABLE 3.

TABLE 2

| SMARTPool™ siRNAs | |
| --- | --- |
| siRNA | Catalog ID |
| Control: ON-TARGETplus Non-targeting Pool | D-001810-10 |
| ON-TARGETplus Human ACLY siRNA | L-004915-00-0005 |
| ON-TARGETplus Human PDHA1 siRNA | L-010329-00-0005 |
| ON-TARGETplus Human ACSS2 siRNA | L-010396-00-0005 |
| ON-TARGETplus Human CRAT siRNA | L-009524-00-0005 |
| ON-TARGETplus Human EP300 siRNA | L-003486-00-0005 |
| ON-TARGETplus Human ACACA siRNA | L-004551-00-0005 |
| ON-TARGETplus Human ACACB siRNA | L-004759-00-0005 |

TABLE 3

| Antibodies | | |
| --- | --- | --- |
| Antibody | Manufacturer | Catalog ID |
| Mouse anti-actin mAb | Cell Signaling Technologies (Danvers, MA) | 3700 |
| Rabbit anti-ACLY mAb | Cell Signaling Technologies (Danvers, MA) | 13390 |
| Rabbit anti-ACSS2 mAb | Cell Signaling Technologies (Danvers, MA) | 3658 |
| Rabbit anti-PDH mAb | Cell Signaling Technologies (Danvers, MA) | 3205 |
| Rabbit anti-CrAT pAb | Proteintech ® | 15170-1-AP |
| Rabbit anti-p300 mAb | Cell Signaling Technologies (Danvers, MA) | 57625 |
| Rabbit anti-ACC mAb | Cell Signaling Technologies (Danvers, MA) | 3676 |

The cells were imaged 48 hours after transfection. Immediately before beginning the microscopy session, the media was changed to phenol red and serum free media containing 4.5 g/L glucose and 4 mM glutamine.

Fluorescence microscopy data collection. The cells were maintained at 37° C. and 5% $CO_2$ during imaging using an Oko Lab (Pozzuoli NA, Italy) stage top incubator. A Leica SP8 White Light Confocal microscope (Leica Microsystems, Wetzlar, Germany) was used for imaging. A Leica 20× dry objective was used (Leica Microsystems, Wetzlar, Germany). Excitation was performed at 405 nm and 488 nm, and emission was measured at 515 nm. Both excitation lasers were operated at 6% power. The gain of the PMT detector varied depending on the overall brightness of the cells on a given day such that pixel saturation was avoided. The scan parameters were set to 200× scan speed, 2.00 zoom factor, 3.5 μm pinhole. For each well, 10 FOVs were collected encompassing about 100 cells per FOV.

Fluorescence microscopy data analysis. The images were processed using Fiji (ImageJ, National Institutes of Health). A custom Python script was used for batch processing. Each pair of 405 nm and 488 nm images was subjected to a background subtraction (sliding rolling ball 50 px width) and a gaussian blur of 2, and then the ratio image was generated by dividing the 488 nm/405 nm. A mask for the ratio image was prepared by summing the 405 nm and 488 nm images that had a background subtraction and a gaussian blur applied as above. This mask was then applied to the ratio image. The mean pixel density was measured for the masked ratio image using an Otsu threshold. For the 10 FOVs per well, outliers were first removed, and an outlier were defined as a FOV that was more than three standard deviations outside the mean of the 10 FOVs. Then the total pixel area of the final processed ratio images was calculated and used to weigh the average mean pixel density of the 10 FOVs (minus any outliers). This value was taken as the measurement for each well. Next, the PancAce measurement was divided by the corresponding cpGFP measurement for a given condition (i.e., PancAce/cpGFP). For visualizing data, it was further normalized by dividing the experimental by the corresponding control condition (e.g., Fed/deprived) to give a fold change. For some plots, the percentage change is displayed from the following calculation: −(1-(fold-change))*100. The statistical analyses are described in detail in the Statistics section below.

Immunoblotting. Hela cell samples were treated as described in the section above for nutrient deprivation or siRNA transfections. The only difference was that conditions for immunoblotting were scaled up to a 6-well plate format. The cells were washed with cold PBS and then harvested in cold PBS. The Epiquik™ Histone Extraction Kit (Epigentek, Farmingdale, NY) was used for lysis and histone extraction as directed by the manufacturer. Briefly, the cell pellets were resuspended in 100 μL of 1× Pre-Lysis buffer and lysed on ice for 10 minutes. The cells were pelleted at high speed for 1 minute, and the supernatant was reserved ("lysate" or "total soluble fraction"). The pellet was resuspended in 30 μL of the Lysis buffer and incubated on ice for 30 minutes. The material was pelleted, and the supernatant was reserved ("histones") and neutralized with 9 μL of Balance buffer as directed. SDS loading buffer was added to both lysate and histone samples for immunoblotting.

The protein samples were separated by SDS-PAGE gel (either 12% Bis Tris or 4-12% Bis Tris as indicated for each blot) and transferred to a PVDF membrane by semi-dry transfer in Towbin buffer. The membranes were blocked with 3% or 5% milk according to the antibody manufacturer's instructions for 1 hour at room temperature. The membranes were incubated with primary antibodies at 4° C. overnight and then washed with TBST 3×. The membranes were incubated with secondary antibodies (Licor) in TBST for 1 hour at room temperature and then washed with TBST 3× before imaging using an Odyssey® Imager. Densitometry was performed in the LI-COR software (LI-COR Biosciences, Lincoln, NE).

Figure 16:
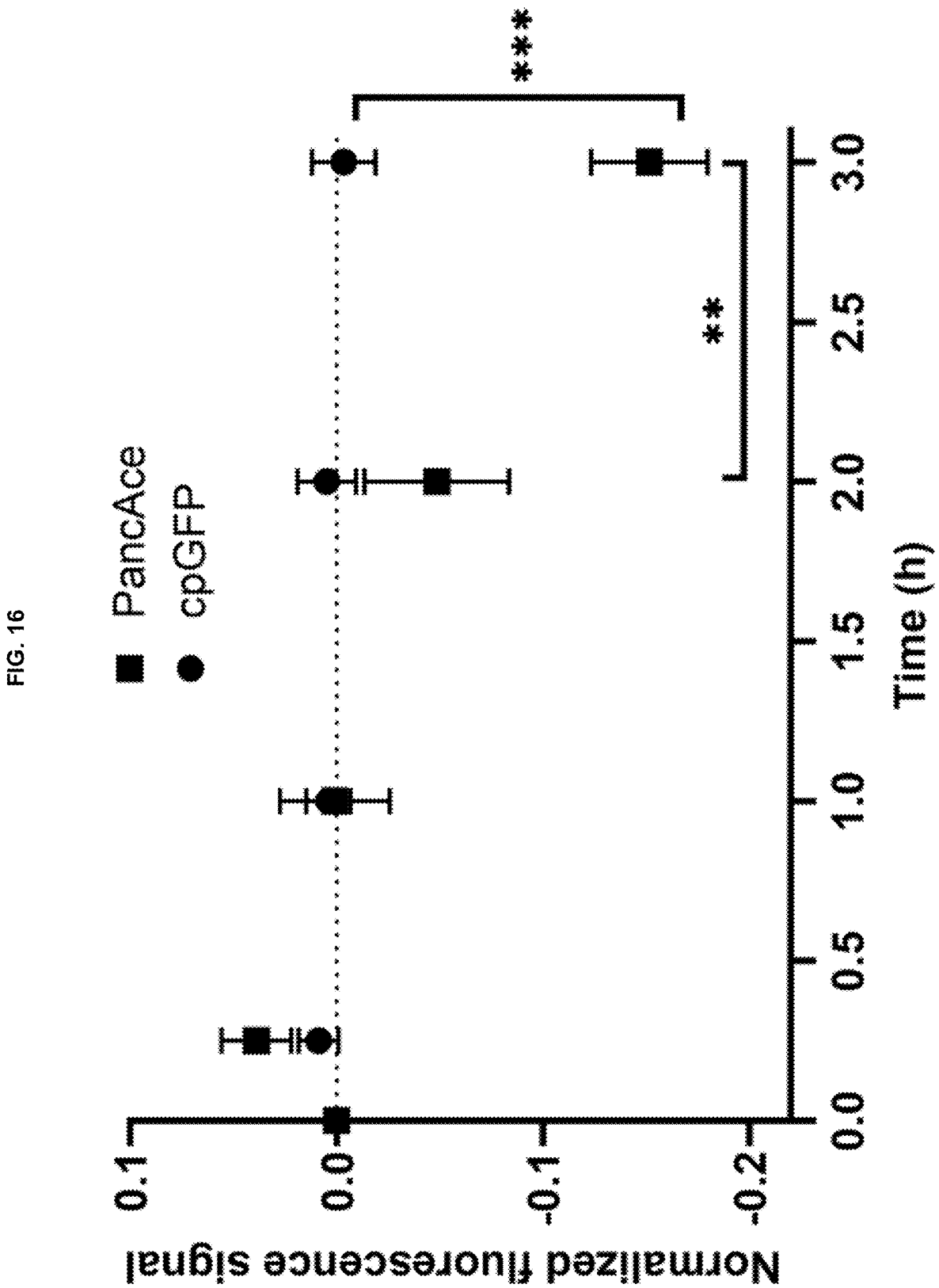
FIG. 16 is a dot plot showing the fluorescence of live *E. coli* that express either PancAce (sensor) or cpGFP and were deprived of all glucose over the time period shown on the X-axis of the plot. Depriving the *E. coli* of glucose in their media should cause their acetyl-CoA levels to drop over time because glucose is their main metabolic precursor of acetyl-CoA. The fluorescence ($\lambda_{ex}$=405 nm, 485 nm; $\lambda_{em}$=514 nm) was measured by flow cytometry. The fluorescence was normalized by dividing $F_{488}/F_{405}$ and then ($F_1-F_0)/F_0$ where $F_0$ were non-deprived cells, n=3, p<0.005, *p<0.0005.

Statistics. Prism GraphPad (version 10) was used for statistical analysis. A one-way ANOVA was applied to the data in FIG. 16 and FIG. 17. A two-way ANOVA was applied to the non-normalized data in FIG. 23A, FIG. 23B, FIG. 23C, FIG. 24, FIG. 25A, FIG. 25B, FIG. 25C, and FIG. 27. These tests yielded p-values, and each plot caption indicates the p-value ranges. The error bars shown in the plots and text are the standard deviations.

Example 2

Biosensor Engineering

First, an acetyl-CoA binding protein was selected that was predicted to be amenable to forming a biosensor. The protein PanZ was chosen, which is an endogenous acetyl-CoA sensor in *E. coli* that participates in the regulation of pantothenate synthesis. PanZ has a GNAT (GCN5-related N-acetyltransferase) domain but was shown to lack acetyltransferase activity. Instead of acting as an enzyme itself, PanZ binds acetyl-CoA, and this bound state is competent to bind the zymogen PanD (and to the activated form, aspartate α-decarboxylase). A structure of the PanZ/acetyl-CoA/PanD complex (PDB: 5LS7) and other biochemical data suggested that PanZ might be a suitable basis for a fluorescent acetyl-CoA sensor. However, one concern was that previous data was unclear as to the selectivity of PanZ for acetyl-CoA versus CoA. Poor selectivity would limit the utility of a biosensor for directly measuring acetyl-CoA in cells where acetyl-CoA and CoA levels are comparable under some conditions. The binding of purified PanZ to acetyl-CoA and CoA was tested using surface plasmon resonance (SPR) and measured a 7-fold higher affinity for acetyl-CoA versus CoA (FIGS. 1A-1D). The $K_d$ for acetyl-CoA agreed with the previously published value. Based on this data, it was concluded that PanZ was a promising starting point for a biosensor.

Figure 2:
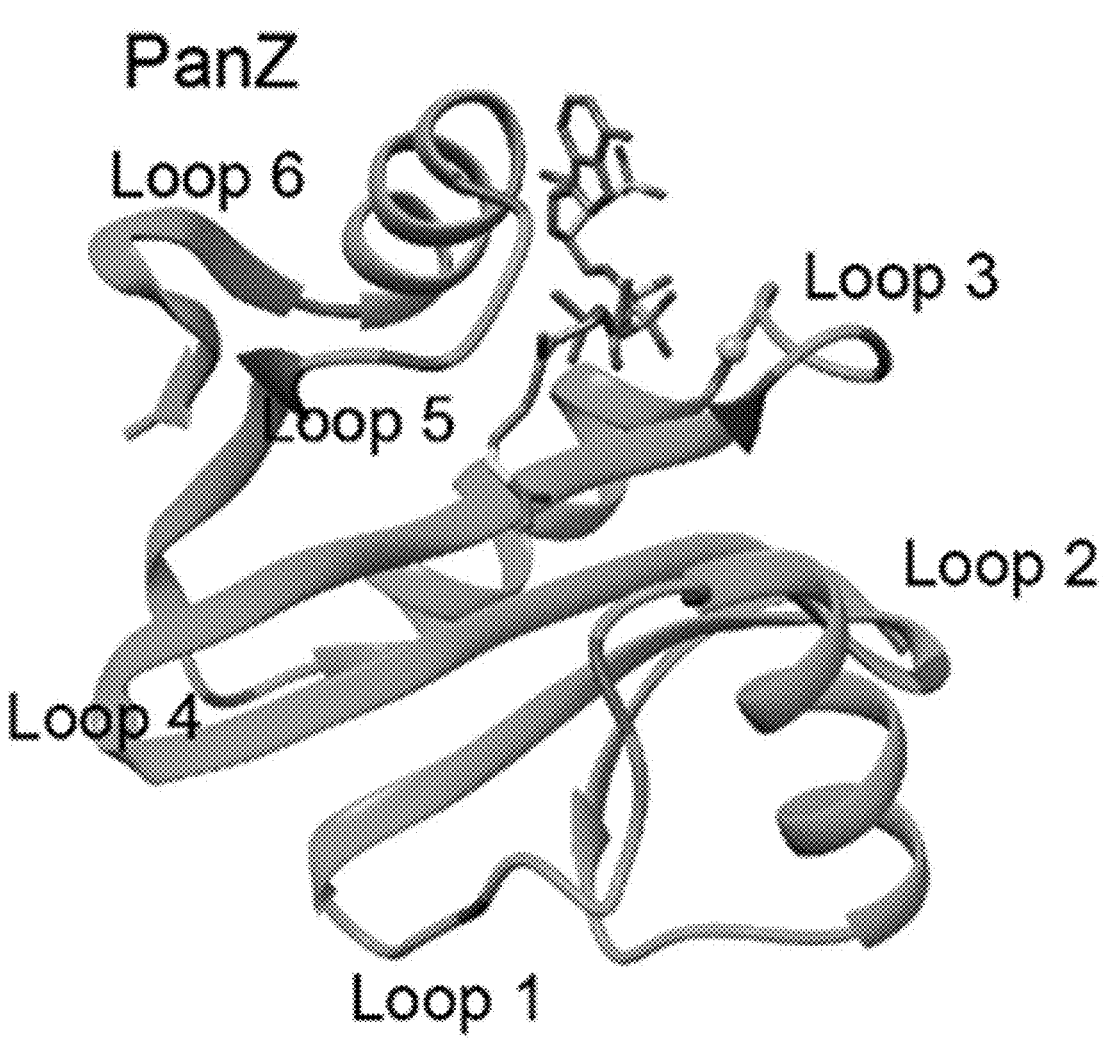
FIG. 2 is a model depicting the structure of PanZ (PDB 4CRZ) with its six unstructured loops labeled that were tested as cpGFP insertion sites to make an acetyl-CoA biosensor described herein.
Figure 3:
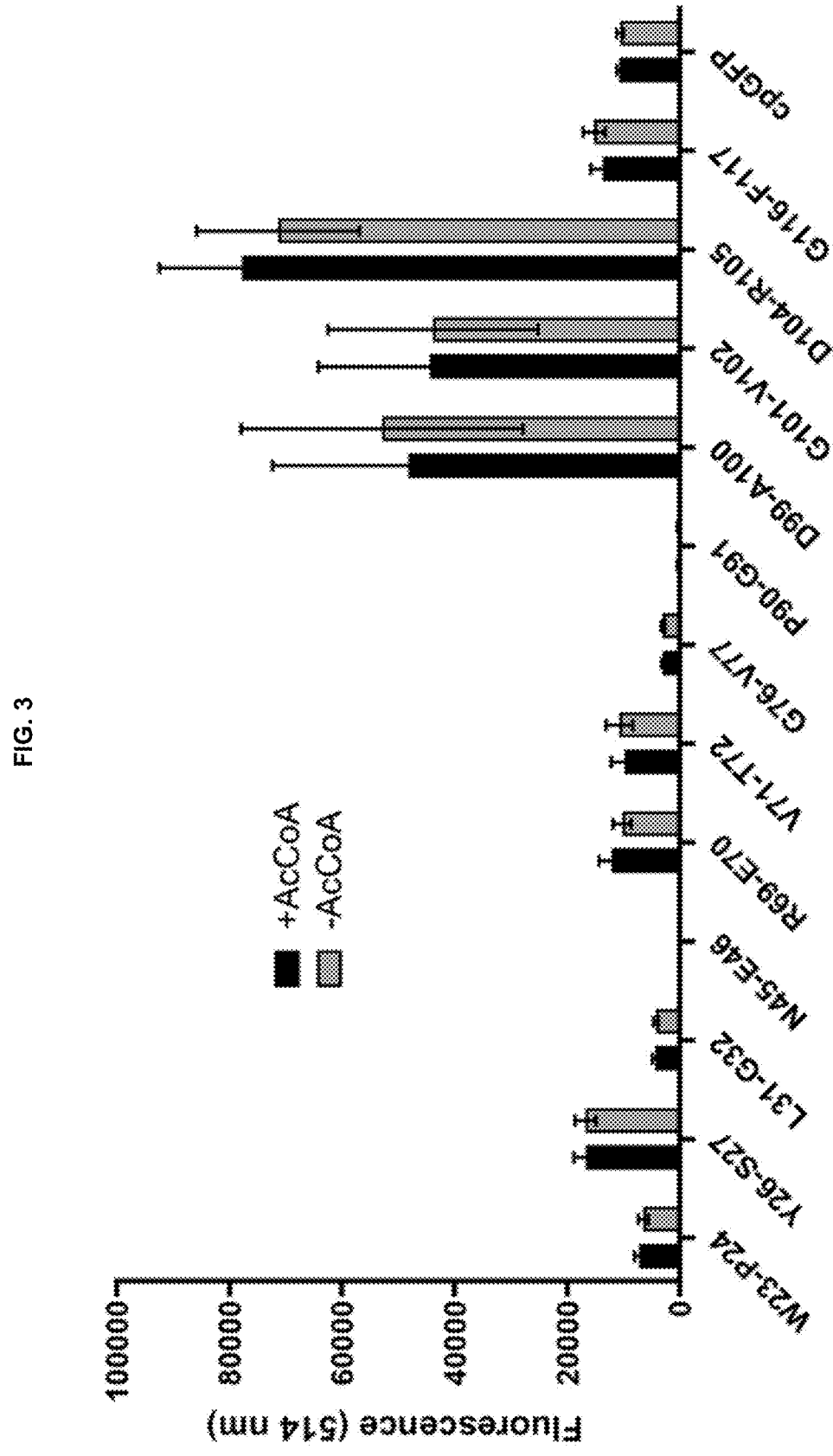
FIG. 3 is a bar graph showing the fluorescence intensity of a series of PanZ-cpGFP fusion proteins in the presence of 1 mM acetyl-CoA or in the absence of acetyl-CoA. λex=485 nm, λem=514 nm, n=3. All of these fusions contain an Ala-Ser (AS) linker at each junction, i.e., (Nterm)PanZ-AS-cpGFP-AS-PanZ(Cterm). The PanZ-cpGFP fusion proteins vary in their overall intensity depending on the site of cpGFP insertion. Some of these proteins, such as when the linker is attached to asparagine at position 45 and proline at position 90, have a very low fluorescence intensity, suggesting they would be poor sensors.
Figure 5:
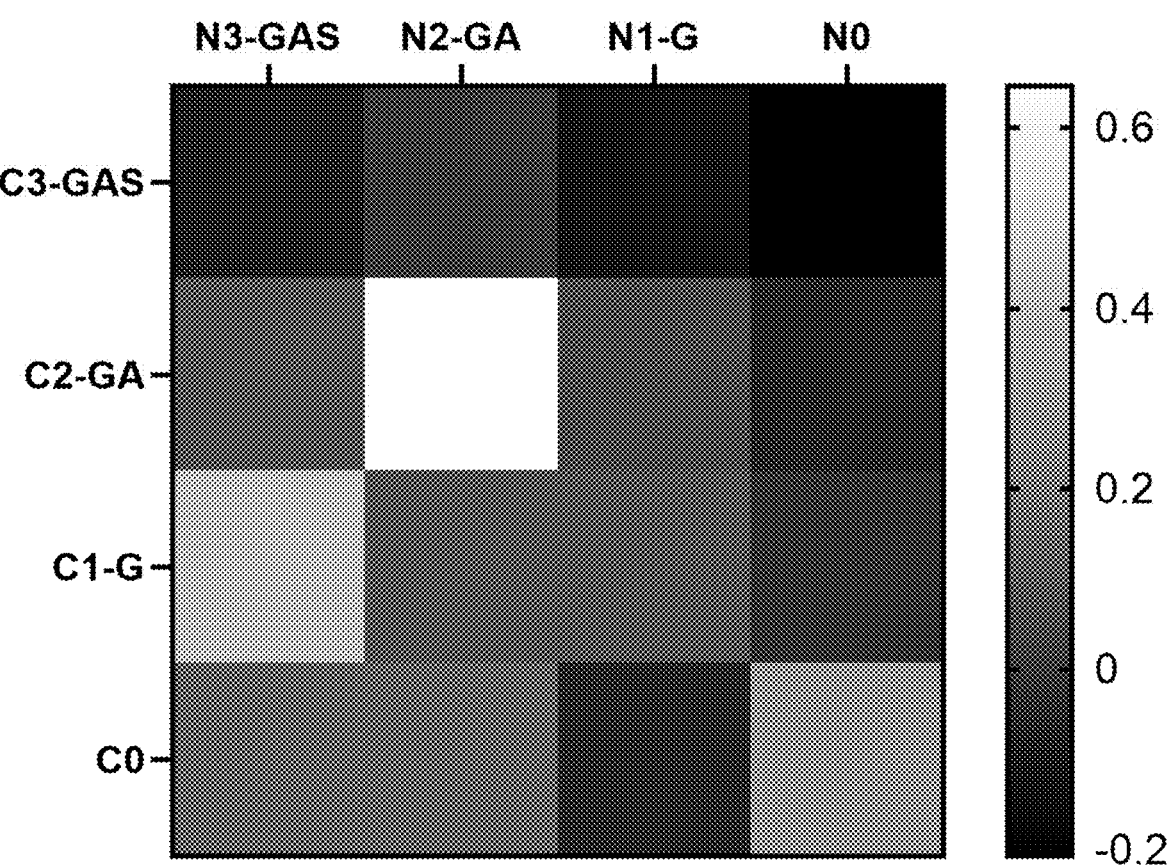
FIG. 5 is a heat map showing the fluorescence response of a series of linker variations of the PanZ(R69)-N-termlinker-cpGFP-C-termlinker-(E70)PanZ fusion protein, where in this instance, the N-termlinker is the peptide linker that attaches the N-terminal end of the fluorescent protein cpGFP to the C terminal end of the PanZ(R69) acetyl CoA binding protein fragment, and the C-termlinker is the peptide linker that attaches the C-terminal end of the fluorescent protein to the N-terminal end of the PanZ (E70) acetyl-CoA binding protein fragment. The N-terminal linker was either Gly-Ala-Ser (GAS), Gly-Ala (GA), Gly (G), or no linker and was paired with a C-terminal linker of either Gly-Ala-Ser (GAS), Gly-Ala (GA), Gly (G), or no linker as shown on the axes of the heat map. The data was quantified as a fold-change in each fusion protein's fluorescence emission in the presence of 1 mM acetyl-CoA compared to in the absence of acetyl-CoA. $((F_1-F_0)/F_0)$. $\lambda_{ex}=485$, $\lambda_{em}=514$ nm. From this data, it is shown that the N-terminal GA (N-GA)/C-terminal GA (C-GA) linker combination gives the largest magnitude of sensor response (about 0.6-fold). However, the N-terminal GAS (N-GAS)/C-terminal G (C-G), no linker on the N-terminal (NO)/no linker on the C-terminal (CO), and no linker on the N-terminal (NO)/C-terminal GAS (C-GAS) linker combinations are also well above the background defined by cpGFP alone in FIGS. 3-4. N-GAS/CO, N-GA/CO, and N-terminal G (N-G)/C-GAS are also above that background level, performing similarly to the original N-terminal AS (N-AS)/C-terminal AS (C-AS) linker. The N-GA/C-GA linker was further studied because it had the highest fluorescence response when compared to the other linkers that were tested.
Figure 6:
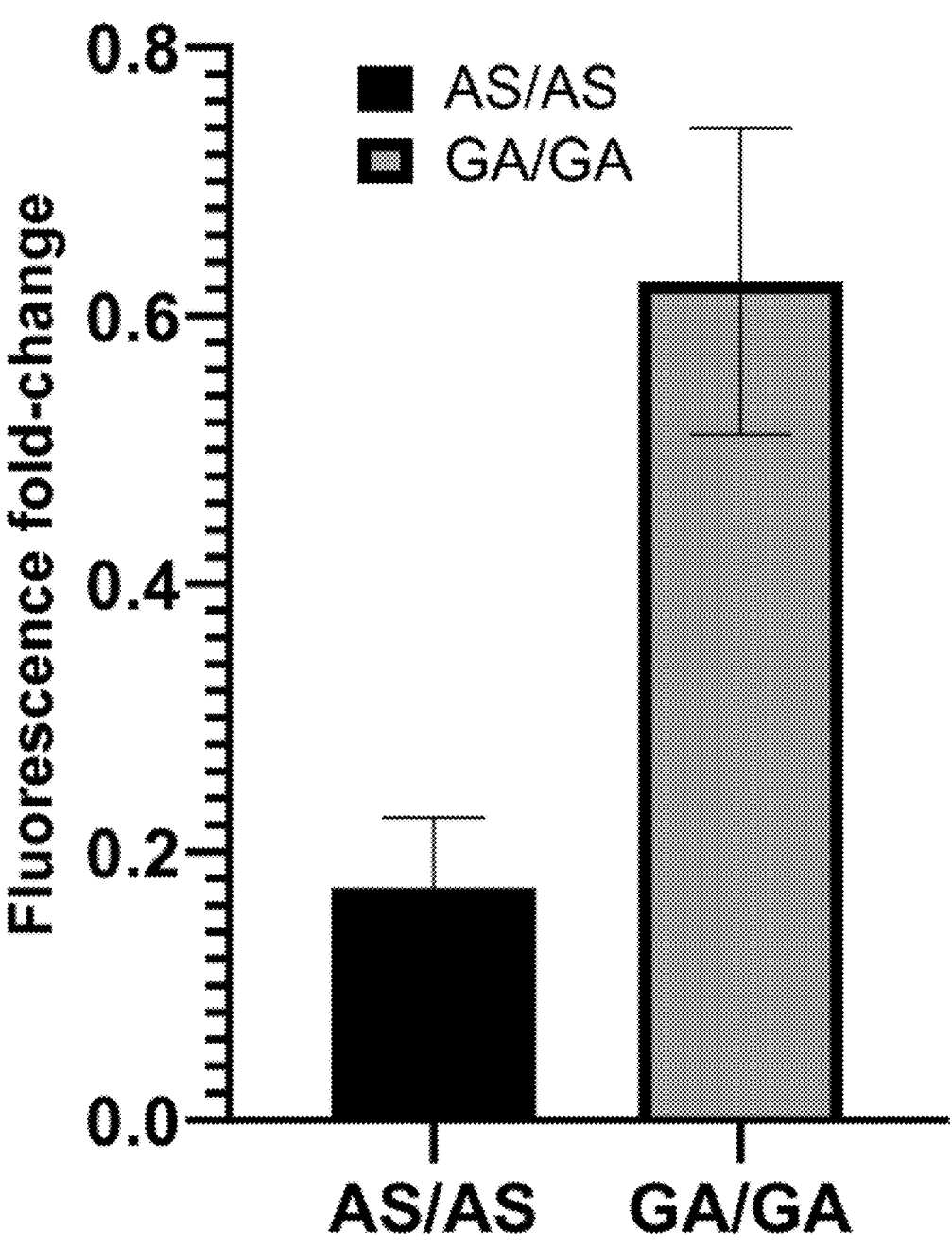
FIG. 6 is a bar graph depicting the fluorescence response of the PanZ(R69)-AS-cpGFP-AS-(E70)PanZ fusion protein from FIG. 4 and of the PanZ(R69)-GA-cpGFP-GA-(E70)PanZ fusion protein from FIG. 5 as a comparison. The N-GA/C-GA linker combination significantly enhanced the magnitude of the fluorescence change of the sensor compared to N-AS/C-AS linker combination. A big dynamic range equates to a better detection sensitivity, so the N-GA/C-GA linker combination was further studied.
Figure 7:
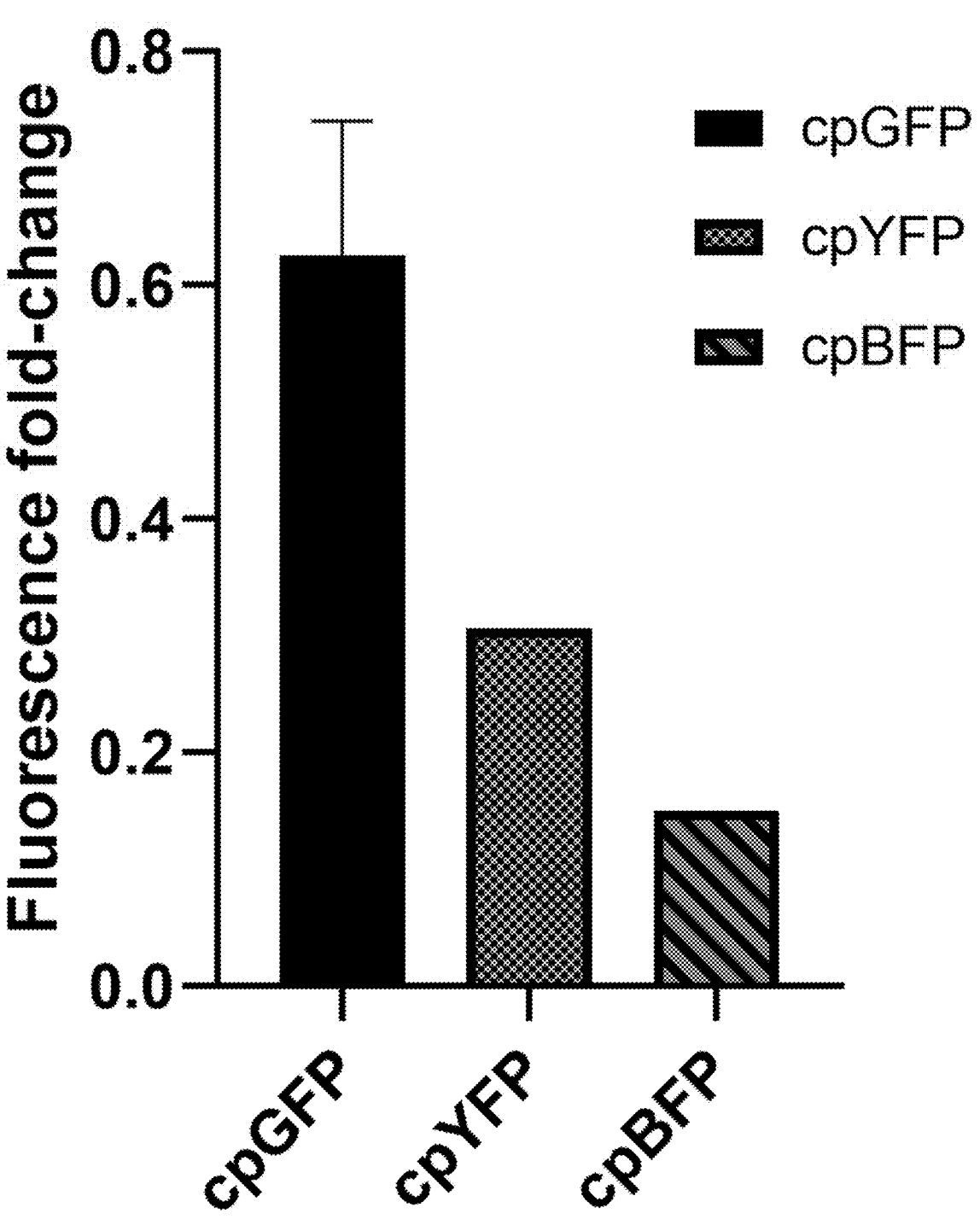
FIG. 7 is a bar graph showing the fluorescence response of the PanZ(R69)-GA-cpGFP-GA-(E70)PanZ fusion protein from FIG. 4 compared to the same yellow and blue fluorescent protein fusions (i.e., PanZ(R69)-GA-cpYFP-GA-(E70)PanZ and PanZ(R69)-GA-cpBFP-GA-(E70)PanZ) to acetyl-CoA. $((F_1-F_0)/F_0)$. cpGFP: $\lambda_{ex}=485$, $\lambda_{em}=514$ nm; cpYFP: $\lambda_{ex}=505$, $\lambda_{em}=535$ nm; cpBFP: $\lambda_{ex}=389$, $\lambda_{em}=440$ nm. The fluorescence response of the fusion protein comprising cpGFP had the largest dynamic range of the three fusion proteins, but the fluorescence response of the fusion protein comprising cpYFP was above background fluorescence. The fluorescence response of the fusion protein comprising cpBFP was similar to that of the fusion protein comprising cpGFP and the N-AS/C-AS linker combination shown in FIG. 6.
Figure 8:
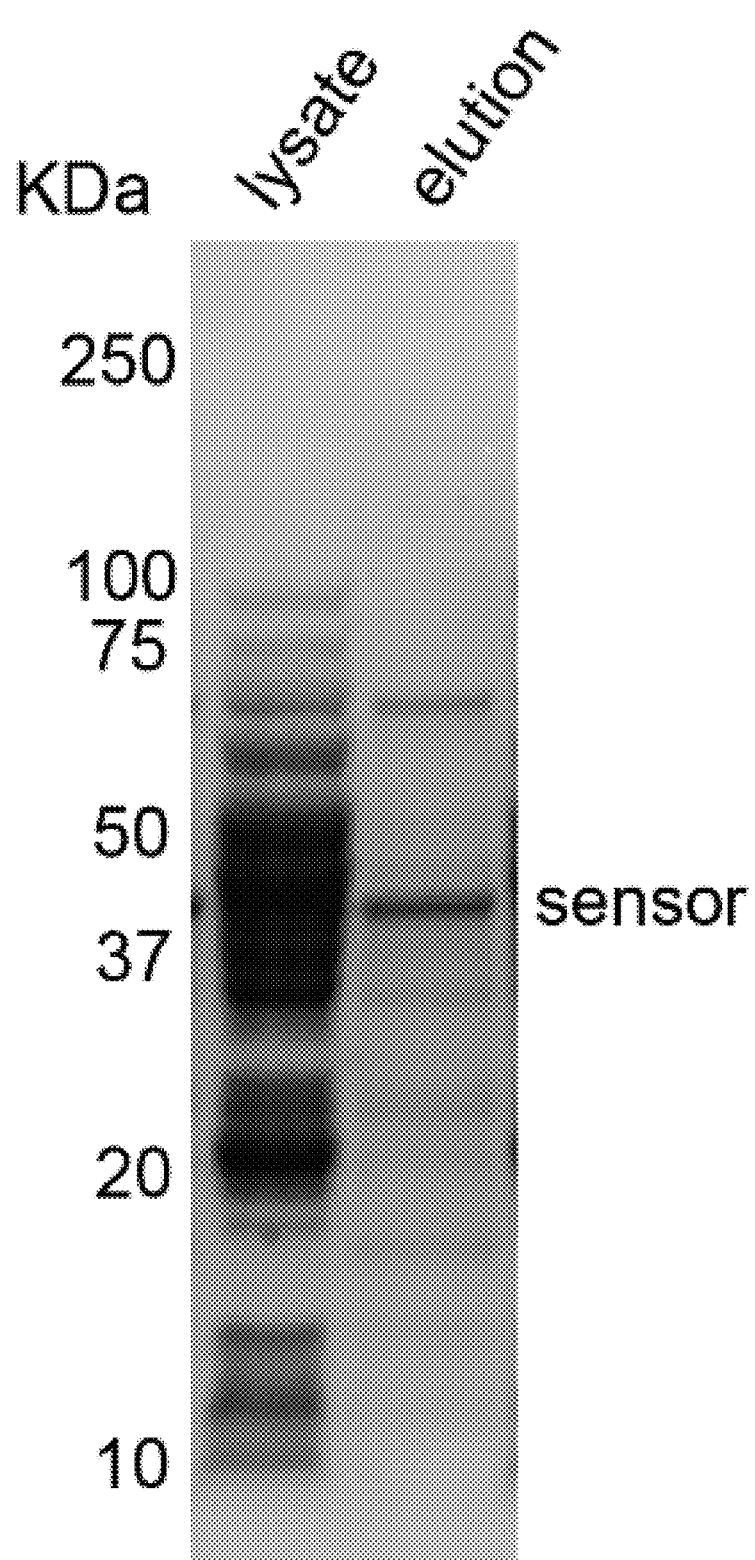
FIG. 8 is an image of a Coomassie stained SDS-PAGE gel of the purified PanZ(R69)-GA-cpGFP-GA-(E70)PanZ fusion protein ("sensor"; "elution" lane).

To engineer a fluorescent sensor, insertion sites of circularly permuted GFP (cpGFP) in loop regions of PanZ (FIG. 2) were screened (FIG. 3 and FIG. 4). The variants ranged widely in terms of fluorescence intensity and yield (FIG. 3 and FIG. 4). Considering the fold-change between the +/− acetyl-CoA conditions, the overall fluorescence intensity, and the yield of each variant, the R69-E70 insertion site was selected as the best-performing from the panel. Next, a linker length screen based on this R69-E70 variant was performed. The original R69-E70 construct contained an AS linker on either side of the cpGFP (i.e., Nterm-PanZ-AS-cpGFP-AS-PanZ-Cterm). The linker combinations shown were purified and tested, and the GA linker at both the N-terminus and C-terminus of cpGFP was revealed to perform best (FIG. 5) and was even better than the original AS linker by about 2.5-fold in terms of response (FIG. 6). This version of the biosensor is termed PancAce (pronounced "pancake"; for PanZ Acetyl-CoA sensor, FIG. 8). CpYFP and cpBFP (yellow and blue cpFPs, respectively) were tested with the PancAce variant and were found to perform as acetyl-CoA biosensors, although they have a lower response range than PancAce (FIG. 7).

Example 3

Biochemical Characterization of PancAce

Figure 9:
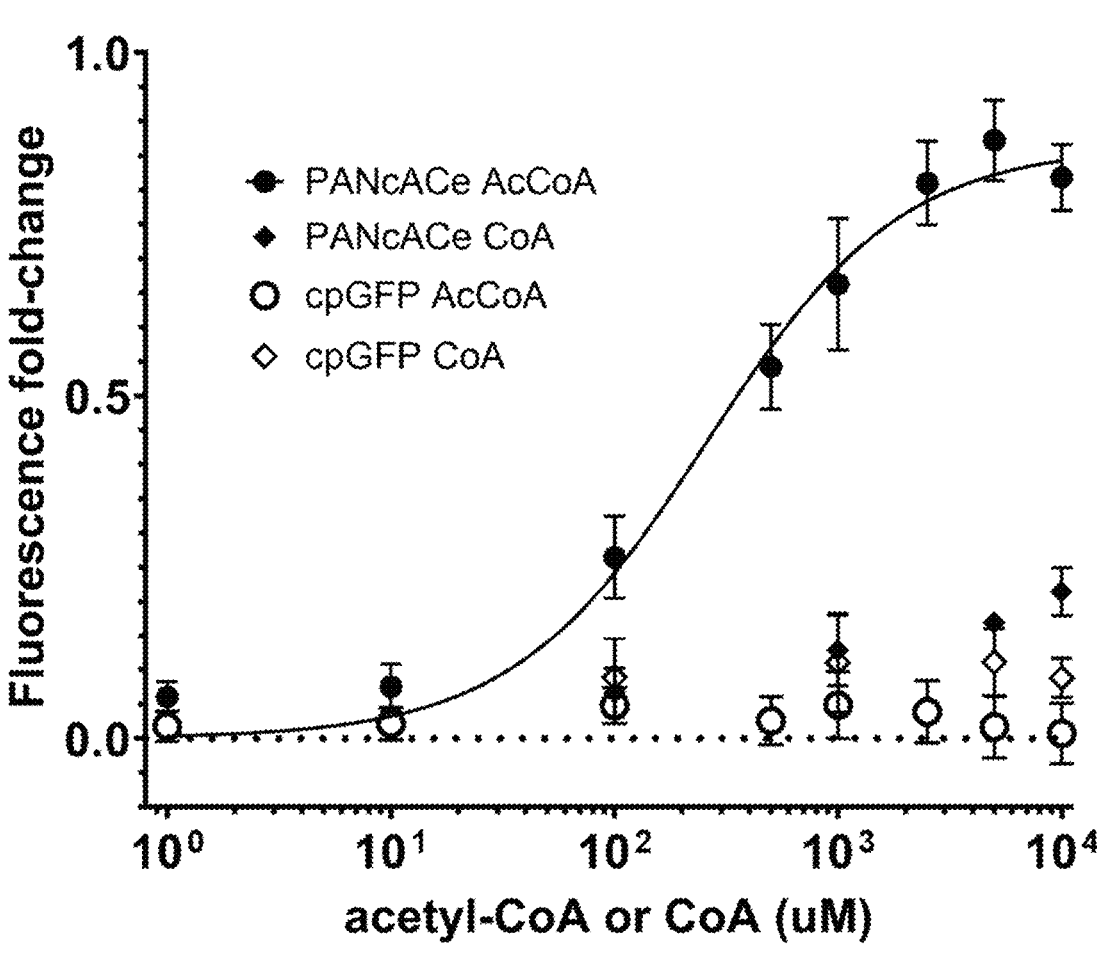
FIG. 9 is a line graph depicting the fluorescence response of the sensor (i.e., PanZ(R69)-GA-cpGFP-GA-(E70)PanZ fusion protein or "PancAce") and of cpGFP alone to a range of concentrations of acetyl-CoA or CoA as indicated on the X-axis of the line graph. $((F_1-F_0)/F_0)$. $\lambda_{ex}=485$, $\lambda_{em}=514$ nm, n=3-5. This line graph shows that the sensor responds only to acetyl-CoA and not CoA, which is consistent with FIGS. 1A-1D. This line graph also shows the range of concentrations of acetyl-CoA that the sensor can detect (from about 10 UM up to about 2 mM with a KD of about 250 UM).
Figure 10A:
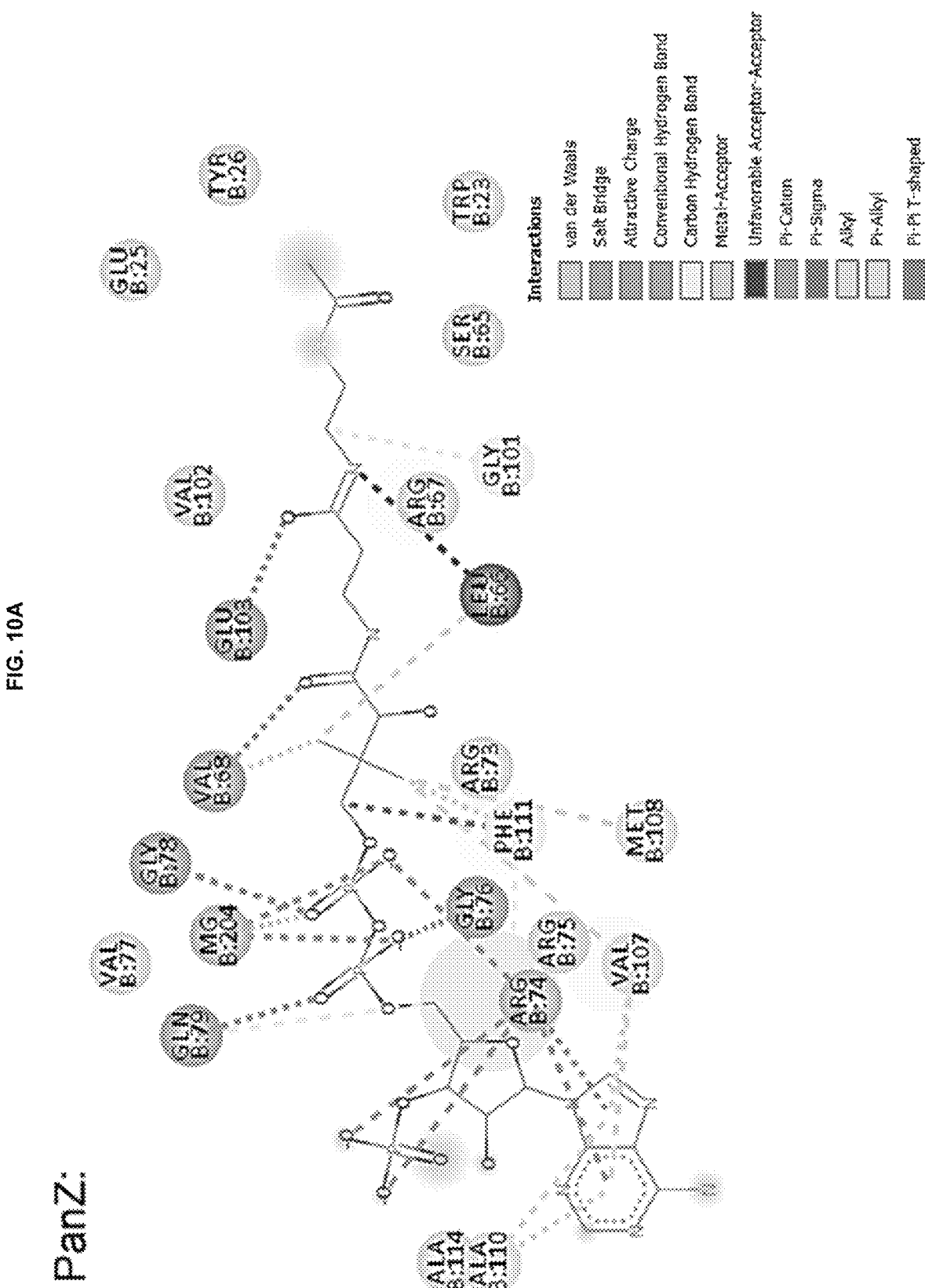
FIG. 10A and FIG. 10B are molecular models showing the acetyl-CoA binding sites of PanZ from Protein Data Bank (PDB) 4CRZ (FIG. 10A) and the sensor (i.e., PanZ (R69)-AS-cpGFP-AS-(E70)PanZ or "PancAce") from molecular modeling (FIG. 10B). The schematics highlight the interactions between the amino acids in each protein with the acetyl-CoA molecule. This shows that the insertion of the cpGFP appears to disrupt the acetyl-CoA binding site in PanZ to an extent and explains why the affinity of the sensor for acetyl-CoA is lower than that of PanZ by itself.
Figure 10B:
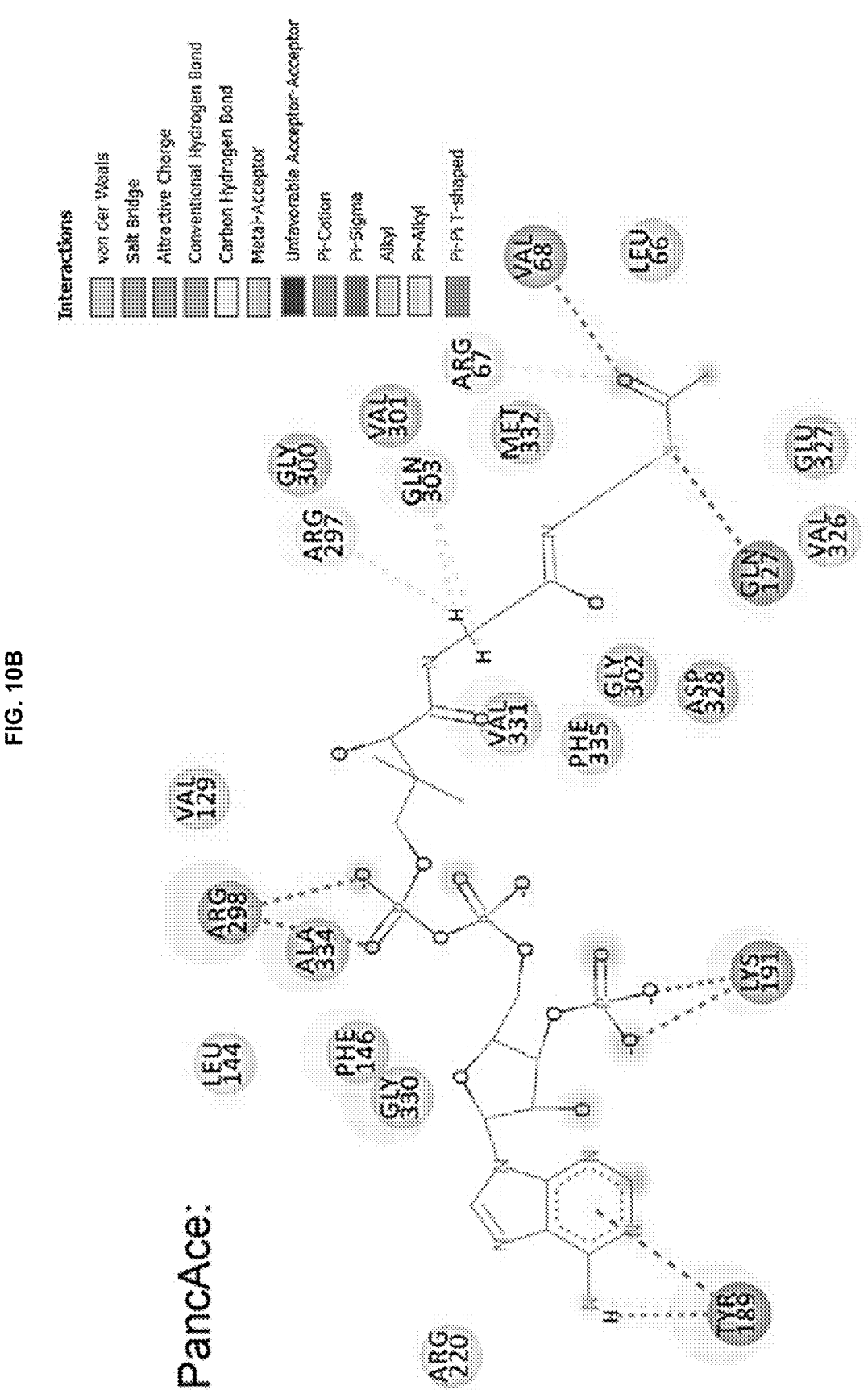
Figure 11:
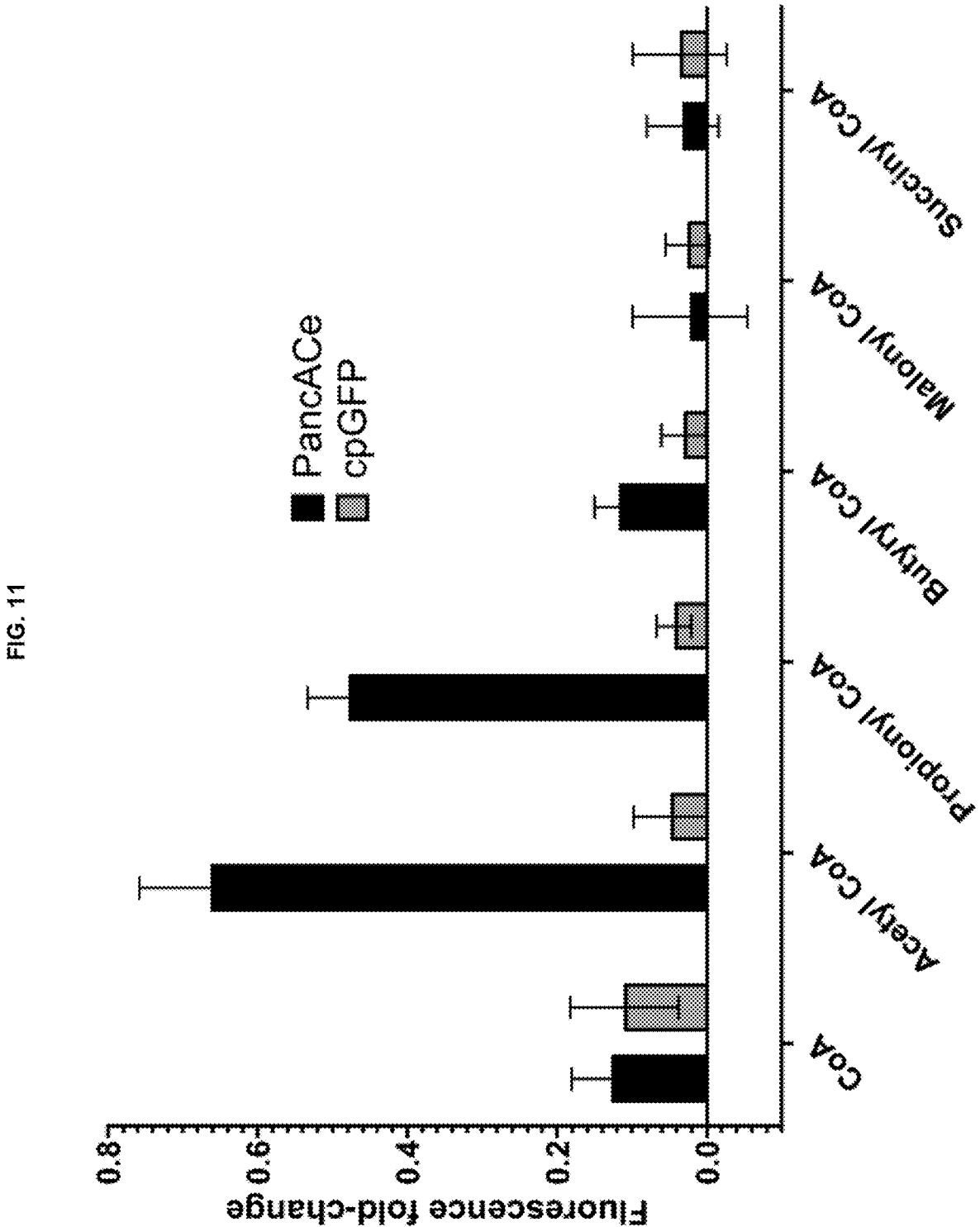
FIG. 11 is a bar graph showing the fluorescence response of the sensor (i.e., PanZ(R69)-GA-cpGFP-GA-(E70)PanZ or "PancAce") and of cpGFP alone to a 1 mM concentration of different biologically-relevant acyl-CoAs as indicated on the X-axis. $(F_1-F_0)/F_0)$. $\lambda_{ex}=485$, $\lambda_{em}=514$ nm, n=3. These data show how selective the sensor is for acetyl-CoA over other structurally similar molecules that would be expected to be in samples that would be used for detection of acetyl-CoA with the sensor. The sensor is highly selective for acetyl-CoA over most of the acyl-CoA species, but the sensor does have some response to propionyl-CoA, which varies from acetyl-CoA by only one CH2 group.
Figure 12:
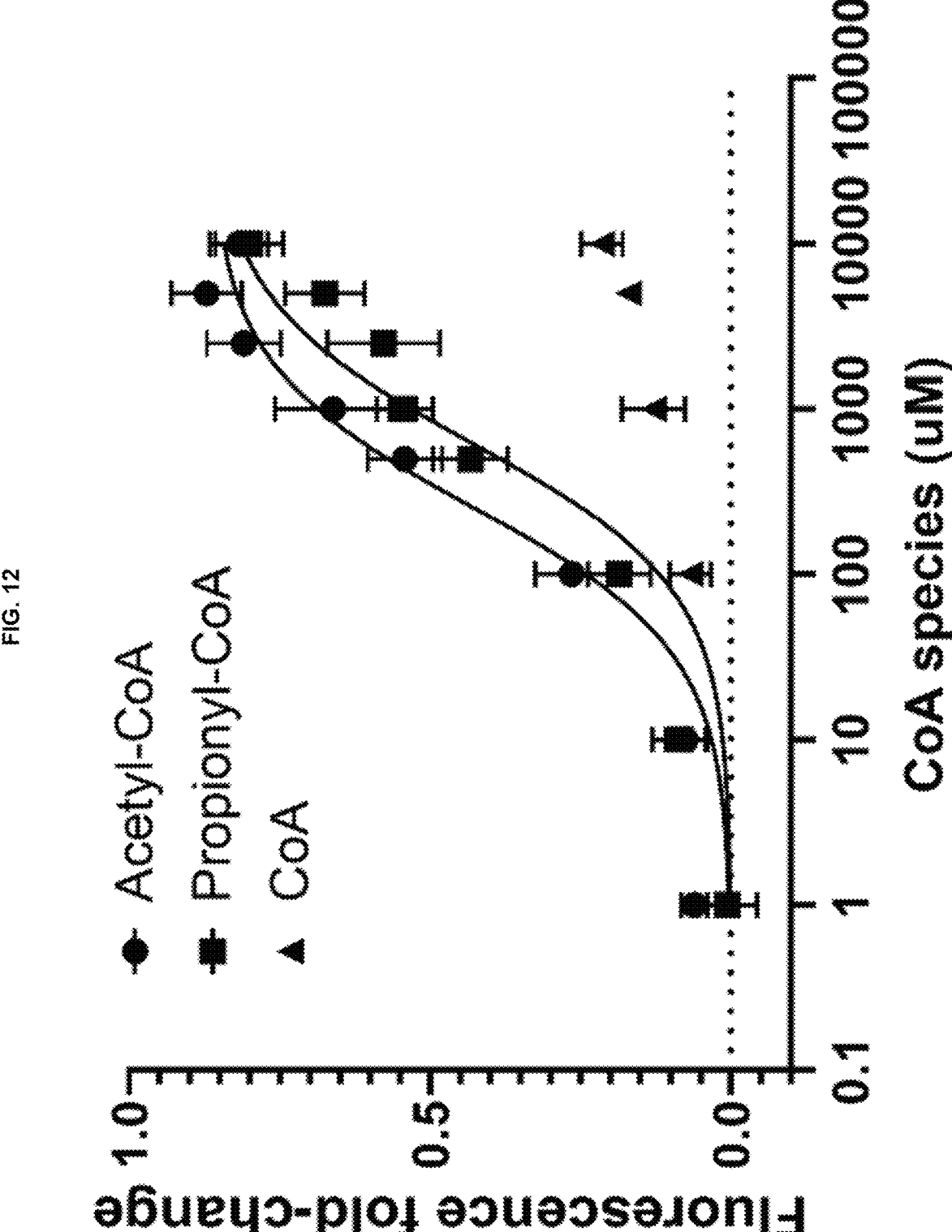
FIG. 12 is a line graph showing the fluorescence response of the sensor (i.e., PanZ(R69)-GA-cpGFP-GA-(E70)PanZ or "PancAce") and of cpGFP alone to a range of propionyl-CoA concentrations $(F_1-F_0)/F_0)$. The data for acetyl-CoA and CoA are reproduced here from FIG. 9. The sensor has an approximately 2.5-fold higher affinity for acetyl-CoA compared to propionyl-CoA. $\lambda_{ex}=485$, $\lambda_{em}=514$ nm, n=3-5. This graph quantifies the selectivity of the sensor for acetyl-CoA over propionyl-CoA since propionyl-CoA was the only potential interferent based on FIG. 11. The sensor prefers acetyl-CoA by a factor of about 2.5-fold. Based on the amount of propionyl-CoA in cells compared to acetyl-CoA, this margin should not affect the accuracy of the sensor for detecting acetyl-CoA.
Figure 13:
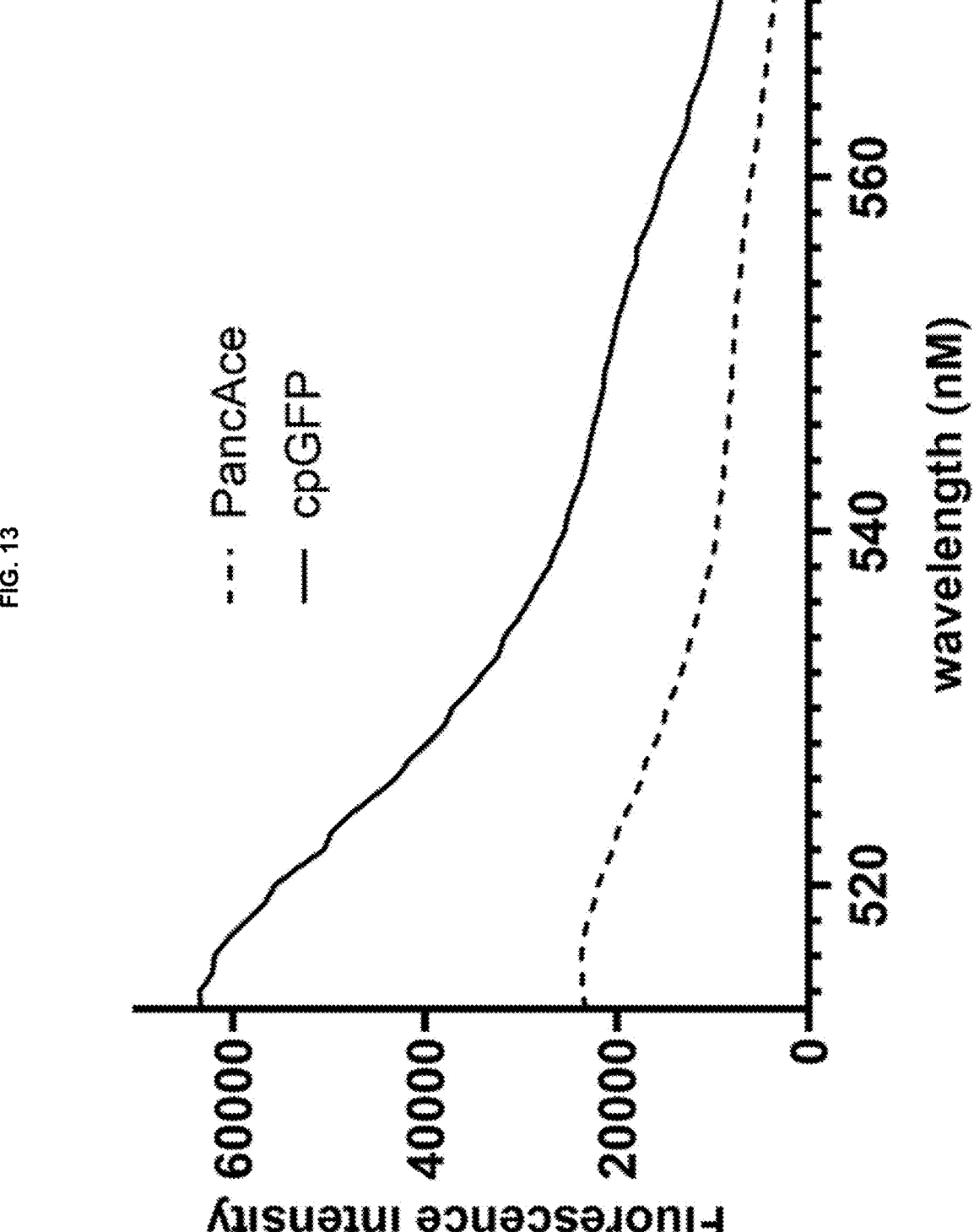
FIG. 13 is a line graph depicting the fluorescence emission spectra of the sensor (i.e., PanZ(R69)-GA-cpGFP-GA-(E70)PanZ or "PancAce") and of cpGFP alone collected using an excitation wavelength of 485 nm. The emission peak of the sensor is from 513-540 nm. 514 nm was used for other experiments herein because it is at the top of the emission spectra peak.

Titrations of acetyl-CoA and CoA with PANcACe and cpGFP alone were performed (FIG. 9). PANcACe displays an increase in fluorescence upon binding to acetyl-CoA and has a maximum response of almost 2-fold at saturating acetyl-CoA. This response range is comparable to many other reported metabolite biosensors derived from a cpFP. The affinity of PANcACe for acetyl-CoA ($K_{d,app}$=258±38 μM from fluorescence data) is about 150-fold lower compared to PanZ ($K_d$=1.7±0.2 μM from SPR data). Since the insertion site of cpGFP is very close to the acetyl-CoA binding site, this effect was not surprising. Indeed, a molecular model of the sensor shows that the cpGFP insertion alters the acetyl-CoA binding site of the PanZ significantly (FIGS. 10A-10B). PANcACe shows good selectivity for acetyl-CoA over CoA (FIG. 9), which is consistent with the SPR binding data for PanZ (7-fold, FIG. 1A). Even though the PancAce-CoA data cannot be fitted to obtain a Kd since saturation was not achieved, interpolation between the PancAce-AcCoA and -CoA data indicate that 10 mM CoA is required to elicit the same sensor response as 100 μM acetyl-CoA. Further, the selectivity of PANcACe for short-chain acyl-CoAs was tested (FIG. 11). The only acyl-CoA that was also recognized by the sensor was propionyl-CoA, and based on the single concentration experiment, the affinity of PancAce for propionyl-CoA was lower than for acetyl-CoA. A propionyl-CoA titration confirmed this apparent affinity difference (FIG. 12). Since saturation was not achieved up to 10 mM propionyl-CoA, it was assumed that the same maximal sensor response would be achieved for propionyl-CoA as for acetyl-CoA. Based on this assumption, the data was fit and a $K_d=626\pm75$ µM was estimated for propionyl-CoA, a 2.4-fold lower affinity compared to acetyl-CoA.

Figure 14:
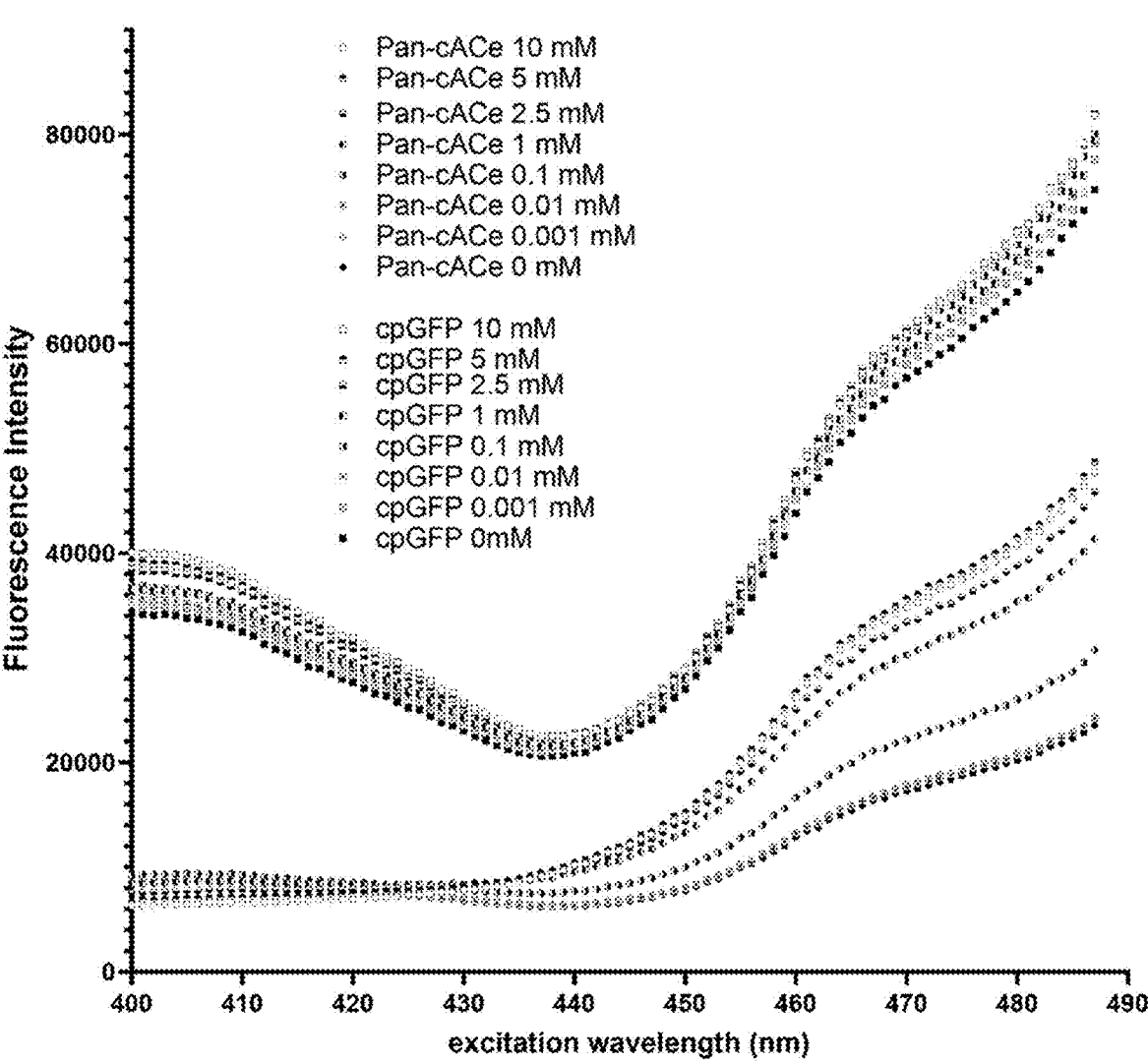
FIG. 14 is a line graph showing the fluorescence excitation spectra of the sensor (i.e., PanZ(R69)-GA-cpGFP-GA-(E70)PanZ or "PancAce") and of cpGFP when incubated with concentrations of acetyl-CoA that are specified on the X-axis. The data was collected using an emission wavelength of 514 nm. There are two excitation peaks, one at 405 nm (400-430 nm) and one at 485 nm (460-490 nm). This figure shows the 405 nm and 485 nm excitation peaks of the sensor. It further shows that the 405 nm excitation is essentially invariant to the presence of acetyl-CoA, while the 485 nm peak is highly sensitive to the presence of acetyl-CoA. This shows that the 485 nm/405 nm enables ratiometric imaging, which can improve the accuracy of the sensor measurements, especially in cell imaging applications.
Figure 15:
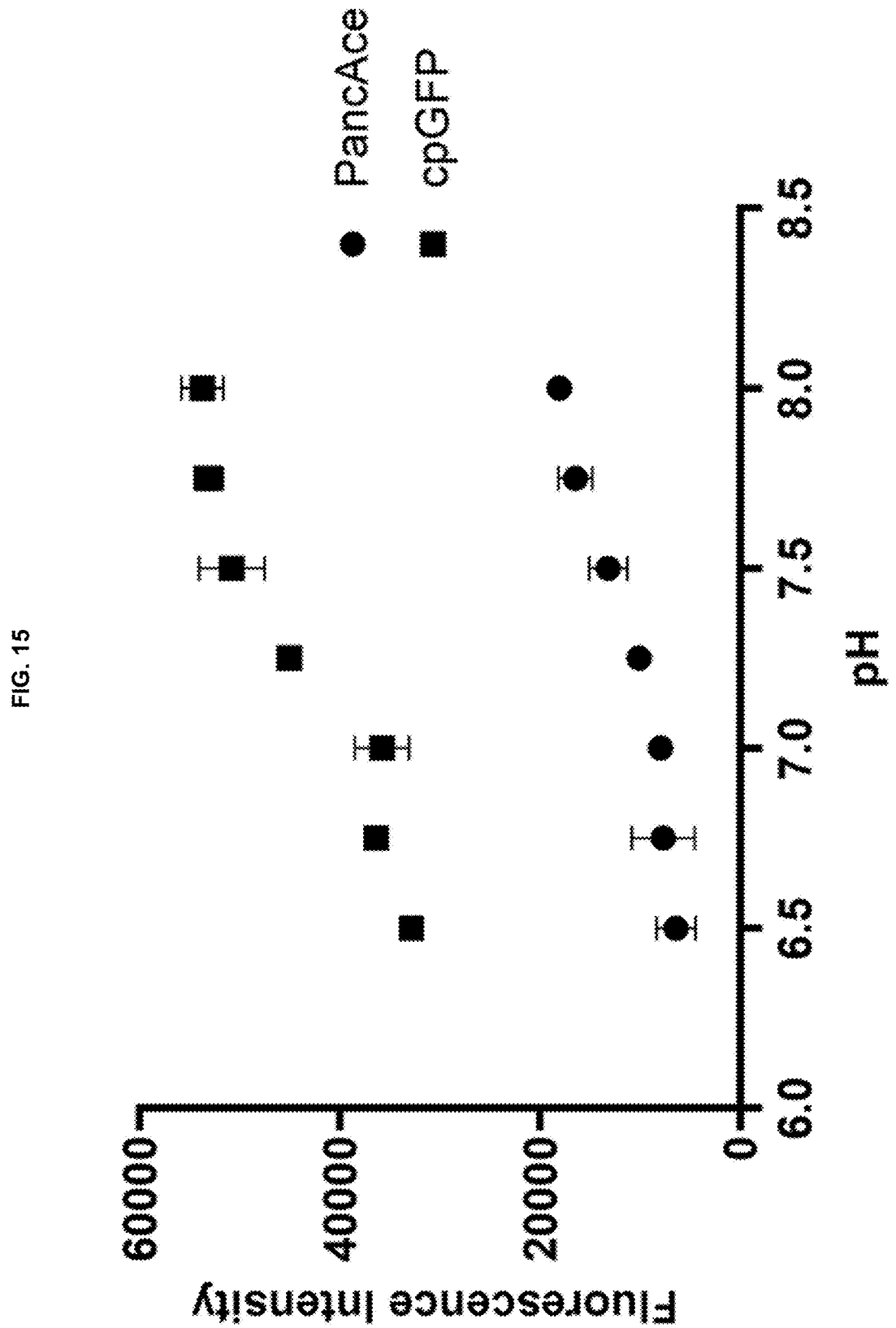
FIG. 15 is a dot plot showing the fluorescence intensity of the sensor (i.e., PanZ(R69)-GA-cpGFP-GA-(E70)PanZ or "PancAce") and of cpGFP alone in response to a range of pHs ($F_1-F_0)/F_0$). $\lambda_{ex}$=485, $\lambda_{em}$=514 nm, n=3. This figure shows that the sensor has a similar emission intensity dependence on pH (i.e., pH sensitivity) to cpGFP alone.

Since fluorescent proteins display pH sensitivity, the fluorescence of PANcACe and cpGFP over a range of pH values (6.5-8, FIG. 15) were measured and it was observed that there was similar behavior as has been reported previously for fluorescent proteins and biosensors constructed from them. Finally, it was determined whether the same type of internal control that was used by another group with their cpVenus (cpV)-derived NAD+ biosensor could be used (Cambronne et al., Science (2016) 352, 1474-1477). Cambronne et al. found that a second excitation wavelength ($\lambda_{ex}=405$ nm, $\lambda_{em}=520$ nm) of cpV was largely invariant in the presence of NAD+ and used this wavelength as an internal control for the amount of sensor present in their cell-based assays. PancAce also has this 405 nm excitation peak that is invariant to acetyl-CoA (FIG. 14) that could be used in the same way for live cell experiments.

Example 4

Acetyl-CoA Measurements in Live *E. coli*

Either PancAce or cpGFP was expressed in *E. coli* (Rosetta DE3 cells) and their nutrient status was manipulated to measure changes in acetyl-CoA levels by measuring the sensor response via flow cytometry or well plate reader. $\lambda_{ex}=405$ nm and 485 nm (both with $\lambda_{em}=514$ nm) was measured to allow for normalizing the data to account for changes due to pH, protein expression, photobleaching, or other factors that might influence the fluorescence signal that are not indicative of acetyl-CoA.

Figure 17:
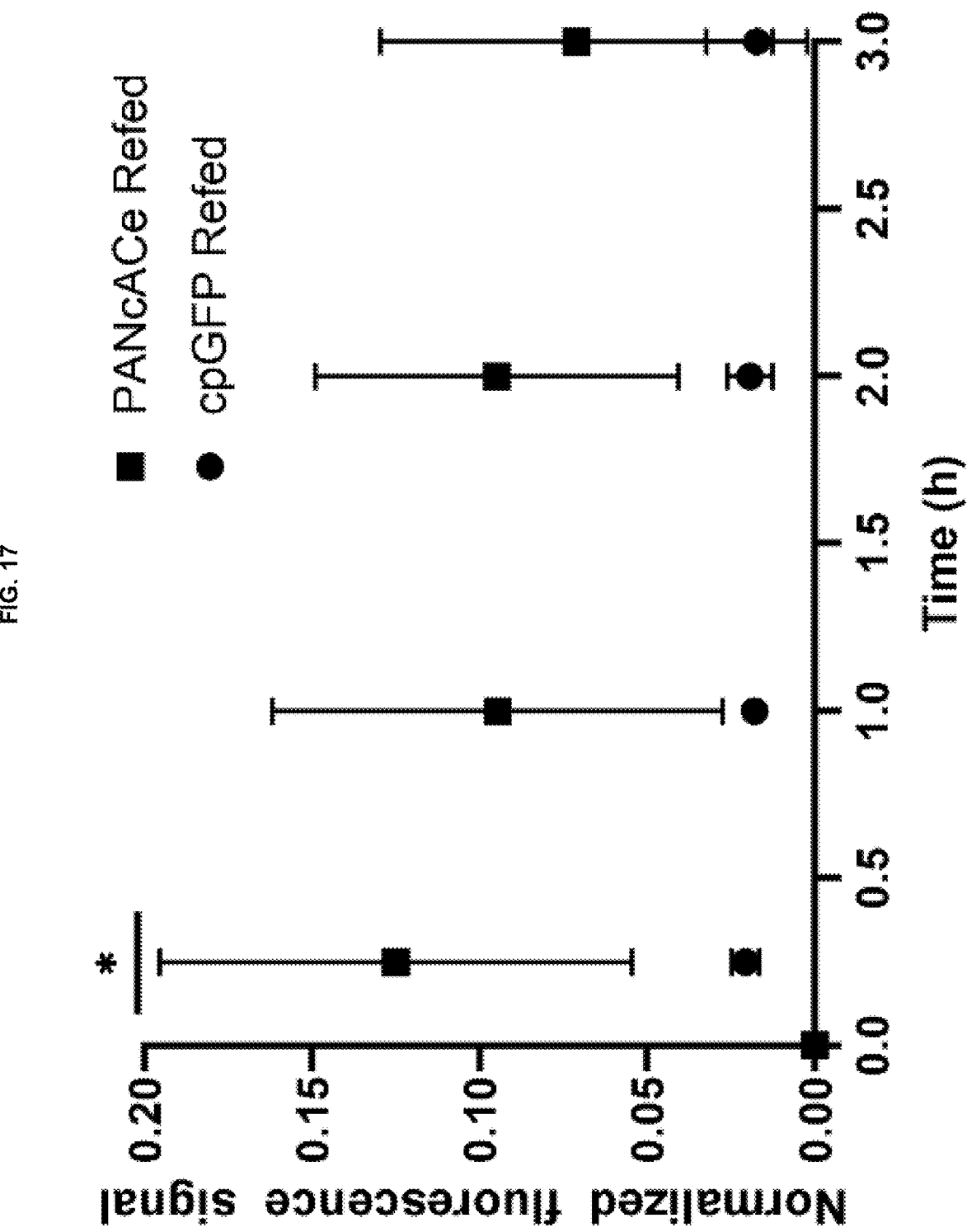
FIG. 17 is a dot plot showing the fluorescence of live *E. coli* that express either PancAce (sensor) or cpGFP and were first deprived of all glucose for 3 hours and then refed with 28 mM glucose for the time periods shown on the X-axis of the plot. If *E. coli* were deprived of glucose for 3 h, it is known from FIG. 16 that their acetyl-CoA levels drop. Here, if the *E. coli* are refed, the acetyl-CoA levels should go back up again (as shown). The fluorescence ($\lambda_{ex}$=405 nm, 485 nm; $\lambda_{em}$=514 nm) was measured by flow cytometry. The fluorescence was normalized by dividing $F_{488}/F_{405}$ and then ($F_1-F_0)/F_0$ where $F_0$ were cells that were not refed with glucose, n=3, *p<0.05.

First, cells were incubated in phosphate-buffered saline (PBS) with no glucose or other nutrients for increasing periods of time. Flow cytometry was used to measure fluorescence, and the signal from each starvation time point was normalized to the signal from fed cells (PBS+28 mM glucose) expressing the corresponding construct (fed=0, FIG. 16). cpGFP-expressing cells that were treated identically to the PancAce-expressing cells were used as a control. After 2 hours of nutrient deprivation, PancAce showed a decrease in its fluorescence response while the cpGFP signal remained invariant over the entire time course. Next, a refeeding experiment was performed in which cells were first starved in PBS for 3 hours and then were refed with 28 mM glucose for different periods of time (FIG. 17). For this experiment, the time points were normalized to the signal from starved cells expressing the corresponding construct (starved=0). Within 15 minutes, PancAce displayed an increase in signal that was much greater than the small increase in the signal of cpGFP, suggesting that the cells recovered their intracellular acetyl-CoA levels rapidly upon refeeding.

Figure 18:
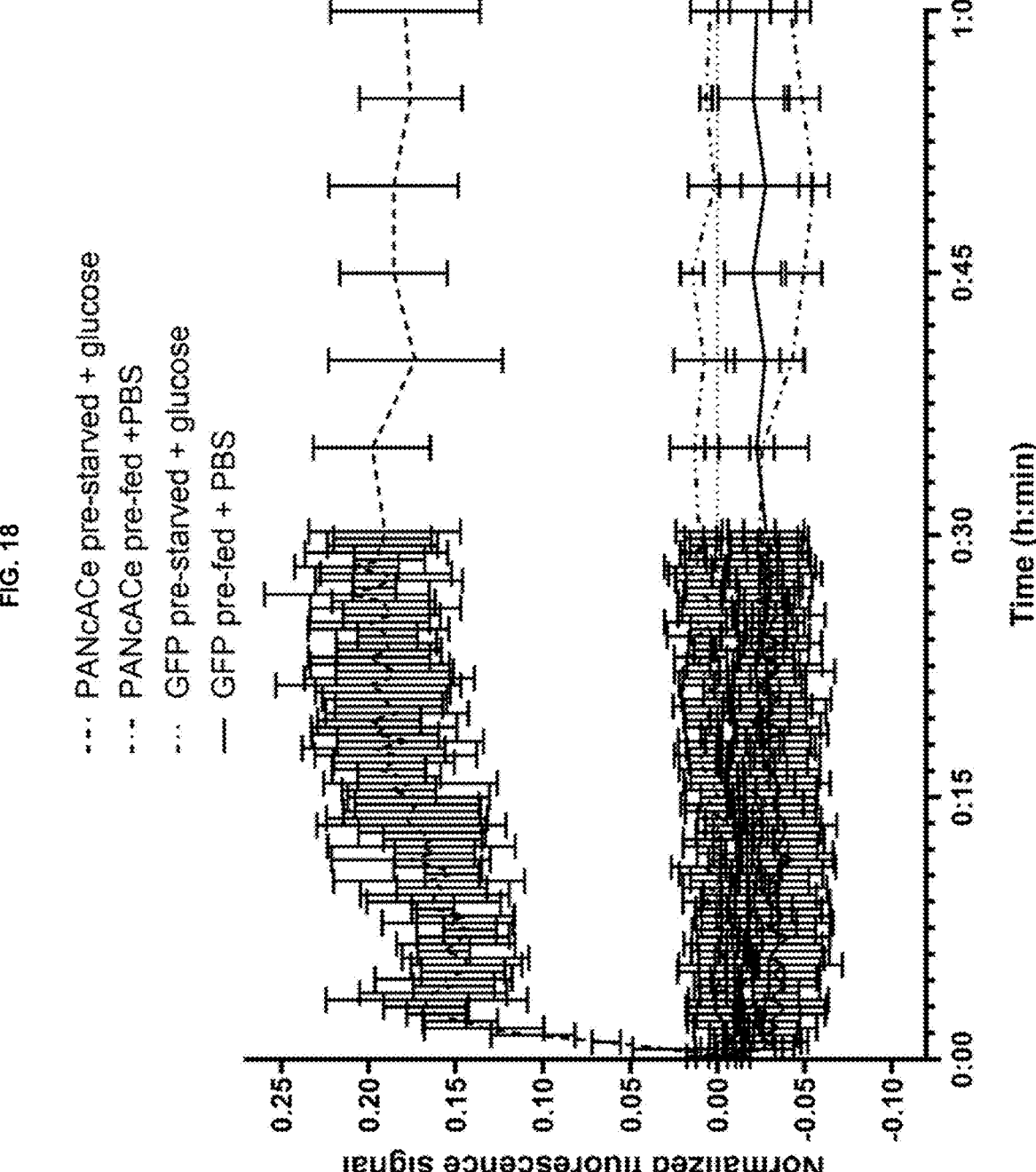
FIG. 18 is a line graph showing the fluorescence of live *E. coli* that express either PancAce (sensor) or cpGFP that were either fed 28 mM glucose for 3 hours prior ("pre-fed") or deprived of glucose for 3 hours prior ("pre-starved"). At time 0:00, the cells were given either phosphate buffered saline ("+PBS") or 28 mM glucose ("+glucose"), and the fluorescence was measured by a plate reader ($\lambda_{ex}$=405 nm, 485 nm; $\lambda_{em}$=514 nm) over 1 hour as shown on the X-axis. The fluorescence was normalized by dividing $F_{488}/F_{405}$ and then ($F_1-F_0)/F_0$ where $F_0$ is defined by the fluorescence from each population of cells prior to time 0:00, n=3. Only the cells that express the sensor and were pre-starved of glucose showed a large jump in signal, which is indicative of those cells having relatively low acetyl-CoA to start and then recovering their acetyl-CoA levels once they were given glucose.
Figure 21:
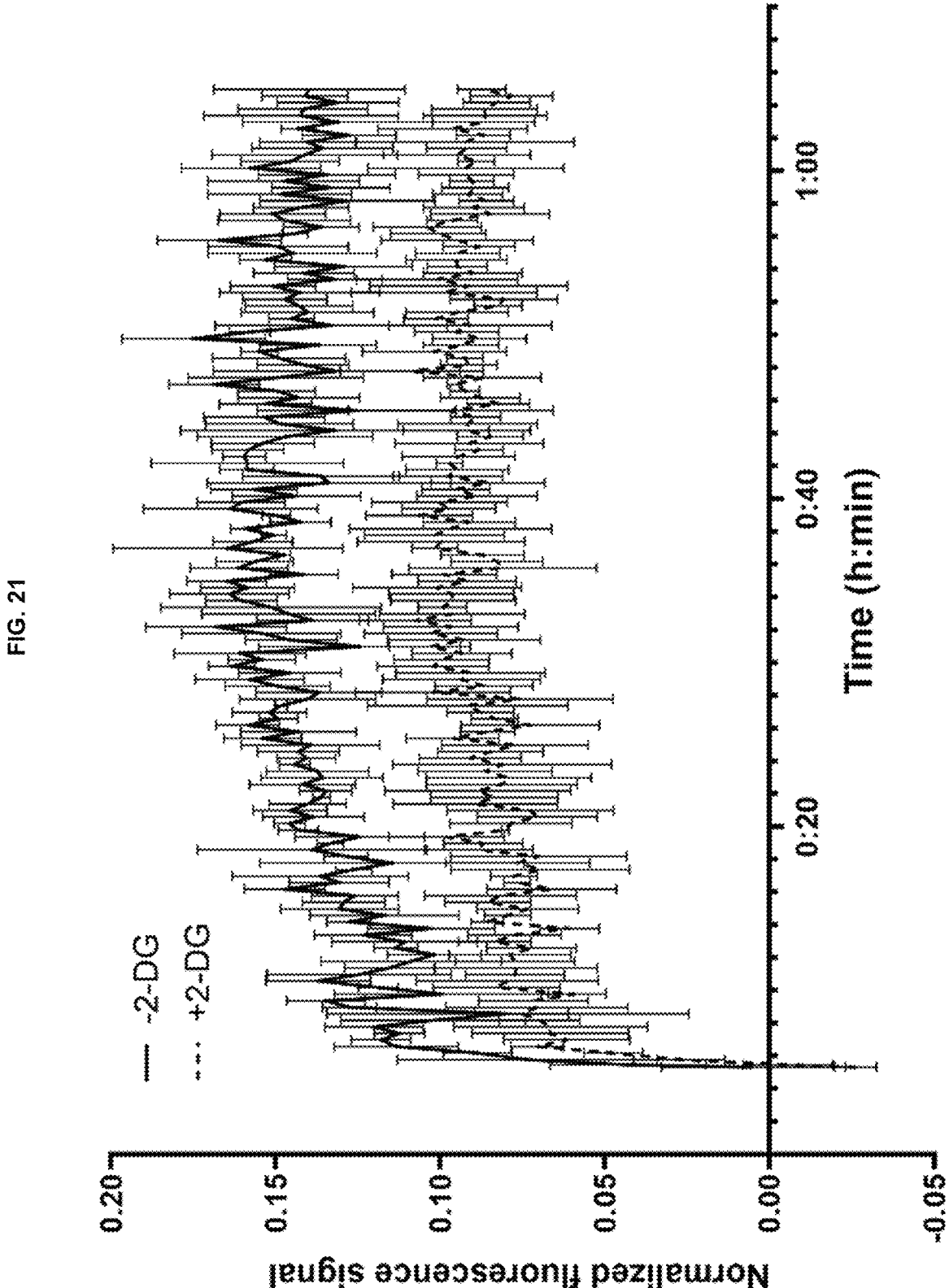
FIG. 21 is a line graph showing the fluorescence of live *E. coli* that express PancAce (sensor) that were deprived of glucose for 3 prior with or without 28 mM 2-deoxyglucose ("−2-DG" or "+2-DG"). 2-DG was used to inhibit glycolysis, which is the metabolic process that converts glucose to acetyl-CoA. At time 0:05, the cells were given 28 mM glucose, and the fluorescence was measured by a plate reader ($\lambda_{ex}$=405 nm, 485 nm; $\lambda_{em}$=514 nm) over 1 hour as shown on the X-axis. The fluorescence was normalized by dividing $F_{488}/F_{405}$ and then ($F_1-F_0)/F_0$ where $F_0$ is defined by the fluorescence from each population of cells prior to time 0:05, n=3. The data shows that in the presence of 2-DG, the cells are less able to recover acetyl-CoA levels because glycolysis is inhibited.

Since this change happened fast and was pushing the limits of how quickly the experimental workflow could be performed, a well plate reader was used instead to measure the fluorescence in situ so that repeated measurements of a cell population could be taken in increments of less than 1 minute. Injectors were used to rapidly add assays components. First, cells that had either been pre-starved (no glucose for 3 h) or fed (+28 mM glucose for 3 h) were used. After briefly measuring the baseline signal, 28 mM glucose was added to the starved cells or buffer without glucose to the fed cells (FIG. 18). Only the PancAce-expressing starved cells that were fed with glucose showed a sharp increase in signal, and this occurred in just a few minutes, which was consistent with our refeeding flow cytometry experiment. Next, the cells were treated with 2-deoxyglucose (2-DG), an inhibitor of glycolysis (FIG. 21). Both sets of cells were deprived of glucose for 3 hours, but one set was also given 2-DG during that time period. Then the cells were refed with 28 mM glucose, and the sensor response was monitored over 1 hour. As expected, the cells treated with 2-DG showed a lower recovery of acetyl-CoA levels upon refeeding, but they were still able to largely recover.

Figure 19:
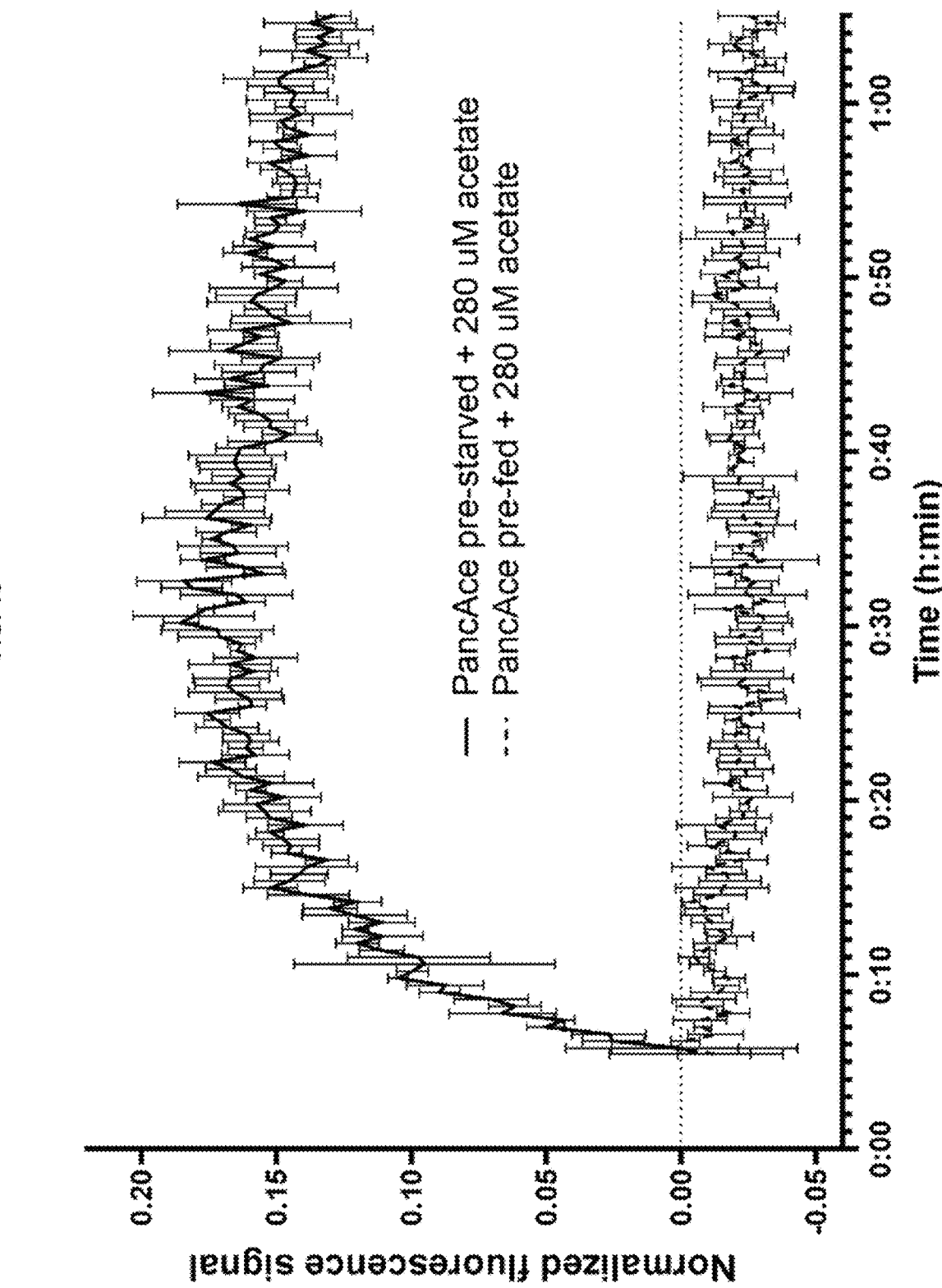
FIG. 19 is a line graph showing the fluorescence of live *E. coli* that express PancAce (sensor) that were either fed 28 mM glucose for 3 hours prior ("pre-fed") or deprived of glucose for 3 hours prior ("pre-starved"). At time 0:05, the cells were given 280 μM acetate, and the fluorescence was measured by a plate reader ($\lambda_{ex}$=405 nm, 485 nm; $\lambda_{em}$=514 nm) over 1 hour as shown on the X-axis. The fluorescence was normalized by dividing $F_{488}/F_{405}$ and then ($F_1-F_0)/F_0$ where $F_0$ is defined by the fluorescence from each population of cells prior to time 0:05, n=3. Acetate can be an alternative source of acetyl-CoA for the cells, so here shows that if the cells have been deprived of glucose and have low acetyl-CoA levels, then they will use acetate to make acetyl-CoA. However, if the cells have had access to glucose (pre-fed), then the infusion of acetate causes no change in the cells because they continue to use the glucose that they have to produce acetyl-CoA.
Figure 20:
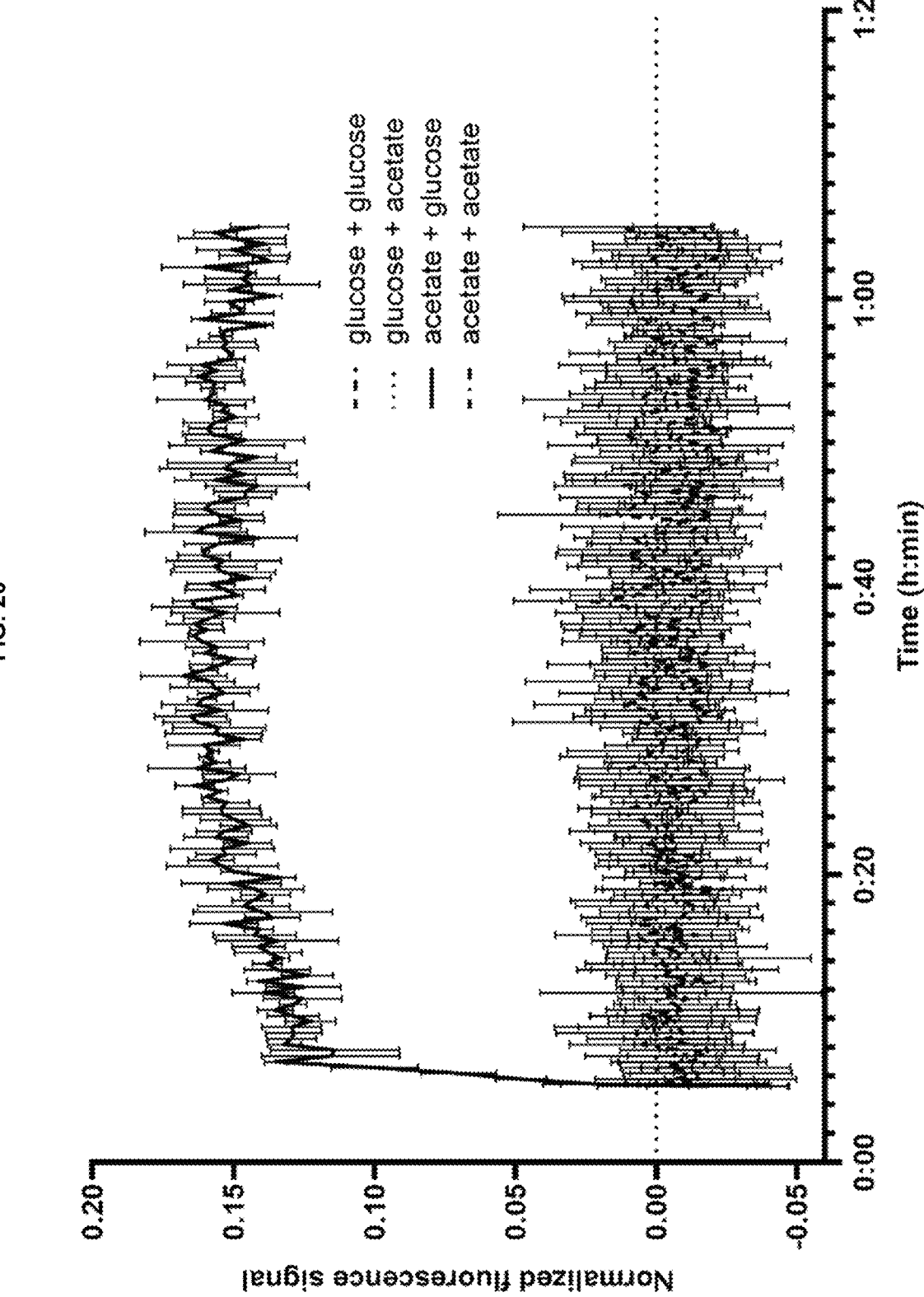
FIG. 20 is a line graph showing the fluorescence of live *E. coli* that express PancAce (sensor) that were either fed 28 mM glucose or 280 μM acetate for 3 hours prior. At time 0:05, the cells were given either 28 mM glucose or 280 UM acetate as indicated in the figure legend, and the fluorescence was measured by a plate reader ($\lambda_{ex}$=405 nm, 485 nm; $\lambda_{em}$=514 nm) over 1 hour as shown on the X-axis. The fluorescence was normalized by dividing $F_{488}/F_{405}$ and then ($F_1-F_0)/F_0$ where $F_0$ is defined by the fluorescence from each population of cells prior to time 0:05, n=3. This data shows that *E. coli* prefer glucose as their acetyl-CoA source compared to acetate.

Finally, starved or glucose-fed cells were fed with acetate instead of glucose since acetate can be converted to acetyl-CoA via non-glycolytic pathways. Based on the use of 100 µM acetate for experiments in mammalian cells, 280 µM acetate was chosen. The starved cells exhibited a relatively gradual increase in PancAce signal upon acetate feeding (increase over about 30 minutes), compared to the sharp change observed with glucose feeding (FIGS. 19-20). The fed cells exhibited no change upon addition of acetate.

Example 5

Acetyl-CoA Measurements in Hela Cells

Figure 22:
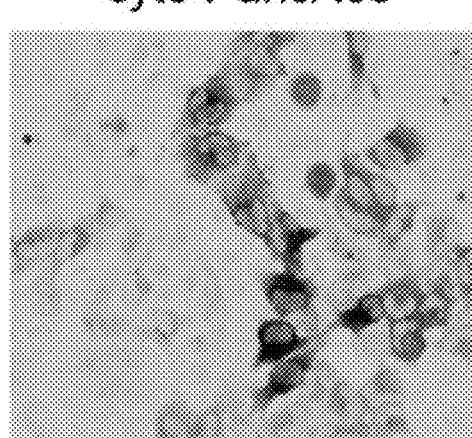
FIG. 22 is images showing fluorescence confocal microscopy of Hela cells that stably express PancAce ("sensor") or cpGFP with a cytoplasmic localization sequence ("cyto"), nuclear localization sequence ("nuc"), or mitochondrial localization sequence ("mito"). The scale bars represent 80 μm. $\lambda_{ex}$=485, $\lambda_{em}$=514 nm. This shows that the Hela cells are expressing the fluorescent protein constructs and that the protein translated from the constructs is going to the correct compartment corresponding to the localization sequence comprised by the protein.
Figure 22:
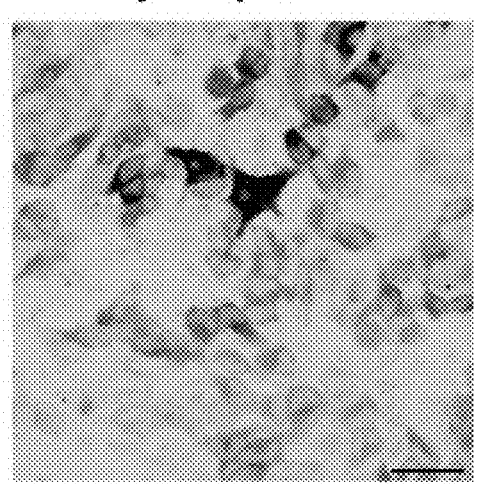
Figure 22:
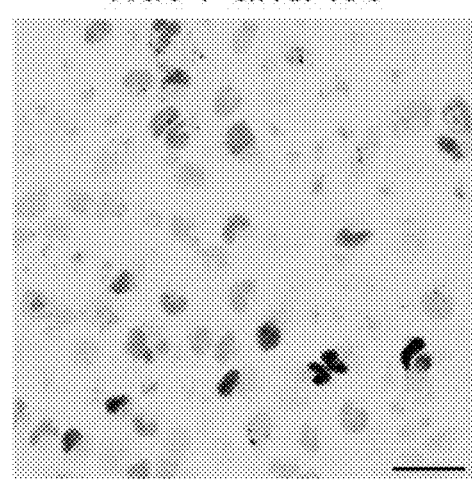
Figure 22:
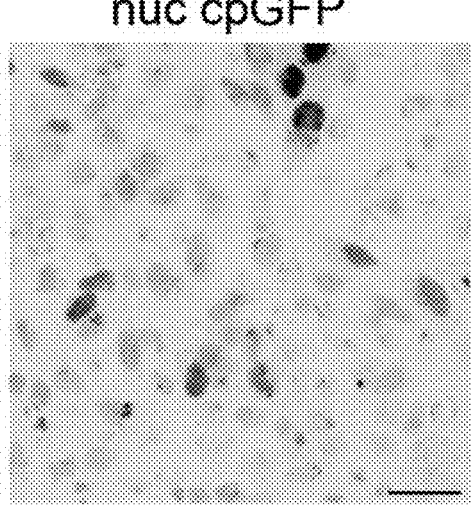
Figure 22:
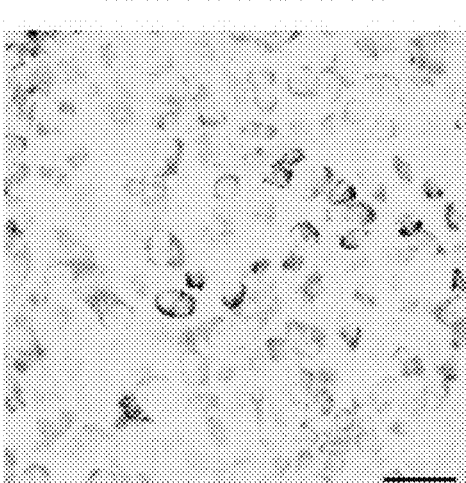
Figure 22:
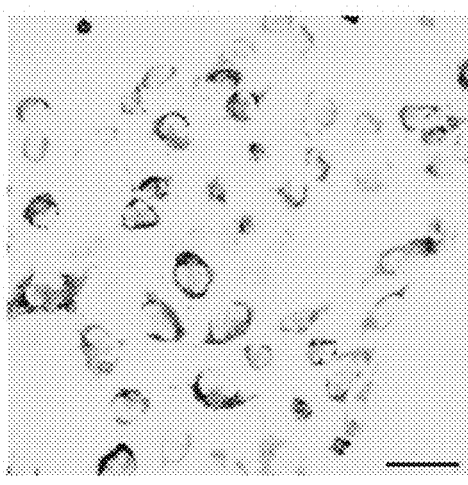
Figure 23A:
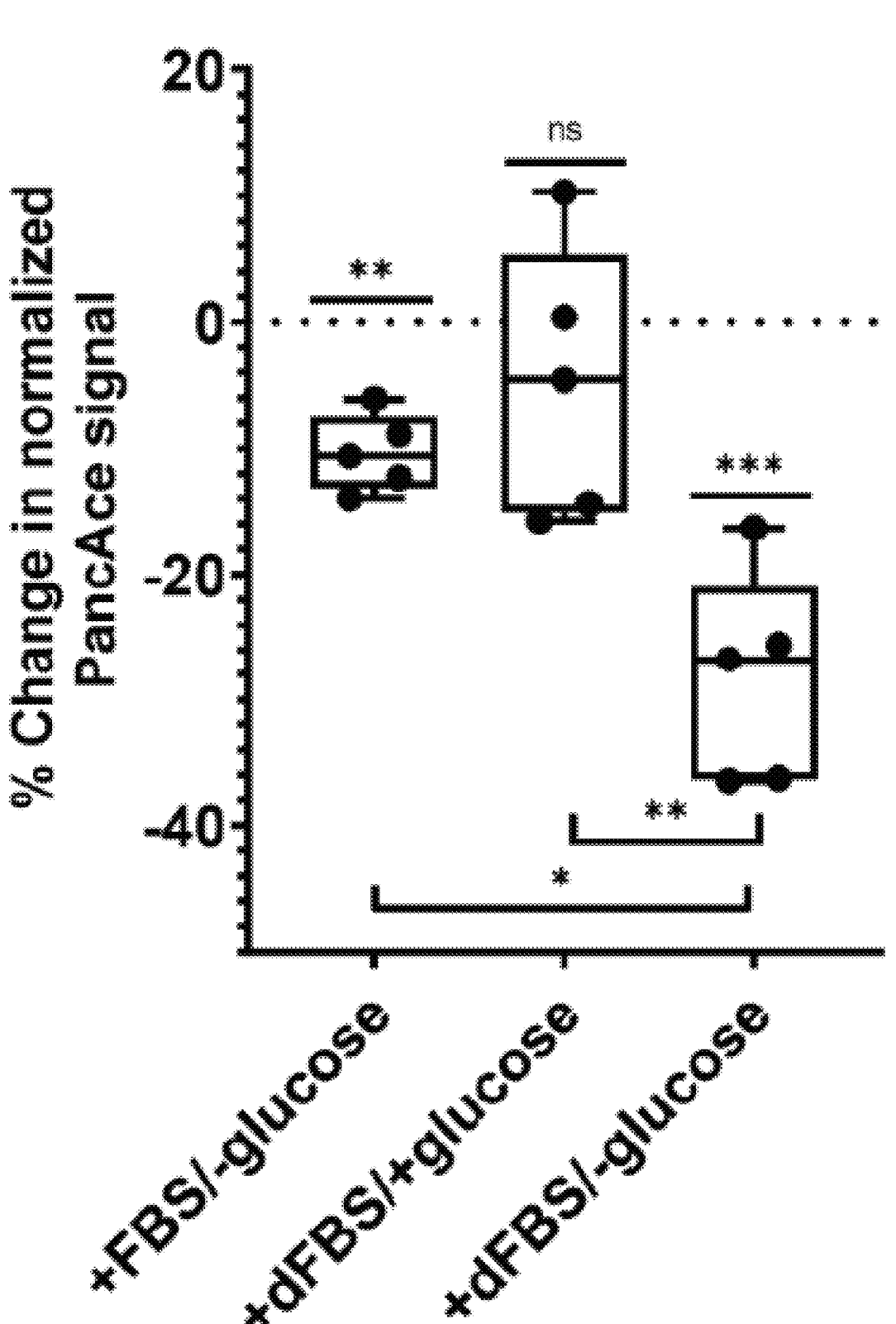
FIG. 23A, FIG. 23B, and FIG. 23C are bar graphs showing the normalized sensor signal from live Hela cells that express the sensor in the nucleus (FIG. 23A), cytoplasm (FIG. 23B), or mitochondrion (FIG. 23C). In these experiments the Hela cells were deprived of different combinations of acetyl-CoA precursor nutrients and the effect on acetyl-CoA levels in the different compartments of the cell were measured. The cells were given either fetal bovine serum (FBS) and deprived of glucose ("+FBS/−glucose"), given dialyzed fetal bovine serum ("dFBS") instead of FBS and given glucose ("+dFBS/+glucose), or given dFBS and deprived of glucose ("+dFBS/−glucose") for 18 hours prior to imaging the cells by confocal fluorescence microscopy ($\lambda_{ex}$=405 nm, 485 nm; $\lambda_{em}$=514 nm). To obtain the normalized signal, the signal from PancAce was normalized by dividing $F_{488}/F_{405}$, then $F_{Pan}/F_{GFP}$, then normalizing to the signal from cells that were given+FBS/+glucose for the same time interval ("$F_0$"): ($F_1-F_0)/F_0$. n=5-6. *p<0.05, p<0.005, *p<0.0005, ****<0.0001. This data shows that the sensor can detect compartment-specific changes in acetyl-CoA in live cells.
Figure 23B:
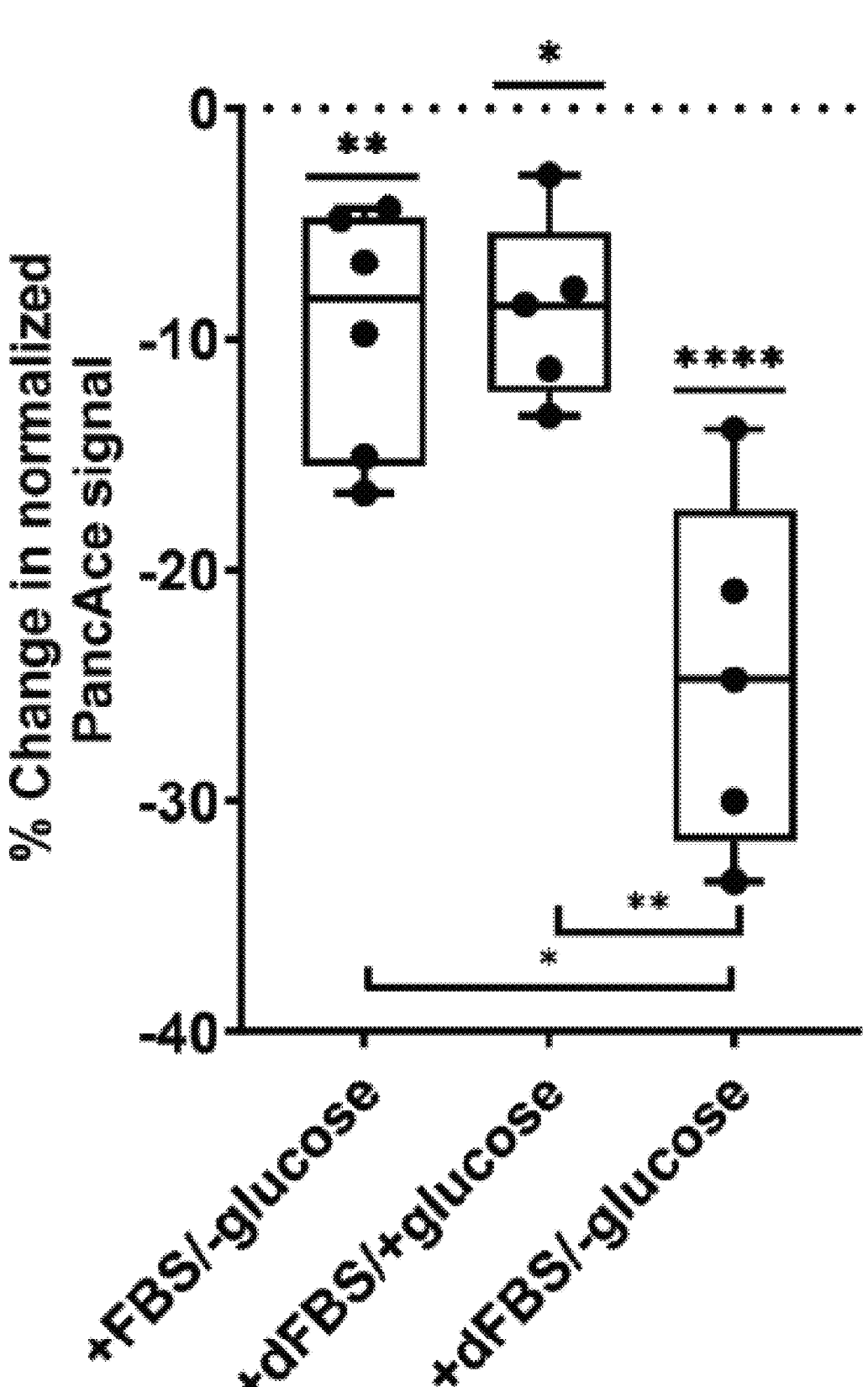
Figure 23C:
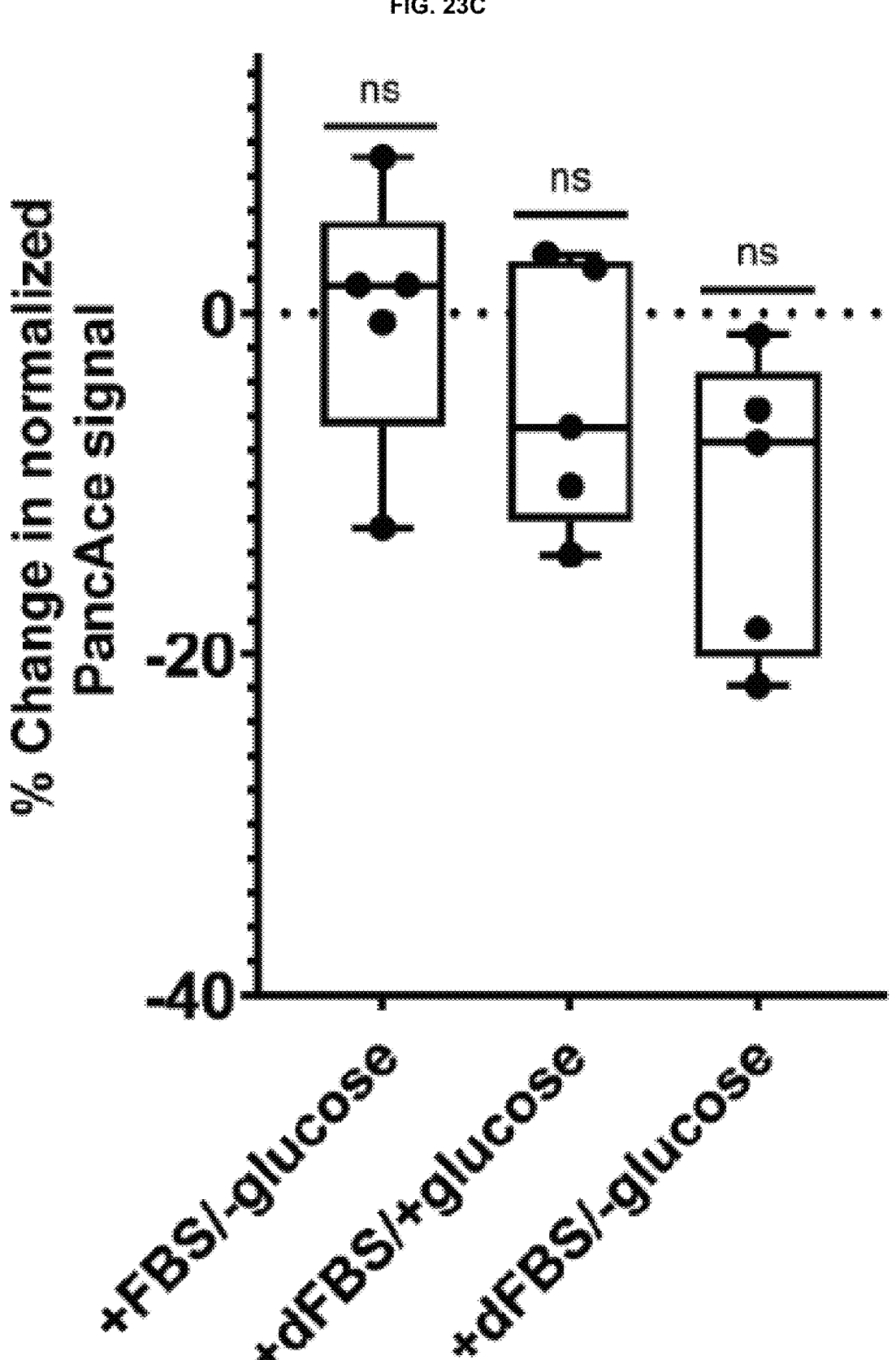

HeLa cell lines stably expressing PancAce or cpGFP with a nuclear, cytoplasmic, or mitochondrial localization tag were prepared (FIG. 22) and fluorescence microscopy was used to quantify the PancAce and cpGFP signals. To perturb intracellular acetyl-CoA levels, the cells were deprived of glucose, complete serum (i.e., cells given dialyzed fetal bovine serum, dFBS), or both for 18 hours and then compared the sensor response to fed cells given glucose and complete serum during that same period (FIGS. 23A-23C). The dFBS was used since FBS contains acetate and glucose both of which can feed into acetyl-CoA. Nuclear acetyl-CoA levels were sensitive to glucose deprivation as expected based on previous findings. Serum deprivation did not significantly affect nuclear acetyl-CoA levels, but deprivation of both nutrients had a synergistic impact. Cytoplasmic acetyl-CoA levels decreased under all of the deprivation conditions with the deprivation of both glucose and serum causing a larger decrease than either deprivation alone. Mitochondrial acetyl-CoA levels did not change according to the PancAce sensor.

Figure 24:
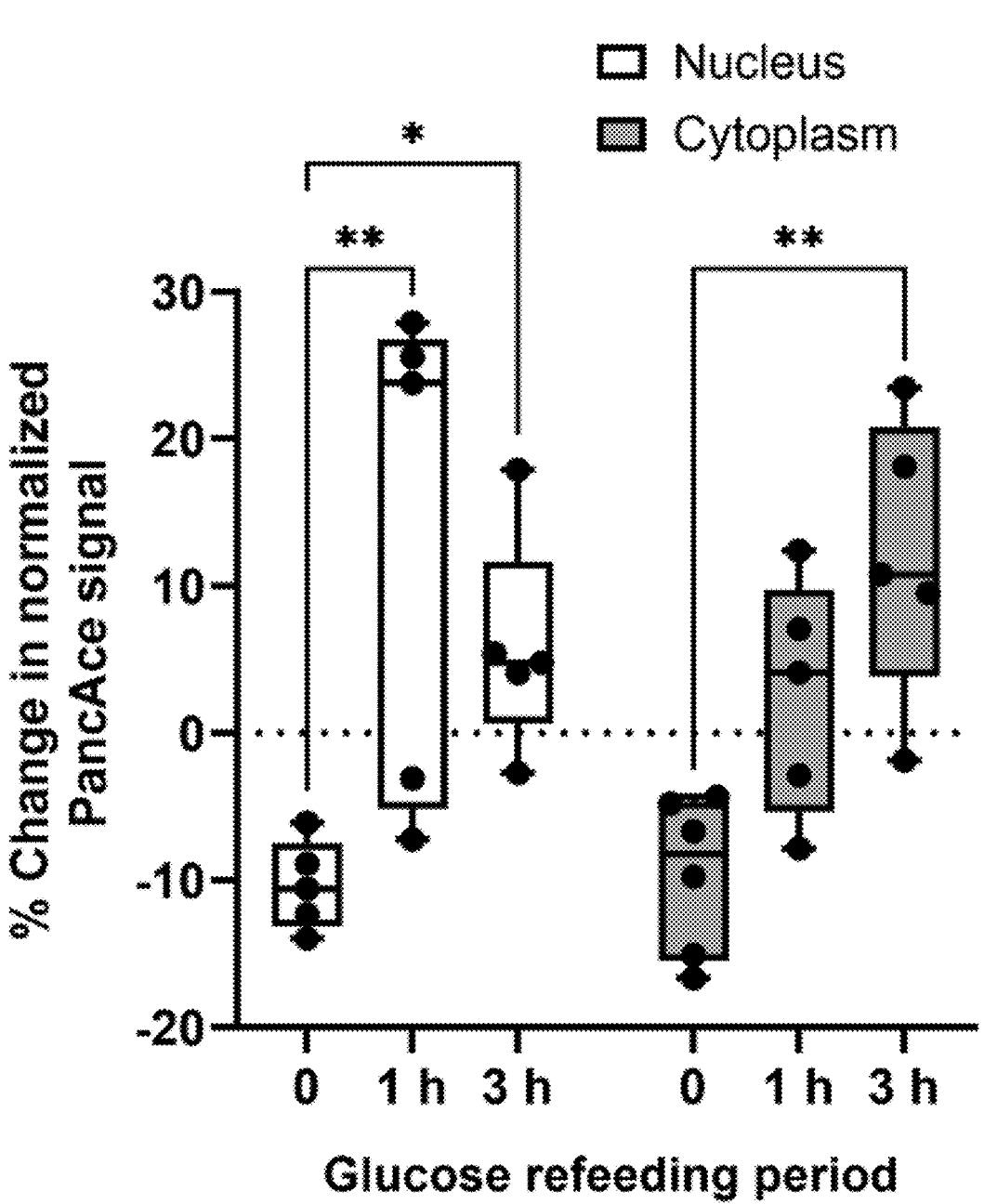
FIG. 24 is bar graphs showing the normalized sensor signal from live Hela cells that express the sensor in the nucleus or cytoplasm. Similar to the *E. coli* experiments, here the cells were deprived of glucose and then refed with glucose to see whether the acetyl-CoA levels were recovered in the Hela cells after the Hela cells had access to glucose again. The cells were deprived of glucose for 18 hours and then given 4.5 g/L glucose for 1 hour or 3 hours prior to imaging the cells by confocal fluorescence microscopy ($\lambda_{ex}$=405 nm, 485 nm; $\lambda_{em}$=514 nm). To obtain the normalized signal, the signal from PancAce was normalized by dividing $F_{488}/F_{405}$, then $F_{Pan}/F_{GFP}$, then normalizing to the signal from cells that were given+FBS/+glucose for the same time intervals ("$F_0$"): $(F_1-F_0)/F_0$. n=5-6. *p<0.05, **p<0.005.
Figure 27:
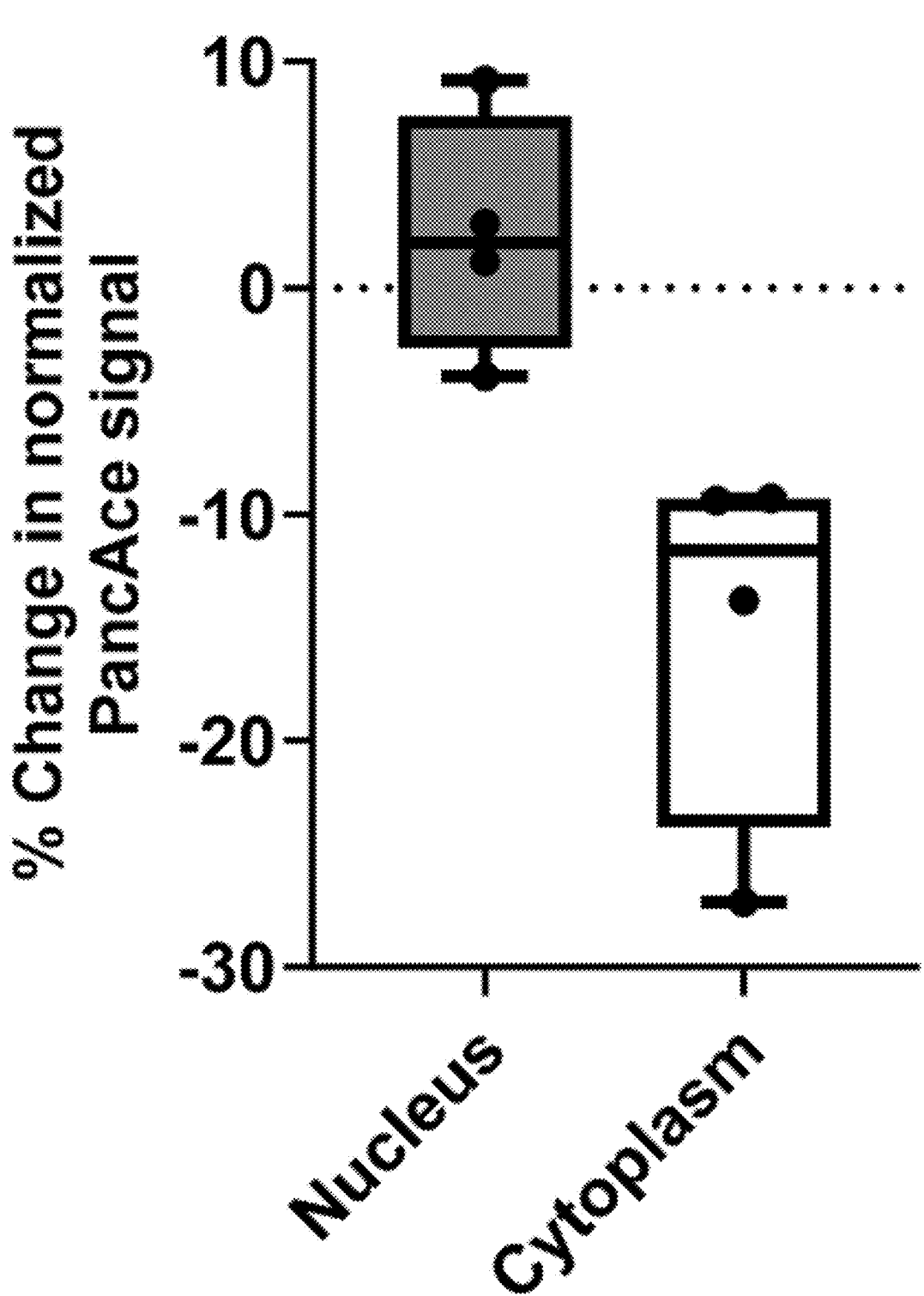
FIG. 27 is a bar graph showing the normalized sensor signal from live Hela cells that express the sensor in the nucleus or cytoplasm. The biochemical data herein (FIG. 11 and FIG. 12) indicated that the sensor might also bind to propionyl-CoA in addition to acetyl-CoA in a cell. It has been shown that branched-chain amino acids ("BCAAs") deprivation causes propionyl-CoA levels to significantly increase in the nucleus of cells, but not acetyl-CoA levels. The cells were deprived of the BCAAs, isoleucine and valine, for 24 hours before the cells were imaged by confocal fluorescence microscopy ($\lambda_{ex}$=405 nm, 485 nm; $\lambda_{em}$=514 nm). To obtain the normalized signal, the signal from PancAce was normalized by dividing $F_{488}/F_{405}$, then $F_{Pan}/F_{GFP}$, then normalizing to the signal from cells that were given BCAAs for the same time interval ("$F_0$"): $(F_1-F_0)/F_0$. n=5-6. *p<0.05, **p<0.005. In the cytoplasm, both propionyl-CoA and acetyl-CoA levels decreased by about the same amount. These data indicate a reduction in the cytoplasm and not the nucleus, which implies that the sensor is in fact selective for acetyl-CoA in cells.

Next, how long it would take for acetyl-CoA levels to recover in cells that were glucose deprived and then refed with glucose was analyzed (FIG. 24). It was observed that the nucleus acetyl-CoA levels were at least partially restored after 1 hour and fully restored after 3 hours. Cytoplasmic acetyl-CoA levels were restored after 3 hours and were trending up after only 1 hour. Since PancAce only has a 2.4-fold lower affinity for propionyl-CoA, how sensitive the sensor was in responding to changes in propionyl-CoA instead of acetyl-CoA was evaluated. Based on previous work that showed that branched chain amino acid (BCAA) deprivation lowered nuclear propionyl-CoA levels much more than acetyl-CoA levels (Trefely, et al., *Mol. Cell* (2022) 82, 447-462), this perturbation with PancACe was used. In Trefely, et al, cells deprived of BCAAs showed a reduction in both acetyl-CoA and propionyl-CoA in the non-nuclear fraction of the cells, while the nucleus showed a reduction in propionyl-CoA but not acetyl-CoA. Cells were either given complete media or starved of BCAAs (valine and isoleucine) for 24 h (FIG. 27). The nuclear compartment showed no significant change in the sensor response, while the cytoplasm displayed a decrease in the PancAce signal. Based on this data and the data from Trefely, et al, PancAce appears to be selective for acetyl-CoA over propionyl-CoA in cells.

Figure 25A:
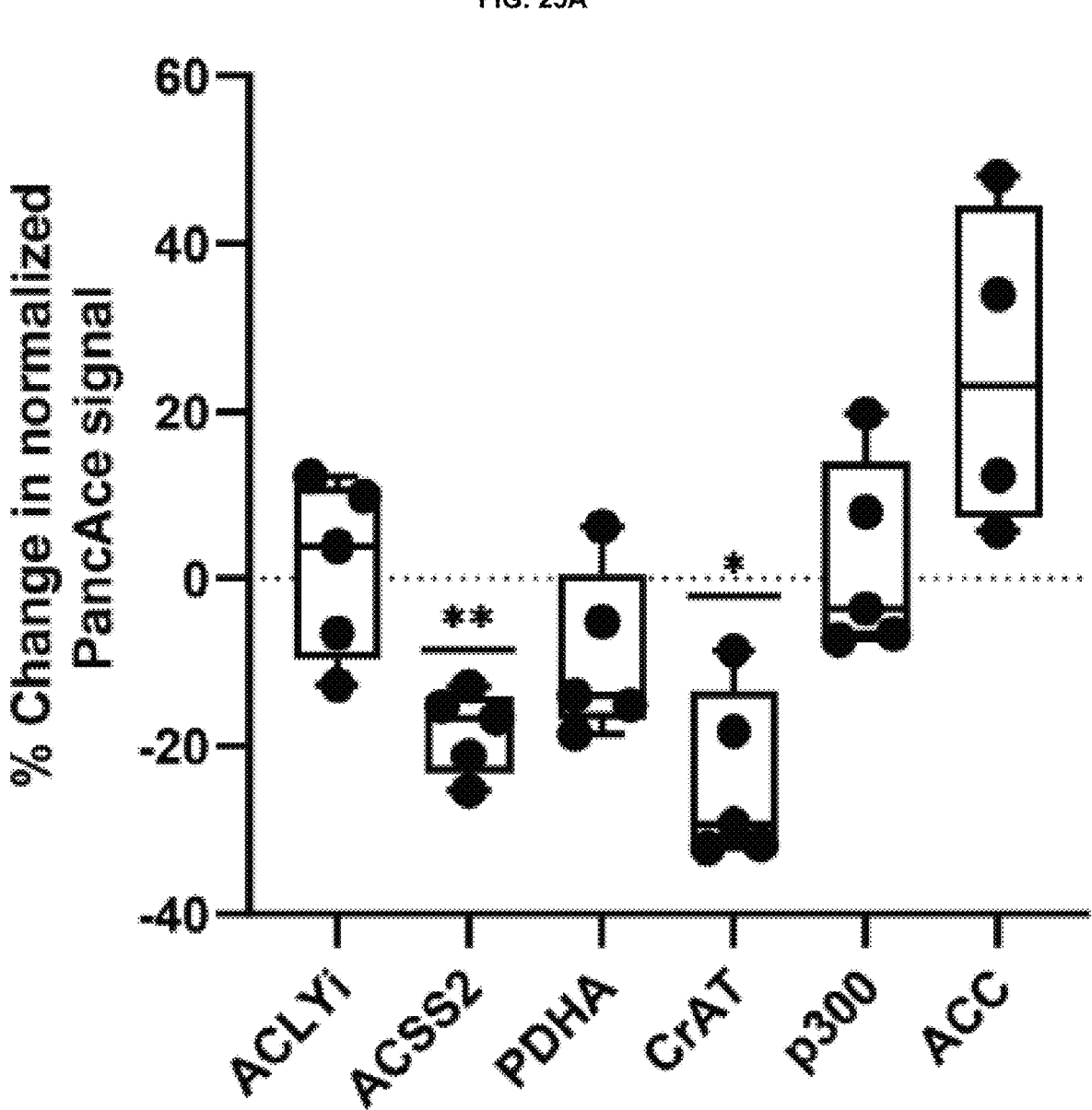
Figure 25B:
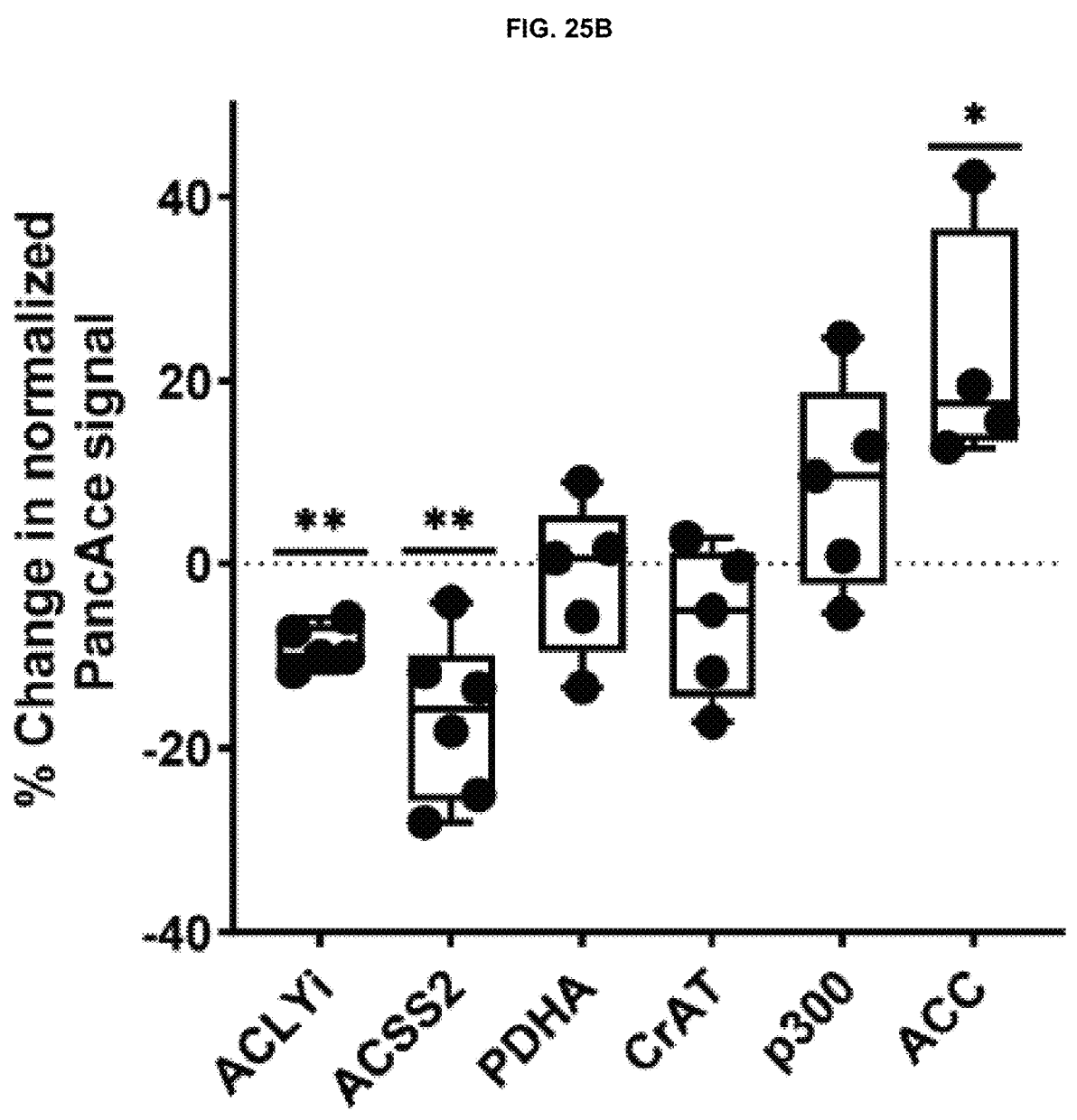
Figure 25C:
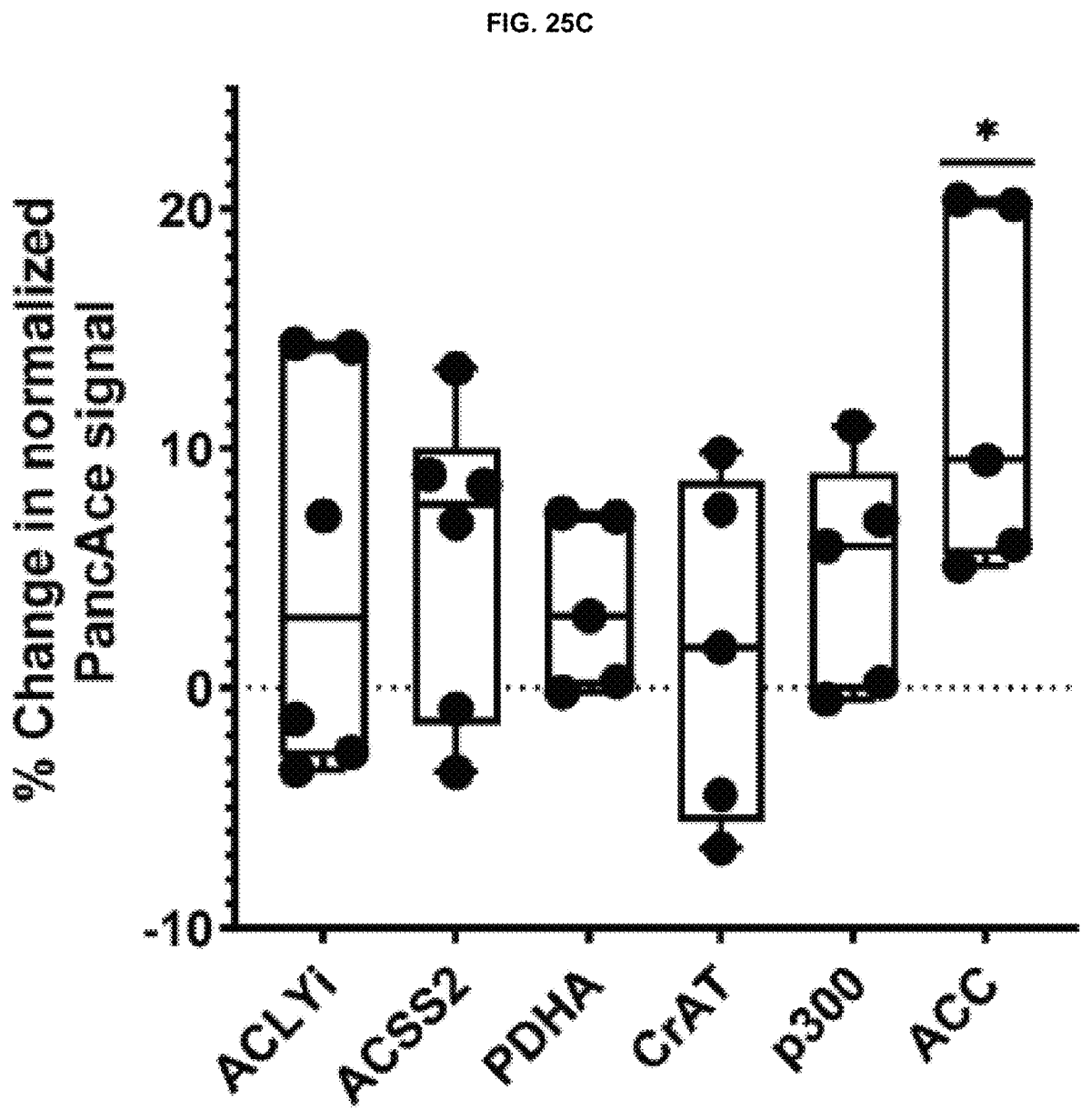
Figure 26:
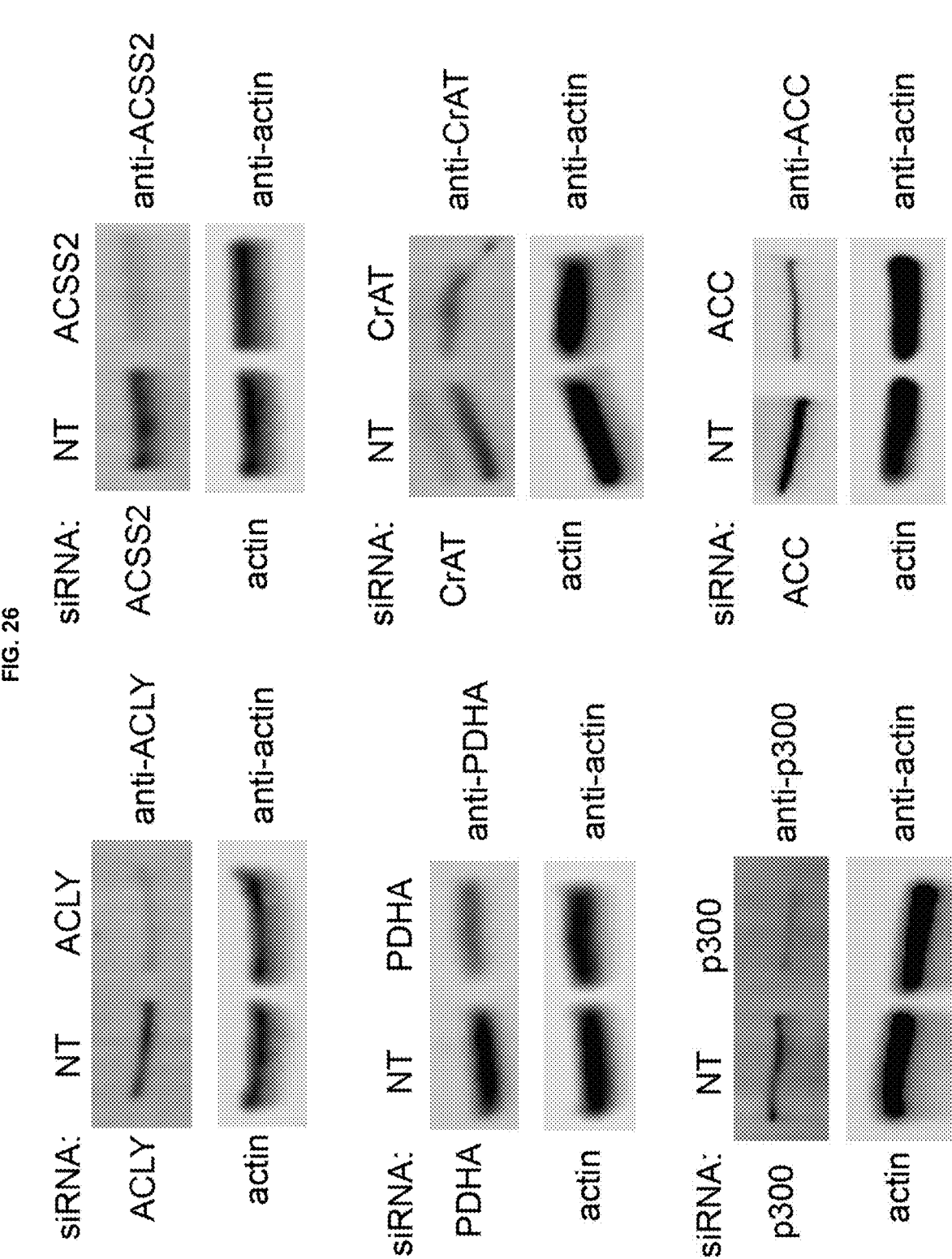
FIG. 26 is images depicting a series of immunoblots that show the knockdown of the specified protein via the siRNAs that were used in the Hela cells in FIGS. 25A-25C. Site-specific antibodies were used for each siRNA target ("NT"=non-targeting siRNA). Actin is shown as a control for protein loading.

Acetyl-CoA is produced and consumed by disparate pathways in the cell in a compartmentalized fashion. Thus, a panel of proteins was knocked-down (FIG. 26) that modulate acetyl-CoA by producing, transporting, or consuming acetyl-CoA and PancAce was used to measure compartspecific changes in acetyl-CoA levels (FIGS. 25A-25C). The data for the nuclear-localized PancAce shows that acyl-CoA short chain synthetase 2 (ACSS2) and carnitine acetyltransferase (CrAT) are primarily responsible for producing acetyl-CoA there, while ACLY (ATP citrate lyase) and PDHA (pyruvate dehydrogenase, isoform A) do not measurably contribute to nuclear acetyl-CoA. Knockdown of the acetyltransferase p300 did not result in accumulation of acetyl-CoA in the nucleus, but knockdown of acetyl-CoA carboxylase (ACC, isoforms A and B) did cause accumulation of acetyl-CoA in the nucleus. In the cytoplasm, the data indicates that ACLY and ACSS2 are the major contributors to acetyl-CoA. Like in the nucleus, ACC knockdown causes accumulation of cytoplasmic acetyl-CoA, as expected. No major changes occurred to acetyl-CoA in the mitochondria except, when ACC was knocked down, there was accumulation of acetyl-CoA like in the other compartments. These data show that PancAce can measure acetyl-CoA levels in different cell compartments and be used to characterize the compartment-specific effects of modulating metabolic enzymes.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A recombinant acetyl-coenzyme A (acetyl-CoA) biosensor polypeptide comprising: an acetyl-CoA binding protein having an amino acid sequence at least 95% identical to SEQ ID NO: 1, wherein the acetyl-CoA binding protein is divided into: a first acetyl-CoA binding protein fragment comprising an N-terminal portion of the acetyl-CoA binding protein; and a second acetyl-CoA binding protein fragment comprising a C-terminal portion of the acetyl-CoA binding protein; wherein the first and second acetyl-CoA binding protein fragments collectively include all of the amino acids of the acetyl-CoA binding protein; and a fluorescent protein inserted between the first and second acetyl-CoA binding protein fragments and attached to a C-terminus of the first acetyl-CoA binding protein fragment and an N-terminus of the second acetyl-CoA binding protein fragment; and wherein: (i) the C-terminus is an arginine at position 69 of SEQ ID NO: 1 (Arg69) and the N-terminus is a glutamic acid at position 70 of SEQ ID NO: 1 (Glu70); (ii) the C-terminus is a tryptophan at position 23 of SEQ ID NO: 1 (Trp23) and the N-terminus is a proline at position 24 of SEQ ID NO: 1 (Pro24); (iii) the C-terminus is a valine at position 71 of SEQ ID NO: 1 (Val71) and the N-terminus is a threonine at position 72 of SEQ ID NO: 1 (Thr72); (iv) the C-terminus is an aspartic acid at position 99 of SEQ ID NO: 1 (Asp99) and the N-terminus is an alanine at position 100 of SEQ ID NO: 1 (Ala100); (v) the C-terminus is an aspartic acid at 104 of SEQ ID NO: 1 (Asp104) and the N-terminus is an arginine at position 105 of SEQ ID NO: 1 (Arg105); or (vi) the C-terminus is a glycine at position 116 of SEQ ID NO: 1 (Gly116) and the N-terminus is a phenylalanine at position 117 of SEQ ID NO: 1 (Phe117); and wherein the recombinant acetyl-CoA biosensor polypeptide selectively binds acetyl-CoA, and the binding of acetyl-CoA induces a change in the fluorescence of the fluorescent protein.

Clause 2. The recombinant acetyl-CoA biosensor polypeptide of clause 1, wherein the fluorescent protein is a circularly permuted GFP (cpGFP), a circularly permuted yellow fluorescent protein (cpYFP), or a circularly permuted blue fluorescent protein (cpBFP).

Clause 3. The recombinant acetyl-CoA biosensor polypeptide of clause 2, wherein the cpGFP comprises an amino acid sequence of SEQ ID NO: 2, the cpYFP comprises an amino acid sequence of SEQ ID NO: 3, and the cpBFP comprises an amino acid sequence of SEQ ID NO: 4.

Clause 4. The recombinant acetyl-CoA biosensor polypeptide of any one of clauses 1-3, wherein the acetyl-CoA binding protein comprises an amino acid sequence at least 99% identical to SEQ ID NO: 1.

Clause 5. The recombinant acetyl-CoA biosensor polypeptide of any one of clauses 1-4, wherein the acetyl-CoA binding protein comprises the amino acid sequence of SEQ ID NO: 1.

Clause 6. The recombinant acetyl-CoA biosensor polypeptide of any one of clauses 1-5, wherein: the fluorescent protein is either directly attached to the C-terminus of the first acetyl-CoA binding protein fragment or is attached by a first amino acid linker that is from 1 to 3 amino acids in length; and the fluorescent protein is either directly attached to the N-terminus of the second acetyl-CoA binding protein fragment or is attached by a second linker that is from 1 to 3 amino acids in length.

Clause 7. The recombinant acetyl-CoA biosensor polypeptide of clause 6, wherein the first and second amino acid linkers are each independently selected from the group consisting of a Gly, Gly-Ala, Ala-Ser, and Gly-Ala-Ser.

Clause 8. The recombinant acetyl-CoA biosensor poly-
peptide of clause 6 or clause 7, wherein: (i) the first
linker is Gly-Ala and the second linker is Gly-Ala; (ii)
the first linker is Ala-Ser and the second linker is
Ala-Ser; (iii) the first linker is Gly-Ala-Ser and the
second linker is Gly; (iv) the C-terminus and N-termi-
nus are directly attached to the fluorescent protein; (v)
the C-terminus is directly attached to the fluorescent
protein and the second linker is Gly-Ala-Ser; (vi) the
first linker is Gly-Ala-Ser and the N-terminus is
directly attached to the fluorescent protein; (vii) the first
linker is Gly-Ala and the N-terminus is directly
attached to the fluorescent protein; or (viii) the first
linker is Gly and the second linker is Gly-Ala-Ser.
Clause 9. The recombinant acetyl-CoA biosensor poly-
peptide of any one of clauses 1-8, further comprising
one or more of a histidine tag, a TEV cleavage site, a
FLAG® tag, a human influenza hemagglutinin (HA)
tag, a nuclear export signal, a nuclear localization
signal, a cytoplasmic localization signal, and a mito-
chondrial localization signal at the N-terminal portion
of the acetyl-CoA binding protein.
Clause 10. The recombinant acetyl-CoA biosensor poly-
peptide of any one of clauses 1-9, wherein: (i) the
recombinant acetyl-CoA biosensor polypeptide com-
prises the amino acid sequence of SEQ ID NO: 5; (ii)
the recombinant acetyl-CoA biosensor polypeptide
comprises the amino acid sequence of SEQ ID NO: 6;
(iii) the recombinant acetyl-CoA biosensor polypeptide
comprises the amino acid sequence of SEQ ID NO: 7;
(iv) the recombinant acetyl-CoA biosensor polypeptide
comprises the amino acid sequence of SEQ ID NO: 8;
(v) the recombinant acetyl-CoA biosensor polypeptide
comprises the amino acid sequence of SEQ ID NO: 9;
(vi) the recombinant acetyl-CoA biosensor polypeptide
comprises the amino acid sequence of SEQ ID NO: 10;
(vii) the recombinant acetyl-CoA biosensor polypep-
tide comprises the amino acid sequence of SEQ ID NO:
11; (viii) the recombinant acetyl-CoA biosensor poly-
peptide comprises the amino acid sequence of SEQ ID
NO: 12; (ix) the recombinant acetyl-CoA biosensor
polypeptide comprises the amino acid sequence of SEQ
ID NO: 13; (x) the recombinant acetyl-CoA biosensor
polypeptide comprises the amino acid sequence of SEQ
ID NO: 14; (xi) the recombinant acetyl-CoA biosensor
polypeptide comprises the amino acid sequence of SEQ
ID NO: 15; (xii) the recombinant acetyl-CoA biosensor
polypeptide comprises the amino acid sequence of SEQ
ID NO: 16; (xiii) the recombinant acetyl-CoA biosen-
sor polypeptide comprises the amino acid sequence of
SEQ ID NO: 17; (xiv) the recombinant acetyl-CoA
biosensor polypeptide comprises the amino acid
sequence of SEQ ID NO: 18; or (xv) the recombinant
acetyl-CoA biosensor polypeptide comprises the amino
acid sequence of SEQ ID NO: 19.
Clause 11. The recombinant acetyl-CoA biosensor poly-
peptide of clause 10, wherein the recombinant acetyl-
CoA biosensor polypeptide comprises the amino acid
of SEQ ID NO: 5.
Clause 12. An expression vector comprising: a nucleic
acid that encodes the recombinant acetyl-CoA biosen-
sor polypeptide of any one of clauses 1-11; and a
promoter operably linked to the nucleic acid.
Clause 13. The expression vector of clause 12, wherein
the expression vector is a lentiviral vector, an adeno-
associated virus (AAV) vector, or a cytomegalovirus
(CMV) vector.

Clause 14. A method of detecting acetyl-CoA in a sample
comprising: contacting the sample with the recombi-
nant acetyl-CoA biosensor polypeptide of any one of
clauses 1-11; exciting the recombinant acetyl-CoA
biosensor polypeptide in the sample at an excitation
wavelength; measuring a fluorescence intensity of the
recombinant acetyl-CoA biosensor polypeptide in the
sample at an emission wavelength; and comparing the
fluorescence intensity to a standard curve, wherein the
fluorescence intensity correlates with a concentration
of acetyl-CoA in the sample.
Clause 15. The method of clause 14, wherein the excita-
tion wavelength is from about 460 nm to about 490 nm.
Clause 16. The method of clause 14 or clause 15, wherein
the excitation wavelength is 485 nm. Clause 17. The
method of any one of clauses 14-16, wherein the
emission wavelength is from about 513 nm to about
540 nm.
Clause 18. The method of any one of clauses 14-17,
wherein the emission wavelength is 514 nm.
Clause 19. The method of any one of clauses 14-18,
wherein the pH of the sample is maintained at a pH of
6.5-8.0.
Clause 20. A method of monitoring acetyl-CoA activity in
a cell, comprising: providing a cell with the recombi-
nant acetyl-CoA biosensor polypeptide of any one of
clauses 1-11; exciting the recombinant acetyl-CoA
biosensor polypeptide in the cell at a first excitation
wavelength between about 400 nm and about 430 nm
while measuring a first fluorescence intensity at an
emission wavelength between about 513 nm and about
540 nm; exciting the recombinant acetyl-CoA biosen-
sor polypeptide in the cell at a second excitation
wavelength between about 460 nm and about 490 nm
while measuring a second fluorescence intensity at the
emission wavelength; and normalizing the second fluo-
rescence intensity based on the first fluorescence inten-
sity.
Clause 21. The method of clause 20, wherein normalizing
comprises dividing the second fluorescence intensity
by the first fluorescence intensity.
Clause 22. The method of clause 20 or clause 21, further
comprising treating the cell with an acetyl-CoA pre-
cursor or nutrient affecting the function of the cell and
comparing the normalized fluorescence intensity of the
cell to the normalized fluorescence intensity of a con-
trol cell.
Clause 23. The method of clause 22, wherein one or more
of a nuclear export signal, a nuclear localization signal,
a cytoplasmic localization signal, and a mitochondrial
localization signal is attached to an N-terminus of the
recombinant acetyl-CoA biosensor polypeptide.
Clause 24. The method of clause 23, further comprising
determining where acetyl-CoA is localized in the cell.
Clause 25. The method of any one of clauses 20-24,
wherein the first excitation wavelength is 405 nm.
Clause 26. The method of any one of clauses 20-25,
wherein the second excitation wavelength is 485 nm.
Clause 27. The method of any one of clauses 20-26,
wherein the emission wavelength is 514 nm.
Clause 28. The method of any one of clauses 20-27,
wherein the providing step comprises transforming the
cell with a plasmid comprising a polynucleotide that
encodes the recombinant acetyl-CoA biosensor poly-
peptide.

| | SEQUENCES | |
|---|---|---|
| Name | Amino Acid or Nucleotide Sequence (N→C or 5'→3') | SEQ ID NO |
| PanZ Amino AcidSequence | MKLTIIRLEKFSDQDRIDLQKIWPEYSPSSLQVDDNHRIYAARFNERLLAAVRV<br>TLSGTEGALDSLRVREVTRRRGVGQYLLEEVLRNNPGVSCWWMADAGVEDRGVM<br>TAFMQALGFTAQQGGWEKC | 1 |
| cpGFP Amino AcidSequence | NVYIKADKQKNGIKANFKIRHNIEDGGVQLAYHYQQNTPIGDGPVLLPDNHYLS<br>VQSKLSKDPNEKRDHMVLLEFVTAAGITLGMDELYKGGTGGSMVSKGEELFTGV<br>VPILVELDGDVNGHKFSVSGEGEGDATYGKLTLKFICTTGKLPVPWPTLVTTLT<br>YGVQCFSRYPDHMKQHDFFKSAMPEGYIQERTIFFKDDGNYKTRAEVKFEGDTL<br>VNRIELKGIDFKEDGNILGHKLEYN | 2 |
| cpYFP Amino AcidSequence | NVYIKADKQKNGIKANFKIRHNIEDGGVQLAYHYQQNTPIGDGPVLLPDNHYLS<br>YQSVLSKDPNEKRDHMVLLEFVTAAGITLGMDELYKGGTGGSMVSKGEELFTGV<br>VPILVELDGDVNGHKFSVSGEGEGDATYGKLTLKFICTTGKLPVPWPTLVTTLT<br>YGVQCFSRYPDHMKQHDFFKSAMPEGYIQERTIFFKDDGNYKTRAEVKFEGDTL<br>VNRIELKGIDFKEDGNILGHKLEYN | 3 |
| cpBFP Amino AcidSequence | NVYIKADKQKNGIKANFKIRHNIEDGGVQLAYHYQQNTPIGDGPVLLPDNHYLS<br>VQSKLSKDPNEKRDHMVLLEFVTAAGITLGMDELYKGGTGGSMVSKGEELFTGV<br>VPILVELDGDVNGHKFSVSGEGEGDATYGKLTLKFICTTGKLPVPWPTLVTTLS<br>HGVQCFSRYPDHMKQHDFFKSAMPEGYIQERTIFFKDDGNYKTRAEVKFEGDTL<br>VNRIELKGIDFKEDGNILGHKLEYN | 4 |
| PanZ(R69)-GA-cpGFP-GA-(E70)PanZ ("PANcACe") Amino AcidSequence | MKLTIIRLEKESDQDRIDLQKIWPEYSPSSLQVDDNHRIYAARFNERLLAAVRV<br>TLSGTEGALDSLRVRGANVYIKADKQKNGIKANFKIRHNIEDGGVQLAYHYQQN<br>TPIGDGPVLLPDNHYLSVQSKLSKDPNEKRDHMVLLEFVTAAGITLGMDELYKG<br>GTGGSMVSKGEELFTGVVPILVELDGDVNGHKFSVSGEGEGDATYGKLTLKFIC<br>TTGKLPVPWPTLVTTLTYGVQCFSRYPDHMKQHDFFKSAMPEGYIQERTIFFKD<br>DGNYKTRAEVKFEGDTLVNRIELKGIDFKEDGNILGHKLEYNGAEVTRRRGVGQ<br>YLLEEVLRNNPGVSCWWMADAGVEDRGVMTAFMQALGFTAQQGGWEKC | 5 |
| PanZ(W23)-AS-cpGFP-AS-(P24)PanZ Amino AcidSequence | MKLTIIRLEKFSDQDRIDLQKIWASNVYIKADKQKNGIKANFKIRHNIEDGGVQ<br>LAYHYQQNTPIGDGPVLLPDNHYLSVQSKLSKDPNEKRDHMVLLEFVTAAGITL<br>GMDELYKGGTGGSMVSKGEELFTGVVPILVELDGDVNGHKFSVSGEGEGDATYG<br>KLTLKFICTTGKLPVPWPTLVTTLTYGVQCFSRYPDHMKQHDFFKSAMPEGYIQ<br>ERTIFFKDDGNYKTRAEVKFEGDTLVNRIELKGIDFKEDGNILGHKLEYNASPE<br>YSPSSLQVDDNHRIYAARFNERLLAAVRVTLSGTEGALDSLRVREVTRRRGVGQ<br>YLLEEVLRNNPGVSCWWMADAGVEDRGVMTAFMQALGFTAQQGGWEKC | 6 |
| PanZ(V71)-AS-cpGFP-AS-(T72)PanZ Amino AcidSequence | MKLTIIRLEKFSDQDRIDLQKIWPEYSPSSLQVDDNHRIYAARFNERLLAAVRV<br>TLSGTEGALDSLRVREVASNVYIKADKQKNGIKANFKIRHNIEDGGVQLAYHYQ<br>QNTPIGDGPVLLPDNHYLSVQSKLSKDPNEKRDHMVLLEFVTAAGITLGMDELY<br>KGGTGGSMVSKGEELFTGVVPILVELDGDVNGHKFSVSGEGEGDATYGKLTLKF<br>ICTTGKLPVPWPTLVTTLTYGVQCFSRYPDHMKQHDFFKSAMPEGYIQERTIFF<br>KDDGNYKTRAEVKFEGDTLVNRIELKGIDFKEDGNILGHKLEYNASTRRRGVGQ<br>YLLEEVLRNNPGVSCWWMADAGVEDRGVMTAFMQALGFTAQQGGWEKC | 7 |
| PanZ(R69)-AS-cpGFP-AS-(E70)PanZ Amino AcidSequence | MKLTIIRLEKFSDQDRIDLQKIWPEYSPSSLQVDDNHRIYAARFNERLLAAVRV<br>TLSGTEGALDSLRVRASNVYIKADKQKNGIKANFKIRHNIEDGGVQLAYHYQQN<br>TPIGDGPVLLPDNHYLSVQSKLSKDPNEKRDHMVLLEFVTAAGITLGMDELYKG<br>GTGGSMVSKGEELFTGVVPILVELDGDVNGHKFSVSGEGEGDATYGKLTLKFIC<br>TTGKLPVPWPTLVTTLTYGVQCFSRYPDHMKQHDFFKSAMPEGYIQERTIFFKD<br>DGNYKTRAEVKFEGDTLVNRIELKGIDFKEDGNILGHKLEYNASEVTRRRGVGQ<br>YLLEEVLRNNPGVSCWWMADAGVEDRGVMTAFMQALGFTAQQGGWEKC | 8 |
| PanZ(D99)-AS-cpGFP-AS-(A100)PanZ Amino AcidSequence | MKLTIIRLEKFSDQDRIDLQKIWPEYSPSSLQVDDNHRIYAARFNERLLAAVRV<br>TLSGTEGALDSLRVREVTRRRGVGQYLLEEVLRNNPGVSCWWMADASNVYIKAD<br>KQKNGIKANFKIRHNIEDGGVQLAYHYQQNTPIGDGPVLLPDNHYLSVQSKLSK<br>DPNEKRDHMVLLEFVTAAGITLGMDELYKGGTGGSMVSKGEELFTGVVPILVEL<br>DGDVNGHKFSVSGEGEGDATYGKLTLKFICTTGKLPVPWPTLVTTLTYGVQCFS<br>RYPDHMKQHDFFKSAMPEGYIQERTIFFKDDGNYKTRAEVKFEGDTLVNRIELK<br>GIDFKEDGNILGHKLEYNASAGVEDRGVMTAFMQALGFTAQQGGWEKC | 9 |
| PanZ(D104)-AS-cpGFP-AS-(R105)PanZ Amino Acid | MKLTIIRLEKFSDQDRIDLQKIWPEYSPSSLQVDDNHRIYAARFNERLLAAVRV<br>TLSGTEGALDSLRVREVTRRRGVGQYLLEEVLRNNPGVSCWWMADAGVEDASNV<br>YIKADKQKNGIKANFKIRHNIEDGGVQLAYHYQQNTPIGDGPVLLPDNHYLSVQ<br>SKLSKDPNEKRDHMVLLEFVTAAGITLGMDELYKGGTGGSMVSKGEELFTGVVP<br>ILVELDGDVNGHKFSVSGEGEGDATYGKLTLKFICTTGKLPVPWPTLVTTLTYG<br>VQCFSRYPDHMKQHDFFKSAMPEGYIQERTIFFKDDGNYKTRAEVKFEGDTLVN<br>RIELKGIDFKEDGNILGHKLEYNASRGVMTAFMQALGFTAQQGGWEKC | 10 |
| PanZ(G116)-AS-cpGFP-AS-(F117)PanZ Amino Acid | MKLTIIRLEKFSDQDRIDLQKIWPEYSPSSLQVDDNHRIYAARFNERLLAAVRV<br>TLSGTEGALDSLRVREVTRRRGVGQYLLEEVLRNNPGVSCWWMADAGVEDRGVM<br>TAFMQALGASNVYIKADKQKNGIKANFKIRHNIEDGGVQLAYHYQQNTPIGDGP<br>VLLPDNHYLSVQSKLSKDPNEKRDHMVLLEFVTAAGITLGMDELYKGGTGGSMV<br>SKGEELFTGVVPILVELDGDVNGHKFSVSGEGEGDATYGKLTLKFICTTGKLPV | 11 |

-continued

| | SEQUENCES | |
|---|---|---|
| Name | Amino Acid or Nucleotide Sequence (N→C or 5'→3') | SEQ ID NO |
| | PWPTLVTTLTYGVQCFSRYPDHMKQHDFFKSAMPEGYIQERTIFFKDDGNYKTR AEVKFEGDTLVNRIELKGIDFKEDGNILGHKLEYNASFTAQQGGWEKC | |
| PanZ(R69)-GAS-cpGFP-G-(E70)PanZ Amino Acid | KLTIIRLEKFSDQDRIDLQKIWPEYSPSSLQVDDNHRIYAARFNERLLAAVRVT LSGTEGALDSLRVRGASNVYIKADKQKNGIKANFKIRHNIEDGGVQLAYHYQQN TPIGDGPVLLPDNHYLSVQSKLSKDPNEKRDHMVLLEFVTAAGITLGMDELYKG GTGGSMVSKGEELFTGVVPILVELDGDVNGHKFSVSGEGEGDATYGKLTLKFIC TTGKLPVPWPTLVTTLTYGVQCFSRYPDHMKQHDFFKSAMPEGYIQERTIFFKD DGNYKTRAEVKFEGDTLVNRIELKGIDFKEDGNILGHKLEYNGEVTRRRGVGQY LLEEVLRNNPGVSCWWMADAGVEDRGVMTAFMQALGFTAQQGGWEKC | 12 |
| PanZ(R69)-GAS-cpGFP-(E70)PanZ Amino Acid | MKLTIIRLEKFSDQDRIDLQKIWPEYSPSSLQVDDNHRIYAARFNERLLAAVRV TLSGTEGALDSLRVRGASNVYIKADKQKNGIKANFKIRHNIEDGGVQLAYHYQQ NTPIGDGPVLLPDNHYLSVQSKLSKDPNEKRDHMVLLEFVTAAGITLGMDELYK GGTGGSMVSKGEELFTGVVPILVELDGDVNGHKFSVSGEGEGDATYGKLTLKFI CTTGKLPVPWPTLVTTLTYGVQCFSRYPDHMKQHDFFKSAMPEGYIQERTIFFK DDGNYKTRAEVKFEGDTLVNRIELKGIDFKEDGNILGHKLEYNEVTRRRGVGQY LLEEVLRNNPGVSCWWMADAGVEDRGVMTAFMQALGFTAQQGGWEKC | 13 |
| PanZ(R69)-GA-cpGFP-(E70)PanZ Amino Acid | MKLTIIRLEKFSDQDRIDLQKIWPEYSPSSLQVDDNHRIYAARFNERLLAAVRV TLSGTEGALDSLRVRGANVYIKADKQKNGIKANFKIRHNIEDGGVQLAYHYQQN TPIGDGPVLLPDNHYLSVQSKLSKDPNEKRDHMVLLEFVTAAGITLGMDELYKG GTGGSMVSKGEELFTGVVPILVELDGDVNGHKFSVSGEGEGDATYGKLTLKFIC TTGKLPVPWPTLVTTLTYGVQCFSRYPDHMKQHDFFKSAMPEGYIQERTIFFKD DGNYKTRAEVKFEGDTLVNRIELKGIDFKEDGNILGHKLEYNEVTRRRGVGQYL LEEVLRNNPGVSCWWMADAGVEDRGVMTAFMQALGFTAQQGGWEKC | 14 |
| PanZ(R69)-cpGFP-(E70)PanZ Amino Acid | MKLTIIRLEKFSDQDRIDLQKIWPEYSPSSLQVDDNHRIYAARFNERLLAAVRV TLSGTEGALDSLRVRNVYIKADKQKNGIKANFKIRHNIEDGGVQLAYHYQQNTP IGDGPVLLPDNHYLSVQSKLSKDPNEKRDHMVLLEFVTAAGITLGMDELYKGGT GGSMVSKGEELFTGVVPILVELDGDVNGHKFSVSGEGEGDATYGKLTLKFICTT GKLPVPWPTLVTTLTYGVQCFSRYPDHMKQHDFFKSAMPEGYIQERTIFFKDDG NYKTRAEVKFEGDTLVNRIELKGIDFKEDGNILGHKLEYNEVTRRRGVGQYLLE EVLRNNPGVSCWWMADAGVEDRGVMTAFMQALGFTAQQGGWEKC | 15 |
| PanZ(69)-G-cpGFP-GAS-(E70)PanZ Amino Acid | MKLTIIRLEKFSDQDRIDLQKIWPEYSPSSLQVDDNHRIYAARFNERLLAAVRV TLSGTEGALDSLRVRGNVYIKADKQKNGIKANFKIRHNIEDGGVQLAYHYQQNT PIGDGPVLLPDNHYLSVQSKLSKDPNEKRDHMVLLEFVTAAGITLGMDELYKGG TGGSMVSKGEELFTGVVPILVELDGDVNGHKFSVSGEGEGDATYGKLTLKFICT TGKLPVPWPTLVTTLTYGVQCFSRYPDHMKQHDFFKSAMPEGYIQERTIFFKDD GNYKTRAEVKFEGDTLVNRIELKGIDFKEDGNILGHKLEYNGASEVTRRRGVGQ YLLEEVLRNNPGVSCWWMADAGVEDRGVMTAFMQALGFTAQQGGWEKC | 16 |
| PanZ(R69)-cpGFP-GAS-(E70)PanZ Amino Acid | MKLTIIRLEKFSDQDRIDLQKIWPEYSPSSLQVDDNHRIYAARFNERLLAAVRV TLSGTEGALDSLRVRNVYIKADKQKNGIKANFKIRHNIEDGGVQLAYHYQQNTP IGDGPVLLPDNHYLSVQSKLSKDPNEKRDHMVLLEFVTAAGITLGMDELYKGGT GGSMVSKGEELFTGVVPILVELDGDVNGHKFSVSGEGEGDATYGKLTLKFICTT GKLPVPWPTLVTTLTYGVQCFSRYPDHMKQHDFFKSAMPEGYIQERTIFFKDDG NYKTRAEVKFEGDTLVNRIELKGIDFKEDGNILGHKLEYNGASEVTRRRGVGQY LLEEVLRNNPGVSCWWMADAGVEDRGVMTAFMQALGFTAQQGGWEKC | 17 |
| PanZ(R69)-GA-cpYFP-GA-(E70)PanZ Amino Acid | MKLTIIRLEKFSDQDRIDLQKIWPEYSPSSLQVDDNHRIYAARFNERLLAAVRV TLSGTEGALDSLRVRGANVYIKADKQKNGIKANFKIRHNIEDGGVQLAYHYQQN TPIGDGPVLLPDNHYLSYQSVLSKDPNEKRDHMVLLEFVTAAGITLGMDELYKG GTGGSMVSKGEELFTGVVPILVELDGDVNGHKFSVSGEGEGDATYGKLTLKFIC TTGKLPVPWPTLVTTLTYGVQCFSRYPDHMKQHDFFKSAMPEGYIQERTIFFKD DGNYKTRAEVKFEGDTLVNRIELKGIDFKEDGNILGHKLEYNGAEVTRRRGVGQ YLLEEVLRNNPGVSCWWMADAGVEDRGVMTAFMQALGFTAQQGGWEKC | 18 |
| PanZ(R69)-GA-cpBFP-GA-(E70)PanZ Amino Acid | MKLTIIRLEKFSDQDRIDLQKIWPEYSPSSLQVDDNHRIYAARFNERLLAAVRV TLSGTEGALDSLRVRGANVYIKADKQKNGIKANFKIRHNIEDGGVQLAYHYQQN TPIGDGPVLLPDNHYLSVQSKLSKDPNEKRDHMVLLEFVTAAGITLGMDELYKG GTGGSMVSKGEELFTGVVPILVELDGDVNGHKFSVSGEGEGDATYGKLTLKFIC TTGKLPVPWPTLVTTLSHGVQCFSRYPDHMKQHDFFKSAMPEGYIQERTIFFKD DGNYKTRAEVKFEGDTLVNRIELKGIDFKEDGNILGHKLEYNGAEVTRRRGVGQ YLLEEVLRNNPGVSCWWMADAGVEDRGVMTAFMQALGFTAQQGGWEKC | 19 |
| PanZ Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCCGGTTAGGGTA ACCCTCAGCGGTACGGAAGGTGCTCTGGACTCCCTGCGGGTCCGAGAGGTGACA | 20 |

-continued

| | SEQUENCES | |
|---|---|---|
| Name | Amino Acid or Nucleotide Sequence (N→C or 5'→3') | SEQ ID NO |
| | AGACGGAGAGGGGTAGGACAATATTTGCTCGAGGAGGTCCTTAGAAATAACCCC GGAGTAAGTTGCTGGTGGATGGCGGACGCTGGAGTTGAGGATCGCGGAGTCATG ACGGCTTTCATGCAGGCCCTTGGGTTCACCGCACAGCAAGGGGGCTGGGAGAAG TGC | |
| cpGFP Nucleic Acid | AACGTCTATATCAAGGCCGACAAGCAGAAGAACGGCATCAAGGCGAACTTCAAG ATCCGCCACAACATCGAGGACGGCGGCGTGCAGCTCGCCTACCACTACCAGCAG AACACCCCCATCGGCGACGGCCCCGTGCTGCTGCCCGACAACCACTACCTGAGC GTGCAGTCCAAACTTTCGAAAGACCCCAACGAGAAGCGCGATCACATGGTCCTG CTGGAGTTCGTGACCGCCGCCGGGATCACTCTCGGCATGGACGAGCTGTACAAG GGCGGTACCGGAGGGAGCATGGTGAGCAAGGGCGAGGAGCTGTTCACCGGGGTG GTGCCCATCCTGGTCGAGCTGGACGGCGACGTAAACGGCCACAAGTTCAGCGTG TCCGGCGAGGGTGAGGGCGATGCCACCTACGGCAAGCTGACCCTGAAGTTCATC TGCACCACCGGCAAGCTGCCCGTGCCCTGGCCCACCCTCGTGACCACCCTGACC TACGGCGTGCAGTGCTTCAGCCGCTACCCCGACCACATGAAGCAGCACGACTTC TTCAAGTCCGCCATGCCCGAAGGCTACATCCAGGAGCGCACCATCTTCTTCAAG GACGACGGCAACTACAAGACCCGCGCCGAGGTGAAGTTCGAGGGCGACACCCTG GTGAACCGCATCGAGCTGAAGGGCATCGACTTCAAGGAGGACGGCAACATCCTG GGGCACAAGCTGGAGTACAAC | 21 |
| cpYFP Nucleic Acid | AACGTCTATATCAAGGCCGACAAGCAGAAGAACGGCATCAAGGCGAACTTCAAG ATCCGCCACAACATCGAGGACGGCGGCGTGCAGCTCGCCTACCACTACCAGCAG AACACCCCCATCGGCGACGGCCCCGTGCTGCTGCCCGACAACCACTACCTGAGC TATCAGTCCGTACTTTCGAAAGACCCCAACGAGAAGCGCGATCACATGGTCCTG CTGGAGTTCGTGACCGCCGCCGGGATCACTCTCGGCATGGACGAGCTGTACAAG GGCGGTACCGGAGGGAGCATGGTGAGCAAGGGCGAGGAGCTGTTCACCGGGGTG GTGCCCATCCTGGTCGAGCTGGACGGCGACGTAAACGGCCACAAGTTCAGCGTG TCCGGCGAGGGTGAGGGCGATGCCACCTACGGCAAGCTGACCCTGAAGTTCATC TGCACCACCGGCAAGCTGCCCGTGCCCTGGCCCACCCTCGTGACCACCCTGACC TACGGCGTGCAGTGCTTCAGCCGCTACCCCGACCACATGAAGCAGCACGACTTC TTCAAGTCCGCCATGCCCGAAGGCTACATCCAGGAGCGCACCATCTTCTTCAAG GACGACGGCAACTACAAGACCCGCGCCGAGGTGAAGTTCGAGGGCGACACCCTG GTGAACCGCATCGAGCTGAAGGGCATCGACTTCAAGGAGGACGGCAACATCCTG GGGCACAAGCTGGAGTACAAC | 22 |
| cpBFP Nucleic Acid | AACGTCTATATCAAGGCCGACAAGCAGAAGAACGGCATCAAGGCGAACTTCAAG ATCCGCCACAACATCGAGGACGGCGGCGTGCAGCTCGCCTACCACTACCAGCAG AACACCCCCATCGGCGACGGCCCCGTGCTGCTGCCCGACAACCACTACCTGAGC GTGCAGTCCAAACTTTCGAAAGACCCCAACGAGAAGCGCGATCACATGGTCCTG CTGGAGTTCGTGACCGCCGCCGGGATCACTCTCGGCATGGACGAGCTGTACAAG GGCGGTACCGGAGGGAGCATGGTGAGCAAGGGCGAGGAGCTGTTCACCGGGGTG GTGCCCATCCTGGTCGAGCTGGACGGCGACGTAAACGGCCACAAGTTCAGCGTG TCCGGCGAGGGTGAGGGCGATGCCACCTACGGCAAGCTGACCCTGAAGTTCATC TGCACCACCGGCAAGCTGCCCGTGCCCTGGCCCACCCTCGTGACCACCCTGTCC CACGGCGTGCAGTGCTTCAGCCGCTACCCCGACCACATGAAGCAGCACGACTTC TTCAAGTCCGCCATGCCCGAAGGCTACATCCAGGAGCGCACCATCTTCTTCAAG GACGACGGCAACTACAAGACCCGCGCCGAGGTGAAGTTCGAGGGCGACACCCTG GTGAACCGCATCGAGCTGAAGGGCATCGACTTCAAGGAGGACGGCAACATCCTG GGGCACAAGCTGGAGTACAAC | 23 |
| PanZ(R69)-GA-cpGFP-GA-(E70)PanZ ("PANcACe") Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAGGAGCAAAC GTCTATATCAAGGCCGACAAGCAGAAGAACGGCATCAAGGCGAACTTCAAGATC CGCCACAACATCGAGGACGGCGGCGTGCAGCTCGCCTACCACTACCAGCAGATC ACCCCCATCGGCGACGGCCCCGTGCTGCTGCCCGACAACCACTACCTGAGCGTG CAGTCCAAACTTTCGAAAGACCCCAACGAGAAGCGCGATCACATGGTCCTGCTG GAGTTCGTGACCGCCGCCGGGATCACTCTCGGCATGGACGAGCTGTACAAGGGC GGTACCGGAGGGAGCATGGTGAGCAAGGGCGAGGAGCTGTTCACCGGGGTGGTG CCCATCCTGGTCGAGCTGGACGGCGACGTAAACGGCCACAAGTTCAGCGTGTCC GGCGAGGGTGAGGGCGATGCCACCTACGGCAAGCTGACCCTGAAGTTCATCTGC ACCACCGGCAAGCTGCCCGTGCCCTGGCCCACCCTCGTGACCACCCTGACCTAC GGCGTGCAGTGCTTCAGCCGCTACCCCGACCACATGAAGCAGCACGACTTCTTC AAGTCCGCCATGCCCGAAGGCTACATCCAGGAGCGCACCATCTTCTTCAAGGAC GACGGCAACTACAAGACCCGCGCCGAGGTGAAGTTCGAGGGCGACACCCTGGTG AACCGCATCGAGCTGAAGGGCATCGACTTCAAGGAGGACGGCAACATCCTGGGG CACAAGCTGGAGTACAACGGTGCTGAGGTGACAAGACGGAGAGGGGTAGGACAA TATTTGCTCGAGGAGGTCCTTAGAAATAACCCCGGAGTAAGTTGCTGGTGGATG GCGGACGCTGGAGTTGAGGATCGCGGAGTCATGACGGCTTTCATGCAGGCCCTT GGGTTCACCGCACAGCAAGGGGGCTGGGAGAAGTGC | 24 |

-continued

| | SEQUENCES | |
|---|---|---|
| Name | Amino Acid or Nucleotide Sequence (N→C or 5'→3') | SEQ ID NO |
| PanZ(W23)-AS-cpGFP-AS-(P24)PanZ Nucleic Acid | ATGAAGCTGACAATCATTCGCCTGGAGAAATTTTCCGACCAGGATAGAATCGAC CTTCAGAAGATCTGGGCATCTAACGTCTATATCAAGGCCGACAAGCAGAAGAAC GGCATCAAGGCGAACTTCAAGATCCGCCACAACATCGAGGACGGCGGCGTGCAG CTCGCCTACCACTACCAGCAGAACACCCCCATCGGCGACGGCCCCGTGCTGCTG CCCGACAACCACTACCTGAGCGTGCAGTCCAAACTTTCGAAAGACCCCAACGAG AAGCGCGATCACATGGTCCTGCTGGAGTTCGTGACCGCCGCCGGGATCACTCTC GGCATGGACGAGCTGTACAAGGGCGGTACCGGAGGGAGCATGGTGAGCAAGGGC GAGGAGCTGTTCACCGGGGTGGTGCCCATCCTGGTCGAGCTGGACGGCGACGTA AACGGCCACAAGTTCAGCGTGTCCGGCGAGGGTGAGGGCGATGCCACCTACGGC AAGCTGACCCTGAAGTTCATCTGCACCACCGGCAAGCTGCCCGTGCCCTGGCCC ACCCTCGTGACCACCCTGACCTACGGCGTGCAGTGCTTCAGCCGCTACCCCGAC CACATGAAGCAGCACGACTTCTTCAAGTCCGCCATGCCCGAAGGCTACATCCAG GAGCGCACCATCTTCTTCAAGGACGACGGCAACTACAAGACCCGCGCCGAGGTG AAGTTCGAGGGCGACACCCTGGTGAACCGCATCGAGCTGAAGGGCATCGACTTC AAGGAGGACGGCAACATCCTGGGGCACAAGCTGGAGTACAACGCGTCACCCGAA TATTCTCCCAGTAGCCTCCAAGTAGACGACAACCATCGAATCTACGCCGCGAGA TTTAATGAACGACTGCTTGCGGCGGTTAGGGTAACCCTCAGCGGTACGGAAGGT GCTCTGGACTCCCTGCGGGTCCGAGAGGTGACAAGACGGAGAGGGGTAGGACAA TATTTGCTCGAGGAGGTCCTTAGAAATAACCCCGGAGTAAGTTGCTGGTGGATG GCGGACGCTGGAGTTGAGGATCGCGGAGTCATGACGGCTTTCATGCAGGCCCTT GGGTTCACCGCACAGCAAGGGGGCTGGGAGAAGTGC | 25 |
| PanZ(V71)-AS-cpGFP-AS-(T72)PanZ Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAGAGGTGGCA TCTAACGTCTATATCAAGGCCGACAAGCAGAAGAACGGCATCAAGGCGAACTTC AAGATCCGCCACAACATCGAGGACGGCGGCGTGCAGCTCGCCTACCACTACCAG CAGAACACCCCCATCGGCGACGGCCCCGTGCTGCTGCCCGACAACCACTACCTG AGCGTGCAGTCCAAACTTTCGAAAGACCCCAACGAGAAGCGCGATCACATGGTC CTGCTGGAGTTCGTGACCGCCGCCGGGATCACTCTCGGCATGGACGAGCTGTAC AAGGGCGGTACCGGAGGGAGCATGGTGAGCAAGGGCGAGGAGCTGTTCACCGGG GTGGTGCCCATCCTGGTCGAGCTGGACGGCGACGTAAACGGCCACAAGTTCAGC GTGTCCGGCGAGGGTGAGGGCGATGCCACCTACGGCAAGCTGACCCTGAAGTTC ATCTGCACCACCGGCAAGCTGCCCGTGCCCTGGCCCACCCTCGTGACCACCCTG ACCTACGGCGTGCAGTGCTTCAGCCGCTACCCCGACCACATGAAGCAGCACGAC TTCTTCAAGTCCGCCATGCCCGAAGGCTACATCCAGGAGCGCACCATCTTCTTC AAGGACGACGGCAACTACAAGACCCGCGCCGAGGTGAAGTTCGAGGGCGACACC CTGGTGAACCGCATCGAGCTGAAGGGCATCGACTTCAAGGAGGACGGCAACATC CTGGGGCACAAGCTGGAGTACAACGCGTCAACAAGACGGAGAGGGGTAGGACAA TATTTGCTCGAGGAGGTCCTTAGAAATAACCCCGGAGTAAGTTGCTGGTGGATG GCGGACGCTGGAGTTGAGGATCGCGGAGTCATGACGGCTTTCATGCAGGCCCTT GGGTTCACCGCACAGCAAGGGGGCTGGGAGAAGTGC | 26 |
| PanZ(R69)-AS-cpGFP-AS-(E70)PanZ Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAGCATCTAAC GTCTATATCAAGGCCGACAAGCAGAAGAACGGCATCAAGGCGAACTTCAAGATC CGCCACAACATCGAGGACGGCGGCGTGCAGCTCGCCTACCACTACCAGCAGAAC ACCCCCATCGGCGACGGCCCCGTGCTGCTGCCCGACAACCACTACCTGAGCGTG CAGTCCAAACTTTCGAAAGACCCCAACGAGAAGCGCGATCACATGGTCCTGCTG GAGTTCGTGACCGCCGCCGGGATCACTCTCGGCATGGACGAGCTGTACAAGGGC GGTACCGGAGGGAGCATGGTGAGCAAGGGCGAGGAGCTGTTCACCGGGGTGGTG CCCATCCTGGTCGAGCTGGACGGCGACGTAAACGGCCACAAGTTCAGCGTGTCC GGCGAGGGTGAGGGCGATGCCACCTACGGCAAGCTGACCCTGAAGTTCATCTGC ACCACCGGCAAGCTGCCCGTGCCCTGGCCCACCCTCGTGACCACCCTGACCTAC GGCGTGCAGTGCTTCAGCCGCTACCCCGACCACATGAAGCAGCACGACTTCTTC AAGTCCGCCATGCCCGAAGGCTACATCCAGGAGCGCACCATCTTCTTCAAGGAC GACGGCAACTACAAGACCCGCGCCGAGGTGAAGTTCGAGGGCGACACCCTGGTG AACCGCATCGAGCTGAAGGGCATCGACTTCAAGGAGGACGGCAACATCCTGGGG CACAAGCTGGAGTACAACGCGTCAGAGGTGACAAGACGGAGAGGGGTAGGACAA TATTTGCTCGAGGAGGTCCTTAGAAATAACCCCGGAGTAAGTTGCTGGTGGATG GCGGACGCTGGAGTTGAGGATCGCGGAGTCATGACGGCTTTCATGCAGGCCCTT GGGTTCACCGCACAGCAAGGGGGCTGGGAGAAGTGC | 27 |
| PanZ(D99)-AS-cpGFP-AS-(A100)PanZ Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAGAGGTGACA AGACGGAGAGGGGTAGGACAATATTTGCTCGAGGAGGTCCTTAGAAATAACCCC GGAGTAAGTTGCTGGTGGATGGCGGACGCATCTAACGTCTATATCAAGGCCGAC AAGCAGAAGAACGGCATCAAGGCGAACTTCAAGATCCGCCACAACATCGAGGAC | 28 |

-continued

| | SEQUENCES | |
|---|---|---|
| Name | Amino Acid or Nucleotide Sequence (N→C or 5'→3') | SEQ ID NO |

GGCGGCGTGCAGCTCGCCTACCACTACCAGCAGAACACCCCCATCGGCGACGGC
CCCGTGCTGCTGCCCGACAACCACTACCTGAGCGTGCAGTCCAAACTTTCGAAA
GACCCCAACGAGAAGCGCGATCACATGGTCCTGCTGGAGTTCGTGACCGCCGCC
GGGATCACTCTCGGCATGGACGAGCTGTACAAGGGCGGTACCGGAGGGGAGCATG
GTGAGCAAGGGCGAGGAGCTGTTCACCGGGGTGGTGCCCATCCTGGTCGAGCTG
GACGGCGACGTAAACGGCCACAAGTTCAGCGTGTCCGGCGAGGGTGAGGGCGAT
GCCACCTACGGCAAGCTGACCCTGAAGTTCATCTGCACCACCGGCAAGCTGCCC
GTGCCCTGGCCCACCCTCGTGACCACCCTGACCTACGGCGTGCAGTGCTTCAGC
CGCTACCCCGACCACATGAAGCAGCACGACTTCTTCAAGTCCGCCATGCCCGAA
GGCTACATCCAGGAGCGCACCATCTTCTTCAAGGACGACGGCAACTACAAGACC
CGCGCCGAGGTGAAGTTCGAGGGCGACACCCTGGTGAACCGCATCGAGCTGAAG
GGCATCGACTTCAAGGAGGACGGCAACATCCTGGGGCACAAGCTGGAGTACAAC
GCGTCAGCTGGAGTTGAGGATCGCGGAGTCATGACGGCTTTCATGCAGGCCCTT
GGGTTCACCGCACAGCAAGGGGGCTGGGAGAAGTGC

| PanZ(D104)-AS-cpGFP-AS-(R105)PanZ Nucleic Acid | ATGAAGCTGACAATCATTCGCCTGGAGAAATTTTCCGACCAGGATAGAATCGAC<br>CTTCAGAAGATCTGGCCCGAATATTCTCCCAGTAGCCTCCAAGTAGACGACAAC<br>CATCGAATCTACGCCGCGAGATTTAATGAACGACTGCTTGCGGCGGTTAGGGTA<br>ACCCTCAGCGGTACGGAAGGTGCTCTGGACTCCCTGCGGGTCCGAGAGGTGACA<br>AGACGGAGAGGGGTAGGACAATATTTGCTCGAGGAGGTCCTTAGAAATAACCCC<br>GGAGTAAGTTGCTGGTGGATGGCGGACGCTGGAGTTGAGGATGCATCTAACGTC<br>TATATCAAGGCCGACAAGCAGAAGAACGGCATCAAGGCGAACTTCAAGATCCGC<br>CACAACATCGAGGACGGCGGCGTGCAGCTCGCCTACCACTACCAGCAGAACACC<br>CCCATCGGCGACGGCCCCGTGCTGCTGCCCGACAACCACTACCTGAGCGTGCAG<br>TCCAAACTTTCGAAAGACCCCAACGAGAAGCGCGATCACATGGTCCTGCTGGAG<br>TTCGTGACCGCCGCCGGGATCACTCTCGGCATGGACGAGCTGTACAAGGGCGGT<br>ACCGGAGGGGAGCATGGTGAGCAAGGGCGAGGAGCTGTTCACCGGGGTGGTGCCC<br>ATCCTGGTCGAGCTGGACGGCGACGTAAACGGCCACAAGTTCAGCGTGTCCGGC<br>GAGGGTGAGGGCGATGCCACCTACGGCAAGCTGACCCTGAAGTTCATCTGCACC<br>ACCGGCAAGCTGCCCGTGCCCTGGCCCACCCTCGTGACCACCCTGACCTACGGC<br>GTGCAGTGCTTCAGCCGCTACCCCGACCACATGAAGCAGCACGACTTCTTCAAG<br>TCCGCCATGCCCGAAGGCTACATCCAGGAGCGCACCATCTTCTTCAAGGACGAC<br>GGCAACTACAAGACCCGCGCCGAGGTGAAGTTCGAGGGCGACACCCTGGTGAAC<br>CGCATCGAGCTGAAGGGCATCGACTTCAAGGAGGACGGCAACATCCTGGGGCAC<br>AAGCTGGAGTACAACGCGTCACGCGGAGTCATGACGGCTTTCATGCAGGCCCTT<br>GGGTTCACCGCACAGCAAGGGGGCTGGGAGAAGTGC | 29 |

| PanZ(G116)-AS-cpGFP-AS-(F117)PanZ Nucleic Acid | ATGAAGCTGACAATCATTCGCCTGGAGAAATTTTCCGACCAGGATAGAATCGAC<br>CTTCAGAAGATCTGGCCCGAATATTCTCCCAGTAGCCTCCAAGTAGACGACAAC<br>CATCGAATCTACGCCGCGAGATTTAATGAACGACTGCTTGCGGCGGTTAGGGTA<br>ACCCTCAGCGGTACGGAAGGTGCTCTGGACTCCCTGCGGGTCCGAGAGGTGACA<br>AGACGGAGAGGGGTAGGACAATATTTGCTCGAGGAGGTCCTTAGAAATAACCCC<br>GGAGTAAGTTGCTGGTGGATGGCGGACGCTGGAGTTGAGGATCGCGGAGTCATG<br>ACGGCTTTCATGCAGGCCCTTGGGGCATCTAACGTCTATATCAAGGCCGACAAG<br>CAGAAGAACGGCATCAAGGCGAACTTCAAGATCCGCCACAACATCGAGGACGGC<br>GGCGTGCAGCTCGCCTACCACTACCAGCAGAACACCCCCATCGGCGACGGCCCC<br>GTGCTGCTGCCCGACAACCACTACCTGAGCGTGCAGTCCAAACTTTCGAAAGAC<br>CCCAACGAGAAGCGCGATCACATGGTCCTGCTGGAGTTCGTGACCGCCGCCGGG<br>ATCACTCTCGGCATGGACGAGCTGTACAAGGGCGGTACCGGAGGGGAGCATGGTG<br>AGCAAGGGCGAGGAGCTGTTCACCGGGGTGGTGCCCATCCTGGTCGAGCTGGAC<br>GGCGACGTAAACGGCCACAAGTTCAGCGTGTCCGGCGAGGGTGAGGGCGATGCC<br>ACCTACGGCAAGCTGACCCTGAAGTTCATCTGCACCACCGGCAAGCTGCCCGTG<br>CCCTGGCCCACCCTCGTGACCACCCTGACCTACGGCGTGCAGTGCTTCAGCCGC<br>TACCCCGACCACATGAAGCAGCACGACTTCTTCAAGTCCGCCATGCCCGAAGGC<br>TACATCCAGGAGCGCACCATCTTCTTCAAGGACGACGGCAACTACAAGACCCGC<br>GCCGAGGTGAAGTTCGAGGGCGACACCCTGGTGAACCGCATCGAGCTGAAGGGC<br>ATCGACTTCAAGGAGGACGGCAACATCCTGGGGCACAAGCTGGAGTACAACGCG<br>TCATTCACCGCACAGCAAGGGGGCTGGGAGAAGTGC | 30 |

| PanZ(R69)-GAS-cpGFP-G-(E70)PanZ Nucleic Acid | ATGAAGCTGACAATCATTCGCCTGGAGAAATTTTCCGACCAGGATAGAATCGAC<br>CTTCAGAAGATCTGGCCCGAATATTCTCCCAGTAGCCTCCAAGTAGACGACAAC<br>CATCGAATCTACGCCGCGAGATTTAATGAACGACTGCTTGCGGCGGTTAGGGTA<br>ACCCTCAGCGGTACGGAAGGTGCTCTGGACTCCCTGCGGGTCCGAGGAGCAAGT<br>AACGTCTATATCAAGGCCGACAAGCAGAAGAACGGCATCAAGGCGAACTTCAAG<br>ATCCGCCACAACATCGAGGACGGCGGCGTGCAGCTCGCCTACCACTACCAGCAG<br>AACACCCCCATCGGCGACGGCCCCGTGCTGCTGCCCGACAACCACTACCTGAGC<br>GTGCAGTCCAAACTTTCGAAAGACCCCAACGAGAAGCGCGATCACATGGTCCTG<br>CTGGAGTTCGTGACCGCCGCCGGGATCACTCTCGGCATGGACGAGCTGTACAAG<br>GGCGGTACCGGAGGGAGCATGGTGAGCAAGGGCGAGGAGCTGTTCACCGGGGTG<br>GTGCCCATCCTGGTCGAGCTGGACGGCGACGTAAACGGCCACAAGTTCAGCGTG<br>TCCGGCGAGGGTGAGGGCGATGCCACCTACGGCAAGCTGACCCTGAAGTTCATC<br>TGCACCACCGGCAAGCTGCCCGTGCCCTGGCCCACCCTCGTGACCACCCTGACC<br>TACGGCGTGCAGTGCTTCAGCCGCTACCCCGACCACATGAAGCAGCACGACTTC<br>TTCAAGTCCGCCATGCCCGAAGGCTACATCCAGGAGCGCACCATCTTCTTCAAG | 31 |

-continued

| | SEQUENCES | |
|---|---|---|
| Name | Amino Acid or Nucleotide Sequence (N→C or 5'→3') | SEQ ID NO |

|   |   |   |
|---|---|---|
| | GACGACGGCAACTACAAGACCCGCGCCGAGGTGAAGTTCGAGGGCGACACCCTG<br>GTGAACCGCATCGAGCTGAAGGGCATCGACTTCAAGGAGGACGGCAACATCCTG<br>GGGCACAAGCTGGAGTACAACGGTGAGGTGACAAGACGGAGAGGGGTAGGACAA<br>TATTTGCTCGAGGAGGTCCTTAGAAATAACCCCGGAGTAAGTTGCTGGTGGATG<br>GCGGACGCTGGAGTTGAGGATCGCGGAGTCATGACGGCTTTCATGCAGGCCCTT<br>GGGTTCACCGCACAGCAAGGGGGCTGGGAGAAGTGC | |
| PanZ(R69)-GAS-<br>cpGFP-<br>(E70)PanZ<br>Nucleic Acid | ATGAAGCTGACAATCATTCGCCTGGAGAAATTTTCCGACCAGGATAGAATCGAC<br>CTTCAGAAGATCTGGCCCGAATATTCTCCCAGTAGCCTCCAAGTAGACGACAAC<br>CATCGAATCTACGCCGCGAGATTTAATGAACGACTGCTTGCGGCGGTTAGGGTA<br>ACCCTCAGCGGTACGGAAGGTGCTCTGGACTCCCTGCGGGTCCGAGGAGCAAGT<br>AACGTCTATATCAAGGCCGACAAGCAGAAGAACGGCATCAAGGCGAACTTCAAG<br>ATCCGCCACAACATCGAGGACGGCGGCGTGCAGCTCGCCTACCACTACCAGCAG<br>AACACCCCCATCGGCGACGGCCCCGTGCTGCTGCCCGACAACCACTACCTGAGC<br>GTGCAGTCCAAACTTTCGAAAGACCCCAACGAGAAGCGCGATCACATGGTCCTG<br>CTGGAGTTCGTGACCGCCGCCGGGATCACTCTCGGCATGGACGAGCTGTACAAG<br>GGCGGTACCGGAGGGAGCATGGTGAGCAAGGGCGAGGAGCTGTTCACCGGGGTG<br>GTGCCCATCCTGGTCGAGCTGGACGGCGACGTAAACGGCCACAAGTTCAGCGTG<br>TCCGGCGAGGGTGAGGGCGATGCCACCTACGGCAAGCTGACCCTGAAGTTCATC<br>TGCACCACCGGCAAGCTGCCCGTGCCCTGGCCCACCCTCGTGACCACCCTGACC<br>TACGGCGTGCAGTGCTTCAGCCGCTACCCCGACCACATGAAGCAGCACGACTTC<br>TTCAAGTCCGCCATGCCCGAAGGCTACATCCAGGAGCGCACCATCTTCTTCAAG<br>GACGACGGCAACTACAAGACCCGCGCCGAGGTGAAGTTCGAGGGCGACACCCTG<br>GTGAACCGCATCGAGCTGAAGGGCATCGACTTCAAGGAGGACGGCAACATCCTG<br>GGGCACAAGCTGGAGTACAACGAGGTGACAAGACGGAGAGGGGTAGGACAATAT<br>TTGCTCGAGGAGGTCCTTAGAAATAACCCCGGAGTAAGTTGCTGGTGGATGGCG<br>GACGCTGGAGTTGAGGATCGCGGAGTCATGACGGCTTTCATGCAGGCCCTTGGG<br>TTCACCGCACAGCAAGGGGGCTGGGAGAAGTGC | 32 |
| PanZ(R69)-GA-<br>cpGFP-<br>(E70)PanZ<br>Nucleic Acid | ATGAAGCTGACAATCATTCGCCTGGAGAAATTTTCCGACCAGGATAGAATCGAC<br>CTTCAGAAGATCTGGCCCGAATATTCTCCCAGTAGCCTCCAAGTAGACGACAAC<br>CATCGAATCTACGCCGCGAGATTTAATGAACGACTGCTTGCGGCGGTTAGGGTA<br>ACCCTCAGCGGTACGGAAGGTGCTCTGGACTCCCTGCGGGTCCGAGGAGCAAAC<br>GTCTATATCAAGGCCGACAAGCAGAAGAACGGCATCAAGGCGAACTTCAAGATC<br>CGCCACAACATCGAGGACGGCGGCGTGCAGCTCGCCTACCACTACCAGCAGAAC<br>ACCCCCATCGGCGACGGCCCCGTGCTGCTGCCCGACAACCACTACCTGAGCGTG<br>CAGTCCAAACTTTCGAAAGACCCCAACGAGAAGCGCGATCACATGGTCCTGCTG<br>GAGTTCGTGACCGCCGCCGGGATCACTCTCGGCATGGACGAGCTGTACAAGGGC<br>GGTACCGGAGGGAGCATGGTGAGCAAGGGCGAGGAGCTGTTCACCGGGGTGGTG<br>CCCATCCTGGTCGAGCTGGACGGCGACGTAAACGGCCACAAGTTCAGCGTGTCC<br>GGCGAGGGTGAGGGCGATGCCACCTACGGCAAGCTGACCCTGAAGTTCATCTGC<br>ACCACCGGCAAGCTGCCCGTGCCCTGGCCCACCCTCGTGACCACCCTGACCTAC<br>GGCGTGCAGTGCTTCAGCCGCTACCCCGACCACATGAAGCAGCACGACTTCTTC<br>AAGTCCGCCATGCCCGAAGGCTACATCCAGGAGCGCACCATCTTCTTCAAGGAC<br>GACGGCAACTACAAGACCCGCGCCGAGGTGAAGTTCGAGGGCGACACCCTGGTG<br>AACCGCATCGAGCTGAAGGGCATCGACTTCAAGGAGGACGGCAACATCCTGGGG<br>CACAAGCTGGAGTACAACGAGGTGACAAGACGGAGAGGGGTAGGACAATATTTG<br>CTCGAGGAGGTCCTTAGAAATAACCCCGGAGTAAGTTGCTGGTGGATGGCGGAC<br>GCTGGAGTTGAGGATCGCGGAGTCATGACGGCTTTCATGCAGGCCCTTGGGTTC<br>ACCGCACAGCAAGGGGGCTGGGAGAAGTGC | 33 |
| PanZ(R69)-<br>cpGFP-<br>(E70)PanZ<br>Nucleic Acid | ATGAAGCTGACAATCATTCGCCTGGAGAAATTTTCCGACCAGGATAGAATCGAC<br>CTTCAGAAGATCTGGCCCGAATATTCTCCCAGTAGCCTCCAAGTAGACGACAAC<br>CATCGAATCTACGCCGCGAGATTTAATGAACGACTGCTTGCGGCGGTTAGGGTA<br>ACCCTCAGCGGTACGGAAGGTGCTCTGGACTCCCTGCGGGTCCGAAACGTCTAT<br>ATCAAGGCCGACAAGCAGAAGAACGGCATCAAGGCGAACTTCAAGATCCGCCAC<br>AACATCGAGGACGGCGGCGTGCAGCTCGCCTACCACTACCAGCAGAACACCCCC<br>ATCGGCGACGGCCCCGTGCTGCTGCCCGACAACCACTACCTGAGCGTGCAGTCC<br>AAACTTTCGAAAGACCCCAACGAGAAGCGCGATCACATGGTCCTGCTGGAGTTC<br>GTGACCGCCGCCGGGATCACTCTCGGCATGGACGAGCTGTACAAGGGCGGTACC<br>GGAGGGAGCATGGTGAGCAAGGGCGAGGAGCTGTTCACCGGGGTGGTGCCCATC<br>CTGGTCGAGCTGGACGGCGACGTAAACGGCCACAAGTTCAGCGTGTCCGGCGAG<br>GGTGAGGGCGATGCCACCTACGGCAAGCTGACCCTGAAGTTCATCTGCACCACC<br>GGCAAGCTGCCCGTGCCCTGGCCCACCCTCGTGACCACCCTGACCTACGGCGTG<br>CAGTGCTTCAGCCGCTACCCCGACCACATGAAGCAGCACGACTTCTTCAAGTCC<br>GCCATGCCCGAAGGCTACATCCAGGAGCGCACCATCTTCTTCAAGGACGACGGC<br>AACTACAAGACCCGCGCCGAGGTGAAGTTCGAGGGCGACACCCTGGTGAACCGC<br>ATCGAGCTGAAGGGCATCGACTTCAAGGAGGACGGCAACATCCTGGGGCACAAG<br>CTGGAGTACAACGAGGTGACAAGACGGAGAGGGGTAGGACAATATTTGCTCGAG<br>GAGGTCCTTAGAAATAACCCCGGAGTAAGTTGCTGGTGGATGGCGGACGCTGGA<br>GTTGAGGATCGCGGAGTCATGACGGCTTTCATGCAGGCCCTTGGGTTCACCGCA<br>CAGCAAGGGGGCTGGGAGAAGTGC | 34 |

-continued

| | SEQUENCES | |
|---|---|---|
| Name | Amino Acid or Nucleotide Sequence (N→C or 5'→3') | SEQ ID NO |
| PanZ(69)-G-cpGFP-GAS-(E70)PanZ Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAGGGAAACGTC TATATCAAGGCCGACAAGCAGAAGAACGGCATCAAGGCGAACTTCAAGATCCGC CACAACATCGAGGACGGCGGCGTGCAGCTCGCCTACCACTACCAGCAGAACACC CCCATCGGCGACGGCCCCGTGCTGCTGCCCGACAACCACTACCTGAGCGTGCAG TCCAAACTTTCGAAAGACCCCAACGAGAAGCGCGATCACATGGTCCTGCTGGAG TTCGTGACCGCCGCCGGGATCACTCTCGGCATGGACGAGCTGTACAAGGGCGGT ACCGGAGGGAGCATGGTGAGCAAGGGCGAGGAGCTGTTCACCGGGGTGGTGCCC ATCCTGGTCGAGCTGGACGGCGACGTAAACGGCCACAAGTTCAGCGTGTCCGGC GAGGGTGAGGGCGATGCCACCTACGGCAAGCTGACCCTGAAGTTCATCTGCACC ACCGGCAAGCTGCCCGTGCCCTGGCCCACCCTCGTGACCACCCTGACCTACGGC GTGCAGTGCTTCAGCCGCTACCCCGACCACATGAAGCAGCACGACTTCTTCAAG TCCGCCATGCCCGAAGGCTACATCCAGGAGCGCACCATCTTCTTCAAGGACGAC GGCAACTACAAGACCCGCGCCGAGGTGAAGTTCGAGGGCGACACCCTGGTGAAC CGCATCGAGCTGAAGGGCATCGACTTCAAGGAGGACGGCAACATCCTGGGGCAC AAGCTGGAGTACAACGGTGCTTCAGAGGTGACAAGACGGAGAGGGGTAGGACAA TATTTGCTCGAGGAGGTCCTTAGAAATAACCCCGGAGTAAGTTGCTGGTGGATG GCGGACGCTGGAGTTGAGGATCGCGGAGTCATGACGGCTTTCATGCAGGCCCTT GGGTTCACCGCACAGCAAGGGGGCTGGGAGAAGTGC | 35 |
| PanZ(R69)-cpGFP-GAS-(E70)PanZ Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAAACGTCTAT ATCAAGGCCGACAAGCAGAAGAACGGCATCAAGGCGAACTTCAAGATCCGCCAC AACATCGAGGACGGCGGCGTGCAGCTCGCCTACCACTACCAGCAGAACACCCCC ATCGGCGACGGCCCCGTGCTGCTGCCCGACAACCACTACCTGAGCGTGCAGTCC AAACTTTCGAAAGACCCCAACGAGAAGCGCGATCACATGGTCCTGCTGGAGTTC GTGACCGCCGCCGGGATCACTCTCGGCATGGACGAGCTGTACAAGGGCGGTACC GGAGGGAGCATGGTGAGCAAGGGCGAGGAGCTGTTCACCGGGGTGGTGCCCATC CTGGTCGAGCTGGACGGCGACGTAAACGGCCACAAGTTCAGCGTGTCCGGCGAG GGTGAGGGCGATGCCACCTACGGCAAGCTGACCCTGAAGTTCATCTGCACCACC GGCAAGCTGCCCGTGCCCTGGCCCACCCTCGTGACCACCCTGACCTACGGCGTG CAGTGCTTCAGCCGCTACCCCGACCACATGAAGCAGCACGACTTCTTCAAGTCC GCCATGCCCGAAGGCTACATCCAGGAGCGCACCATCTTCTTCAAGGACGACGGC AACTACAAGACCCGCGCCGAGGTGAAGTTCGAGGGCGACACCCTGGTGAACCGC ATCGAGCTGAAGGGCATCGACTTCAAGGAGGACGGCAACATCCTGGGGCACAAG CTGGAGTACAACGGTGCTTCAGAGGTGACAAGACGGAGAGGGGTAGGACAATAT TTGCTCGAGGAGGTCCTTAGAAATAACCCCGGAGTAAGTTGCTGGTGGATGGCG GACGCTGGAGTTGAGGATCGCGGAGTCATGACGGCTTTCATGCAGGCCCTTGGG TTCACCGCACAGCAAGGGGGCTGGGAGAAGTGC | 36 |
| PanZ(R69)-GA-cpYFP-GA-(E70)PanZ Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAGGAGCAAAC GTCTATATCAAGGCCGACAAGCAGAAGAACGGCATCAAGGCGAACTTCAAGATC CGCCACAACATCGAGGACGGCGGCGTGCAGCTCGCCTACCACTACCAGCAGAAC ACCCCCATCGGCGACGGCCCCGTGCTGCTGCCCGACAACCACTACCTGAGCTAT CAGTCCGTACTTTCGAAAGACCCCAACGAGAAGCGCGATCACATGGTCCTGCTG GAGTTCGTGACCGCCGCCGGGATCACTCTCGGCATGGACGAGCTGTACAAGGGC GGTACCGGAGGGAGCATGGTGAGCAAGGGCGAGGAGCTGTTCACCGGGGTGGTG CCCATCCTGGTCGAGCTGGACGGCGACGTAAACGGCCACAAGTTCAGCGTGTCC GGCGAGGGTGAGGGCGATGCCACCTACGGCAAGCTGACCCTGAAGTTCATCTGC ACCACCGGCAAGCTGCCCGTGCCCTGGCCCACCCTCGTGACCACCCTGACCTAC GGCGTGCAGTGCTTCAGCCGCTACCCCGACCACATGAAGCAGCACGACTTCTTC AAGTCCGCCATGCCCGAAGGCTACATCCAGGAGCGCACCATCTTCTTCAAGGAC GACGGCAACTACAAGACCCGCGCCGAGGTGAAGTTCGAGGGCGACACCCTGGTG AACCGCATCGAGCTGAAGGGCATCGACTTCAAGGAGGACGGCAACATCCTGGGG CACAAGCTGGAGTACAACGGTGCTGAGGTGACAAGACGGAGAGGGGTAGGACAA TATTTGCTCGAGGAGGTCCTTAGAAATAACCCCGGAGTAAGTTGCTGGTGGATG GCGGACGCTGGAGTTGAGGATCGCGGAGTCATGACGGCTTTCATGCAGGCCCTT GGGTTCACCGCACAGCAAGGGGGCTGGGAGAAGTGC | 37 |
| PanZ(R69)-GA-cpBFP-GA-(E70)PanZ Nucleic Acid | ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAGGAGCAAAC GTCTATATCAAGGCCGACAAGCAGAAGAACGGCATCAAGGCGAACTTCAAGATC CGCCACAACATCGAGGACGGCGGCGTGCAGCTCGCCTACCACTACCAGCAGAAC ACCCCCATCGGCGACGGCCCCGTGCTGCTGCCCGACAACCACTACCTGAGCGTG | 38 |

| | SEQUENCES | |
|---|---|---|
| Name | Amino Acid or Nucleotide Sequence (N→C or 5'→3') | SEQ ID NO |
| | CAGTCCAAACTTTCGAAAGACCCCAACGAGAAGCGCGATCACATGGTCCTGCTG GAGTTCGTGACCGCCGCCGGGATCACTCTCGGCATGGACGAGCTGTACAAGGGC GGTACCGGAGGGAGCATGGTGAGCAAGGGCGAGGAGCTGTTCACCGGGGTGGTG CCCATCCTGGTCGAGCTGGACGGCGACGTAAACGGCCACAAGTTCAGCGTGTCC GGCGAGGGTGAGGGCGATGCCACCTACGGCAAGCTGACCCTGAAGTTCATCTGC ACCACCGGCAAGCTGCCCGTGCCCTGGCCCACCCTCGTGACCACCCTGTCCCAC GGCGTGCAGTGCTTCAGCCGCTACCCCGACCACATGAAGCAGCACGACTTCTTC AAGTCCGCCATGCCCGAAGGCTACATCCAGGAGCGCACCATCTTCTTCAAGGAC GACGGCAACTACAAGACCCGCGCCGAGGTGAAGTTCGAGGGCGACACCCTGGTG AACCGCATCGAGCTGAAGGGCATCGACTTCAAGGAGGACGGCAACATCCTGGGG CACAAGCTGGAGTACAACGGTGCTGAGGTGACAAGACGGAGAGGGGTAGGACAA TATTTGCTCGAGGAGGTCCTTAGAAATAACCCCGGAGTAAGTTGCTGGTGGATG GCGGACGCTGGAGTTGAGGATCGCGGAGTCATGACGGCTTTCATGCAGGCCCTT GGGTTCACCGCACAGCAAGGGGGCTGGGAGAAGTGC | |
| 6xHistidine-TEV-PanZ Amino Acid | MHHHHHHENLYFQSMKLTIIRLEKFSDQDRIDLQKIWPEYSPSSLQVDDNHRIY AARFNERLLAAVRVTLSGTEGALDSLRVREVTRRRGVGQYLLEEVLRNNPGVSC WWMADAGVEDRGVMTAFMQALGFTAQQGGWEKC | 39 |
| 6xHistidine-TEV-cpGFP Amino Acid | MHHHHHHENLYFQSNVYIKADKQKNGIKANFKIRHNIEDGGVQLAYHYQQNTPI GDGPVLLPDNHYLSVQSKLSKDPNEKRDHMVLLEFVTAAGITLGMDELYKGGTG GSMVSKGEELFTGVVPILVELDGDVNGHKFSVSGEGEGDATYGKLTLKFICTTG KLPVPWPTLVTTLTYGVQCFSRYPDHMKQHDFFKSAMPEGYIQERTIFFKDDGN YKTRAEVKFEGDTLVNRIELKGIDFKEDGNILGHKLEYN | 40 |
| 6xHistidine-TEV-cpYFP Amino Acid | MHHHHHHENLYFQSNVYIKADKQKNGIKANFKIRHNIEDGGVQLAYHYQQNTPI GDGPVLLPDNHYLSYQSVLSKDPNEKRDHMVLLEFVTAAGITLGMDELYKGGTG GSMVSKGEELFTGVVPILVELDGDVNGHKFSVSGEGEGDATYGKLTLKFICTTG KLPVPWPTLVTTLTYGVQCFSRYPDHMKQHDFFKSAMPEGYIQERTIFFKDDGN YKTRAEVKFEGDTLVNRIELKGIDFKEDGNILGHKLEYN | 41 |
| 6xHistidine-TEV-cpBFP Amino Acid | MHHHHHHENLYFQSNVYIKADKQKNGIKANFKIRHNIEDGGVQLAYHYQQNTPI GDGPVLLPDNHYLSVQSKLSKDPNEKRDHMVLLEFVTAAGITLGMDELYKGGTG GSMVSKGEELFTGVVPILVELDGDVNGHKFSVSGEGEGDATYGKLTLKFICTTG KLPVPWPTLVTTLSHGVQCFSRYPDHMKQHDFFKSAMPEGYIQERTIFFKDDGN YKTRAEVKFEGDTLVNRIELKGIDFKEDGNILGHKLEYN | 42 |
| 6xHistidine-TEV-PanZ(R69)-GA-cpGFP-GA-(E70)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVRGANVYIKADKQKNGIKANFKIRHNI EDGGVQLAYHYQQNTPIGDGPVLLPDNHYLSVQSKLSKDPNEKRDHMVLLEFVT AAGITLGMDELYKGGTGGSMVSKGEELFTGVVPILVELDGDVNGHKFSVSGEGE GDATYGKLTLKFICTTGKLPVPWPTLVTTLTYGVQCFSRYPDHMKQHDFFKSAM PEGYIQERTIFFKDDGNYKTRAEVKFEGDTLVNRIELKGIDFKEDGNILGHKLE YNGAEVTRRRGVGQYLLEEVLRNNPGVSCWWMADAGVEDRGVMTAFMQALGFTA QQGGWEKC | 43 |
| 6xHistidine-TEV-PanZ(W23)-AS-cpGFP-AS-(P24)PanZ Amino Acid | MHHHHHHENLYFQSMKLTIIRLEKFSDQDRIDLQKIWASNVYIKADKQKNGIKA NFKIRHNIEDGGVQLAYHYQQNTPIGDGPVLLPDNHYLSVQSKLSKDPNEKRDH MVLLEFVTAAGITLGMDELYKGGTGGSMVSKGEELFTGVVPILVELDGDVNGHK FSVSGEGEGDATYGKLTLKFICTTGKLPVPWPTLVTTLTYGVQCFSRYPDHMKQ HDFFKSAMPEGYIQERTIFFKDDGNYKTRAEVKFEGDTLVNRIELKGIDFKEDG NILGHKLEYNASPEYSPSSLQVDDNHRIYAARFNERLLAAVRVTLSGTEGALDS LRVREVTRRRGVGQYLLEEVLRNNPGVSCWWMADAGVEDRGVMTAFMQALGFTA QQGGWEKC | 44 |
| 6xHistidine-TEV-PanZ(V71)-AS-cpGFP-AS-(T72)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVREVASNVYIKADKQKNGIKANFKIRH NIEDGGVQLAYHYQQNTPIGDGPVLLPDNHYLSVQSKLSKDPNEKRDHMVLLEF VTAAGITLGMDELYKGGTGGSMVSKGEELFTGVVPILVELDGDVNGHKFSVSGE GEGDATYGKLTLKFICTTGKLPVPWPTLVTTLTYGVQCFSRYPDHMKQHDFFKS AMPEGYIQERTIFFKDDGNYKTRAEVKFEGDTLVNRIELKGIDFKEDGNILGHK LEYNASTRRRGVGQYLLEEVLRNNPGVSCWWMADAGVEDRGVMTAFMQALGFTA QQGGWEKC | 45 |
| 6xHistidine-TEV-PanZ(R69)-AS-cpGFP-AS-(E70)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVRASNVYIKADKQKNGIKANFKIRHNI EDGGVQLAYHYQQNTPIGDGPVLLPDNHYLSVQSKLSKDPNEKRDHMVLLEFVT AAGITLGMDELYKGGTGGSMVSKGEELFTGVVPILVELDGDVNGHKFSVSGEGE GDATYGKLTLKFICTTGKLPVPWPTLVTTLTYGVQCFSRYPDHMKQHDFFKSAM PEGYIQERTIFFKDDGNYKTRAEVKFEGDTLVNRIELKGIDFKEDGNILGHKLE YNASEVTRRRGVGQYLLEEVLRNNPGVSCWWMADAGVEDRGVMTAFMQALGFTA QQGGWEKC | 46 |

| Name | Amino Acid or Nucleotide Sequence (N→C or 5'→3') | SEQ ID NO |
|------|--------------------------------------------------|-----------|
| 6xHistidine-TEV-PanZ(D99)-AS-cpGFP-AS-(A100)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVREVTRRRGVGQYLLEEVLRNNPGVSC WWMADASNVYIKADQKNGIKANFKIRHNIEDGGVQLAYHYQQNTPIGDGPVLL PDNHYLSVQSKLSKDPNEKRDHMVLLEFVTAAGITLGMDELYKGGTGGSMVSKG EELFTGVVPILVELDGDVNGHKFSVSGEGEGDATYGKLTLKFICTTGKLPVPWP TLVTTLTYGVQCFSRYPDHMKQHDFFKSAMPEGYIQERTIFFKDDGNYKTRAEV KFEGDTLVNRIELKGIDFKEDGNILGHKLEYNASAGVEDRGVMTAFMQALGFTA QQGGWEKC | 47 |
| 6xHistidine-TEV-PanZ(D104)-AS-cpGFP-AS-(R105)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVREVTRRRGVGQYLLEEVLRNNPGVSC WWMADAGVEDASNVYIKADQKNGIKANFKIRHNIEDGGVQLAYHYQQNTPIGD GPVLLPDNHYLSVQSKLSKDPNEKRDHMVLLEFVTAAGITLGMDELYKGGTGGS MVSKGEELFTGVVPILVELDGDVNGHKESVSGEGEGDATYGKLTLKFICTTGKL PVPWPTLVTTLTYGVQCFSRYPDHMKQHDFFKSAMPEGYIQERTIFFKDDGNYK TRAEVKFEGDTLVNRIELKGIDFKEDGNILGHKLEYNASRGVMTAFMQALGFTA QQGGWEKC | 48 |
| 6xHistidine-TEV-PanZ(G116)-AS-cpGFP-AS-(F117)PanZ Amino Acid | MHHHHHHENLYFQSMKLTIIRLEKESDQDRIDLQKIWPEYSPSSLQVDDNHRIY AARFNERLLAAVRVTLSGTEGALDSLRVREVTRRRGVGQYLLEEVLRNNPGVSC WWMADAGVEDRGVMTAFMQALGASNVYIKADQKNGIKANFKIRHNIEDGGVQL AYHYQQNTPIGDGPVLLPDNHYLSVQSKLSKDPNEKRDHMVLLEFVTAAGITLG MDELYKGGTGGSMVSKGEELFTGVVPILVELDGDVNGHKFSVSGEGEGDATYGK LTLKFICTTGKLPVPWPTLVTTLTYGVQCFSRYPDHMKQHDFFKSAMPEGYIQE RTIFFKDDGNYKTRAEVKFEGDTLVNRIELKGIDFKEDGNILGHKLEYNASFTA QQGGWEKC | 49 |
| 6xHistidine-TEV-PanZ(R69)-GAS-cpGFP-G-(E70)PanZ Amino Acid | KLTIIRLEKFSDQDRIDLQKIWPEYSPSSLQVDDNHRIYAARFNERLLAAVRVT LSGTEGALDSLRVRGASNVYIKADQKNGIKANFKIRHNIEDGGVQLAYHYQQN TPIGDGPVLLPDNHYLSVQSKLSKDPNEKRDHMVLLEFVTAAGITLGMDELYKG GTGGSMVSKGEELFTGVVPILVELDGDVNGHKFSVSGEGEGDATYGKLTLKFIC TTGKLPVPWPTLVTTLTYGVQCFSRYPDHMKQHDFFKSAMPEGYIQERTIFFKD DGNYKTRAEVKFEGDTLVNRIELKGIDFKEDGNILGHKLEYNGEVTRRRGVGQY LLEEVLRNNPGVSCWWMADAGVEDRGVMTAFMQALGFTAQQGGWEKC | 50 |
| 6xHistidine-TEV-PanZ(R69)-GAS-cpGFP-(E70)PanZ Amino Acid | MHHHHHHENLYFQSMKLTIIRLEKESDQDRIDLQKIWPEYSPSSLQVDDNHRIY AARFNERLLAAVRVTLSGTEGALDSLRVRGASNVYIKADQKNGIKANFKIRHN IEDGGVQLAYHYQQNTPIGDGPVLLPDNHYLSVQSKLSKDPNEKRDHMVLLEFV TAAGITLGMDELYKGGTGGSMVSKGEELFTGVVPILVELDGDVNGHKFSVSGEG EGDATYGKLTLKFICTTGKLPVPWPTLVTTLTYGVQCESRYPDHMKQHDFFKSA MPEGYIQERTIFFKDDGNYKTRAEVKFEGDTLVNRIELKGIDFKEDGNILGHKL EYNEVTRRRGVGQYLLEEVLRNNPGVSCWWMADAGVEDRGVMTAFMQALGFTAQ QGGWEKC | 51 |
| 6xHistidine-TEV-PanZ(R69)-GA-cpGFP-(E70)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVRGANVYIKADQKNGIKANFKIRHNI EDGGVQLAYHYQQNTPIGDGPVLLPDNHYLSVQSKLSKDPNEKRDHMVLLEFVT AAGITLGMDELYKGGTGGSMVSKGEELFTGVVPILVELDGDVNGHKFSVSGEGE GDATYGKLTLKFICTTGKLPVPWPTLVTTLTYGVQCFSRYPDHMKQHDFFKSAM PEGYIQERTIFFKDDGNYKTRAEVKFEGDTLVNRIELKGIDFKEDGNILGHKLE YNEVTRRRGVGQYLLEEVLRNNPGVSCWWMADAGVEDRGVMTAFMQALGFTAQQ GGWEKC | 52 |
| 6xHistidine-TEV-PanZ(R69)-cpGFP-(E70)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVRNVYIKADKQKNGIKANFKIRHNIED GGVQLAYHYQQNTPIGDGPVLLPDNHYLSVQSKLSKDPNEKRDHMVLLEFVTAA GITLGMDELYKGGTGGSMVSKGEELFTGVVPILVELDGDVNGHKFSVSGEGEGD ATYGKLTLKFICTTGKLPVPWPTLVTTLTYGVQCFSRYPDHMKQHDFFKSAMPE GYIQERTIFFKDDGNYKTRAEVKFEGDTLVNRIELKGIDFKEDGNILGHKLEYN EVTRRRGVGQYLLEEVLRNNPGVSCWWMADAGVEDRGVMTAFMQALGFTAQQGG WEKC | 53 |
| 6xHistidine-TEV-PanZ(69)-G-cpGFP-GAS-(E70)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVRGNVYIKADQKNGIKANFKIRHNIE DGGVQLAYHYQQNTPIGDGPVLLPDNHYLSVQSKLSKDPNEKRDHMVLLEFVTA AGITLGMDELYKGGTGGSMVSKGEELFTGVVPILVELDGDVNGHKFSVSGEGEG DATYGKLTLKFICTTGKLPVPWPTLVTTLTYGVQCFSRYPDHMKQHDFFKSAMP EGYIQERTIFFKDDGNYKTRAEVKFEGDTLVNRIELKGIDFKEDGNILGHKLEY NGASEVTRRRGVGQYLLEEVLRNNPGVSCWWMADAGVEDRGVMTAFMQALGFTA QQGGWEKC | 54 |
| 6xHistidine-TEV-PanZ(R69)- | MHHHHHHENLYFQSMKLTIIRLEKFSDQDRIDLQKIWPEYSPSSLQVDDNHRIY AARFNERLLAAVRVTLSGTEGALDSLRVRNVYIKADKQKNGIKANFKIRHNIED | 55 |

| | SEQUENCES | |
|---|---|---|
| Name | Amino Acid or Nucleotide Sequence (N→C or 5'→3') | SEQ ID NO |
| cpGFP-GAS-(E70)PanZ Amino Acid | GGVQLAYHYQQNTPIGDGPVLLPDNHYLSVQSKLSKDPNEKRDHMVLLEFVTAA GITLGMDELYKGGTGGSMVSKGEELFTGVVPILVELDGDVNGHKFSVSGEGEGD ATYGKLTLKFICTTGKLPVPWPTLVTTLTYGVQCFSRYPDHMKQHDFFKSAMPE GYIQERTIFFKDDGNYKTRAEVKFEGDTLVNRIELKGIDFKEDGNILGHKLEYN GASEVTRRRGVGQYLLEEVLRNNPGVSCWWMADAGVEDRGVMTAFMQALGFTAQ QGGWEKC | |
| 6xHistidine-TEV-PanZ(R69)-GA-cpYFP-GA-(E70)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVRGANVYIKADKQKNGIKANFKIRHNI EDGGVQLAYHYQQNTPIGDGPVLLPDNHYLSYQSVLSKDPNEKRDHMVLLEFVT AAGITLGMDELYKGGTGGSMVSKGEELFTGVVPILVELDGDVNGHKFSVSGEGE GDATYGKLTLKFICTTGKLPVPWPTLVTTLTYGVQCFSRYPDHMKQHDFFKSAM PEGYIQERTIFFKDDGNYKTRAEVKFEGDTLVNRIELKGIDFKEDGNILGHKLE YNGAEVTRRRGVGQYLLEEVLRNNPGVSCWWMADAGVEDRGVMTAFMQALGFTA QQGGWEKC | 56 |
| 6xHistidine-TEV-PanZ(R69)-GA-cpBFP-GA-(E70)PanZ Amino Acid | MHHHHHHENLYFQSMKLTIIRLEKFSDQDRIDLQKIWPEYSPSSLQVDDNHRIY AARFNERLLAAVRVTLSGTEGALDSLRVRGANVYIKADKQKNGIKANFKIRHNI EDGGVQLAYHYQQNTPIGDGPVLLPDNHYLSVQSKLSKDPNEKRDHMVLLEFVT AAGITLGMDELYKGGTGGSMVSKGEELFTGVVPILVELDGDVNGHKESVSGEGE GDATYGKLTLKFICTTGKLPVPWPTLVTTLSHGVQCFSRYPDHMKQHDFFKSAM PEGYIQERTIFFKDDGNYKTRAEVKFEGDTLVNRIELKGIDFKEDGNILGHKLE YNGAEVTRRRGVGQYLLEEVLRNNPGVSCWWMADAGVEDRGVMTAFMQALGFTA QQGGWEKC | 57 |
| 6xHistidine-TEV-PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGAGGTGACAAGACGGAGAGGG GTAGGACAATATTTGCTCGAGGAGGTCCTTAGAAATAACCCCGGAGTAAGTTGC TGGTGGATGGCGGACGCTGGAGTTGAGGATCGCGGAGTCATGACGGCTTTCATG CAGGCCCTTGGGTTCACCGCACAGCAAGGGGCTGGGAGAAGTGC | 58 |
| 6xHistidine-TEV-cpGFP Nucleic Acid | ATGCATCACCATCACCATCACGAAAACCTGTACTTCCAAAGCAACGTCTATATC AAGGCCGACAAGCAGAAGAACGGCATCAAGGCGAACTTCAAGATCCGCCACAAC ATCGAGGACGGCGGCGTGCAGCTCGCCTACCACTACCAGCAGAACACCCCCATC GGCGACGGCCCCGTGCTGCTGCCCGACAACCACTACCTGAGCGTGCAGTCCAAA CTTTCGAAAGACCCCAACGAGAAGCGCGATCACATGGTCCTGCTGGAGTTCGTG ACCGCCGCCGGGATCACTCTCGGCATGGACGAGCTGTACAAGGGCGGTACCGGA GGGAGCATGGTGAGCAAGGGCGAGGAGCTGTTCACCGGGGTGGTGCCCATCCTG GTCGAGCTGGACGGCGACGTAAACGGCCACAAGTTCAGCGTGTCCGGCGAGGGT GAGGGCGATGCCACCTACGGCAAGCTGACCCTGAAGTTCATCTGCACCACCGGC AAGCTGCCCGTGCCCTGGCCCACCCTCGTGACCACCCTGACCTACGGCGTGCAG TGCTTCAGCCGCTACCCCGACCACATGAAGCAGCACGACTTCTTCAAGTCCGCC ATGCCCGAAGGCTACATCCAGGACGCGCACCATCTTCTTCAAGGACGACGGCAAC TACAAGACCCGCGCCGAGGTGAAGTTCGAGGGCGACACCCTGGTGAACCGCATC GAGCTGAAGGGCATCGACTTCAAGGAGGACGGCAACATCCTGGGGCACAAGCTG GAGTACAAC | 59 |
| 6xHistidine-TEV-cpYFP Nucleic Acid | ATGCATCACCATCACCATCACGAAAACCTGTACTTCCAAAGCAACGTCTATATC AAGGCCGACAAGCAGAAGAACGGCATCAAGGCGAACTTCAAGATCCGCCACAAC ATCGAGGACGGCGGCGTGCAGCTCGCCTACCACTACCAGCAGAACACCCCCATC GGCGACGGCCCCGTGCTGCTGCCCGACAACCACTACCTGAGCTATCAGTCCGTA CTTTCGAAAGACCCCAACGAGAAGCGCGATCACATGGTCCTGCTGGAGTTCGTG ACCGCCGCCGGGATCACTCTCGGCATGGACGAGCTGTACAAGGGCGGTACCGGA GGGAGCATGGTGAGCAAGGGCGAGGAGCTGTTCACCGGGGTGGTGCCCATCCTG GTCGAGCTGGACGGCGACGTAAACGGCCACAAGTTCAGCGTGTCCGGCGAGGGT GAGGGCGATGCCACCTACGGCAAGCTGACCCTGAAGTTCATCTGCACCACCGGC AAGCTGCCCGTGCCCTGGCCCACCCTCGTGACCACCCTGACCTACGGCGTGCAG TGCTTCAGCCGCTACCCCGACCACATGAAGCAGCACGACTTCTTCAAGTCCGCC ATGCCCGAAGGCTACATCCAGGAGCGCACCATCTTCTTCAAGGACGACGGCAAC TACAAGACCCGCGCCGAGGTGAAGTTCGAGGGCGACACCCTGGTGAACCGCATC GAGCTGAAGGGCATCGACTTCAAGGAGGACGGCAACATCCTGGGGCACAAGCTG GAGTACAAC | 60 |
| 6xHistidine-TEV-cpBFP Nucleic Acid | ATGCATCACCATCACCATCACGAAAACCTGTACTTCCAAAGCAACGTCTATATC AAGGCCGACAAGCAGAAGAACGGCATCAAGGCGAACTTCAAGATCCGCCACAAC ATCGAGGACGGCGGCGTGCAGCTCGCCTACCACTACCAGCAGAACACCCCCATC GGCGACGGCCCCGTGCTGCTGCCCGACAACCACTACCTGAGCGTGCAGTCCAAA CTTTCGAAAGACCCCAACGAGAAGCGCGATCACATGGTCCTGCTGGAGTTCGTG ACCGCCGCCGGGATCACTCTCGGCATGGACGAGCTGTACAAGGGCGGTACCGGA GGGAGCATGGTGAGCAAGGGCGAGGAGCTGTTCACCGGGGTGGTGCCCATCCTG GTCGAGCTGGACGGCGACGTAAACGGCCACAAGTTCAGCGTGTCCGGCGAGGGT | 61 |

-continued

| SEQUENCES | | |
|---|---|---|
| Name | Amino Acid or Nucleotide Sequence (N→C or 5'→3') | SEQ ID NO |
| | GAGGGCGATGCCACCTACGGCAAGCTGACCCTGAAGTTCATCTGCACCACCGGC AAGCTGCCCGTGCCCTGGCCCACCCTCGTGACCACCCTGTCCCACGGCGTGCAG TGCTTCAGCCGCTACCCCGACCACATGAAGCAGCACGACTTCTTCAAGTCCGCC ATGCCCGAAGGCTACATCCAGGAGCGCACCATCTTCTTCAAGGACGACGGCAAC TACAAGACCCGCGCCGAGGTGAAGTTCGAGGGCGACACCCTGGTGAACCGCATC GAGCTGAAGGGCATCGACTTCAAGGAGGACGGCAACATCCTGGGGCACAAGCTG GAGTACAAC | |
| 6xHistidine-TEV-PanZ(R69)-GA-cpGFP-GA-(E70)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGGAGCAAACGTCTATATCAAG GCCGACAAGCAGAAGAACGGCATCAAGGCGAACTTCAAGATCCGCCACAACATC GAGGACGGCGGCGTGCAGCTCGCCTACCACTACCAGCAGAACACCCCCATCGGC GACGGCCCCGTGCTGCTGCCCGACAACCACTACCTGAGCGTGCAGTCCAAACTT TCGAAAGACCCCAACGAGAAGCGCGATCACATGGTCCTGCTGGAGTTCGTGACC GCCGCCGGGATCACTCTCGGCATGGACGAGCTGTACAAGGGCGGTACCGGAGGG AGCATGGTGAGCAAGGGCGAGGAGCTGTTCACCGGGGTGGTGCCCATCCTGGTC GAGCTGGACGGCGACGTAAACGGCCACAAGTTCAGCGTGTCCGGCGAGGGTGAG GGCGATGCCACCTACGGCAAGCTGACCCTGAAGTTCATCTGCACCACCGGCAAG CTGCCCGTGCCCTGGCCCACCCTCGTGACCACCCTGACCTACGGCGTGCAGTGC TTCAGCCGCTACCCCGACCACATGAAGCAGCACGACTTCTTCAAGTCCGCCATG CCCGAAGGCTACATCCAGGAGCGCACCATCTTCTTCAAGGACGACGGCAACTAC AAGACCCGCGCCGAGGTGAAGTTCGAGGGCGACACCCTGGTGAACCGCATCGAG CTGAAGGGCATCGACTTCAAGGAGGACGGCAACATCCTGGGGCACAAGCTGGAG TACAACGGTGCTGAGGTGACAAGACGGAGAGGGGTAGGACAATATTTGCTCGAG GAGGTCCTTAGAAATAACCCCGGAGTAAGTTGCTGGTGGATGGCGGACGCTGGA GTTGAGGATCGCGGAGTCATGACGGCTTTCATGCAGGCCCTTGGGTTCACCGCA CAGCAAGGGGGCTGGGAGAAGTGC | 62 |
| 6xHistidine-TEV-PanZ(W23)-AS-cpGFP-AS-(P24)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGGCATCTAACGTCTATATCAAGGCCGACAAGCAGAAGAACGGCATCAAGGCG AACTTCAAGATCCGCCACAACATCGAGGACGGCGGCGTGCAGCTCGCCTACCAC TACCAGCAGAACACCCCCATCGGCGACGGCCCCGTGCTGCTGCCCGACAACCAC TACCTGAGCGTGCAGTCCAAACTTTCGAAAGACCCCAACGAGAAGCGCGATCAC ATGGTCCTGCTGGAGTTCGTGACCGCCGCCGGGATCACTCTCGGCATGGACGAG CTGTACAAGGGCGGTACCGGAGGGAGCATGGTGAGCAAGGGCGAGGAGCTGTTC ACCGGGGTGGTGCCCATCCTGGTCGAGCTGGACGGCGACGTAAACGGCCACAAG TTCAGCGTGTCCGGCGAGGGTGAGGGCGATGCCACCTACGGCAAGCTGACCCTG AAGTTCATCTGCACCACCGGCAAGCTGCCCGTGCCCTGGCCCACCCTCGTGACC ACCCTGACCTACGGCGTGCAGTGCTTCAGCCGCTACCCCGACCACATGAAGCAG CACGACTTCTTCAAGTCCGCCATGCCCGAAGGCTACATCCAGGAGCGCACCATC TTCTTCAAGGACGACGGCAACTACAAGACCCGCGCCGAGGTGAAGTTCGAGGGC GACACCCTGGTGAACCGCATCGAGCTGAAGGGCATCGACTTCAAGGAGGACGGC AACATCCTGGGGCACAAGCTGGAGTACAACGCGTCACCCGAATATTCTCCCAGT AGCCTCCAAGTAGACGACAACCATCGAATCTACGCCGCGAGATTTAATGAACGA CTGCTTGCGGCGGTTAGGGTAACCCTCAGCGGTACGGAAGGTGCTCTGGACTCC CTGCGGGTCCGAGAGGTGACAAGACGGAGAGGGGTAGGACAATATTTGCTCGAG GAGGTCCTTAGAAATAACCCCGGAGTAAGTTGCTGGTGGATGGCGGACGCTGGA GTTGAGGATCGCGGAGTCATGACGGCTTTCATGCAGGCCCTTGGGTTCACCGCA CAGCAAGGGGGCTGGGAGAAGTGC | 63 |
| 6xHistidine-TEV-PanZ(V71)-AS-cpGFP-AS-(T72)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGAGGTGGCATCTAACGTCTAT ATCAAGGCCGACAAGCAGAAGAACGGCATCAAGGCGAACTTCAAGATCCGCCAC AACATCGAGGACGGCGGCGTGCAGCTCGCCTACCACTACCAGCAGAACACCCCC ATCGGCGACGGCCCCGTGCTGCTGCCCGACAACCACTACCTGAGCGTGCAGTCC AAACTTTCGAAAGACCCCAACGAGAAGCGCGATCACATGGTCCTGCTGGAGTTC GTGACCGCCGCCGGGATCACTCTCGGCATGGACGAGCTGTACAAGGGCGGTACC GGAGGGAGCATGGTGAGCAAGGGCGAGGAGCTGTTCACCGGGGTGGTGCCCATC CTGGTCGAGCTGGACGGCGACGTAAACGGCCACAAGTTCAGCGTGTCCGGCGAG GGTGAGGGCGATGCCACCTACGGCAAGCTGACCCTGAAGTTCATCTGCACCACC GGCAAGCTGCCCGTGCCCTGGCCCACCCTCGTGACCACCCTGACCTACGGCGTG CAGTGCTTCAGCCGCTACCCCGACCACATGAAGCAGCACGACTTCTTCAAGTCC GCCATGCCCGAAGGCTACATCCAGGAGCGCACCATCTTCTTCAAGGACGACGGC AACTACAAGACCCGCGCCGAGGTGAAGTTCGAGGGCGACACCCTGGTGAACCGC ATCGAGCTGAAGGGCATCGACTTCAAGGAGGACGGCAACATCCTGGGGCACAAG CTGGAGTACAACGCGTCAACAAGACGGAGAGGGGTAGGACAATATTTGCTCGAG GAGGTCCTTAGAAATAACCCCGGAGTAAGTTGCTGGTGGATGGCGGACGCTGGA | 64 |

-continued

| | SEQUENCES | |
|---|---|---|
| Name | Amino Acid or Nucleotide Sequence (N→C or 5'→3') | SEQ ID NO |
| | GTTGAGGATCGCGGAGTCATGACGGCTTTCATGCAGGCCCTTGGGTTCACCGCA CAGCAAGGGGGCTGGGAGAAGTGC | |
| 6xHistidine-TEV-PanZ(R69)-AS-cpGFP-AS-(E70)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGCATCTAACGTCTATATCAAG GCCGACAAGCAGAAGAACGGCATCAAGGCGAACTTCAAGATCCGCCACAACATC GAGGACGGCGGCGTGCAGCTCGCCTACCACTACCAGCAGAACACCCCCATCGGC GACGGCCCCGTGCTGCTGCCCGACAACCACTACCTGAGCGTGCAGTCCAAACTT TCGAAAGACCCCAACGAGAAGCGCGATCACATGGTCCTGCTGGAGTTCGTGACC GCCGCCGGGATCACTCTCGGCATGGACGAGCTGTACAAGGGCGGTACCGGAGGG AGCATGGTGAGCAAGGGCGAGGAGCTGTTCACCGGGGTGGTGCCCATCCTGGTC GAGCTGGACGGCGACGTAAACGGCCACAAGTTCAGCGTGTCCGGCGAGGGTGAG GGCGATGCCACCTACGGCAAGCTGACCCTGAAGTTCATCTGCACCACCGGCAAG CTGCCCGTGCCCTGGCCCACCCTCGTGACCACCCTGACCTACGGCGTGCAGTGC TTCAGCCGCTACCCCGACCACATGAAGCAGCACGACTTCTTCAAGTCCGCCATG CCCGAAGGCTACATCCAGGAGCGCACCATCTTCTTCAAGGACGACGGCAACTAC AAGACCCGCGCCGAGGTGAAGTTCGAGGGCGACACCCTGGTGAACCGCATCGAG CTGAAGGGCATCGACTTCAAGGAGGACGGCAACATCCTGGGGCACAAGCTGGAA TACAACGCGTCAGAGGTGACAAGACGGAGAGGGGTAGGACAATATTTGCTCGAG GAGGTCCTTAGAAATAACCCCGGAGTAAGTTGCTGGTGGATGGCGGACGCTGGA GTTGAGGATCGCGGAGTCATGACGGCTTTCATGCAGGCCCTTGGGTTCACCGCA CAGCAAGGGGGCTGGGAGAAGTGC | 65 |
| 6xHistidine-TEV-PanZ(D99)-AS-cpGFP-AS-(A100)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGAGGTGACAAGACGGAGAGGG GTAGGACAATATTTGCTCGAGGAGGTCCTTAGAAATAACCCCGGAGTAAGTTGC TGGTGGATGGCGGACGCATCTAACGTCTATATCAAGGCCGACAAGCAGAAGAAC GGCATCAAGGCGAACTTCAAGATCCGCCACAACATCGAGGACGGCGGCGTGCAG CTCGCCTACCACTACCAGCAGAACACCCCCATCGGCGACGGCCCCGTGCTGCTG CCCGACAACCACTACCTGAGCGTGCAGTCCAAACTTTCGAAAGACCCCAACGAG AAGCGCGATCACATGGTCCTGCTGGAGTTCGTGACCGCCGCCGGGATCACTCTC GGCATGGACGAGCTGTACAAGGGCGGTACCGGAGGGAGCATGGTGAGCAAGGGC GAGGAGCTGTTCACCGGGGTGGTGCCCATCCTGGTCGAGCTGGACGGCGACGTA AACGGCCACAAGTTCAGCGTGTCCGGCGAGGGTGAGGGCGATGCCACCTACGGC AAGCTGACCCTGAAGTTCATCTGCACCACCGGCAAGCTGCCCGTGCCCTGGCCC ACCCTCGTGACCACCCTGACCTACGGCGTGCAGTGCTTCAGCCGCTACCCCGAC CACATGAAGCAGCACGACTTCTTCAAGTCCGCCATGCCCGAAGGCTACATCCAG GAGCGCACCATCTTCTTCAAGGACGACGGCAACTACAAGACCCGCGCCGAGGTG AAGTTCGAGGGCGACACCCTGGTGAACCGCATCGAGCTGAAGGGCATCGACTTC AAGGAGGACGGCAACATCCTGGGGCACAAGCTGGAGTACAACGCGTCAGCTGGA GTTGAGGATCGCGGAGTCATGACGGCTTTCATGCAGGCCCTTGGGTTCACCGCA CAGCAAGGGGGCTGGGAGAAGTGC | 66 |
| 6xHistidine-TEV-PanZ(D104)-AS-cpGFP-AS-(R105)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGAGGTGACAAGACGGAGAGGG GTAGGACAATATTTGCTCGAGGAGGTCCTTAGAAATAACCCCGGAGTAAGTTGC TGGTGGATGGCGGACGCTGGAGTTGAGGATGCATCTAACGTCTATATCAAGGCC GACAAGCAGAAGAACGGCATCAAGGCGAACTTCAAGATCCGCCACAACATCGAG GACGGCGGCGTGCAGCTCGCCTACCACTACCAGCAGAACACCCCCATCGGCGAC GGCCCCGTGCTGCTGCCCGACAACCACTACCTGAGCGTGCAGTCCAAACTTTCG AAAGACCCCAACGAGAAGCGCGATCACATGGTCCTGCTGGAGTTCGTGACCGCC GCCGGGATCACTCTCGGCATGGACGAGCTGTACAAGGGCGGTACCGGAGGGAGC ATGGTGAGCAAGGGCGAGGAGCTGTTCACCGGGGTGGTGCCCATCCTGGTCGAG CTGGACGGCGACGTAAACGGCCACAAGTTCAGCGTGTCCGGCGAGGGTGAGGGC GATGCCACCTACGGCAAGCTGACCCTGAAGTTCATCTGCACCACCGGCAAGCTG CCCGTGCCCTGGCCCACCCTCGTGACCACCCTGACCTACGGCGTGCAGTGCTTC AGCCGCTACCCCGACCACATGAAGCAGCACGACTTCTTCAAGTCCGCCATGCCC GAAGGCTACATCCAGGAGCGCACCATCTTCTTCAAGGACGACGGCAACTACAAG ACCCGCGCCGAGGTGAAGTTCGAGGGCGACACCCTGGTGAACCGCATCGAGCTG AAGGGCATCGACTTCAAGGAGGACGGCAACATCCTGGGGCACAAGCTGGAGTAC AACGCGTCACGCGAGTCATGACGGCTTTCATGCAGGCCCTTGGGTTCACCGCA CAGCAAGGGGGCTGGGAGAAGTGC | 67 |
| 6xHistidine-TEV-PanZ(G116)-AS- | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC | 68 |

-continued

| | SEQUENCES | |
|---|---|---|
| Name | Amino Acid or Nucleotide Sequence (N→C or 5'→3') | SEQ ID NO |
| cpGFP-AS-(F117)PanZ Nucleic Acid | TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGAGGTGACAAGACGGAGAGGG GTAGGACAATATTTGCTCGAGGAGGTCCTTAGAAATAACCCCGGAGTAAGTTGC TGGTGGATGGCGGACGCTGGAGTTGAGGATCGCGGAGTCATGACGGCTTTCATG CAGGCCCTTGGGGCATCTAACGTCTATATCAAGGCCGACAAGCAGAAGAACGGC ATCAAGGCGAACTTCAAGATCCGCCACAACATCGAGGACGGCGGCGTGCAGCTC GCCTACCACTACCAGCAGAACACCCCCATCGGCGACGGCCCCGTGCTGCTGCCC GACAACCACTACCTGAGCGTGCAGTCCAAACTTTCGAAAGACCCCAACGAGAAG CGCGATCACATGGTCCTGCTGGAGTTCGTGACCGCCGCCGGGATCACTCTCGGC ATGGACGAGCTGTACAAGGGCGGTACCGGAGGGAGCATGGTGAGCAAGGGCGAG GAGCTGTTCACCGGGGTGGTGCCCATCCTGGTCGAGCTGGACGGCGACGTAAAC GGCCACAAGTTCAGCGTGTCCGGCGAGGGTGAGGGCGATGCCACCTACGGCAAG CTGACCCTGAAGTTCATCTGCACCACCGGCAAGCTGCCCGTGCCCTGGCCCACC CTCGTGACCACCCTGACCTACGGCGTGCAGTGCTTCAGCCGCTACCCCGACCAC ATGAAGCAGCACGACTTCTTCAAGTCCGCCATGCCCGAAGGCTACATCCAGGAG CGCACCATCTTCTTCAAGGACGACGGCAACTACAAGACCCGCGCCGAGGTGAAG TTCGAGGGCGACACCCTGGTGAACCGCATCGAGCTGAAGGGCATCGACTTCAAG GAGGACGGCAACATCCTGGGGCACAAGCTGGAGTACAACGCGTCATTCACCGCA CAGCAAGGGGGCTGGGAGAAGTGC | |
| 6xHistidine-TEV-PanZ(R69)-GAS-cpGFP-G-(E70)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGGAGCAAGTAACGTCTATATC AAGGCCGACAAGCAGAAGAACGGCATCAAGGCGAACTTCAAGATCCGCCACAAC ATCGAGGACGGCGGCGTGCAGCTCGCCTACCACTACCAGCAGAACACCCCCATC GGCGACGGCCCCGTGCTGCTGCCCGACAACCACTACCTGAGCGTGCAGTCCAAA CTTTCGAAAGACCCCAACGAGAAGCGCGATCACATGGTCCTGCTGGAGTTCGTG ACCGCCGCCGGGATCACTCTCGGCATGGACGAGCTGTACAAGGGCGGTACCGGA GGGAGCATGGTGAGCAAGGGCGAGGAGCTGTTCACCGGGGTGGTGCCCATCCTG GTCGAGCTGGACGGCGACGTAAACGGCCACAAGTTCAGCGTGTCCGGCGAGGGT GAGGGCGATGCCACCTACGGCAAGCTGACCCTGAAGTTCATCTGCACCACCGGC AAGCTGCCCGTGCCCTGGCCCACCCTCGTGACCACCCTGACCTACGGCGTGCAG TGCTTCAGCCGCTACCCCGACCACATGAAGCAGCACGACTTCTTCAAGTCCGCC ATGCCCGAAGGCTACATCCAGGAGCGCACCATCTTCTTCAAGGACGACGGCAAC TACAAGACCCGCGCCGAGGTGAAGTTCGAGGGCGACACCCTGGTGAACCGCATC GAGCTGAAGGGCATCGACTTCAAGGAGGACGGCAACATCCTGGGGCACAAGCTG GAGTACAACGGTGAGGTGACAAGACGGAGAGGGGTAGGACAATATTTGCTCGAG GAGGTCCTTAGAAATAACCCCGGAGTAAGTTGCTGGTGGATGGCGGACGCTGGA GTTGAGGATCGCGGAGTCATGACGGCTTTCATGCAGGCCCTTGGGTTCACCGCA CAGCAAGGGGGCTGGGAGAAGTGC | 69 |
| 6xHistidine-TEV-PanZ(R69)-GAS-cpGFP-(E70)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGGAGCAAGTAACGTCTATATC AAGGCCGACAAGCAGAAGAACGGCATCAAGGCGAACTTCAAGATCCGCCACAAC ATCGAGGACGGCGGCGTGCAGCTCGCCTACCACTACCAGCAGAACACCCCCATC GGCGACGGCCCCGTGCTGCTGCCCGACAACCACTACCTGAGCGTGCAGTCCAAA CTTTCGAAAGACCCCAACGAGAAGCGCGATCACATGGTCCTGCTGGAGTTCGTG ACCGCCGCCGGGATCACTCTCGGCATGGACGAGCTGTACAAGGGCGGTACCGGA GGGAGCATGGTGAGCAAGGGCGAGGAGCTGTTCACCGGGGTGGTGCCCATCCTG GTCGAGCTGGACGGCGACGTAAACGGCCACAAGTTCAGCGTGTCCGGCGAGGGT GAGGGCGATGCCACCTACGGCAAGCTGACCCTGAAGTTCATCTGCACCACCGGC AAGCTGCCCGTGCCCTGGCCCACCCTCGTGACCACCCTGACCTACGGCGTGCAG TGCTTCAGCCGCTACCCCGACCACATGAAGCAGCACGACTTCTTCAAGTCCGCC ATGCCCGAAGGCTACATCCAGGAGCGCACCATCTTCTTCAAGGACGACGGCAAC TACAAGACCCGCGCCGAGGTGAAGTTCGAGGGCGACACCCTGGTGAACCGCATC GAGCTGAAGGGCATCGACTTCAAGGAGGACGGCAACATCCTGGGGCACAAGCTG GAGTACAACGGTGAGGTGACAAGACGGAGAGGGGTAGGACAATATTTGCTCGAG GTCCTTAGAAATAACCCCGGAGTAAGTTGCTGGTGGATGGCGGACGCTGGAGTT GAGGATCGCGGAGTCATGACGGCTTTCATGCAGGCCCTTGGGTTCACCGCACAG CAAGGGGGCTGGGAGAAGTGC | 70 |
| 6xHistidine-TEV-PanZ(R69)-GA-cpGFP-(E70)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGGAGCAAACGTCTATATCAAG GCCGACAAGCAGAAGAACGGCATCAAGGCGAACTTCAAGATCCGCCACAACATC GAGGACGGCGGCGTGCAGCTCGCCTACCACTACCAGCAGAACACCCCCATCGGC | 71 |

-continued

| | SEQUENCES | |
|---|---|---|
| Name | Amino Acid or Nucleotide Sequence (N→C or 5'→3') | SEQ ID NO |

| | | |
|---|---|---|
| | GACGGCCCCGTGCTGCTGCCCGACAACCACTACCTGAGCGTGCAGTCCAAACTT<br>TCGAAAGACCCCAACGAGAAGCGCGATCACATGGTCCTGCTGGAGTTCGTGACC<br>GCCGCCGGGATCACTCTCGGCATGGACGAGCTGTACAAGGGCGGTACCGGAGGG<br>AGCATGGTGAGCAAGGGCGAGGAGCTGTTCACCGGGGTGGTGCCCATCCTGGTC<br>GAGCTGGACGGCGACGTAAACGGCCACAAGTTCAGCGTGTCCGGCGAGGGTGAG<br>GGCGATGCCACCTACGGCAAGCTGACCCTGAAGTTCATCTGCACCACCGGCAAG<br>CTGCCCGTGCCCTGGCCCACCCTCGTGACCACCCTGACCTACGGCGTGCAGTGC<br>TTCAGCCGCTACCCCGACCACATGAAGCAGCACGACTTCTTCAAGTCCGCCATG<br>CCCGAAGGCTACATCCAGGAGCGCACCATCTTCTTCAAGGACGACGGCAACTAC<br>AAGACCCGCGCCGAGGTGAAGTTCGAGGGCGACACCCTGGTGAACCGCATCGAG<br>CTGAAGGGCATCGACTTCAAGGAGGACGGCAACATCCTGGGGCACAAGCTGGAG<br>TACAACGAGGTGACAAGACGGAGAGGGGTAGGACAATATTTGCTCGAGGAGGTC<br>CTTAGAAATAACCCCGGAGTAAGTTGCTGGTGGATGGCGGACGCTGGAGTTGAG<br>GATCGCGGAGTCATGACGGCTTTCATGCAGGCCCTTGGGTTCACCGCACAGCAA<br>GGGGGCTGGGAGAAGTGC | |
| 6xHistidine-TEV-<br>PanZ(R69)-<br>cpGFP-<br>(E70)PanZ<br>Nucleic Acid | ATGCATCACCATCACCATCACGAAAACCTGTACTTCCAAAGCATGAAGCTGACA<br>ATCATTCGCCTGGAGAAATTTTCCGACCAGGATAGAATCGACCTTCAGAAGATC<br>TGGCCCGAATATTCTCCCAGTAGCCTCCAAGTAGACGACAACCATCGAATCTAC<br>GCCGCGAGATTTAATGAACGACTGCTTGCGGCGGTTAGGGTAACCCTCAGCGGT<br>ACGGAAGGTGCTCTGGACTCCCTGCGGGTCCGAAACGTCTATATCAAGGCCGAC<br>AAGCAGAAGAACGGCATCAAGGCGAACTTCAAGATCCGCCACAACATCGAGGAC<br>GGCGGCGTGCAGCTCGCCTACCACTACCAGCAGAACACCCCCATCGGCGACGGC<br>CCCGTGCTGCTGCCCGACAACCACTACCTGAGCGTGCAGTCCAAACTTTCGAAA<br>GACCCCAACGAGAAGCGCGATCACATGGTCCTGCTGGAGTTCGTGACCGCCGCC<br>GGGATCACTCTCGGCATGGACGAGCTGTACAAGGGCGGTACCGGAGGGAGCATG<br>GTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGTGAGGGCGAT<br>GCCACCTACGGCAAGCTGACCCTGAAGTTCATCTGCACCACCGGCAAGCTGCCC<br>GTGCCCTGGCCCACCCTCGTGACCACCCTGACCTACGGCGTGCAGTGCTTCAGC<br>CGCTACCCCGACCACATGAAGCAGCACGACTTCTTCAAGTCCGCCATGCCCGAA<br>GGCTACATCCAGGAGCGCACCATCTTCTTCAAGGACGACGGCAACTACAAGACC<br>CGCGCCGAGGTGAAGTTCGAGGGCGACACCCTGGTGAACCGCATCGAGCTGAAG<br>GGCATCGACTTCAAGGAGGACGGCAACATCCTGGGGCACAAGCTGGAGTACAAC<br>GAGGTGACAAGACGGAGAGGGGTAGGACAATATTTGCTCGAGGAGGTCCTTAGA<br>AATAACCCCGGAGTAAGTTGCTGGTGGATGGCGGACGCTGGAGTTGAGGATCGC<br>GGAGTCATGACGGCTTTCATGCAGGCCCTTGGGTTCACCGCACAGCAAGGGGGC<br>TGGGAGAAGTGC | 72 |
| 6xHistidine-TEV-<br>PanZ(69)-G-<br>cpGFP-GAS-<br>(E70)PanZ<br>Nucleic Acid | ATGCATCACCATCACCATCACGAAAACCTGTACTTCCAAAGCATGAAGCTGACA<br>ATCATTCGCCTGGAGAAATTTTCCGACCAGGATAGAATCGACCTTCAGAAGATC<br>TGGCCCGAATATTCTCCCAGTAGCCTCCAAGTAGACGACAACCATCGAATCTAC<br>GCCGCGAGATTTAATGAACGACTGCTTGCGGCGGTTAGGGTAACCCTCAGCGGT<br>ACGGAAGGTGCTCTGGACTCCCTGCGGGTCCGAGGAAACGTCTATATCAAGGCC<br>GACAAGCAGAAGAACGGCATCAAGGCGAACTTCAAGATCCGCCACAACATCGAG<br>GACGGCGGCGTGCAGCTCGCCTACCACTACCAGCAGAACACCCCCATCGGCGAC<br>GGCCCCGTGCTGCTGCCCGACAACCACTACCTGAGCGTGCAGTCCAAACTTTCG<br>AAAGACCCCAACGAGAAGCGCGATCACATGGTCCTGCTGGAGTTCGTGACCGCC<br>GCCGGGATCACTCTCGGCATGGACGAGCTGTACAAGGGCGGTACCGGAGGGAGC<br>ATGGTGAGCAAGGGCGAGGAGCTGTTCACCGGGGTGGTGCCCATCCTGGTCGAG<br>CTGGACGGCGACGTAAACGGCCACAAGTTCAGCGTGTCCGGCGAGGGTGAGGGC<br>GATGCCACCTACGGCAAGCTGACCCTGAAGTTCATCTGCACCACCGGCAAGCTG<br>CCCGTGCCCTGGCCCACCCTCGTGACCACCCTGACCTACGGCGTGCAGTGCTTC<br>AGCCGCTACCCCGACCACATGAAGCAGCACGACTTCTTCAAGTCCGCCATGCCC<br>GAAGGCTACATCCAGGAGCGCACCATCTTCTTCAAGGACGACGGCAACTACAAG<br>ACCCGCGCCGAGGTGAAGTTCGAGGGCGACACCCTGGTGAACCGCATCGAGCTG<br>AAGGGCATCGACTTCAAGGAGGACGGCAACATCCTGGGGCACAAGCTGGAGTAC<br>AACGGTGCTTCAGAGGTGACAAGACGGAGAGGGGTAGGACAATATTTGCTCGAG<br>GAGGTCCTTAGAAATAACCCCGGAGTAAGTTGCTGGTGGATGGCGGACGCTGGA<br>GTTGAGGATCGCGGAGTCATGACGGCTTTCATGCAGGCCCTTGGGTTCACCGCA<br>CAGCAAGGGGGCTGGGAGAAGTGC | 73 |
| 6xHistidine-TEV-<br>PanZ(R69)-<br>cpGFP-GAS-<br>(E70)PanZ<br>Nucleic Acid | ATGCATCACCATCACCATCACGAAAACCTGTACTTCCAAAGCATGAAGCTGACA<br>ATCATTCGCCTGGAGAAATTTTCCGACCAGGATAGAATCGACCTTCAGAAGATC<br>TGGCCCGAATATTCTCCCAGTAGCCTCCAAGTAGACGACAACCATCGAATCTAC<br>GCCGCGAGATTTAATGAACGACTGCTTGCGGCGGTTAGGGTAACCCTCAGCGGT<br>ACGGAAGGTGCTCTGGACTCCCTGCGGGTCCGAAACGTCTATATCAAGGCCGAC<br>AAGCAGAAGAACGGCATCAAGGCGAACTTCAAGATCCGCCACAACATCGAGGAC<br>GGCGGCGTGCAGCTCGCCTACCACTACCAGCAGAACACCCCCATCGGCGACGGC<br>CCCGTGCTGCTGCCCGACAACCACTACCTGAGCGTGCAGTCCAAACTTTCGAAA<br>GACCCCAACGAGAAGCGCGATCACATGGTCCTGCTGGAGTTCGTGACCGCCGCC<br>GGGATCACTCTCGGCATGGACGAGCTGTACAAGGGCGGTACCGGAGGGAGCATG<br>GTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGTGAGGGCGAT | 74 |

-continued

| | SEQUENCES | |
|---|---|---|
| Name | Amino Acid or Nucleotide Sequence (N→C or 5'→3') | SEQ ID NO |
| | GCCACCTACGGCAAGCTGACCCTGAAGTTCATCTGCACCACCGGCAAGCTGCCC GTGCCCTGGCCCACCCTCGTGACCACCCTGACCTACGGCGTGCAGTGCTTCAGC CGCTACCCCGACCACATGAAGCAGCACGACTTCTTCAAGTCCGCCATGCCCGAA GGCTACATCCAGGAGCGCACCATCTTCTTCAAGGACGACGGCAACTACAAGACC CGCGCCGAGGTGAAGTTCGAGGGCGACACCCTGGTGAACCGCATCGAGCTGAAG GGCATCGACTTCAAGGAGGACGGCAACATCCTGGGGCACAAGCTGGAGTACAAC GGTGCTTCAGAGGTGACAAGACGGAGAGGGGTAGGACAATATTTGCTCGAGGAG GTCCTTAGAAATAACCCCGGAGTAAGTTGCTGGTGGATGGCGGACGCTGGAGTT GAGGATCGCGGAGTCATGACGGCTTTCATGCAGGCCCTTGGGTTCACCGCACAG CAAGGGGGCTGGGAGAAGTGC | |
| 6xHistidine-TEV-PanZ(R69)-GA-cpYFP-GA-(E70)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGGAGCAAACGTCTATATCAAG GCCGACAAGCAGAAGAACGGCATCAAGGCGAACTTCAAGATCCGCCACAACATC GAGGACGGCGGCGTGCAGCTCGCCTACCACTACCAGCAGAACACCCCCATCGGC GACGGCCCCGTGCTGCTGCCCGACAACCACTACCTGAGCTATCAGTCCGTACTT TCGAAAGACCCCAACGAGAAGCGCGATCACATGGTCCTGCTGGAGTTCGTGACC GCCGCCGGGATCACTCTCGGCATGGACGAGCTGTACAAGGGCGGTACCGGAGGG AGCATGGTGAGCAAGGGCGAGGAGCTGTTCACCGGGGTGGTGCCCATCCTGGTC GAGCTGGACGGCGACGTAAACGGCCACAAGTTCAGCGTGTCCGGCGAGGGTGAG GGCGATGCCACCTACGGCAAGCTGACCCTGAAGTTCATCTGCACCACCGGCAAG CTGCCCGTGCCCTGGCCCACCCTCGTGACCACCCTGACCTACGGCGTGCAGTGC TTCAGCCGCTACCCCGACCACATGAAGCAGCACGACTTCTTCAAGTCCGCCATG CCCGAAGGCTACATCCAGGAGCGCACCATCTTCTTCAAGGACGACGGCAACTAC AAGACCCGCGCCGAGGTGAAGTTCGAGGGCGACACCCTGGTGAACCGCATCGAG CTGAAGGGCATCGACTTCAAGGAGGACGGCAACATCCTGGGGCACAAGCTGGAG TACAACGGTGCTGAGGTGACAAGACGGAGAGGGGTAGGACAATATTTGCTCGAG GAGGTCCTTAGAAATAACCCCGGAGTAAGTTGCTGGTGGATGGCGGACGCTGGA GTTGAGGATCGCGGAGTCATGACGGCTTTCATGCAGGCCCTTGGGTTCACCGCA CAGCAAGGGGGCTGGGAGAAGTGC | 75 |
| 6xHistidine-TEV-PanZ(R69)-GA-cpBFP-GA-(E70)PanZ Nucleic Acid | ATGCATCACCATCACCATCACGAAAACCTGTACTTCCAAAGCATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGGAGCAAACGTCTATATCAAG GCCGACAAGCAGAAGAACGGCATCAAGGCGAACTTCAAGATCCGCCACAACATC GAGGACGGCGGCGTGCAGCTCGCCTACCACTACCAGCAGAACACCCCCATCGGC GACGGCCCCGTGCTGCTGCCCGACAACCACTACCTGAGCGTGCAGTCCAAACTT TCGAAAGACCCCAACGAGAAGCGCGATCACATGGTCCTGCTGGAGTTCGTGACC GCCGCCGGGATCACTCTCGGCATGGACGAGCTGTACAAGGGCGGTACCGGAGGG AGCATGGTGAGCAAGGGCGAGGAGCTGTTCACCGGGGTGGTGCCCATCCTGGTC GAGCTGGACGGCGACGTAAACGGCCACAAGTTCAGCGTGTCCGGCGAGGGTGAG GGCGATGCCACCTACGGCAAGCTGACCCTGAAGTTCATCTGCACCACCGGCAAG CTGCCCGTGCCCTGGCCCACCCTCGTGACCACCCTGTCCCACGGCGTGCAGTGC TTCAGCCGCTACCCCGACCACATGAAGCAGCACGACTTCTTCAAGTCCGCCATG CCCGAAGGCTACATCCAGGAGCGCACCATCTTCTTCAAGGACGACGGCAACTAC AAGACCCGCGCCGAGGTGAAGTTCGAGGGCGACACCCTGGTGAACCGCATCGAG CTGAAGGGCATCGACTTCAAGGAGGACGGCAACATCCTGGGGCACAAGCTGGAG TACAACGGTGCTGAGGTGACAAGACGGAGAGGGGTAGGACAATATTTGCTCGAG GAGGTCCTTAGAAATAACCCCGGAGTAAGTTGCTGGTGGATGGCGGACGCTGGA GTTGAGGATCGCGGAGTCATGACGGCTTTCATGCAGGCCCTTGGGTTCACCGCA CAGCAAGGGGGCTGGGAGAAGTGC | 76 |
| PanZ(R69)-GA-cpGFP-GA-(E70)PanZ ("PANcACe") with NLS Amino Acid | MVTGPKKKRKVDYKDDDDKLDGGYPYDVPDYAARGYQTSLYKKAGSTMGHMKLT IIRLEKFSDQDRIDLQKIWPEYSPSSLQVDDNHRIYAARFNERLLAAVRVTLSG TEGALDSLRVRGANVYIKADKQKNGIKANFKIRHNIEDGGVQLAYHYQQNTPIG DGPVLLPDNHYLSVQSKLSKDPNEKRDHMVLLEFVTAAGITLGMDELYKGGTGG SMVSKGEELFTGVVPILVELDGDVNGHKFSVSGEGEGDATYGKLTLKFICTTGK LPVPWPTLVTTLTYGVQCFSRYPDHMKQHDFFKSAMPEGYIQERTIFFKDDGNY KTRAEVKFEGDTLVNRIELKGIDFKEDGNILGHKLEYNGAEVTRRRGVGQYLLE EVLRNNPGVSCWWMADAGVEDRGVMTAFMQALGFTAQQGGWEKC | 77 |
| cpGFP with NLS Amino Acid | MVTGPKKKRKVDYKDDDDKLDGGYPYDVPDYAARGYQTSLYKKAGSTMGHNVYI KADKQKNGIKANFKIRHNIEDGGVQLAYHYQQNTPIGDGPVLLPDNHYLSVQSK LSKDPNEKRDHMVLLEFVTAAGITLGMDELYKGGTGGSMVSKGEELFTGVVPIL VELDGDVNGHKFSVSGEGEGDATYGKLTLKFICTTGKLPVPWPTLVTTLTYGVQ CFSRYPDHMKQHDFFKSAMPEGYIQERTIFFKDDGNYKTRAEVKFEGDTLVNRI ELKGIDFKEDGNILGHKLEYN | 78 |

-continued

| Name | Amino Acid or Nucleotide Sequence (N→C or 5'→3') | SEQ ID NO |
|------|--------------------------------------------------|-----------|
| PanZ(R69)-GA-cpGFP-GA-(E70)PanZ ("PANcACe") with CLS Amino Acid | MVTGLQKKLEELELDDYKDDDDKLDGGYPYDVPDYAARGYQTSLYKKAGSTMGH MKLTIIRLEKFSDQDRIDLQKIWPEYSPSSLQVDDNHRIYAARFNERLLAAVRV TLSGTEGALDSLRVRGANVYIKADKQKNGIKANFKIRHNIEDGGVQLAYHYQQN TPIGDGPVLLPDNHYLSVQSKLSKDPNEKRDHMVLLEFVTAAGITLGMDELYKG GTGGSMVSKGEELFTGVVPILVELDGDVNGHKFSVSGEGEGDATYGKLTLKFIC TTGKLPVPWPTLVTTLTYGVQCFSRYPDHMKQHDFFKSAMPEGYIQERTIFFKD DGNYKTRAEVKFEGDTLVNRIELKGIDFKEDGNILGHKLEYNGAEVTRRRGVGQ YLLEEVLRNNPGVSCWWMADAGVEDRGVMTAFMQALGFTAQQGGWEKC | 79 |
| cpGFP with CLS Amino Acid | MVTGLQKKLEELELDDYKDDDDKLDGGYPYDVPDYAARGYQTSLYKKAGSTMGH NVYIKADKQKNGIKANFKIRHNIEDGGVQLAYHYQQNTPIGDGPVLLPDNHYLS VQSKLSKDPNEKRDHMVLLEFVTAAGITLGMDELYKGGTGGSMVSKGEELFTGV VPILVELDGDVNGHKFSVSGEGEGDATYGKLTLKFICTTGKLPVPWPTLVTTLT YGVQCFSRYPDHMKQHDFFKSAMPEGYIQERTIFFKDDGNYKTRAEVKFEGDTL VNRIELKGIDFKEDGNILGHKLEYN | 80 |
| PanZ(R69)-GA-cpGFP-GA-(E70)PanZ ("PANcACe") with MLS Amino Acid | MVLATRVESLVGKRAISTSVCVRAHTGDYKDDDDKLDGGYPYDVPDYAARGYQT SLYKKAGSTMGHMKLTIIRLEKFSDQDRIDLQKIWPEYSPSSLQVDDNHRIYAA RFNERLLAAVRVTLSGTEGALDSLRVRGANVYIKADKQKNGIKANFKIRHNIED GGVQLAYHYQQNTPIGDGPVLLPDNHYLSVQSKLSKDPNEKRDHMVLLEFVTAA GITLGMDELYKGGTGGSMVSKGEELFTGVVPILVELDGDVNGHKFSVSGEGEGD ATYGKLTLKFICTTGKLPVPWPTLVTTLTYGVQCFSRYPDHMKQHDFFKSAMPE GYIQERTIFFKDDGNYKTRAEVKFEGDTLVNRIELKGIDFKEDGNILGHKLEYN GAEVTRRRGVGQYLLEEVLRNNPGVSCWWMADAGVEDRGVMTAFMQALGFTAQQ GGWEKC | 81 |
| cpGFP with MLS Amino Acid | MVLATRVESLVGKRAISTSVCVRAHTGDYKDDDDKLDGGYPYDVPDYAARGYQT SLYKKAGSTMGHNVYIKADKQKNGIKANFKIRHNIEDGGVQLAYHYQQNTPIGD GPVLLPDNHYLSVQSKLSKDPNEKRDHMVLLEFVTAAGITLGMDELYKGGTGGS MVSKGEELFTGVVPILVELDGDVNGHKFSVSGEGEGDATYGKLTLKFICTTGKL PVPWPTLVTTLTYGVQCFSRYPDHMKQHDFFKSAMPEGYIQERTIFFKDDGNYK TRAEVKFEGDTLVNRIELKGIDFKEDGNILGHKLEYN | 82 |
| PanZ(R69)-GA-cpGFP-GA-(E70)PanZ ("PANcACe") with NLS Nucleic Acid | ATGGTGACCGGTCCAAAGAAGAAGCGTAAGGTAGACTACAAGGATGACGATGAC AAGCTCGATGGAGGATACCCATACGATGTTCCAGATTACGCTGCTCGAGGTTAT CAAACAAGTTTGTACAAAAAAGCAGGCTCCACCATGGGGCATATGAAGCTGACA ATCATTCGCCTGGAGAAATTTTCCGACCAGGATAGAATCGACCTTCAGAAGATC TGGCCCGAATATTCTCCCAGTAGCCTCCAAGTAGACGACAACCATCGAATCTAC GCCGCGAGATTTAATGAACGACTGCTTGCGGCGGTTAGGGTAACCCTCAGCGGT ACGGAAGGTGCTCTGGACTCCCTGCGGGTCCGAGGAGCAAACGTCTATATCAAG GCCGACAAGCAGAAGAACGGCATCAAGGCGAACTTCAAGATCCGCCACAACATC GAGGACGGCGGCGTGCAGCTCGCCTACCACTACCAGCAGAACACCCCCATCGGC GACGGCCCCGTGCTGCTGCCCGACAACCACTACCTGAGCGTGCAGTCCAAACTT TCGAAAGACCCCAACGAGAAGCGCGATCACATGGTCCTGCTGGAGTTCGTGACC GCCGCCGGGATCACTCTCGGCATGGACGAGCTGTACAAGGGCGGTACCGGAGGG AGCATGGTGAGCAAGGGCGAGGAGCTGTTCACCGGGGTGGTGCCCATCCTGGTC GAGCTGGACGGCGACGTAAACGGCCACAAGTTCAGCGTGTCCGGCGAGGGTGAG GGCGATGCCACCTACGGCAAGCTGACCCTGAAGTTCATCTGCACCACCGGCAAG CTGCCCGTGCCCTGGCCCACCCTCGTGACCACCCTGACCTACGGCGTGCAGTGC TTCAGCCGCTACCCCGACCACATGAAGCAGCACGACTTCTTCAAGTCCGCCATG CCCGAAGGCTACATCCAGGAGCGCACCATCTTCTTCAAGGACGACGGCAACTAC AAGACCCGCGCCGAGGTGAAGTTCGAGGGCGACACCCTGGTGAACCGCATCGAG CTGAAGGGCATCGACTTCAAGGAGGACGGCAACATCCTGGGGCACAAGCTGGAG TACAACGGTGCTGAGGTGACAAGACGGAGAGGGGTAGGACAATATTTGCTCGAG GAGGTCCTTAGAAATAACCCCGGAGTAAGTTGCTGGTGGATGGCGGACGCTGGA GTTGAGGATCGCGCGAGTCATGACGGCTTTCATGCAGGCCCTTGGGTTCACCGCA CAGCAAGGGGGCTGGGAGAAGTGCTAA | 83 |
| cpGFP with NLS Nucleic Acid | ATGGTGACCGGTCCAAAGAAGAAGCGTAAGGTAGACTACAAGGATGACGATGAC AAGCTCGATGGAGGATACCCATACGATGTTCCAGATTACGCTGCTCGAGGTTAT CAAACAAGTTTGTACAAAAAAGCAGGCTCCACCATGGGGCATAACGTCTATATC AAGGCCGACAAGCAGAAGAACGGCATCAAGGCGAACTTCAAGATCCGCCACAAC ATCGAGGACGGCGGCGTGCAGCTCGCCTACCACTACCAGCAGAACACCCCCATC GGCGACGGCCCCGTGCTGCTGCCCGACAACCACTACCTGAGCGTGCAGTCCAAA CTTTCGAAAGACCCCAACGAGAAGCGCGATCACATGGTCCTGCTGGAGTTCGTG ACCGCCGCCGGGATCACTCTCGGCATGGACGAGCTGTACAAGGGCGGTACCGGA GGGAGCATGGTGAGCAAGGGCGAGGAGCTGTTCACCGGGGTGGTGCCCATCCTG GTCGAGCTGGACGGCGACGTAAACGGCCACAAGTTCAGCGTGTCCGGCGAGGGT GAGGGCGATGCCACCTACGGCAAGCTGACCCTGAAGTTCATCTGCACCACCGGC AAGCTGCCCGTGCCCTGGCCCACCCTCGTGACCACCCTGACCTACGGCGTGCAG TGCTTCAGCCGCTACCCCGACCACATGAAGCAGCACGACTTCTTCAAGTCCGCC ATGCCCGAAGGCTACATCCAGGAGCGCACCATCTTCTTCAAGGACGACGGCAAC TACAAGACCCGCGCCGAGGTGAAGTTCGAGGGCGACACCCTGGTGAACCGCATC | 84 |

-continued

| | SEQUENCES | |
|---|---|---|
| Name | Amino Acid or Nucleotide Sequence (N→C or 5'→3') | SEQ ID NO |

| | GAGCTGAAGGGCATCGACTTCAAGGAGGACGGCAACATCCTGGGGCACAAGCTG GAGTACAACTAA | |
|---|---|---|
| PanZ(R69)-GA-cpGFP-GA-(E70)PanZ ("PANcACe") with CLS Nucleic Acid | ATGGTGACCGGTCTGCAGAAAAAGCTGGAAGAGCTGGAACTGGACGACTACAAG GATGACGATGACAAGCTCGATGGAGGATACCCATACGATGTTCCAGATTACGCT GCTCGAGGTTATCAAACAAGTTTGTACAAAAAAGCAGGCTCCACCATGGGGCAT ATGAAGCTGACAATCATTCGCCTGGAGAAATTTTCCGACCAGGATAGAATCGAC CTTCAGAAGATCTGGCCCGAATATTCTCCCAGTAGCCTCCAAGTAGACGACAAC CATCGAATCTACGCCGCGAGATTTAATGAACGACTGCTTGCGGCGGTTAGGGTA ACCCTCAGCGGTACGGAAGGTGCTCTGGACTCCCTGCGGGTCCGAGGAGCAAAC GTCTATATCAAGGCCGACAAGCAGAAGAACGGCATCAAGGCGAACTTCAAGATC CGCCACAACATCGAGGACGGCGGCGTGCAGCTCGCCTACCACTACCAGCAGAAC ACCCCCATCGGCGACGGCCCCGTGCTGCTGCCCGACAACCACTACCTGAGCGTG CAGTCCAAACTTTCGAAAGACCCCAACGAGAAGCGCGATCACATGGTCCTGCTG GAGTTCGTGACCGCCGCGGGATCACTCTCGGCATGGACGAGCTGTACAAGGGC GGTACCGGAGGGGAGCATGGTGAGCAAGGGCGAGGAGCTGTTCACCGGGGTGGTG CCCATCCTGGTCGAGCTGGACGGCGACGTAAACGGCCACAAGTTCAGCGTGTCC GGCGAGGGTGAGGGCGATGCCACCTACGGCAAGCTGACCCTGAAGTTCATCTGC ACCACCGGCAAGCTGCCCGTGCCCTGGCCCACCCTCGTGACCACCCTGACCTAC GGCGTGCAGTGCTTCAGCCGCTACCCCGACCACATGAAGCAGCACGACTTCTTC AAGTCCGCCATGCCCGAAGGCTACATCCAGGAGCGCACCATCTTCTTCAAGGAC GACGGCAACTACAAGACCCGCGCCGAGGTGAAGTTCGAGGGCGACACCCTGGTG AACCGCATCGAGCTGAAGGGCATCGACTTCAAGGAGGACGGCAACATCCTGGGG CACAAGCTGGAGTACAACGGTGCTGAGGTGACAAGACGGAGAGGGGTAGGACAA TATTTGCTCGAGGAGGTCCTTAGAAATAACCCCGGAGTAAGTTGCTGGTGGATG GCGGACGCTGGAGTTGAGGATCGCGGAGTCATGACGGCTTTCATGCAGGCCCTT GGGTTCACCGCACAGCAAGGGGGCTGGGAGAAGTGCTAA | 85 |
| cpGFP with CLS Nucleic Acid | ATGGTGACCGGTCTGCAGAAAAAGCTGGAAGAGCTGGAACTGGACGACTACAAG GATGACGATGACAAGCTCGATGGAGGATACCCATACGATGTTCCAGATTACGCT GCTCGAGGTTATCAAACAAGTTTGTACAAAAAAGCAGGCTCCACCATGGGGCAT AACGTCTATATCAAGGCCGACAAGCAGAAGAACGGCATCAAGGCGAACTTCAAG ATCCGCCACAACATCGAGGACGGCGGCGTGCAGCTCGCCTACCACTACCAGCAG AACACCCCCATCGGCGACGGCCCCGTGCTGCTGCCCGACAACCACTACCTGAGC GTGCAGTCCAAACTTTCGAAAGACCCCAACGAGAAGCGCGATCACATGGTCCTG CTGGAGTTCGTGACCGCCGCGGGATCACTCTCGGCATGGACGAGCTGTACAAG GGCGGTACCGGAGGGGAGCATGGTGAGCAAGGGCGAGGAGCTGTTCACCGGGGTG GTGCCCATCCTGGTCGAGCTGGACGGCGACGTAAACGGCCACAAGTTCAGCGTG TCCGGCGAGGGTGAGGGCGATGCCACCTACGGCAAGCTGACCCTGAAGTTCATC TGCACCACCGGCAAGCTGCCCGTGCCCTGGCCCACCCTCGTGACCACCCTGACC TACGGCGTGCAGTGCTTCAGCCGCTACCCCGACCACATGAAGCAGCACGACTTC TTCAAGTCCGCCATGCCCGAAGGCTACATCCAGGAGCGCACCATCTTCTTCAAG GACGACGGCAACTACAAGACCCGCGCCGAGGTGAAGTTCGAGGGCGACACCCTG GTGAACCGCATCGAGCTGAAGGGCATCGACTTCAAGGAGGACGGCAACATCCTG GGGCACAAGCTGGAGTACAACTAA | 86 |
| PanZ(R69)-GA-cpGFP-GA-(E70)PanZ ("PANcACe") with MLS Nucleic Acid | ATGGTGCTGGCCACCCGCGTGTTCAGCCTGGTGGGCAAGCGCGCCATCAGCACC AGCGTGTGCGTGCGCGCCCACACCGGTGACTACAAGGATGACGATGACAAGCTC GATGGAGGATACCCATACGATGTTCCAGATTACGCTGCTCGAGGTTATCAAACA AGTTTGTACAAAAAAGCAGGCTCCACCATGGGGCATATGAAGCTGACAATCATT CGCCTGGAGAAATTTTCCGACCAGGATAGAATCGACCTTCAGAAGATCTGGCCC GAATATTCTCCCAGTAGCCTCCAAGTAGACGACAACCATCGAATCTACGCCGCG AGATTTAATGAACGACTGCTTGCGGCGGTTAGGGTAACCCTCAGCGGTACGGAA GGTGCTCTGGACTCCCTGCGGGTCCGAGGAGCAAACGTCTATATCAAGGCCGAC AAGCAGAAGAACGGCATCAAGGCGAACTTCAAGATCCGCCACAACATCGAGGAC GGCGGCGTGCAGCTCGCCTACCACTACCAGCAGAACACCCCCATCGGCGACGGC CCCGTGCTGCTGCCCGACAACCACTACCTGAGCGTGCAGTCCAAACTTTCGAAA GACCCCAACGAGAAGCGCGATCACATGGTCCTGCTGGAGTTCGTGACCGCC GGGATCACTCTCGGCATGGACGAGCTGTACAAGGGCGGTACCGGAGGGGAGCATG GTGAGCAAGGGCGAGGAGCTGTTCACCGGGGTGGTGCCCATCCTGGTCGAGCTG GACGGCGACGTAAACGGCCACAAGTTCAGCGTGTCCGGCGAGGGTGAGGGCGAT GCCACCTACGGCAAGCTGACCCTGAAGTTCATCTGCACCACCGGCAAGCTGCCC GTGCCCTGGCCCACCCTCGTGACCACCCTGACCTACGGCGTGCAGTGCTTCAGC CGCTACCCCGACCACATGAAGCAGCACGACTTCTTCAAGTCCGCCATGCCCGAA GGCTACATCCAGGAGCGCACCATCTTCTTCAAGGACGACGGCAACTACAAGACC CGCGCCGAGGTGAAGTTCGAGGGCGACACCCTGGTGAACCGCATCGAGCTGAAG GGCATCGACTTCAAGGAGGACGGCAACATCCTGGGGCACAAGCTGGAGTACAAC GGTGCTGAGGTGACAAGACGGAGAGGGGTAGGACAATATTTGCTCGAGGAGGTC CTTAGAAATAACCCCGGAGTAAGTTGCTGGTGGATGGCGGACGCTGGAGTTGAG GATCGCGGAGTCATGACGGCTTTCATGCAGGCCCTTGGGTTCACCGCACAGCAA GGGGGCTGGGAGAAGTGCTAA | 87 |
| cpGFP with MLS Nucleic Acid | ATGGTGCTGGCCACCCGCGTGTTCAGCCTGGTGGGCAAGCGCGCCATCAGCACC AGCGTGTGCGTGCGCGCCCACACCGGTGACTACAAGGATGACGATGACAAGCTC | 88 |

-continued

| | SEQUENCES | |
|---|---|---|
| Name | Amino Acid or Nucleotide Sequence (N→C or 5'→3') | SEQ ID NO |
| | GATGGAGGATACCCATACGATGTTCCAGATTACGCTGCTCGAGGTTATCAAACA<br>AGTTTGTACAAAAAAGCAGGCTCCACCATGGGGCATAACGTCTATATCAAGGCC<br>GACAAGCAGAAGAACGGCATCAAGGCGAACTTCAAGATCCGCCACAACATCGAG<br>GACGGCGGCGTGCAGCTCGCCTACCACTACCAGCAGAACACCCCCATCGGCGAC<br>GGCCCCGTGCTGCTGCCCGACAACCACTACCTGAGCGTGCAGTCCAAACTTTCG<br>AAAGACCCCAACGAGAAGCGCGATCACATGGTCCTGCTGGAGTTCGTGACCGCC<br>GCCGGGATCACTCTCGGCATGGACGAGCTGTACAAGGGCGGTACCGGAGGGAGC<br>ATGGTGAGCAAGGGCGAGGAGCTGTTCACCGGGGTGGTGCCCATCCTGGTCGAG<br>CTGGACGGCGACGTAAACGGCCACAAGTTCAGCGTGTCCGGCGAGGGTGAGGGC<br>GATGCCACCTACGGCAAGCTGACCCTGAAGTTCATCTGCACCACCGGCAAGCTG<br>CCCGTGCCCTGGCCCACCCTCGTGACCACCCTGACCTACGGCGTGCAGTGCTTC<br>AGCCGCTACCCCGACCACATGAAGCAGCACGACTTCTTCAAGTCCGCCATGCCC<br>GAAGGCTACATCCAGGAGCGCACCATCTTCTTCAAGGACGACGGCAACTACAAG<br>ACCCGCGCCGAGGTGAAGTTCGAGGGCGACACCCTGGTGAACCGCATCGAGCTG<br>AAGGGCATCGACTTCAAGGAGGACGGCAACATCCTGGGGCACAAGCTGGAGTAC<br>AACTAA | |
| FLAG Tag | DYKDDDDK | 89 |

SEQUENCE LISTING

Sequence total quantity: 89
SEQ ID NO: 1              moltype = AA   length = 127
FEATURE                   Location/Qualifiers
source                    1..127
                          mol_type = protein
                          organism = synthetic construct
SEQUENCE: 1
MKLTIIRLEK FSDQDRIDLQ KIWPEYSPSS LQVDDNHRIY AARFNERLLA AVRVTLSGTE   60
GALDSLRVRE VTRRRGVGQY LLEEVLRNNP GVSCWWMADA GVEDRGVMTA FMQALGFTAQ   120
QGGWEKC                                                             127

SEQ ID NO: 2              moltype = AA   length = 241
FEATURE                   Location/Qualifiers
source                    1..241
                          mol_type = protein
                          organism = synthetic construct
SEQUENCE: 2
NVYIKADKQK NGIKANFKIR HNIEDGGVQL AYHYQQNTPI GDGPVLLPDN HYLSVQSKLS   60
KDPNEKRDHM VLLEFVTAAG ITLGMDELYK GGTGGSMVSK GEELFTGVVP ILVELDGDVN   120
GHKFSVSGEG EGDATYGKLT LKFICTTGKL PVPWPTLVTT LTYGVQCFSR YPDHMKQHDF   180
FKSAMPEGYI QERTIFFKDD GNYKTRAEVK FEGDTLVNRI ELKGIDFKED GNILGHKLEY   240
N                                                                   241

SEQ ID NO: 3              moltype = AA   length = 241
FEATURE                   Location/Qualifiers
source                    1..241
                          mol_type = protein
                          organism = synthetic construct
SEQUENCE: 3
NVYIKADKQK NGIKANFKIR HNIEDGGVQL AYHYQQNTPI GDGPVLLPDN HYLSYQSVLS   60
KDPNEKRDHM VLLEFVTAAG ITLGMDELYK GGTGGSMVSK GEELFTGVVP ILVELDGDVN   120
GHKFSVSGEG EGDATYGKLT LKFICTTGKL PVPWPTLVTT LTYGVQCFSR YPDHMKQHDF   180
FKSAMPEGYI QERTIFFKDD GNYKTRAEVK FEGDTLVNRI ELKGIDFKED GNILGHKLEY   240
N                                                                   241

SEQ ID NO: 4              moltype = AA   length = 241
FEATURE                   Location/Qualifiers
source                    1..241
                          mol_type = protein
                          organism = synthetic construct
SEQUENCE: 4
NVYIKADKQK NGIKANFKIR HNIEDGGVQL AYHYQQNTPI GDGPVLLPDN HYLSVQSKLS   60
KDPNEKRDHM VLLEFVTAAG ITLGMDELYK GGTGGSMVSK GEELFTGVVP ILVELDGDVN   120
GHKFSVSGEG EGDATYGKLT LKFICTTGKL PVPWPTLVTT LSHGVQCFSR YPDHMKQHDF   180
FKSAMPEGYI QERTIFFKDD GNYKTRAEVK FEGDTLVNRI ELKGIDFKED GNILGHKLEY   240
N                                                                   241

SEQ ID NO: 5              moltype = AA   length = 372
FEATURE                   Location/Qualifiers -continued

```
source                     1..372
                           mol_type = protein
                           organism = synthetic construct
SEQUENCE: 5
MKLTIIRLEK FSDQDRIDLQ KIWPEYSPSS LQVDDNHRIY AARFNERLLA AVRVTLSGTE  60
GALDSLRVRG ANVYIKADKQ KNGIKANFKI RHNIEDGGVQ LAYHYQQNTP IGDGPVLLPD  120
NHYLSVQSKL SKDPNEKRDH MVLLEFVTAA GITLGMDELY KGGTGGSMVS KGEELFTGVV  180
PILVELDGDV NGHKFSVSGE GEGDATYGKL TLKFICTTGK LPVPWPTLVT TLTYGVQCFS  240
RYPDHMKQHD FFKSAMPEGY IQERTIFFKD DGNYKTRAEV KFEGDTLVNR IELKGIDFKE  300
DGNILGHKLE YNGAEVTRRR GVGQYLLEEV LRNNPGVSCW WMADAGVEDR GVMTAFMQAL  360
GFTAQQGGWE KC                                                       372

SEQ ID NO: 6              moltype = AA   length = 372
FEATURE                   Location/Qualifiers
source                    1..372
                          mol_type = protein
                          organism = synthetic construct
SEQUENCE: 6
MKLTIIRLEK FSDQDRIDLQ KIWASNVYIK ADKQKNGIKA NFKIRHNIED GGVQLAYHYQ  60
QNTPIGDGPV LLPDNHYLSV QSKLSKDPNE KRDHMVLLEF VTAAGITLGM DELYKGGTGG  120
SMVSKGEELF TGVVPILVEL DGDVNGHKFS VSGEGEGDAT YGKLTLKFIC TTGKLPVPWP  180
TLVTTLTYGV QCFSRYPDHM KQHDFFKSAM PEGYIQERTI FFKDDGNYKT RAEVKFEGDT  240
LVNRIELKGI DFKEDGNILG HKLEYNASPE YSPSSLQVDD NHRIYAARFN ERLLAAVRVT  300
LSGTEGALDS LRVREVTRRR GVGQYLLEEV LRNNPGVSCW WMADAGVEDR GVMTAFMQAL  360
GFTAQQGGWE KC                                                       372

SEQ ID NO: 7              moltype = AA   length = 372
FEATURE                   Location/Qualifiers
source                    1..372
                          mol_type = protein
                          organism = synthetic construct
SEQUENCE: 7
MKLTIIRLEK FSDQDRIDLQ KIWPEYSPSS LQVDDNHRIY AARFNERLLA AVRVTLSGTE  60
GALDSLRVRE VASNVYIKAD KQKNGIKANF KIRHNIEDGG VQLAYHYQQN TPIGDGPVLL  120
PDNHYLSVQS KLSKDPNEKR DHMVLLEFVT AAGITLGMDE LYKGGTGGSM VSKGEELFTG  180
VVPILVELDG DVNGHKFSVS GEGEGDATYG KLTLKFICTT GKLPVPWPTL VTTLTYGVQC  240
FSRYPDHMKQ HDFFKSAMPE GYIQERTIFF KDDGNYKTRA EVKFEGDTLV NRIELKGIDF  300
KEDGNILGHK LEYNASTRRR GVGQYLLEEV LRNNPGVSCW WMADAGVEDR GVMTAFMQAL  360
GFTAQQGGWE KC                                                       372

SEQ ID NO: 8              moltype = AA   length = 372
FEATURE                   Location/Qualifiers
source                    1..372
                          mol_type = protein
                          organism = synthetic construct
SEQUENCE: 8
MKLTIIRLEK FSDQDRIDLQ KIWPEYSPSS LQVDDNHRIY AARFNERLLA AVRVTLSGTE  60
GALDSLRVRA SNVYIKADKQ KNGIKANFKI RHNIEDGGVQ LAYHYQQNTP IGDGPVLLPD  120
NHYLSVQSKL SKDPNEKRDH MVLLEFVTAA GITLGMDELY KGGTGGSMVS KGEELFTGVV  180
PILVELDGDV NGHKFSVSGE GEGDATYGKL TLKFICTTGK LPVPWPTLVT TLTYGVQCFS  240
RYPDHMKQHD FFKSAMPEGY IQERTIFFKD DGNYKTRAEV KFEGDTLVNR IELKGIDFKE  300
DGNILGHKLE YNASEVTRRR GVGQYLLEEV LRNNPGVSCW WMADAGVEDR GVMTAFMQAL  360
GFTAQQGGWE KC                                                       372

SEQ ID NO: 9              moltype = AA   length = 372
FEATURE                   Location/Qualifiers
source                    1..372
                          mol_type = protein
                          organism = synthetic construct
SEQUENCE: 9
MKLTIIRLEK FSDQDRIDLQ KIWPEYSPSS LQVDDNHRIY AARFNERLLA AVRVTLSGTE  60
GALDSLRVRE VTRRRGVGQY LLEEVLRNNP GVSCWWMADA SNVYIKADKQ KNGIKANFKI  120
RHNIEDGGVQ LAYHYQQNTP IGDGPVLLPD NHYLSVQSKL SKDPNEKRDH MVLLEFVTAA  180
GITLGMDELY KGGTGGSMVS KGEELFTGVV PILVELDGDV NGHKFSVSGE GEGDATYGKL  240
TLKFICTTGK LPVPWPTLVT TLTYGVQCFS RYPDHMKQHD FFKSAMPEGY IQERTIFFKD  300
DGNYKTRAEV KFEGDTLVNR IELKGIDFKE DGNILGHKLE YNASAGVEDR GVMTAFMQAL  360
GFTAQQGGWE KC                                                       372

SEQ ID NO: 10             moltype = AA   length = 372
FEATURE                   Location/Qualifiers
source                    1..372
                          mol_type = protein
                          organism = synthetic construct
SEQUENCE: 10
MKLTIIRLEK FSDQDRIDLQ KIWPEYSPSS LQVDDNHRIY AARFNERLLA AVRVTLSGTE  60
GALDSLRVRE VTRRRGVGQY LLEEVLRNNP GVSCWWMADA GVEDASNVYI KADKQKNGIK  120
ANFKIRHNIE DGGVQLAYHY QQNTPIGDGP VLLPDNHYLS VQSKLSKDPN EKRDHMVLLE  180
FVTAAGITLG MDELYKGGTG GSMVSKGEEL FTGVVPILVE LDGDVNGHKF SVSGEGEGDA  240
TYGKLTLKFI CTTGKLPVPW PTLVTTLTYG VQCFSRYPDH MKQHDFFKSA MPEGYIQERT  300
```

```
IFFKDDGNYK TRAEVKFEGD TLVNRIELKG IDFKEDGNIL GHKLEYNASR GVMTAFMQAL   360
GFTAQQGGWE KC                                                        372

SEQ ID NO: 11              moltype = AA  length = 372
FEATURE                    Location/Qualifiers
source                     1..372
                           mol_type = protein
                           organism = synthetic construct
SEQUENCE: 11
MKLTIIRLEK FSDQDRIDLQ KIWPEYSPSS LQVDDNHRIY AARFNERLLA AVRVTLSGTE   60
GALDSLRVRE VTRRRGVGQY LLEEVLRNNP GVSCWWMADA GVEDRGVMTA FMQALGASNV   120
YIKADKQKNG IKANFKIRHN IEDGGVQLAY HYQQNTPIGD GPVLLPDNHY LSVQSKLSKD   180
PNEKRDHMVL LEFVTAAGIT LGMDELYKGG TGGSMVSKGE ELFTGVVPIL VELDGDVNGH   240
KFSVSGEGEG DATYGKLTLK FICTTGKLPV PWPTLVTTLT YGVQCFSRYP DHMKQHDFFK   300
SAMPEGYIQE RTIFFKDDGN YKTRAEVKFE GDTLVNRIEL KGIDFKEDGN ILGHKLEYNA   360
SFTAQQGGWE KC                                                        372

SEQ ID NO: 12              moltype = AA  length = 371
FEATURE                    Location/Qualifiers
source                     1..371
                           mol_type = protein
                           organism = synthetic construct
SEQUENCE: 12
KLTIIRLEKF SDQDRIDLQK IWPEYSPSSL QVDDNHRIYA ARFNERLLAA VRVTLSGTEG   60
ALDSLRVRGA SNVYIKADKQ KNGIKANFKI RHNIEDGGVQ LAYHYQQNTP IGDGPVLLPD   120
NHYLSVQSKL SKDPNEKRDH MVLLEFVTAA GITLGMDELY KGGTGGSMVS KGEELFTGVV   180
PILVELDGDV NGHKFSVSGE GEGDATYGKL TLKFICTTGK LPVPWPTLVT TLTYGVQCFS   240
RYPDHMKQHD FFKSAMPEGY IQERTIFFKD DGNYKTRAEV KFEGDTLVNR IELKGIDFKE   300
DGNILGHKLE YNGEVTRRRG VGQYLLEEVL RNNPGVSCWW MADAGVEDRG VMTAFMQALG   360
FTAQQGGWEK C                                                         371

SEQ ID NO: 13              moltype = AA  length = 371
FEATURE                    Location/Qualifiers
source                     1..371
                           mol_type = protein
                           organism = synthetic construct
SEQUENCE: 13
MKLTIIRLEK FSDQDRIDLQ KIWPEYSPSS LQVDDNHRIY AARFNERLLA AVRVTLSGTE   60
GALDSLRVRG ASNVYIKADK QKNGIKANFK IRHNIEDGGV QLAYHYQQNT PIGDGPVLLP   120
DNHYLSVQSK LSKDPNEKRD HMVLLEFVTA AGITLGMDEL YKGGTGGSMV SKGEELFTGV   180
VPILVELDGD VNGHKFSVSG EGEGDATYGK LTLKFICTTG KLPVPWPTLV TTLTYGVQCF   240
SRYPDHMKQH DFFKSAMPEG YIQERTIFFK DDGNYKTRAE VKFEGDTLVN RIELKGIDFK   300
EDGNILGHKL EYNEVTRRRG VGQYLLEEVL RNNPGVSCWW MADAGVEDRG VMTAFMQALG   360
FTAQQGGWEK C                                                         371

SEQ ID NO: 14              moltype = AA  length = 370
FEATURE                    Location/Qualifiers
source                     1..370
                           mol_type = protein
                           organism = synthetic construct
SEQUENCE: 14
MKLTIIRLEK FSDQDRIDLQ KIWPEYSPSS LQVDDNHRIY AARFNERLLA AVRVTLSGTE   60
GALDSLRVRG ANVYIKADKQ KNGIKANFKI RHNIEDGGVQ LAYHYQQNTP IGDGPVLLPD   120
NHYLSVQSKL SKDPNEKRDH MVLLEFVTAA GITLGMDELY KGGTGGSMVS KGEELFTGVV   180
PILVELDGDV NGHKFSVSGE GEGDATYGKL TLKFICTTGK LPVPWPTLVT TLTYGVQCFS   240
RYPDHMKQHD FFKSAMPEGY IQERTIFFKD DGNYKTRAEV KFEGDTLVNR IELKGIDFKE   300
DGNILGHKLE YNEVTRRGV GQYLLEEVLR NNPGVSCWWM ADAGVEDRGV MTAFMQALGF   360
TAQQGGWEKC                                                           370

SEQ ID NO: 15              moltype = AA  length = 368
FEATURE                    Location/Qualifiers
source                     1..368
                           mol_type = protein
                           organism = synthetic construct
SEQUENCE: 15
MKLTIIRLEK FSDQDRIDLQ KIWPEYSPSS LQVDDNHRIY AARFNERLLA AVRVTLSGTE   60
GALDSLRVRN VYIKADKQKN GIKANFKIRH NIEDGGVQLA YHYQQNTPIG DGPVLLPDNH   120
YLSVQSKLSK DPNEKRDHMV LLEFVTAAGI TLGMDELYKG GTGGSMVSKG EELFTGVVPI   180
LVELDGDVNG HKFSVSGEGE GDATYGKLTL KFICTTGKLP VPWPTLVTTL TYGVQCFSRY   240
PDHMKQHDFF KSAMPEGYIQ ERTIFFKDDG NYKTRAEVKF EGDTLVNRIE LKGIDFKEDG   300
NILGHKLEYN EVTRRGVGQ YLLEEVLRNN PGVSCWWMAD AGVEDRGVMT AFMQALGFTA   360
QQGGWEKC                                                             368

SEQ ID NO: 16              moltype = AA  length = 372
FEATURE                    Location/Qualifiers
source                     1..372
                           mol_type = protein
                           organism = synthetic construct
SEQUENCE: 16
```

```
MKLTIIRLEK FSDQDRIDLQ KIWPEYSPSS LQVDDNHRIY AARFNERLLA AVRVTLSGTE 60
GALDSLRVRG NVYIKADKQK NGIKANFKIR HNIEDGGVQL AYHYQQNTPI GDGPVLLPDN 120
HYLSVQSKLS KDPNEKRDHM VLLEFVTAAG ITLGMDELYK GGTGGSMVSK GEEELFTGVVP 180
ILVELDGDVN GHKFSVSGEG EGDATYGKLT LKFICTTGKL PVPWPTLVTT LTYGVQCFSR 240
YPDHMKQHDF FKSAMPEGYI QERTIFFKDD GNYKTRAEVK FEGDTLVNRI ELKGIDFKED 300
GNILGHKLEY NGASEVTRRR GVGQYLLEEV LRNNPGVSCW WMADAGVEDR GVMTAFMQAL 360
GFTAQQGGWE KC 372
```

SEQ ID NO: 17          moltype = AA   length = 371
FEATURE                Location/Qualifiers
source                 1..371
                       mol_type = protein
                       organism = synthetic construct
SEQUENCE: 17

```
MKLTIIRLEK FSDQDRIDLQ KIWPEYSPSS LQVDDNHRIY AARFNERLLA AVRVTLSGTE 60
GALDSLRVRN VYIKADKQKN GIKANFKIRH NIEDGGVQLA YHYQQNTPIG DGPVLLPDNH 120
YLSVQSKLSK DPNEKRDHMV LLEFVTAAGI TLGMDELYKG GTGGSMVSKG EELFTGVVPI 180
LVELDGDVNG HKFSVSGEGE GDATYGKLTL KFICTTGKLP VPWPTLVTTL TYGVQCFSRY 240
PDHMKQHDFF KSAMPEGYIQ ERTIFFKDDG NYKTRAEVKF EGDTLVNRIE LKGIDFKEDG 300
NILGHKLEYN GASEVTRRRG VGQYLLEEVL RNNPGVSCWW MADAGVEDRG VMTAFMQALG 360
FTAQQGGWEK C 371
```

SEQ ID NO: 18          moltype = AA   length = 372
FEATURE                Location/Qualifiers
source                 1..372
                       mol_type = protein
                       organism = synthetic construct
SEQUENCE: 18

```
MKLTIIRLEK FSDQDRIDLQ KIWPEYSPSS LQVDDNHRIY AARFNERLLA AVRVTLSGTE 60
GALDSLRVRG ANVYIKADKQ KNGIKANFKI RHNIEDGGVQ LAYHYQQNTP IGDGPVLLPD 120
NHYLSYQSVL SKDPNEKRDH MVLLEFVTAA GITLGMDELY KGGTGGSMVS KGEELFTGVV 180
PILVELDGDV NGHKFSVSGE GEGDATYGKL TLKFICTTGK LPVPWPTLVT TLTYGVQCFS 240
RYPDHMKQHD FFKSAMPEGY IQERTIFFKD DGNYKTRAEV KFEGDTLVNR IELKGIDFKE 300
DGNILGHKLE YNGAEVTRRR GVGQYLLEEV LRNNPGVSCW WMADAGVEDR GVMTAFMQAL 360
GFTAQQGGWE KC 372
```

SEQ ID NO: 19          moltype = AA   length = 372
FEATURE                Location/Qualifiers
source                 1..372
                       mol_type = protein
                       organism = synthetic construct
SEQUENCE: 19

```
MKLTIIRLEK FSDQDRIDLQ KIWPEYSPSS LQVDDNHRIY AARFNERLLA AVRVTLSGTE 60
GALDSLRVRG ANVYIKADKQ KNGIKANFKI RHNIEDGGVQ LAYHYQQNTP IGDGPVLLPD 120
NHYLSVQSKL SKDPNEKRDH MVLLEFVTAA GITLGMDELY KGGTGGSMVS KGEELFTGVV 180
PILVELDGDV NGHKFSVSGE GEGDATYGKL TLKFICTTGK LPVPWPTLVT TLSHGVQCFS 240
RYPDHMKQHD FFKSAMPEGY IQERTIFFKD DGNYKTRAEV KFEGDTLVNR IELKGIDFKE 300
DGNILGHKLE YNGAEVTRRR GVGQYLLEEV LRNNPGVSCW WMADAGVEDR GVMTAFMQAL 360
GFTAQQGGWE KC 372
```

SEQ ID NO: 20          moltype = DNA   length = 381
FEATURE                Location/Qualifiers
source                 1..381
                       mol_type = other DNA
                       organism = synthetic construct
SEQUENCE: 20

```
atgaagctga caatcattcg cctggagaaa ttttccgacc aggatagaat cgaccttcag 60
aagatctggc ccgaatattc tcccagtagc ctccaagtag acgacaacca tcgaatctac 120
gccgcgagat ttaatgaacg actgcttgcg gcggttaggc taaccctcag cggtacggaa 180
ggtgctctgg actccctgcg ggtccgagag gtgacaagac ggagaggggt aggacaatat 240
ttgctcgagg aggtccttag aaataacccc ggagtaagtt gctggtggat ggcggacgct 300
ggagttgagg atcgcggagt catgacggct ttcatgcagg cccttgggtt caccgcacag 360
caagggggct gggagaagtg c 381
```

SEQ ID NO: 21          moltype = DNA   length = 723
FEATURE                Location/Qualifiers
source                 1..723
                       mol_type = other DNA
                       organism = synthetic construct
SEQUENCE: 21

```
aacgtctata tcaaggccga caagcagaag aacggcatca aggcgaactt caagatccgc 60
cacaacatcg aggacggcgg cgtgcagctc gcctaccact accagcagaa cacccccatc 120
ggcgacggcc ccgtgctgct gcccgacaac cactacctga gcgtgcagtc caaactttcg 180
aaagaccccca acgagaagcg cgatcacatg gtcctgctgg agttcgtgac cgccgccggt 240
atcactctcg gcatggacga gctgtacaag ggcggtaccg agggagcat ggtgagcaag 300
ggcgaggagc tgttcaccgg ggtggtgccc atcctggtcg agctggacgg cgacgtaaac 360
ggccacaagt tcagcgtgtc cggcgagggt gagggcgatg ccacctacgg caagctgacc 420
ctgaagttca tctgcaccac cggcaagctg cccgtgccct ggcccaccct cgtgaccacc 480
ctgacctacg gcgtgcagtg cttcagccgc taccccgacc acatgaagca gcacgacttc 540
```

-continued

```
ttcaagtccg ccatgcccga aggctacatc caggagcgca ccatcttctt caaggacgac    600
ggcaactaca agacccgcgc cgaggtgaag ttcgagggcg acaccctggt gaaccgcatc    660
gagctgaagg gcatcgactt caaggaggac ggcaacatcc tggggcacaa gctggagtac    720
aac                                                                  723

SEQ ID NO: 22            moltype = DNA   length = 723
FEATURE                  Location/Qualifiers
source                   1..723
                         mol_type = other DNA
                         organism = synthetic construct
SEQUENCE: 22
aacgtctata tcaaggccga caagcagaag aacggcatca aggcgaactt caagatccgc    60
cacaacatcg aggacggcgg cgtgcagctc gcctaccact accagcagaa cacccccatc    120
ggcgacggcc ccgtgctgct gcccgacaac cactacctga gctatcagtc cgtactttcg    180
aaagacccca acgagaagcg cgatcacatg gtcctgctgg agttcgtgac cgccgccggg    240
atcactctcg gcatggacga gctgtacaag ggcggtaccg gagggagcat ggtgagcaag    300
ggcgaggagc tgttcaccgg ggtggtgccc atcctggtcg agctggacgg cgacgtaaac    360
ggccacaagt tcagcgtgtc cggcgagggt gagggcgatg ccacctacgg caagcttgacc    420
ctgaagttca tctgcaccac cggcaagctg cccgtgccct ggcccacccc cgtgaccacc    480
ctgacctacg gcgtgcagtg cttcagccgc taccccgacc acatgaagca gcacgacttc    540
ttcaagtccg ccatgcccga aggctacatc caggagcgca ccatcttctt caaggacgac    600
ggcaactaca agacccgcgc cgaggtgaag ttcgagggcg acaccctggt gaaccgcatc    660
gagctgaagg gcatcgactt caaggaggac ggcaacatcc tggggcacaa gctggagtac    720
aac                                                                  723

SEQ ID NO: 23            moltype = DNA   length = 723
FEATURE                  Location/Qualifiers
source                   1..723
                         mol_type = other DNA
                         organism = synthetic construct
SEQUENCE: 23
aacgtctata tcaaggccga caagcagaag aacggcatca aggcgaactt caagatccgc    60
cacaacatcg aggacggcgg cgtgcagctc gcctaccact accagcagaa cacccccatc    120
ggcgacggcc ccgtgctgct gcccgacaac cactacctga gcgtgcagtc caaactttcg    180
aaagacccca acgagaagcg cgatcacatg gtcctgctgg agttcgtgac cgccgccggg    240
atcactctcg gcatggacga gctgtacaag ggcggtaccg gagggagcat ggtgagcaag    300
ggcgaggagc tgttcaccgg ggtggtgccc atcctggtcg agctggacgg cgacgtaaac    360
ggccacaagt tcagcgtgtc cggcgagggt gagggcgatg ccacctacgg caagctgacc    420
ctgaagttca tctgcaccac cggcaagctg cccgtgccct ggcccacccct cgtgaccacc    480
ctgtcccacg gcgtgcagtg cttcagccgc taccccgacc acatgaagca gcacgacttc    540
ttcaagtccg ccatgcccga aggctacatc caggagcgca ccatcttctt caaggacgac    600
ggcaactaca agacccgcgc cgaggtgaag ttcgagggcg acaccctggt gaaccgcatc    660
gagctgaagg gcatcgactt caaggaggac ggcaacatcc tggggcacaa gctggagtac    720
aac                                                                  723

SEQ ID NO: 24            moltype = DNA   length = 1116
FEATURE                  Location/Qualifiers
source                   1..1116
                         mol_type = other DNA
                         organism = synthetic construct
SEQUENCE: 24
atgaagctga caatcattcg cctggagaaa ttttccgacc aggatagaat cgaccttcag    60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgagga gcaaacgtct atatcaaggc cgacaagcag    240
aagaacggca tcaaggcgaa cttcaagatc cgccacaaca tcgaggacgg cggcgtgcag    300
ctcgcctacc actaccagca gaacaccccc atcggcgacg gccccgtgct gctgcccgac    360
aaccactacc tgagcgtgca gtccaaactt tcgaaagacc ccaacgagaa gcgcgatcac    420
atggtccctgc tggagttcgt gaccgccgcc gggatcactc tcggcatgga cgagctgtac    480
aagggcggta ccggagggag catggtgagc aagggcgagg agctgttcac cggggtggtg    540
cccatcctgg tcgagctgga cggcgacgta aacggccaca gttcagcgt gtccggcgag    600
ggtgagggca tgccacccta cggcaagctg accctgaagt tcatctgcac caccggcaag    660
ctgcccgtgc cctggcccac cctcgtgacc accctgacct acggcgtgca gtgcttcagc    720
cgctacccctg accacatgaa gcagcacgac ttcttcaagt ccgccatgcc cgaaggctac    780
atccaggagc gcaccatctt cttcaaggac gacggcaact acaagacccg cgccgaggtg    840
aagttcgagg gcgacaccct ggtgaaccgc atcgagctga aggcatcga cttcaaggag    900
gacggcaaca tcctggggca aagctggag tacaacggtg ctgaggtgac aagacggaga    960
ggggtaggac aatatttgct cgaggaggtc cttagaaata accccggagt aagttgctgg    1020
tggatggcgg acgctggagt tgaggatcgc ggagtcatga cggctttcat gcaggccctt    1080
gggttcaccg cacagcaagg gggctggag aagtgc                                1116

SEQ ID NO: 25            moltype = DNA   length = 1116
FEATURE                  Location/Qualifiers
source                   1..1116
                         mol_type = other DNA
                         organism = synthetic construct
SEQUENCE: 25
atgaagctga caatcattcg cctggagaaa ttttccgacc aggatagaat cgaccttcag    60
aagatctggg catctaacgt ctatatcaag gccgacaagc agaagaacgg catcaaggcg    120
```

-continued

```
aacttcaaga tccgccacaa catcgaggac ggcggcgtgc agctcgccta ccactaccag    180
cagaacaccc ccatcggcga cggccccgtg ctgctgcccg acaaccacta cctgagcgtg    240
cagtccaaac tttcgaaaga ccccaacgag aagcgcgatc acatggtcct gctggagttc    300
gtgaccgccg ccgggatcac tctcggcatg gacgagctgt acaagggcgg taccggaggg    360
agcatggtga gcaagggcga ggagctgttc accggggtgg tgcccatcct ggtcgagctg    420
gacggcgacg taaacggcca caagttcagc gtgtccggcg agggtgaggg cgatgccacc    480
tacggcaagc tgaccctgaa gttcatctgc accaccggca agctgcccgt gccctggccc    540
accctcgtga ccaccctgac ctacggcgtg cagtgcttca gccgctaccc cgaccacatg    600
aagcagcacg acttcttcaa gtccgccatg cccgaaggct acatccagga gcgcaccatc    660
ttcttcaagg acgacggcaa ctacaagacc cgcgccgagg tgaagttcga gggcgacacc    720
ctggtgaacc gcatcgagct gaagggcatc gacttcaagg aggacggcaa catcctgggg    780
cacaagctgg agtacaacgc gtcacccgaa tattctccca gtagcctcca agtagacgac    840
aaccatcgaa tctacgccgc gagatttaat gaacgactgc ttgcggcggt tagggtaacc    900
ctcagcggta cggaaggtgc tctggactcc ctgcgggtcc gagaggtgac aagacggaga    960
ggggtaggac aatatttgct cgaggaggtc cttagaaata accccggagt aagttgctgg   1020
tggatggcgg acgctggagt tgaggatcgc ggagtcatga cggctttcat gcaggccctt   1080
gggttcaccg cacagcaagg gggctgggag aagtgc                             1116
```

```
SEQ ID NO: 26           moltype = DNA   length = 1116
FEATURE                 Location/Qualifiers
source                  1..1116
                        mol_type = other DNA
                        organism = synthetic construct
SEQUENCE: 26
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgagag gtggcatcta acgtctatat caaggccgac    240
aagcagaaga acggcatcaa ggcgaacttc aagatccgcc acaacatcga ggacggcggc    300
gtgcagctcg cctaccacta ccagcagaac acccccatcg gcgacggcgg cgtgctgctg    360
cccgacaacc actacctgag cgtgcagtcc aaactttcga aagacccca cgagaagcgc    420
gatcacatg tcctgctgga gttcgtgacc gccgcgggga tcactctcgg catggacgag    480
ctgtacaagg cggtaccgg aggagcatg gtgagcaagg cgaggagct gttcaccggg    540
gtggtgccca tcctggtcga gctggacggc gacgtaaacg gccacaagtt cagcgtgtcc    600
ggcgagggtg agggcgatgc cacctacggc aagctgaccc tgaagttcat ctgcaccacc    660
ggcaagctgc ccgtgccctg gcccaccctc gtgaccaccc tgacctacgg cgtgcagtgc    720
ttcagccgct accccgacca catgaagcag cacgacttct tcaagtccgc catgcccgaa    780
ggctacatcc aggagcgcac catcttcttc aaggacgacg gcaactacaa gacccgcgcc    840
gaggtgaagt tcgagggcga cacctggtg aaccgcatcg agctgaaggg catcgacttc    900
aaggaggacg gcaacatcct ggggcacaag ctggagtaca acgcgtcaac aagacggaga    960
ggggtaggac aatatttgct cgaggaggtc cttagaaata accccggagt aagttgctgg   1020
tggatggcgg acgctggagt tgaggatcgc ggagtcatga cggctttcat gcaggccctt   1080
gggttcaccg cacagcaagg gggctgggag aagtgc                             1116
```

```
SEQ ID NO: 27           moltype = DNA   length = 1116
FEATURE                 Location/Qualifiers
source                  1..1116
                        mol_type = other DNA
                        organism = synthetic construct
SEQUENCE: 27
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgagca tctaacgtct atatcaaggc cgacaagcag    240
aagaacggca tcaaggcgaa cttcaagatc cgccacaaca tcgaggacgg cggcgtgcag    300
ctcgcctacc actaccagca gaacacccc atcggcgacg ccccgtgct gctgcccgac    360
aaccactacc tgagcgtgca gtccaaactt tcgaaagacc ccaacgagaa gcgcgatcac    420
atggtcctgc tggagttcgt gaccgccgcc gggatcactc tcggcatgga cgagctgtac    480
aagggcggta ccggagggag catggtgagc aagggcgagg agctgttcac cggggtggtg    540
cccatcctgg tcgagctgga cggcgacgta aacggccaca agttcagcgt gtccggcgag    600
ggtgagggcg atgccaccta cggcaagctg accctgaagt tcatctgcac caccggcaag    660
ctgcccgtgc cctggcccac cctcgtgacc accctgacct acggcgtgca gtgcttcagc    720
cgctacccc accacatgaa gcagcacgac ttcttcaagt ccgccatgcc cgaaggctac    780
atccaggagc gcaccatctt cttcaaggac gacggcaact acaagacccg cgccgaggtg    840
aagttcgagg gcgacaccct ggtgaaccgc atcgagctga agggcatcga cttcaaggag    900
gacggcaaca tcctgggca caagctggag tacaacgcgt cagaggtgac aagacggaga    960
ggggtaggac aatatttgct cgaggaggtc cttagaaata accccggagt aagttgctgg   1020
tggatggcgg acgctggagt tgaggatcgc ggagtcatga cggctttcat gcaggccctt   1080
gggttcaccg cacagcaagg gggctgggag aagtgc                             1116
```

```
SEQ ID NO: 28           moltype = DNA   length = 1116
FEATURE                 Location/Qualifiers
source                  1..1116
                        mol_type = other DNA
                        organism = synthetic construct
SEQUENCE: 28
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
```

-continued

```
ggtgctctgg actccctgcg ggtccgagag gtgacaagac ggagaggggt aggacaatat   240
ttgctcgagg aggtccttag aaataacccc ggagtaagtt gctggtggat ggcggacgca   300
tctaacgtct atatcaaggc cgacaagcag aagaacggca tcaaggcgaa cttcaagatc   360
cgccacaaca tcgaggacgg cggcgtgcag ctcgcctacc actaccagca gaacacccc   420
atcggcgacg gccccgtgct gctgcccgac aaccactacc tgagcgtgca gtccaaactt   480
tcgaaagacc ccaacgagaa gcgcgatcac atggtcctgc tggagttcgt gaccgccgcc   540
gggatcactc tcggcatgga cgagctgtac aaggcggta ccggaggag catggtgagc     600
aagggcgagg agctgttcac cggggtggtg cccatcctgg tcgagctgga cggcgacgta   660
aacggccaca agttcagcgt gtccggcgag ggtgagggcg atgccaccta cggcaagctg   720
accctgaagt tcatctgcac caccggcaag ctgcccgtgc cctggcccac cctcgtgacc   780
accctgacct acggcgtgca gtgcttcagc cgctaccccg accacatgaa gcagcacgac   840
ttcttcaagt ccgccatgcc cgaaggctac atccaggagc gcaccatctt cttcaaggac   900
gacggcaact acaagacccg cgccgaggtg aagttcgagg gcgacaccct ggtgaaccgc   960
atcgagctga agggcatcga cttcaaggag gacggcaaca tcctgggca caagctggag   1020
tacaacgcgt cagctggagt tgaggatcgc ggagtcatga cggctttcat gcaggccctt   1080
gggttcaccg cacagcaagg gggctgggag aagtgc                            1116
```

SEQ ID NO: 29          moltype = DNA   length = 1116
FEATURE                Location/Qualifiers
source                 1..1116
                       mol_type = other DNA
                       organism = synthetic construct
SEQUENCE: 29

```
atgaagctga caatcattcg cctggagaaa ttttccgacc aggatagaat cgaccttcag   60
aagatctggc ccgaatattc tcccagtagc ctccaagtag acgacaacca tcgaatctac   120
gccgcgagat ttaatgaacg actgcttgcg gcggttgcgg taaccctag cggtacggaa    180
ggtgctctgg actccctgcg ggtccgagag gtgacaagac ggagagggt aggacaatat    240
ttgctcgagg aggtccttag aaataacccc ggagtaagtt gctggtggat ggcggacgct   300
ggagttgagg atgcatctaa cgtctatatc aaggccgaca agcagaagaa cggcatcaag   360
gcgaacttca agatccgcca caacatcgag gacggcccc gtgctgctgc ccgacaacca    420
cagcagaaca cccccatcgg cgacggcccc gtgctgctgc ccgacaacca ctacctgagc   480
gtgcagtcca actttcgaa agaccccaac gagaagcgcg atcacatggt cctgctggag     540
ttcgtgaccg ccgcgggat cactctcggc atggacgagc tgtacaaggg cggtaccgga    600
gggagcatgg tgagcaaggg cgaggagctg ttcaccgggg tggtgcccat cctggtcgag   660
ctggacggcg acgtaaacg ccacaagttc agcgtgtccg gcgagggtga gggcgatgcc    720
acctacggca agctgaccct gaagttcatc tgcaccaccg gcaagctgcc cgtgccctgg    780
cccacccctg tgaccaccct gacctacggc gtgcagtgct tcagccgcta ccccgaccac    840
atgaagcagc acgacttctt caagtccgcc atgcccgaag gctacatcca ggagcgcacc    900
atcttcttca aggacgacgg caactacaag acccgcgccg aggtgaagtt cgagggcgac    960
accctggtga accgcatcga gctgaagggc atcgacttca aggaggacgg caacatcctg   1020
gggcacaagc tggagtacaa cgcgtcacgc ggagtcatga cggctttcat gcaggcccctt   1080
gggttcaccg cacagcaagg gggctgggag aagtgc                            1116
```

SEQ ID NO: 30          moltype = DNA   length = 1116
FEATURE                Location/Qualifiers
source                 1..1116
                       mol_type = other DNA
                       organism = synthetic construct
SEQUENCE: 30

```
atgaagctga caatcattcg cctggagaaa ttttccgacc aggatagaat cgaccttcag   60
aagatctggc ccgaatattc tcccagtagc ctccaagtag acgacaacca tcgaatctac   120
gccgcgagat ttaatgaacg actgcttgcg gcggttaggg taaccctcag cggtacggaa   180
ggtgctctgg actccctgcg ggtccgagag gtgacaagac ggagagggt aggacaatat    240
ttgctcgagg aggtccttag aaataacccc ggagtaagtt gctggtggat ggcggacgct   300
ggagttgagg atcgcggagt catgacggct ttcatgggg cccttgggga tctaacggat    360
tatatcaagg ccgacaagca gaagaacggc atcaaggcga acttcaagat ccgccacaac   420
atcgaggacg gcgcgtgca gctcgcctac cactaccagc agaacacccc catcggcgac    480
ggccccgtgc tgctgcccga caaccactac ctgagcgtgc agtccaaact tcgaaagac    540
cccaacgaga agcgcgatca catggtcctg ctggagttcg tgaccgccgc cgggatcact   600
ctcggcatgg acgagctgta caagggcggt accggaggag catggtgag caagggcgag    660
gagctgttca ccggggtggt gcccatcctg gtcgagctgg acggcgacgt aaacggccac   720
aagttcagcg tgtccggcga gggtgagggc gatgccacct acggcaagct gaccctgaag   780
ttcatctgca ccaccggcaa gctgcccgtg ccctggccca ccctcgtgac caccctgacc   840
tacggcgtgc agtgcttcag ccgctacccc gaccacatga agcagcacga cttcttcaag   900
tccgccatgc ccgaaggcta catccaggag cgcaccatct tcttcaagga cgacggcaac   960
tacaagaccc gcgccgaggt gaagttcgag ggcgacaccc tggtgaaccg catcgagctg   1020
aagggcatcg acttcaagga ggacggcaac atcctgggc acaagctgga gtacaacgcg    1080
tcattcaccg cacagcaagg gggctgggag aagtgc                            1116
```

SEQ ID NO: 31          moltype = DNA   length = 1116
FEATURE                Location/Qualifiers
source                 1..1116
                       mol_type = other DNA
                       organism = synthetic construct
SEQUENCE: 31

```
atgaagctga caatcattcg cctggagaaa ttttccgacc aggatagaat cgaccttcag   60
aagatctggc ccgaatattc tcccagtagc ctccaagtag acgacaacca tcgaatctac   120
gccgcgagat ttaatgaacg actgcttgcg gcggttaggg taaccctcag cggtacggaa   180
ggtgctctgg actccctgcg ggtccgagga gcaagtaacg tctatatcaa ggccgacaag   240
```

-continued

```
cagaagaacg gcatcaaggc gaacttcaag atccgccaca acatcgagga cggcggcgtg    300
cagctcgcct accactacca gcagaacacc cccatcggcg acggccccgt gctgctgccc    360
gacaaccact acctgagcgt gcagtccaaa ctttcgaaag accccaacga gaagcgcgat    420
cacatggtcc tgctggagtt cgtgaccgcc gccgggatca ctctcggcat ggacgagctg    480
tacaagggcg gtaccggagg gagcatggtg agcaagggcg aggagctgtt caccggggtg    540
gtgcccatcc tggtcgagct ggacggcgac gtaaacggcc acaagttcag cgtgtccggc    600
gagggtgagg gcgatgccac ctacggcaag ctgaccctga agttcatctg caccaccggc    660
aagctgcccg tgccctggcc caccctcgtg accaccctga cctacggcgt gcagtgcttc    720
agccgctacc ccgaccacat gaagcagcac gacttcttca agtccgccat gcccgaaggc    780
tacatccagg agcgcaccat cttcttcaag gacgacggca actacaagac ccgcgccgag    840
gtgaagttcg agggcgacac cctggtgaac cgcatcgagc tgaagggcat cgacttcaag    900
gaggacggca acatcctggg gcacaagctg gagtacaacg gtgaggtgac aagacggaga    960
ggggtaggac aatatttgct cgaggaggtc cttagaaata accccggagt aagttgctgg    1020
tggatggcgg acgctggagt tgaggatcgc ggagtcatga cggctttcat gcaggccctt    1080
gggttcaccg cacagcaagg gggctgggag aagtgc                              1116

SEQ ID NO: 32           moltype = DNA  length = 1113
FEATURE                 Location/Qualifiers
source                  1..1113
                        mol_type = other DNA
                        organism = synthetic construct
SEQUENCE: 32
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgagga gcaagtaacg tctatatcaa ggccgacaag    240
cagaagaacg gcatcaaggc gaacttcaag atccgccaca acatcgagga cggcggcgtg    300
cagctcgcct accactacca gcagaacacc cccatcggcg acggccccgt gctgctgccc    360
gacaaccact acctgagcgt gcagtccaaa ctttcgaaag accccaacga gaagcgcgat    420
cacatggtcc tgctggagtt cgtgaccgcc gccgggatca ctctcggcat ggacgagctg    480
tacaagggcg gtaccggagg gagcatggtg agcaagggcg aggagctgtt caccggggtg    540
gtgcccatcc tggtcgagct ggacggcgac gtaaacggcc acaagttcag cgtgtccggc    600
gagggtgagg gcgatgccac ctacggcaag ctgaccctga agttcatctg caccaccggc    660
aagctgcccg tgccctggcc caccctcgtg accaccctga cctacggcgt gcagtgcttc    720
agccgctacc ccgaccacat gaagcagcac gacttcttca agtccgccat gcccgaaggc    780
tacatccagg agcgcaccat cttcttcaag gacgacggca actacaagac ccgcgccgag    840
gtgaagttcg agggcgacac cctggtgaac cgcatcgagc tgaagggcat cgacttcaag    900
gaggacggca acatcctggg gcacaagctg gagtacaacg gtgacaag acggagaggg      960
gtaggacaat atttgctcga ggaggtcctt agaaataacc ccgagtaag ttgctggtgg    1020
atggcggacg ctggagttga ggatcgcgga gtcatgacgg ctttcatgca ggcccttggg    1080
ttcaccgcac agcaaggggg ctgggagaag tgc                                1113

SEQ ID NO: 33           moltype = DNA  length = 1110
FEATURE                 Location/Qualifiers
source                  1..1110
                        mol_type = other DNA
                        organism = synthetic construct
SEQUENCE: 33
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgagga gcaaacgtct atatcaaggc cgacaagcag    240
aagaacggca tcaaggcgaa cttcaagatc cgccacaaca tcgaggacgg cggcgtgcag    300
ctcgcctacc actaccagca gaacaccccc atcggcgacg gccccgtgct gctgcccgac    360
aaccactacc tgagcgtgca gtccaaactt cgaaagacaa ccaacgagaa gcgcgatcac    420
atggtcctgc tggagttcgt gaccgccgcc gggatcactc tcggcatgga cgagctgtac    480
aagggcggta ccggagggag catggtgagc aagggcgagg agctgttcac cggggtggtg    540
cccatcctgt cgagctgga cggcgacgta aacggccaca agttcagcgt gtccggcgag    600
ggtgagggc atgccaccta cggcaagctg accctgaagt tcatctgcac caccggcaag    660
ctgcccgtgc cctggcccac cctcgtgacc accctgacct acggcgtgca gtgcttcagc    720
cgctacccc accacatgaa gcagcacgac ttcttcaagt ccgccatgcc cgaaggctac    780
atccaggagc gcaccatctt cttcaaggac gacggcaact acaagacccg cgcgaggtg    840
aagttcgagg gcgacaccct ggtgaaccgc atcgagctga agggcatcga cttcaaggag    900
gacggcaaca tcctggggca caagctggag tacaacggtg acaagacgga gaggggta      960
ggacaatatt tgctcgagga ggtccttaga ataaccccg agtaagttg ctggtggatg    1020
gcggacgctg gagttgagga tcgcggagtc atgacggctt tcatgcaggc ccttgggttc    1080
accgcacagc aagggggctg ggagaagtgc                                    1110

SEQ ID NO: 34           moltype = DNA  length = 1104
FEATURE                 Location/Qualifiers
source                  1..1104
                        mol_type = other DNA
                        organism = synthetic construct
SEQUENCE: 34
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgaaac gtctatatca aggccgacaa gcagaagaac    240
ggcatcaagg cgaacttcaa gatccgccac aacatcgagg acggcggcgt gcagctcgcc    300
```

```
taccactacc agcagaacac ccccatcggc gacggccccg tgctgctgcc cgacaaccac    360
tacctgagcg tgcagtccaa actttcgaaa gaccccaacg agaagcgcga tcacatggtc    420
ctgctggagt tcgtgaccgc cgccgggatc actctcggca tggacgagct gtacaagggc    480
ggtaccggag ggagcatggt gagcaagggc gaggagctgt tcaccggggt ggtgcccatc    540
ctggtcgagc tggacggcga cgtaaacggc cacaagttca gcgtgtccgg cgagggtgag    600
ggcgatgcca cctacggcaa gctgaccctg aagttcatct gcaccaccgg caagctgccc    660
gtgccctggc ccaccctcgt gaccaccctg acctacggcg tgcagtgctt cagccgctac    720
cccgaccaca tgaagcagca cgacttcttc aagtccgcca tgcccgaagg ctacatccag    780
gagcgcacca tcttcttcaa ggacgacggc aactacaaga cccgcgccga ggtgaagttc    840
gagggcgaca ccctggtgaa ccgcatcgag ctgaagggca tcgacttcaa ggaggacggc    900
aacatcctgg ggcacaagct ggagtacaac gaggtgacaa gacggagagg ggtaggacaa    960
tatttgctcg aggaggtcct tagaaataac cccggagtaa gttgctggtg gatggcggac   1020
gctggagttg aggatcgcgg agtcatgacg gctttcatgc aggcccttgg gttcaccgca   1080
cagcaagggg gctgggagaa gtgc                                          1104
```

SEQ ID NO: 35          moltype = DNA  length = 1116
FEATURE                Location/Qualifiers
source                 1..1116
                       mol_type = other DNA
                       organism = synthetic construct
SEQUENCE: 35

```
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgagga aacgtctata tcaaggccga caagcagaag    240
aacggcatca aggcgaactt caagatccgc cacaacatcg aggacggcgg cgtgcagctc    300
gcctaccact accagcagaa cacccccatc ggcgacggcc ccgtgctgct gcccgacaac    360
cactacctga gcgtgcagtc caaactttcg aaagacccca acgagaagcg cgatcacatg    420
gtcctgctgg agttcgtgac cgccgccggg atcactctcg gcatggacga gctgtacaag    480
ggcggtaccg gagggagcat ggtgagcaag ggcgaggagc tgttcaccgg ggtggtgccc    540
atcctggtcg agctggacgg cgacgtaaac ggccacaagt tcagcgtgtc cggcgagggt    600
gagggcgatg ccacctacgg caagctgacc ctgaagttca tctgcaccac cggcaagctg    660
cccgtgccct ggcccaccct cgtgaccacc ctgacctacg gcgtgcagtg cttcagccgc    720
taccccgacc acatgaagca cgacttcttc aagtccgcca tgcccgaagg ctacatcatc    780
caggagcgca ccatcttctt caaggacgac ggcaactaca gacccgcgc gaggtgaag    840
ttcgagggcg acaccctggt gaaccgcatc gagctgaagg gcatcgactt caaggaggac    900
ggcaacatcc tggggcacaa gctggagtac aacggtgctt cagaggtgac aagacggaga    960
ggggtaggac aatatttgct cgaggaggtc cttagaaata accccggagt aagttgctgg   1020
tggatggcgg acgctggagt tgaggatcgc ggagtcatga cggctttcat gcaggccctt   1080
gggttcaccg cacagcaagg gggctgggag aagtgc                             1116
```

SEQ ID NO: 36          moltype = DNA  length = 1113
FEATURE                Location/Qualifiers
source                 1..1113
                       mol_type = other DNA
                       organism = synthetic construct
SEQUENCE: 36

```
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgaaac gtctatatca aggccgacaa gcagaagaac    240
ggcatcaagg cgaacttcaa gatccgccac aacatcgagg acggcggcgt gcagctcgcc    300
taccactacc agcagaacac ccccatcggc gacggccccg tgctgctgcc cgacaaccac    360
tacctgagcg tgcagtccaa actttcgaaa gaccccaacg agaagcgcga tcacatggtc    420
ctgctggagt tcgtgaccgc cgccgggatc actctcggca tggacgagct gtacaagggc    480
ggtaccggag ggagcatggt gagcaagggc gaggagctgt tcaccggggt ggtgcccatc    540
ctggtcgagc tggacggcga cgtaaacggc cacaagttca gcgtgtccgg cgagggtgag    600
ggcgatgcca cctacggcaa gctgaccctg aagttcatct gcaccaccgg caagctgccc    660
gtgccctggc ccaccctcgt gaccaccctg acctacggcg tgcagtgctt cagccgctac    720
cccgaccaca tgaagcagca cgacttcttc aagtccgcca tgcccgaagg ctacatccag    780
gagcgcacca tcttcttcaa ggacgacggc aactacaaga cccgcgccga ggtgaagttc    840
gagggcgaca ccctggtgaa ccgcatcgag ctgaagggca tcgacttcaa ggaggacggc    900
aacatcctgg ggcacaagct ggagtacaac ggtgctcag aggtgacaag acggagaggg    960
gtaggacaat atttgctcga ggaggtcctt agaaataccc cggagtaag ttgctggtgg   1020
atggcggacg ctggagttga ggatcgcgga gtcatgacgg ctttcatgca ggcccttggg   1080
ttcaccgcac agcaaggggg ctgggagaag tgc                                1113
```

SEQ ID NO: 37          moltype = DNA  length = 1116
FEATURE                Location/Qualifiers
source                 1..1116
                       mol_type = other DNA
                       organism = synthetic construct
SEQUENCE: 37

```
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgagga gcaaacgtct atatcaaggc cgacaagcag    240
aagaacggca tcaaggcgaa cttcaagatc cgccacaaca tcgaggacgg cggcgtgcag    300
ctcgcctacc actaccagca gaacaccccc atcggcgacg gccccgtgct gctgcccgac    360
```

```
aaccactacc tgagctatca gtccgtactt tcgaaagacc ccaacgagaa gcgcgatcac    420
atggtcctgc tggagttcgt gaccgccgcc gggatcactc tcggcatgga cgagctgtac    480
aagggcggta ccggagggag catggtgagc aagggcgagg agctgttcac cggggtggtg    540
cccatcctgg tcgagctgga cggcgacgta aacggccaca agttcagcgt gtccggcgag    600
ggtgagggcg atgccaccta cggcaagctg accctgaagt tcatctgcac caccggcaag    660
ctgcccgtgc cctggcccac cctcgtgacc accctgacct acggcgtgca gtgcttcagc    720
cgctaccccg accacatgaa gcagcacgac ttcttcaagt ccgccatgcc cgaaggctac    780
atccaggagc gcaccatctt cttcaaggac gacggcaact acaagacccg cgccgaggtg    840
aagttcgagg gcgacaccct ggtgaaccgc atcgagctga agggcatcga cttcaaggag    900
gacggcaaca tcctggggca caagctggag tacaacggtg ctgaggtgac aagacggaga    960
ggggtaggac aatatttgct cgaggaggtc cttagaaata accccggagt aagttgctgg   1020
tggatggcgg acgctggagt tgaggatcgc ggagtcatga cggctttcat gcaggccctt   1080
gggttcaccg cacagcaagg gggctgggag aagtgc                            1116
```

```
SEQ ID NO: 38          moltype = DNA  length = 1116
FEATURE                Location/Qualifiers
source                 1..1116
                       mol_type = other DNA
                       organism = synthetic construct
SEQUENCE: 38
atgaagctga caatcattcg cctggagaaa ttttccgacc aggatagaat cgaccttcag     60
aagatctggc ccgaatattc tcccagtagc ctccaagtag acgacaacca tcgaatctac    120
gccgcgagat ttaatgaacg actgcttgcg gcggttaggg taaccctcag cggtacggaa    180
ggtgctctgg actccctgcg ggtccgagga gcaaacgtct atatcaaggc cgacaagcag    240
aagaacggca tcaaggcgaa cttcaagatc cgccacaaca tcgaggacgg cggcgtgcag    300
ctcgcctacc actaccagca gaacaccccc atcggcgacg gccccgtgct gctgcccgac    360
aaccactacc tgagcgtgca gtccaaactt tcgaaagacc ccaacgagaa gcgcgatcac    420
atggtcctgc tggagttcgt gaccgccgcc gggatcactc tcggcatgga cgagctgtac    480
aagggcggta ccggagggag catggtgagc aagggcgagg agctgttcac cggggtggtg    540
cccatcctgg tcgagctgga cggcgacgta aacggccaca agttcagcgt gtccggcgag    600
ggtgagggcg atgccaccta cggcaagctg accctgaagt tcatctgcac caccggcaag    660
ctgcccgtgc cctggcccac cctcgtgacc accctgtccc acggcgtgca gtgcttcagc    720
cgctaccccg accacatgaa gcagcacgac ttcttcaagt ccgccatgcc cgaaggctac    780
atccaggagc gcaccatctt cttcaaggac gacggcaact acaagacccg cgccgaggtg    840
aagttcgagg gcgacaccct ggtgaaccgc atcgagctga agggcatcga cttcaaggag    900
gacggcaaca tcctggggca caagctggag tacaacggtg ctgaggtgac aagacggaga    960
ggggtaggac aatatttgct cgaggaggtc cttagaaata accccggagt aagttgctgg   1020
tggatggcgg acgctggagt tgaggatcgc ggagtcatga cggctttcat gcaggccctt   1080
gggttcaccg cacagcaagg gggctgggag aagtgc                            1116
```

```
SEQ ID NO: 39          moltype = AA  length = 141
FEATURE                Location/Qualifiers
source                 1..141
                       mol_type = protein
                       organism = synthetic construct
SEQUENCE: 39
MHHHHHHENL YFQSMKLTII RLEKFSDQDR IDLQKIWPEY SPSSLQVDDN HRIYAARFNE     60
RLLAAVRVTL SGTEGALDSL RVREVTRRRG VGQYLLEEVL RNNPGVSCWW MADAGVEDRG    120
VMTAFMQALG FTAQQGGWEK C                                              141
```

```
SEQ ID NO: 40          moltype = AA  length = 255
FEATURE                Location/Qualifiers
source                 1..255
                       mol_type = protein
                       organism = synthetic construct
SEQUENCE: 40
MHHHHHHENL YFQSNVYIKA DKQKNGIKAN FKIRHNIEDG GVQLAYHYQQ NTPIGDGPVL     60
LPDNHYLSVQ SKLSKDPNEK RDHMVLLEFV TAAGITLGMD ELYKGGTGGS MVSKGEELFT    120
GVVPILVELD GDVNGHKFSV SGEGEGDATY GKLTLKFICT TGKLPVPWPT LVTTLTYGVQ    180
CFSRYPDHMK QHDFFKSAMP EGYIQERTIF FKDDGNYKTR AEVKFEGDTL VNRIELKGID    240
FKEDGNILGH KLEYN                                                     255
```

```
SEQ ID NO: 41          moltype = AA  length = 255
FEATURE                Location/Qualifiers
source                 1..255
                       mol_type = protein
                       organism = synthetic construct
SEQUENCE: 41
MHHHHHHENL YFQSNVYIKA DKQKNGIKAN FKIRHNIEDG GVQLAYHYQQ NTPIGDGPVL     60
LPDNHYLSYQ SVLSKDPNEK RDHMVLLEFV TAAGITLGMD ELYKGGTGGS MVSKGEELFT    120
GVVPILVELD GDVNGHKFSV SGEGEGDATY GKLTLKFICT TGKLPVPWPT LVTTLTYGVQ    180
CFSRYPDHMK QHDFFKSAMP EGYIQERTIF FKDDGNYKTR AEVKFEGDTL VNRIELKGID    240
FKEDGNILGH KLEYN                                                     255
```

```
SEQ ID NO: 42          moltype = AA  length = 255
FEATURE                Location/Qualifiers
source                 1..255
                       mol_type = protein
                       organism = synthetic construct
```

```
SEQUENCE: 42
MHHHHHHENL YFQSNVYIKA DKQKNGIKAN FKIRHNIEDG GVQLAYHYQQ NTPIGDGPVL    60
LPDNHYLSVQ SKLSKDPNEK RDHMVLLEFV TAAGITLGMD ELYKGGTGGS MVSKGEELFT   120
GVVPILVELD GDVNGHKFSV SGEGEGDATY GKLTLKFICT TGKLPVPWPT LVTTLSHGVQ   180
CFSRYPDHMK QHDFFKSAMP EGYIQERTIF FKDDGNYKTR AEVKFEGDTL VNRIELKGID   240
FKEDGNILGH KLEYN                                                     255

SEQ ID NO: 43                    moltype = AA  length = 386
FEATURE                          Location/Qualifiers
source                           1..386
                                 mol_type = protein
                                 organism = synthetic construct
SEQUENCE: 43
MHHHHHHENL YFQSMKLTII RLEKFSDQDR IDLQKIWPEY SPSSLQVDDN HRIYAARFNE    60
RLLAAVRVTL SGTEGALDSL RVRGANVYIK ADKQKNGIKA NFKIRHNIED GGVQLAYHYQ   120
QNTPIGDGPV LLPDNHYLSV QSKLSKDPNE KRDHMVLLEF VTAAGITLGM DELYKGGTGG   180
SMVSKGEELF TGVVPILVEL DGDVNGHKFS VSGEGEGDAT YGKLTLKFIC TTGKLPVPWP   240
TLVTTLTYGV QCFSRYPDHM KQHDFFKSAM PEGYIQERTI FFKDDGNYKT RAEVKFEGDT   300
LVNRIELKGI DFKEDGNILG HKLEYNGAEV TRRRGVGQYL LEEVLRNNPG VSCWWMADAG   360
VEDRGVMTAF MQALGFTAQQ GGWEKC                                        386

SEQ ID NO: 44                    moltype = AA  length = 386
FEATURE                          Location/Qualifiers
source                           1..386
                                 mol_type = protein
                                 organism = synthetic construct
SEQUENCE: 44
MHHHHHHENL YFQSMKLTII RLEKFSDQDR IDLQKIWASN VYIKADKQKN GIKANFKIRH    60
NIEDGGVQLA YHYQQNTPIG DGPVLLPDNH YLSVQSKLSK DPNEKRDHMV LLEFVTAAGI   120
TLGMDELYKG GTGGSMVSKG EELFTGVVPI LVELDGDVNG HKFSVSGEGE GDATYGKLTL   180
KFICTTGKLP VPWPTLVTTL TYGVQCFSRY PDHMKQHDFF KSAMPEGYIQ ERTIFFKDDG   240
NYKTRAEVKF EGDTLVNRIE LKGIDFKEDG NILGHKLEYN ASPEYSPSSL QVDDNHRIYA   300
ARFNERLLAA VRVTLSGTEG ALDSLRVREV TRRRGVGQYL LEEVLRNNPG VSCWWMADAG   360
VEDRGVMTAF MQALGFTAQQ GGWEKC                                        386

SEQ ID NO: 45                    moltype = AA  length = 386
FEATURE                          Location/Qualifiers
source                           1..386
                                 mol_type = protein
                                 organism = synthetic construct
SEQUENCE: 45
MHHHHHHENL YFQSMKLTII RLEKFSDQDR IDLQKIWPEY SPSSLQVDDN HRIYAARFNE    60
RLLAAVRVTL SGTEGALDSL RVREVASNVY IKADKQKNGI KANFKIRHNI EDGGVQLAYH   120
YQQNTPIGDG PVLLPDNHYL SVQSKLSKDP NEKRDHMVLL EFVTAAGITL GMDELYKGGT   180
GGSMVSKGEE LFTGVVPILV ELDGDVNGHK FSVSGEGEGD ATYGKLTLKF ICTTGKLPVP   240
WPTLVTTLTY GVQCFSRYPD HMKQHDFFKS AMPEGYIQER TIFFKDDGNY KTRAEVKFEG   300
DTLVNRIELK GIDFKEDGNI LGHKLEYNAS TRRRGVGQYL LEEVLRNNPG VSCWWMADAG   360
VEDRGVMTAF MQALGFTAQQ GGWEKC                                        386

SEQ ID NO: 46                    moltype = AA  length = 386
FEATURE                          Location/Qualifiers
source                           1..386
                                 mol_type = protein
                                 organism = synthetic construct
SEQUENCE: 46
MHHHHHHENL YFQSMKLTII RLEKFSDQDR IDLQKIWPEY SPSSLQVDDN HRIYAARFNE    60
RLLAAVRVTL SGTEGALDSL RVRASNVYIK ADKQKNGIKA NFKIRHNIED GGVQLAYHYQ   120
QNTPIGDGPV LLPDNHYLSV QSKLSKDPNE KRDHMVLLEF VTAAGITLGM DELYKGGTGG   180
SMVSKGEELF TGVVPILVEL DGDVNGHKFS VSGEGEGDAT YGKLTLKFIC TTGKLPVPWP   240
TLVTTLTYGV QCFSRYPDHM KQHDFFKSAM PEGYIQERTI FFKDDGNYKT RAEVKFEGDT   300
LVNRIELKGI DFKEDGNILG HKLEYNASEV TRRRGVGQYL LEEVLRNNPG VSCWWMADAG   360
VEDRGVMTAF MQALGFTAQQ GGWEKC                                        386

SEQ ID NO: 47                    moltype = AA  length = 386
FEATURE                          Location/Qualifiers
source                           1..386
                                 mol_type = protein
                                 organism = synthetic construct
SEQUENCE: 47
MHHHHHHENL YFQSMKLTII RLEKFSDQDR IDLQKIWPEY SPSSLQVDDN HRIYAARFNE    60
RLLAAVRVTL SGTEGALDSL RVREVTRRRG VGQYLLEEVL RNNPGVSCWW MADASNVYIK   120
ADKQKNGIKA NFKIRHNIED GGVQLAYHYQ QNTPIGDGPV LLPDNHYLSV QSKLSKDPNE   180
KRDHMVLLEF VTAAGITLGM DELYKGGTGG SMVSKGEELF TGVVPILVEL DGDVNGHKFS   240
VSGEGEGDAT YGKLTLKFIC TTGKLPVPWP TLVTTLTYGV QCFSRYPDHM KQHDFFKSAM   300
PEGYIQERTI FFKDDGNYKT RAEVKFEGDT LVNRIELKGI DFKEDGNILG HKLEYNASAG   360
VEDRGVMTAF MQALGFTAQQ GGWEKC                                        386

SEQ ID NO: 48                    moltype = AA  length = 386
FEATURE                          Location/Qualifiers
```

```
source                    1..386
                          mol_type = protein
                          organism = synthetic construct
SEQUENCE: 48
MHHHHHHENL YFQSMKLTII RLEKFSDQDR IDLQKIWPEY SPSSLQVDDN HRIYAARFNE   60
RLLAAVRVTL SGTEGALDSL RVREVTRRRG VGQYLLEEVL RNNPGVSCWW MADAGVEDAS  120
NVYIKADKQK NGIKANFKIR HNIEDGGVQL AYHYQQNTPI GDGPVLLPDN HYLSVQSKLS  180
KDPNEKRDHM VLLEFVTAAG ITLGMDELYK GGTGGSMVSK GEELFTGVVP ILVELDGDVN  240
GHKFSVSGEG EGDATYGKLT LKFICTTGKL PVPWPTLVTT LTYGVQCFSR YPDHMKQHDF  300
FKSAMPEGYI QERTIFFKDD GNYKTRAEVK FEGDTLVNRI ELKGIDFKED GNILGHKLEY  360
NASRGVMTAF MQALGFTAQQ GGWEKC                                      386

SEQ ID NO: 49            moltype = AA   length = 386
FEATURE                  Location/Qualifiers
source                   1..386
                         mol_type = protein
                         organism = synthetic construct
SEQUENCE: 49
MHHHHHHENL YFQSMKLTII RLEKFSDQDR IDLQKIWPEY SPSSLQVDDN HRIYAARFNE   60
RLLAAVRVTL SGTEGALDSL RVREVTRRRG VGQYLLEEVL RNNPGVSCWW MADAGVEDRG  120
VMTAFMQALG ASNVYIKADK QKNGIKANFK IRHNIEDGGV QLAYHYQQNT PIGDGPVLLP  180
DNHYLSVQSK LSKDPNEKRD HMVLLEFVTA AGITLGMDEL YKGGTGGSMV SKGEELFTGV  240
VPILVELDGD VNGHKFSVSG EGEGDATYGK LTLKFICTTG KLPVPWPTLV TTLTYGVQCF  300
SRYPDHMKQH DFFKSAMPEG YIQERTIFFK DDGNYKTRAE VKFEGDTLVN RIELKGIDFK  360
EDGNILGHKL EYNASFTAQQ GGWEKC                                      386

SEQ ID NO: 50            moltype = AA   length = 371
FEATURE                  Location/Qualifiers
source                   1..371
                         mol_type = protein
                         organism = synthetic construct
SEQUENCE: 50
KLTIIRLEKF SDQDRIDLQK IWPEYSPSSL QVDDNHRIYA ARFNERLLAA VRVTLSGTEG   60
ALDSLRVRGA SNVYIKADKQ KNGIKANFKI RHNIEDGGVQ LAYHYQQNTP IGDGPVLLPD  120
NHYLSVQSKL SKDPNEKRDH MVLLEFVTAA GITLGMDELY KGGTGGSMVS KGEELFTGVV  180
PILVELDGDV NGHKFSVSGE GEGDATYGKL TLKFICTTGK LPVPWPTLVT TLTYGVQCFS  240
RYPDHMKQHD FFKSAMPEGY IQERTIFFKD DGNYKTRAEV KFEGDTLVNR IELKGIDFKE  300
DGNILGHKLE YNGEVTRRRG VGQYLLEEVL RNNPGVSCWW MADAGVEDRG VMTAFMQALG  360
FTAQQGGWEK C                                                      371

SEQ ID NO: 51            moltype = AA   length = 385
FEATURE                  Location/Qualifiers
source                   1..385
                         mol_type = protein
                         organism = synthetic construct
SEQUENCE: 51
MHHHHHHENL YFQSMKLTII RLEKFSDQDR IDLQKIWPEY SPSSLQVDDN HRIYAARFNE   60
RLLAAVRVTL SGTEGALDSL RVRGASNVYI KADKQKNGIK ANFKIRHNIE DGGVQLAYHY  120
QQNTPIGDGP VLLPDNHYLS VQSKLSKDPN EKRDHMVLLE FVTAAGITLG MDELYKGGTG  180
GSMVSKGEEL FTGVVPILVE LDGDVNGHKF SVSGEGEGDA TYGKLTLKFI CTTGKLPVPW  240
PTLVTTLTYG VQCFSRYPDH MKQHDFFKSA MPEGYIQERT IFFKDDGNYK TRAEVKFEGD  300
TLVNRIELKG IDFKEDGNIL GHKLEYNEVT RRRGVGQYLL EEVLRNNPGV SCWWMADAGV  360
EDRGVMTAFM QALGFTAQQG GWEKC                                       385

SEQ ID NO: 52            moltype = AA   length = 384
FEATURE                  Location/Qualifiers
source                   1..384
                         mol_type = protein
                         organism = synthetic construct
SEQUENCE: 52
MHHHHHHENL YFQSMKLTII RLEKFSDQDR IDLQKIWPEY SPSSLQVDDN HRIYAARFNE   60
RLLAAVRVTL SGTEGALDSL RVRGANVYIK ADKQKNGIKA NFKIRHNIED GGVQLAYHYQ  120
QNTPIGDGPV LLPDNHYLSV QSKLSKDPNE KRDHMVLLEF VTAAGITLGM DELYKGGTGG  180
SMVSKGEELF TGVVPILVEL DGDVNGHKFS VSGEGEGDAT YGKLTLKFIC TTGKLPVPWP  240
TLVTTLTYGV QCFSRYPDHM KQHDFFKSAM PEGYIQERTI FFKDDGNYKT RAEVKFEGDT  300
LVNRIELKGI DFKEDGNILG HKLEYNEVTR RRGVGQYLLE EVLRNNPGVS CWWMADAGVE  360
DRGVMTAFMQ ALGFTAQQGG WEKC                                        384

SEQ ID NO: 53            moltype = AA   length = 382
FEATURE                  Location/Qualifiers
source                   1..382
                         mol_type = protein
                         organism = synthetic construct
SEQUENCE: 53
MHHHHHHENL YFQSMKLTII RLEKFSDQDR IDLQKIWPEY SPSSLQVDDN HRIYAARFNE   60
RLLAAVRVTL SGTEGALDSL RVRNVYIKAD KQKNGIKANF KIRHNIEDGG VQLAYHYQQN  120
TPIGDGPVLL PDNHYLSVQS KLSKDPNEKR DHMVLLEFVT AAGITLGMDE LYKGGTGGSM  180
VSKGEELFTG VVPILVELDG DVNGHKFSVS GEGEGDATYG KLTLKFICTT GKLPVPWPTL  240
VTTLTYGVQC FSRYPDHMKQ HDFFKSAMPE GYIQERTIFF KDDGNYKTRA EVKFEGDTLV  300
```

-continued

```
NRIELKGIDF KEDGNILGHK LEYNEVTRRR GVGQYLLEEV LRNNPGVSCW WMADAGVEDR   360
GVMTAFMQAL GFTAQQGGWE KC                                            382

SEQ ID NO: 54           moltype = AA  length = 386
FEATURE                 Location/Qualifiers
source                  1..386
                        mol_type = protein
                        organism = synthetic construct
SEQUENCE: 54
MHHHHHHENL YFQSMKLTII RLEKFSDQDR IDLQKIWPEY SPSSLQVDDN HRIYAARFNE   60
RLLAAVRVTL SGTEGALDSL RVRGNVYIKA DKQKNGIKAN FKIRHNIEDG GVQLAYHYQQ   120
NTPIGDGPVL LPDNHYLSVQ SKLSKDPNEK RDHMVLLEFV TAAGITLGMD ELYKGGTGGS   180
MVSKGEELFT GVVPILVELD GDVNGHKFSV SGEGEGDATY GKLTLKFICT TGKLPVPWPT   240
LVTTLTYGVQ CFSRYPDHMK QHDFFKSAMP EGYIQERTIF FKDDGNYKTR AEVKFEGDTL   300
VNRIELKGID FKEDGNILGH KLEYNGASEV TRRRGVGQYL LEEVLRNNPG VSCWWMADAG   360
VEDRGVMTAF MQALGFTAQQ GGWEKC                                        386

SEQ ID NO: 55           moltype = AA  length = 385
FEATURE                 Location/Qualifiers
source                  1..385
                        mol_type = protein
                        organism = synthetic construct
SEQUENCE: 55
MHHHHHHENL YFQSMKLTII RLEKFSDQDR IDLQKIWPEY SPSSLQVDDN HRIYAARFNE   60
RLLAAVRVTL SGTEGALDSL RVRNVYIKAD KQKNGIKANF KIRHNIEDGG VQLAYHYQQN   120
TPIGDGPVLL PDNHYLSVQS KLSKDPNEKR DHMVLLEFV AAGITLGMDE LYKGGTGGSM   180
VSKGEELFTG VVPILVELDG DVNGHKFSVS GEGEGDATYG KLTLKFICTT GKLPVPWPTL   240
VTTLTYGVQC FSRYPDHMKQ HDFFKSAMPE GYIQERTIFF KDDGNYKTRA EVKFEGDTLV   300
NRIELKGIDF KEDGNILGHK LEYNGASEVT RRRGVGQYLL EEVLRNNPGV SCWWMADAGV   360
EDRGVMTAFM QALGFTAQQG GWEKC                                         385

SEQ ID NO: 56           moltype = AA  length = 386
FEATURE                 Location/Qualifiers
source                  1..386
                        mol_type = protein
                        organism = synthetic construct
SEQUENCE: 56
MHHHHHHENL YFQSMKLTII RLEKFSDQDR IDLQKIWPEY SPSSLQVDDN HRIYAARFNE   60
RLLAAVRVTL SGTEGALDSL RVRGANVYIK ADKQKNGIKA NFKIRHNIED GGVQLAYHYQ   120
QNTPIGDGPV LLPDNHYLSY QSVLSKDPNE KRDHMVLLEF VTAAGITLGM DELYKGGTGG   180
SMVSKGEELF TGVVPILVEL DGDVNGHKFS VSGEGEGDAT YGKLTLKFIC TTGKLPVPWP   240
TLVTTLTYGV QCFSRYPDHM KQHDFFKSAM PEGYIQERTI FFKDDGNYKT RAEVKFEGDT   300
LVNRIELKGI DFKEDGNILG HKLEYNGAEV TRRRGVGQYL LEEVLRNNPG VSCWWMADAG   360
VEDRGVMTAF MQALGFTAQQ GGWEKC                                        386

SEQ ID NO: 57           moltype = AA  length = 386
FEATURE                 Location/Qualifiers
source                  1..386
                        mol_type = protein
                        organism = synthetic construct
SEQUENCE: 57
MHHHHHHENL YFQSMKLTII RLEKFSDQDR IDLQKIWPEY SPSSLQVDDN HRIYAARFNE   60
RLLAAVRVTL SGTEGALDSL RVRGANVYIK ADKQKNGIKA NFKIRHNIED GGVQLAYHYQ   120
QNTPIGDGPV LLPDNHYLSV QSKLSKDPNE KRDHMVLLEF VTAAGITLGM DELYKGGTGG   180
SMVSKGEELF TGVVPILVEL DGDVNGHKFS VSGEGEGDAT YGKLTLKFIC TTGKLPVPWP   240
TLVTTLSHGV QCFSRYPDHM KQHDFFKSAM PEGYIQERTI FFKDDGNYKT RAEVKFEGDT   300
LVNRIELKGI DFKEDGNILG HKLEYNGAEV TRRRGVGQYL LEEVLRNNPG VSCWWMADAG   360
VEDRGVMTAF MQALGFTAQQ GGWEKC                                        386

SEQ ID NO: 58           moltype = DNA  length = 423
FEATURE                 Location/Qualifiers
source                  1..423
                        mol_type = other DNA
                        organism = synthetic construct
SEQUENCE: 58
atgcatcacc atcaccatca cgaaaacctg tacttccaaa gcatgaagct gacaatcatt   60
cgcctggaga aattttccga ccaggataga atcgaccttc agaagatctg ccccgaatat   120
tctcccagta gcctccaagt agacgacaac catcgaatct acgccgcgag atttaatgaa   180
cgactgcttg cggcggttag ggtaaccctc agcggtacgg aaggtgctct ggactccctg   240
cgggtccgag aggtgacaag acggagaggg gtaggacaat atttgctcga ggaggtcctt   300
agaaataacc ccgagtaag ttgctggtgg atggcggacg ctggagttga ggatcgcgga   360
gtcatgacgg ctttcatgca ggcccttggg ttcaccgcac agcaagggg ctgggagaag   420
tgc                                                                423

SEQ ID NO: 59           moltype = DNA  length = 765
FEATURE                 Location/Qualifiers
source                  1..765
                        mol_type = other DNA
                        organism = synthetic construct
```

```
SEQUENCE: 59
atgcatcacc atcaccatca cgaaaacctg tacttccaaa gcaacgtcta tatcaaggcc   60
gacaagcaga agaacggcat caaggcgaac ttcaagatcc gccacaacat cgaggacggc   120
ggcgtgcagc tcgcctacca ctaccagcag aacacccca tcggcgacgg ccccgtgctg    180
ctgcccgaca accactacct gagcgtgcag tccaaacttt cgaaagaccc caacgagaag   240
cgcgatcaca tggtcctgct ggagttcgtg accgccgccg ggatcactct cggcatggac   300
gagctgtaca agggcggtac cggagggagc atggtgagca agggcgagga gctgttcacc   360
ggggtggtgc ccatcctggt cgagctggac ggcgacgtaa acggccacaa gttcagcgtg   420
tccggcgagg gtgagggcga tgccacctac ggcaagctga ccctgaagtt catctgcacc   480
accggcaagc tgcccgtgcc ctggcccacc ctcgtgacca ccctgaccta cggcgtgcag   540
tgcttcagcc gctaccccga ccacatgaag cagcacgact tcttcaagtc cgccatgccc   600
gaaggctaca tccaggagcg caccatcttc ttcaaggacg acggcaacta caagacccgc   660
gccgaggtga agttcgaggg cgacaccctg gtgaaccgca tcgagctgaa gggcatcgac   720
ttcaaggagg acggcaacat cctggggcac aagctggagt acaac              765

SEQ ID NO: 60           moltype = DNA  length = 765
FEATURE                 Location/Qualifiers
source                  1..765
                        mol_type = other DNA
                        organism = synthetic construct
SEQUENCE: 60
atgcatcacc atcaccatca cgaaaacctg tacttccaaa gcaacgtcta tatcaaggcc   60
gacaagcaga agaacggcat caaggcgaac ttcaagatcc gccacaacat cgaggacggc   120
ggcgtgcagc tcgcctacca ctaccagcag aacacccca tcggcgacgg ccccgtgctg    180
ctgcccgaca accactacct gagctatcag tccgtacttt cgaaagaccc caacgagaag   240
cgcgatcaca tggtcctgct ggagttcgtg accgccgccg ggatcactct cggcatggac   300
gagctgtaca agggcggtac cggagggagc atggtgagca agggcgagga gctgttcacc   360
ggggtggtgc ccatcctggt cgagctggac ggcgacgtaa acggccacaa gttcagcgtg   420
tccggcgagg gtgagggcga tgccacctac ggcaagctga ccctgaagtt catctgcacc   480
accggcaagc tgcccgtgcc ctggcccacc ctcgtgacca ccctgaccta cggcgtgcag   540
tgcttcagcc gctaccccga ccacatgaag cagcacgact tcttcaagtc cgccatgccc   600
gaaggctaca tccaggagcg caccatcttc ttcaaggacg acggcaacta caagacccgc   660
gccgaggtga agttcgaggg cgacaccctg gtgaaccgca tcgagctgaa gggcatcgac   720
ttcaaggagg acggcaacat cctggggcac aagctggagt acaac              765

SEQ ID NO: 61           moltype = DNA  length = 765
FEATURE                 Location/Qualifiers
source                  1..765
                        mol_type = other DNA
                        organism = synthetic construct
SEQUENCE: 61
atgcatcacc atcaccatca cgaaaacctg tacttccaaa gcaacgtcta tatcaaggcc   60
gacaagcaga agaacggcat caaggcgaac ttcaagatcc gccacaacat cgaggacggc   120
ggcgtgcagc tcgcctacca ctaccagcag aacacccca tcggcgacgg ccccgtgctg    180
ctgcccgaca accactacct gagcgtgcag tccaaacttt cgaaagaccc caacgagaag   240
cgcgatcaca tggtcctgct ggagttcgtg accgccgccg ggatcactct cggcatggac   300
gagctgtaca agggcggtac cggagggagc atggtgagca agggcgagga gctgttcacc   360
ggggtggtgc ccatcctggt cgagctggac ggcgacgtaa acggccacaa gttcagcgtg   420
tccggcgagg gtgagggcga tgccacctac ggcaagctga ccctgaagtt catctgcacc   480
accggcaagc tgcccgtgcc ctggcccacc ctcgtgacca ccctgtccca cggcgtgcag   540
tgcttcagcc gctaccccga ccacatgaag cagcacgact tcttcaagtc cgccatgccc   600
gaaggctaca tccaggagcg caccatcttc ttcaaggacg acggcaacta caagacccgc   660
gccgaggtga agttcgaggg cgacaccctg gtgaaccgca tcgagctgaa gggcatcgac   720
ttcaaggagg acggcaacat cctggggcac aagctggagt acaac              765

SEQ ID NO: 62           moltype = DNA  length = 1158
FEATURE                 Location/Qualifiers
source                  1..1158
                        mol_type = other DNA
                        organism = synthetic construct
SEQUENCE: 62
atgcatcacc atcaccatca cgaaaacctg tacttccaaa gcatgaagct gacaatcatt   60
cgcctggaga aattttccga ccaggataga atcgaccttc agaagatctg gcccgaatat   120
tctcccagta gcctccaagt agacgacaac catcgaatct acgccgcgag atttaatgaa   180
cgactgcttg cggcggttag ggtaaccctc agcggtacgg aaggtgctct ggactccctg   240
cgggtccgag gagcaaacgt ctatatcaag gccgacaagc agaagaacgg catcaaggcg   300
aacttcaaga tccgccacaa catcgaggac ggcgcgtgc agctcgccta ccactaccag   360
cagaacaccc catcggcga cggccccgtg ctgctgcccg acaaccacta cctgagcgtg   420
cagtccaaac tttcgaaaga ccccaacgag aagcgcgatc acatggtcct gctggagttc   480
gtgaccgccg ccgggatcac tctcggcatg gacgagctgt acaagggcgg taccggaggg   540
agcatggtga gcaagggcga ggagctgttc accgggggtgg tgcccatcct ggtcgagctg   600
gacggcgacg taaacggcca caagttcagc gtgtccggcg agggtgaggg cgatgccacc   660
tacggcaagc tgaccctgaa gttcatctgc accaccggca agctgcccgt gccctggccc   720
accctcgtga ccaccctgac ctacggcgtg cagtgcttca gccgctaccc cgaccacatg   780
aagcagcacg acttcttcaa gtccgccatg cccgaaggct acatccagga gcgcaccatc   840
ttcttcaagg acgacggcaa ctacaagacc cgcgccgagg tgaagttcga gggcgacacc   900
ctggtgaacc gcatcgagct gaagggcatc gacttcaagg aggacggcaa catcctgggg   960
cacaagctgg agtacaacgg tgctgaggtg acaagacgga gaggggtagg acaatatttg   1020
ctcgaggagg tccttagaaa taaccccgga gtaagttgct ggtggatggc ggacgctgga   1080
```

```
gttgaggatc gcggagtcat gacggctttc atgcaggccc ttgggttcac cgcacagcaa   1140
gggggctggg agaagtgc                                                  1158

SEQ ID NO: 63              moltype = DNA   length = 1158
FEATURE                    Location/Qualifiers
source                     1..1158
                           mol_type = other DNA
                           organism = synthetic construct
SEQUENCE: 63
atgcatcacc atcaccatca cgaaaacctg tacttccaaa gcatgaagct gacaatcatt   60
cgcctggaga aatttttccga ccaggataga atcgaccttc agaagatctg ggcatctaac  120
gtctatatca aggccgacaa gcagaagaac ggcatcaagg cgaacttcaa gatccgccac   180
aacatcgagg acggcggcgt gcagctcgcc taccactacc agcagaacac ccccatcggc   240
gacggccccg tgctgctgcc cgacaaccac tacctggcca tgcagtccaa actttcgaaa   300
gaccccaacg agaagcgcga tcacatggtc ctgctggagt tcgtgaccgc cgccgggatc   360
actctcggca tggacgagct gtacaagggc ggtaccggag ggagcatggt gagcaagggc   420
gaggagctgt tcaccggggt ggtgcccatc ctggtcgagc tggacggcga cgtaaacggc   480
cacaagttca gcgtgtccgg cgagggtgag ggcgatgcca cctacggcaa gctgaccctg   540
aagttcatct gcaccaccgg caagctgccc gtgccctggc ccacccctcgt gaccaccctg   600
acctacggcg tgcagtgctt cagccgctac cccgaccaca tgaagcagca cgacttcttc   660
aagtccgcca tgcccgaagg ctacatccag gagcgcacca tcttcttcaa ggacgacggc   720
aactacaaga cccgcgccga ggtgaagttc gagggcgacac ccctggtgaa ccgcatcgag   780
ctgaagggca tcgacttcaa ggaggacggc aacatcctgg ggcacaagct ggagtacaac   840
gcgtcacccg aatattctcc cagtagcctc caagtagacg acaaccatcg aatctacgcc   900
gcgagattta atgaacgact gcttgcggcg gttagggtaa ccctcagcgg tacggaaggt   960
gctctggact ccctgcgggt ccgagaggtg acaagacgga gaggggtagg acaatatttg   1020
ctcgaggagg tccttagaaa taaccccgga gtaagttgct ggtggatggc ggacgctgga   1080
gttgaggatc gcggagtcat gacggctttc atgcaggccc ttgggttcac cgcacagcaa   1140
gggggctggg agaagtgc                                                  1158

SEQ ID NO: 64              moltype = DNA   length = 1158
FEATURE                    Location/Qualifiers
source                     1..1158
                           mol_type = other DNA
                           organism = synthetic construct
SEQUENCE: 64
atgcatcacc atcaccatca cgaaaacctg tacttccaaa gcatgaagct gacaatcatt   60
cgcctggaga aatttttccga ccaggataga atcgaccttc agaagatctg gcccgaatat   120
tctcccagta gcctccaagt agacgacaac catcgaatct acgccgcgag atttaatgaa   180
cgactgcttg cggcggttag ggtaaccctc agcggtacgg aaggtgctct ggactccctg   240
cgggtccgag aggtggcatc taacgtctat atcaaggccg acaagcagaa gaacggcatc   300
aaggcgaact tcaagatccg ccacaacatc gaggacggcg gcgtgcagct cgcctaccac   360
taccagcagc acacccccat cggcgcggc cccgtgctgc tgcccgacaa ccactacctg   420
gccgtgcagt ccaaactttc gaaagacccc aacgagaagc gcgatcacat ggtcctgctg   480
gagttcgtga ccgccgccgg gatcactctc ggcatggacg agctgtacaa gggcggtacc   540
ggagggagca tggtgagcaa gggcgaggag ctgttcaccg gggtggtgcc catcctggtc   600
gagctggacg gcgacgtaaa cggccacaag ttcagcgtgt ccggcgaggg tgagggcgat   660
gccacctacg gcaagctgac cctgaagttc atctgcacca ccggcaagct gcccgtgccc   720
tggcccaccc tcgtgaccac cctgacctac ggcgtgcagt gcttcagccg ctaccccgac   780
cacatgaagc agcacgactt cttcaagtcc gccatgcccg aaggctacat ccaggagcgc   840
accatcttct tcaaggacga cggcaactac aagacccgcg ccgaggtgaa gttcgagggc   900
gacaccctgg tgaaccgcat cgagctgaag ggcatcgact tcaaggagga cggcaacatc   960
ctggggcaca agctggagta caacgcgtca caagacgga gaggggtagg acaatatttg   1020
ctcgaggagg tccttagaaa taaccccgga gtaagttgct ggtggatggc ggacgctgga   1080
gttgaggatc gcggagtcat gacggctttc atgcaggccc ttgggttcac cgcacagcaa   1140
gggggctggg agaagtgc                                                  1158

SEQ ID NO: 65              moltype = DNA   length = 1158
FEATURE                    Location/Qualifiers
source                     1..1158
                           mol_type = other DNA
                           organism = synthetic construct
SEQUENCE: 65
atgcatcacc atcaccatca cgaaaacctg tacttccaaa gcatgaagct gacaatcatt   60
cgcctggaga aatttttccga ccaggataga atcgaccttc agaagatctg gcccgaatat   120
tctcccagta gcctccaagt agacgacaac catcgaatct acgccgcgag atttaatgaa   180
cgactgcttg cggcggttag ggtaaccctc agcggtacgg aaggtgctct ggactccctg   240
cgggtccgag catctaacgt ctatatcaag gccgacaagc agaagaacgg catcaaggcg   300
aacttcaaga tccgccacaa catcgaggac ggcggcgtgc agctcgccta ccactaccag   360
cagaacaccc ccatcggcga cggccccgtg ctgctgcccg acaaccacta cctgagcgtg   420
cagtccaaac tttcgaaaga ccccaacgag aagcgcgatc acatggtcct gctggagttc   480
gtgaccgccg ccgggatcac tctcggcatg gacgagctgt acaagggcgg taccggaggg   540
agcatggtga gcaagggcga ggagctgttc accggggtg tgcccatcct ggtcgagctg   600
gacggcgacg taaacggcca caagttcagc gtgtccggcg agggtgaggg cgatgccacc   660
tacggcaagc tgaccctgaa gttcatctgc accaccggca agctgcccgt gcctggccc   720
accctcgtga ccaccctgac ctacggcgtg cagtgcttca gccgctaccc cgaccacatg   780
aagcagcacg acttcttcaa gtccgccatg cccgaaggct acatccagga gcgcaccatc   840
ttcttcaagg acgacggcaa ctacaagacc cgcgccgagt gaagttcga gggcgacacc   900
ctggtgaacc gcatcgagct gaagggcatc gacttcaagg aggacggcaa catcctgggg   960
```

```
cacaagctgg agtacaacgc gtcagaggtg acaagacgga gaggggtagg acaatatttg  1020
ctcgaggagg tccttagaaa taaccccgga gtaagttgct ggtggatggc ggacgctgga  1080
gttgaggatc gcggagtcat gacggctttc atgcaggccc ttgggttcac cgcacagcaa  1140
gggggctggg agaagtgc                                                 1158

SEQ ID NO: 66            moltype = DNA  length = 1158
FEATURE                  Location/Qualifiers
source                   1..1158
                         mol_type = other DNA
                         organism = synthetic construct
SEQUENCE: 66
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgag aggtgacaag acggagaggg gtaggacaat atttgctcga ggaggtcctt  300
agaaataacc ccgagtaag ttgctggtgg atggcggacg catctaacgt ctatatcaag  360
gccgacaagc agaagaacg catcaaggcg aacttcaaga tccgccacaa catcgaggac  420
ggcggcgtgc agctcgccta ccactaccag cagaacaccc ccatcggcga cggcccgtg  480
ctgctgcccg acaaccacta cctgagcgtg cagtccaaac tttcgaaaga ccccaacgag  540
aagcgcgatc acatggtcct gctggagttc gtgaccgccg ccgggatcac tctcggcatg  600
gacgagctgt acaagggcgg taccggaggg agcatggtga caagggcga ggagctgttc  660
accggggtgg tgcccatcct ggtcgagctg gacggcgacg taaacggcca caagttcagc  720
gtgtccggcg agggtgaggg cgatgccacc tacggcaagc tgaccctgaa gttcatctgc  780
accaccggca agctgcccgt gccctggccc accctcgtga ccaccctgac ctacggcgtg  840
cagtgcttca gccgctaccc cgaccacatg aagcagcaag acttcttcaa gtccgccatg  900
cccgaaggct acatccagga gcgcaccatc ttcttcaagg acgacggcaa ctacaagacc  960
cgcgccgagg tgaagttcga gggcgacacc ctggtgaacc gcatcgagct gaagggcatc  1020
gacttcaagg aggacggcaa catcctgggg cacaagctgg agtacaacgc gtcagctgga  1080
gttgaggatc gcggagtcat gacggctttc atgcaggccc ttgggttcac cgcacagcaa  1140
gggggctggg agaagtgc                                                 1158

SEQ ID NO: 67            moltype = DNA  length = 1158
FEATURE                  Location/Qualifiers
source                   1..1158
                         mol_type = other DNA
                         organism = synthetic construct
SEQUENCE: 67
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgag aggtgacaag acggagaggg gtaggacaat atttgctcga ggaggtcctt  300
agaaataacc ccggagtaag ttgctggtgg atggcggacg ctggagttga ggatgcatct  360
aacgtctata tcaaggccga caagcagaag aacggcatca aggcgaactt caagatccgc  420
cacaacatcg aggacggcgg cgtgcagctc gcctaccact accagcagaa cacccccatc  480
ggcgacggcc ccgtgctgct gcccgacaac cactacctga gcgtgcagtc caaactttcg  540
aaagacccca cgagaagcg cgatcacatg gtcctgctgg agttcgtgac cgccgccggg  600
atcactctcg gcatggacga gctgtacaag ggcggtaccg gagggagcat ggtgagcaag  660
ggcgaggagc tgttcaccgg ggtggtgccc atcctggtcg agctggacgg cgacgtaaac  720
ggccacaagt tcagcgtgtc cggcgagggt gagggcgatg ccacctacgg caagctgacc  780
ctgaagttca tctgcaccac cggcaagctg cccgtgccct ggcccaccct cgtgaccacc  840
ctgacctacg gcgtgcagtg cttcagccgc taccccgacc acatgaagca gcacgacttc  900
ttcaagtccg ccatgcccga aggctacatc caggagcgca ccatcttctt caaggacgac  960
ggcaactaca agacccgcgc cgaggtgaag ttcgagggcg acaccctggt gaaccgcatc  1020
gagctgaagg gcatcgactt caaggaggac ggcaacatcc tggggcacaa gctggagtac  1080
aacgcgtcac gcggagtcat gacggctttc atgcaggccc ttgggttcac cgcacagcaa  1140
gggggctggg agaagtgc                                                 1158

SEQ ID NO: 68            moltype = DNA  length = 1158
FEATURE                  Location/Qualifiers
source                   1..1158
                         mol_type = other DNA
                         organism = synthetic construct
SEQUENCE: 68
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgag aggtgacaag acggagaggg gtaggacaat atttgctcga ggaggtcctt  300
agaaataacc ccgagtaag ttgctggtgg atggcggacg ctggagttga ggatcgcgga  360
gtcatgacgc ctttcatgca ggcccttggg gcatctaacg tctatatcaa ggccgacaag  420
cagaagaacg gcatcaaggc gaacttcaag atccgccaca acatcgagga cggcggcgtg  480
cagctcgcct accactacca gcagaacacc cccatcggcga cggcccgt gctgctgccg  540
gacaaccact acctgagcgt gcagtccaaa ctttcgaaag accccaacga gaagcgcgat  600
cacatggtcc tgctggagtt cgtgaccgcc gccgggatca ctctcggcat ggacgagctg  660
tacaagggcg gtaccggagg gagcatggtg agcaagggcg aggagctgtt caccgggtg  720
gtgcccatcc tggtcgagct ggacggcgac gtaaacggcc acaagttcag cgtgtccggc  780
gagggtgagg gcgatgccac ctacggcaag ctgaccctga gttcatctg caccaccggc  840
```

```
aagctgcccg tgccctggcc caccctcgtg accaccctga cctacggcgt gcagtgcttc   900
agccgctacc ccgaccacat gaagcagcac gacttcttca agtccgccat gcccgaaggc   960
tacatccagg agcgcaccat cttcttcaag gacgacggca actacaagac ccgcgccgag  1020
gtgaagttcg agggcgacac cctggtgaac cgcatcgagc tgaagggcat cgacttcaag  1080
gaggacggca acatcctggg gcacaagctg gagtacaacg cgtcattcac cgcacagcaa  1140
gggggctggg agaagtgc                                                 1158
```

SEQ ID NO: 69          moltype = DNA   length = 1158
FEATURE                Location/Qualifiers
source                 1..1158
                       mol_type = other DNA
                       organism = synthetic construct
SEQUENCE: 69

```
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgag gagcaagtaa cgtctatatc aaggccgaca agcagaagaa cggcatcaag  300
gcgaacttca agatccgcca caacatcgag gacggcggcg tgcagctcgc ctaccactac  360
cagcagaaca cccccatcgg cgacggcccc gtgctgctgc ccgacaacca ctacctgagc  420
gtgcagtcca aactttcgaa agaccccaac gagaagcgcg atcacatggt cctgctggag  480
ttcgtgaccg ccgccgggat cactctcggc atggacgagc tgtacaaggg cggtaccgga  540
gggagcatgg tgagcaaggg cgaggagctg ttcaccgggg tggtgcccat cctggtcgag  600
ctggacggcg acgtaaacgg ccacaagttc agcgtgtccg gcgagggtga gggcgatgcc  660
acctacggca agctgaccct gaagttcatc tgcaccaccg gcaagctgcc cgtgccctgg  720
cccaccctcg tgaccaccct gacctacggc gtgcagtgct tcagccgcta ccccgaccac  780
atgaagcagc acgacttctt caagtccgcc atgcccgaag gctacatcca ggagcgcacc  840
atcttcttca aggacgacgg caactacaag acccgcgccg aggtgaagtt cgagggcgac  900
accctggtga accgcatcga gctgaagggc atcgacttca aggaggacgg caacatcctg  960
gggcacaagc tggagtacaa cggtgaggtg acaagacgga gggggtagg acaatatttg  1020
ctcgaggagg tccttagaaa taaccccgga gtaagttgct ggtggatggc ggacgctgga  1080
gttgaggatc gcggagtcat gacggctttc atgcaggccc ttgggttcac cgcacagcaa  1140
gggggctggg agaagtgc                                                 1158
```

SEQ ID NO: 70          moltype = DNA   length = 1155
FEATURE                Location/Qualifiers
source                 1..1155
                       mol_type = other DNA
                       organism = synthetic construct
SEQUENCE: 70

```
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgag gagcaagtaa cgtctatatc aaggccgaca agcagaagaa cggcatcaag  300
gcgaacttca agatccgcca caacatcgag gacggcggcg tgcagctcgc ctaccactac  360
cagcagaaca cccccatcgg cgacggcccc gtgctgctgc ccgacaacca ctacctgagc  420
gtgcagtcca aactttcgaa agaccccaac gagaagcgcg atcacatggt cctgctggag  480
ttcgtgaccg ccgccgggat cactctcggc atggacgagc tgtacaaggg cggtaccgga  540
gggagcatgg tgagcaaggg cgaggagctg ttcaccgggg tggtgcccat cctggtcgag  600
ctggacggcg acgtaaacgg ccacaagttc agcgtgtccg gcgagggtga gggcgatgcc  660
acctacggca agctgaccct gaagttcatc tgcaccaccg gcaagctgcc cgtgccctgg  720
cccaccctcg tgaccaccct gacctacggc gtgcagtgct tcagccgcta ccccgaccac  780
atgaagcagc acgacttctt caagtccgcc atgcccgaag gctacatcca ggagcgcacc  840
atcttcttca aggacgacgg caactacaag acccgcgccg aggtgaagtt cgagggcgac  900
accctggtga accgcatcga gctgaagggc atcgacttca aggaggacgg caacatcctg  960
gggcacaagc tggagtacaa cgaggtgaca agacggagag gggtaggaca atatttgctc  1020
gaggaggtcc ttagaaataa ccccggagta agttgctggt ggatggcgga cgctggagtt  1080
gaggatcgcg agtcatgac ggctttcatg caggcccttg ggttcaccgc acagcaaggg  1140
ggctgggaga agtgc                                                    1155
```

SEQ ID NO: 71          moltype = DNA   length = 1152
FEATURE                Location/Qualifiers
source                 1..1152
                       mol_type = other DNA
                       organism = synthetic construct
SEQUENCE: 71

```
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgag gagcaaacgt ctatatcaag gccgacaagc agaagaacgg catcaaggcg  300
aacttcaaga tccgccacaa catcgaggac ggcggcgtgc agctcgccta ccactaccag  360
cagaacaccc catcggcgac ggccccgtgc tgctgcccga caaccactac ctgagcgtg  420
cagtccaaac tttcgaaaga ccccaacgag aagcgcgatc acatggtcct gctggagttc  480
gtgaccgccg ccgggatcac tctcggcatg gacgagctgt acaagggcgg taccggaggg  540
agcatggtga gcaagggcga ggagctgttc accggggtgg tgcccatcct ggtcgagctg  600
gacggcgacg taaacggcca caagttcagc gtgtccggcg agggtgaggg cgatgccacc  660
tacggcaagc tgaccctgaa gttcatctgc accaccggca agctgcccgt gccctggccc  720
```

-continued

```
accctcgtga ccaccctgac ctacggcgtg cagtgcttca gccgctaccc cgaccacatg   780
aagcagcacg acttcttcaa gtccgccatg cccgaaggct acatccagga gcgcaccatc   840
ttcttcaagg acgacggcaa ctacaagacc cgcgccgagg tgaagttcga gggcgacacc   900
ctggtgaacc gcatcgagct gaagggcatc gacttcaagg aggacggcaa catcctgggg   960
cacaagctgg agtacaacga ggtgacaaga cggagagggg taggacaata tttgctcgag  1020
gaggtcctta gaaataaccc cggagtaagt tgctggtgga tggcggacgc tggagttgag  1080
gatcgcggag tcatgacggc tttcatgcag gcccttgggt tcaccgcaca gcaaggggggc  1140
tgggagaagt gc                                                       1152

SEQ ID NO: 72          moltype = DNA  length = 1146
FEATURE                Location/Qualifiers
source                 1..1146
                       mol_type = other DNA
                       organism = synthetic construct
SEQUENCE: 72
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgaa acgtctatat caaggccgac aagcagaaga acggcatcaa ggcgaacttc  300
aagatccgcc acaacatcga ggacggcggc gtgcagctcg cctaccacta ccagcagaac  360
accccatcg gcgacggccc cgtgctgctg cccgacaacc actacctgag cgtgcagtcc  420
aaactttcga aagaccccaa cgagaagcgc gatcacatgg tcctgctgga gttcgtgacc  480
gccgccggga tcactctcgg catggacgag ctgtacaagg gcggtaccgg agggagcatg  540
gtgagcaagg gcgaggagct gttcaccggg gtggtgccca tcctggtcga gctggacggc  600
gacgtaaacg gccacaagtt cagcgtgtcc ggcgagggtg agggcgatgc cacctacggc  660
aagctgaccc tgaagttcat ctgcaccacc ggcaagctgc ccgtgccctg cccaccctc   720
gtgaccaccc tgacctacgg cgtgcagtgc ttcagccgct accccgacca catgaagcag  780
cacgacttct tcaagtccgc catgcccgaa ggctacatcc aggagcgcac catcttcttc  840
aaggacgacg gcaactacaa gacccgcgcc gaggtgaagt tcgagggcga ccccctgctg  900
aaccgcatcg agctgaaggg catcgacttc aaggaggacg gcaacatcct ggggcacaag  960
ctggagtaca cgaggtgac aagacggaga ggggtaggac aatatttgct cgaggaggtc  1020
cttagaaata accccggagt aagttgctgg tggatggcgg acgctggagt tgaggatcgc  1080
ggagtcatga cggctttcat gcaggcccct gggttcaccg cacagcaagg gggctgggag  1140
aagtgc                                                              1146

SEQ ID NO: 73          moltype = DNA  length = 1158
FEATURE                Location/Qualifiers
source                 1..1158
                       mol_type = other DNA
                       organism = synthetic construct
SEQUENCE: 73
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgag gaaacgtcta tatcaaggcc gacaagcaga agacggcat caaggcgaac  300
ttcaagatcc gccacaacat cgaggacggc ggcgtgcagc tcgcctacca ctaccagcag  360
aacaccccca tcggcgacgg ccccgtgctg ctgcccgaca accactacct gagcgtgcag  420
tccaaacttt cgaaagaccc caacgagaag cgcgatcaca tggtcctgct ggagttcgtg  480
accgccgcg gatcactct cggcatggac gagctgtaca agggcggtac cggagggcga  540
atggtgagca gggcgagga gctgttcacc ggggtggtgc ccatcctggt cgagctggac  600
ggcgacgtaa acgccacaa gttcagcgtg tccggcgagg gtgagggcga tgccacctac  660
ggcaagctga ccctgaagtt catctgcacc accggcaagc tgcccgtgcc ctggcccacc  720
ctcgtgacca ccctgaccta cggcgtgcag tgcttcagcc gctacccga catgaag  780
cagcacgact tcttcaagtc cgccatgccc gaaggctaca tccaggagcg caccatcttc  840
ttcaaggacg acggcaacta caagacccgc gccgaggtga gttcgaggg cgacaccctg  900
gtgaaccgca tcgagctgaa gggcatcgac ttcaaggagg acggcaacat cctggggcac  960
aagctggagt acaacggtgc ttcagaggtg acaagacgga gagggtagg acaatatttg  1020
ctcgaggagg tccttagaaa taaccccgga gtaagttgct ggtggatggc ggacgctgga  1080
gttgaggatc gcggagtcat gacggctttc atgcaggccc ttgggttcac cgcacagcaa  1140
gggggctggg agaagtgc                                                 1158

SEQ ID NO: 74          moltype = DNA  length = 1155
FEATURE                Location/Qualifiers
source                 1..1155
                       mol_type = other DNA
                       organism = synthetic construct
SEQUENCE: 74
atgcatcacc atcaccatca cgaaaacctg tacttccaaa gcatgaagct gacaatcatt   60
cgcctggaga aattttccga ccaggataga atcgaccttc agaagatctg gcccgaatat  120
tctcccagta gcctccaagt agacgacaac catcgaatct acgccgcgag atttaatgaa  180
cgactgcttg cggcggttag ggtaaccctc agcggtacgg aaggtgctct ggactccctg  240
cgggtccgaa acgtctatat caaggccgac aagcagaaga acggcatcaa ggcgaacttc  300
aagatccgcc acaacatcga ggacggcggc gtgcagctcg cctaccacta ccagcagaac  360
accccatcg gcgacggccc cgtgctgctg cccgacaacc actacctgag cgtgcagtcc  420
aaactttcga aagaccccaa cgagaagcgc gatcacatgg tcctgctgga gttcgtgacc  480
gccgccggga tcactctcgg catggacgag ctgtacaagg gcggtaccgg agggagcatg  540
gtgagcaagg gcgaggagct gttcaccggg gtggtgccca tcctggtcga gctggacggc  600
```

```
gacgtaaacg gccacaagtt cagcgtgtcc ggcgagggtg agggcgatgc cacctacggc   660
aagctgaccc tgaagttcat ctgcaccacc ggcaagctgc ccgtgccctg gcccaccctc   720
gtgaccaccc tgacctacgg cgtgcagtgc ttcagccgct accccgacca catgaagcag   780
cacgacttct tcaagtccgc catgcccgaa ggctacatcc aggagcgcac catcttcttc   840
aaggacgacg gcaactacaa gacccgcgcc gaggtgaagt tcgagggcga caccctggtg   900
aaccgcatcg agctgaaggg catcgacttc aaggaggacg gcaacatcct ggggcacaag   960
ctggagtaca cggtgcttc agaggtgaca agacggagag gggtaggaca atatttgctc   1020
gaggaggtcc ttagaaataa ccccggagta agttgctggt ggatggcgga cgctggagtt   1080
gaggatcgcg gagtcatgac ggctttcatg caggcccttg ggttcaccgc acagcaaggg   1140
ggctgggaga agtgc                                                     1155
```

SEQ ID NO: 75          moltype = DNA  length = 1158
FEATURE                Location/Qualifiers
source                 1..1158
                       mol_type = other DNA
                       organism = synthetic construct
SEQUENCE: 75

```
atgcatcacc atcaccatca cgaaaacctg tacttccaaa gcatgaagct gacaatcatt   60
cgcctggaga aattttccga ccaggataga atcgaccttc agaagatctg cccgaatat    120
tctcccagta gcctccaagt agacgacaac catcgaatct acgccgcgag atttaatgaa   180
cgactgcttg cggcggttag ggtaaccctc agcggtacgg aaggtgctct ggactccctg   240
cgggtccgag gagcaaacgt ctatatcaag gccgacaagc agaagaacgg catcaaggcg   300
aacttcaaga tccgccacaa catcgaggac ggcggcgtgc agctcgccta ccactaccag   360
cagaacaccc ccatcggcga cggccccgtg ctgctgcccg acaaccacta cctgagctat   420
cagtccgtac tttcgaaaga ccccaacgag aagcgcgatc acatggtcct gctggagttc   480
gtgaccgccg ccgggatcac tctcggcatg gacgagctgt acaagggcgg taccggaggg   540
agcatggtga gcaagggcga ggagctgttc accggggtgg tgcccatcct ggtcgagctg   600
gacggcgacg taaacggcca caagttcagc gtgtccggcg agggtgaggg cgatgccacc   660
tacggcaagc tgaccctgaa gttcatctgc accaccggca agctgcccgt gccctggccc   720
accctcgtga ccaccctgac ctacggcgtg cagtgcttca gccgctaccc cgaccacatg   780
aagcagcacg acttcttcaa gtccgccatg cccgaaggct acatccagga gcgcaccatc   840
ttcttcaagg acgacggcaa ctacaagacc cgcgccgagg tgaagttcga gggcgacacc   900
ctggtgaacc gcatcgagct gaagggcatc gacttcaagg aggacggcaa catcctgggg   960
cacaagctgg agtacaacgg tgctgaggtg acaagacgga gaggggtagg acaatatttg   1020
ctcgaggagg tccttagaaa taaccccgga gtaagttgct ggtggatggc ggacgctgga   1080
gttgaggatc gcggagtcat gacggctttc atgcaggccc ttgggttcac cgcacagcaa   1140
gggggctggg agaagtgc                                                  1158
```

SEQ ID NO: 76          moltype = DNA  length = 1158
FEATURE                Location/Qualifiers
source                 1..1158
                       mol_type = other DNA
                       organism = synthetic construct
SEQUENCE: 76

```
atgcatcacc atcaccatca cgaaaacctg tacttccaaa gcatgaagct gacaatcatt   60
cgcctggaga aattttccga ccaggataga atcgaccttc agaagatctg cccgaatat    120
tctcccagta gcctccaagt agacgacaac catcgaatct acgccgcgag atttaatgaa   180
cgactgcttg cggcggttag ggtaaccctc agcggtacgg aaggtgctct ggactccctg   240
cgggtccgag gagcaaacgt ctatatcaag gccgacaagc agaagaacgg catcaaggcg   300
aacttcaaga tccgccacaa catcgaggac ggcggcgtgc agctcgccta ccactaccag   360
cagaacaccc ccatcggcga cggccccgtg ctgctgcccg acaaccacta cctgagctat   420
cagtccaaac tttcgaaaga ccccaacgag aagcgcgatc acatggtcct gctggagttc   480
gtgaccgccg ccgggatcac tctcggcatg gacgagctgt acaagggcgg taccggaggg   540
agcatggtga gcaagggcga ggagctgttc accggggtgg tgcccatcct ggtcgagctg   600
gacggcgacg taaacggcca caagttcagc gtgtccggcg agggtgaggg cgatgccacc   660
tacggcaagc tgaccctgaa gttcatctgc accaccggca agctgcccgt gccctggccc   720
accctcgtga ccaccctgtc ccacggcgtg cagtgcttca gccgctaccc cgaccacatg   780
aagcagcacg acttcttcaa gtccgccatg cccgaaggct acatccagga gcgcaccatc   840
ttcttcaagg acgacggcaa ctacaagacc cgcgccgagg tgaagttcga gggcgacacc   900
ctggtgaacc gcatcgagct gaagggcatc gacttcaagg aggacggcaa catcctgggg   960
cacaagctgg agtacaacgg tgctgaggtg acaagacgga gaggggtagg acaatatttg   1020
ctcgaggagg tccttagaaa taaccccgga gtaagttgct ggtggatggc ggacgctgga   1080
gttgaggatc gcggagtcat gacggctttc atgcaggccc ttgggttcac cgcacagcaa   1140
gggggctggg agaagtgc                                                  1158
```

SEQ ID NO: 77          moltype = AA  length = 422
FEATURE                Location/Qualifiers
source                 1..422
                       mol_type = protein
                       organism = synthetic construct
SEQUENCE: 77

```
MVTGPKKKRK VDYKDDDDKL DGGYPYDVPD YAARGYQTSL YKKAGSTMGH MKLTIIRLEK   60
FSDQDRIDLQ KIWPEYSPSS LQVDDNHRIY AARFNERLLA AVRVTLSGTE GALDSLRVRG   120
ANVYIKADKQ KNGIKANFKI RHNIEDGGVQ LAYHYQQNTP IGDGPVLLPD NHYLSVQSKL   180
SKDPNEKRDH MVLLEFVTAA GITLGMDELY KGGTGGSMVS KGEELFTGVV PILVELDGDV   240
NGHKFSVSGE GEGDATYGKL TLKFICTTGK LPVPWPTLVT TLTYGVQCFS RYPDHMKQHD   300
FFKSAMPEGY IQERTIFFKD DGNYKTRAEV KFEGDTLVNR IELKGIDFKE DGNILGHKLE   360
YNGAEVTRRR GVGQYLLEEV LRNNPGVSCW WMADAGVEDR GVMTAFMQAL GFTAQQGGWE   420
KC                                                                   422
```

-continued

```
SEQ ID NO: 78              moltype = AA   length = 291
FEATURE                    Location/Qualifiers
source                     1..291
                           mol_type = protein
                           organism = synthetic construct
SEQUENCE: 78
MVTGPKKKRK VDYKDDDDKL DGGYPYDVPD YAARGYQTSL YKKAGSTMGH NVYIKADKQK   60
NGIKANFKIR HNIEDGGVQL AYHYQQNTPI GDGPVLLPDN HYLSVQSKLS KDPNEKRDHM  120
VLLEFVTAAG ITLGMDELYK GGTGGSMVSK GEELFTGVVP ILVELDGDVN GHKFSVSGEG  180
EGDATYGKLT LKFICTTGKL PVPWPTLVTT LTYGVQCFSR YPDHMKQHDF FKSAMPEGYI  240
QERTIFFKDD GNYKTRAEVK FEGDTLVNRI ELKGIDFKED GNILGHKLEY N           291

SEQ ID NO: 79              moltype = AA   length = 426
FEATURE                    Location/Qualifiers
source                     1..426
                           mol_type = protein
                           organism = synthetic construct
SEQUENCE: 79
MVTGLQKKLE ELELDDYKDD DDKLDGGYPY DVPDYAARGY QTSLYKKAGS TMGHMKLTII   60
RLEKFSDQDR IDLQKIWPEY SPSSLQVDDN HRIYAARFNE RLLAAVRVTL SGTEGALDSL  120
RVRGANVYIK ADKQKNGIKA NFKIRHNIED GGVQLAYHYQ QNTPIGDGPV LLPDNHYLSV  180
QSKLSKDPNE KRDHMVLLEF VTAAGITLGM DELYKGGTGG SMVSKGEELF TGVVPILVEL  240
DGDVNGHKFS VSGEGEGDAT YGKLTLKFIC TTGKLPVPWP TLVTTLTYGV QCFSRYPDHM  300
KQHDFFKSAM PEGYIQERTI FFKDDGNYKT RAEVKFEGDT LVNRIELKGI DFKEDGNILG  360
HKLEYNGAEV TRRRGVGQYL LEEVLRNNPG VSCWWMADAG VEDRGVMTAF MQALGFTAQQ  420
GGWEKC                                                              426

SEQ ID NO: 80              moltype = AA   length = 295
FEATURE                    Location/Qualifiers
source                     1..295
                           mol_type = protein
                           organism = synthetic construct
SEQUENCE: 80
MVTGLQKKLE ELELDDYKDD DDKLDGGYPY DVPDYAARGY QTSLYKKAGS TMGHNVYIKA   60
DKQKNGIKAN FKIRHNIEDG GVQLAYHYQQ NTPIGDGPVL LPDNHYLSVQ SKLSKDPNEK  120
RDHMVLLEFV TAAGITLGMD ELYKGGTGGS MVSKGEELFT GVVPILVELD GDVNGHKFSV  180
SGEGEGDATY GKLTLKFICT TGKLPVPWPT LVTTLTYGVQ CFSRYPDHMK QHDFFKSAMP  240
EGYIQERTIF FKDDGNYKTR AEVKFEGDTL VNRIELKGID FKEDGNILGH KLEYN        295

SEQ ID NO: 81              moltype = AA   length = 438
FEATURE                    Location/Qualifiers
source                     1..438
                           mol_type = protein
                           organism = synthetic construct
SEQUENCE: 81
MVLATRVFSL VGKRAISTSV CVRAHTGDYK DDDDKLDGGY PYDVPDYAAR GYQTSLYKKA   60
GSTMGHMKLT IIRLEKFSDQ DRIDLQKIWP EYSPSSLQVD DNHRIYAARF NERLLAAVRV  120
TLSGTEGALD SLRVRGANVY IKADKQKNGI KANFKIRHNI EDGGVQLAYH YQQNTPIGDG  180
PVLLPDNHYL SVQSKLSKDP NEKRDHMVLL EFVTAAGITL GMDELYKGGT GGSMVSKGEE  240
LFTGVVPILV ELDGDVNGHK FSVSGEGEGD ATYGKLTLKF ICTTGKLPVP WPTLVTTLTY  300
GVQCFSRYPD HMKQHDFFKS AMPEGYIQER TIFFKDDGNY KTRAEVKFEG DTLVNRIELK  360
GIDFKEDGNI LGHKLEYNGA EVTRRRGVGQ YLLEEVLRNN PGVSCWWMAD AGVEDRGVMT  420
AFMQALGFTA QQGGWEKC                                                 438

SEQ ID NO: 82              moltype = AA   length = 307
FEATURE                    Location/Qualifiers
source                     1..307
                           mol_type = protein
                           organism = synthetic construct
SEQUENCE: 82
MVLATRVFSL VGKRAISTSV CVRAHTGDYK DDDDKLDGGY PYDVPDYAAR GYQTSLYKKA   60
GSTMGHNVYI KADKQKNGIK ANFKIRHNIE DGGVQLAYHY QQNTPIGDGP VLLPDNHYLS  120
VQSKLSKDPN EKRDHMVLLE FVTAAGITLG MDELYKGGTG GSMVSKGEEL FTGVVPILVE  180
LDGDVNGHKF SVSGEGEGDA TYGKLTLKFI CTTGKLPVPW PTLVTTLTYG VQCFSRYPDH  240
MKQHDFFKSA MPEGYIQERT IFFKDDGNYK TRAEVKFEGD TLVNRIELKG IDFKEDGNIL  300
GHKLEYN                                                             307

SEQ ID NO: 83              moltype = DNA   length = 1269
FEATURE                    Location/Qualifiers
source                     1..1269
                           mol_type = other DNA
                           organism = synthetic construct
SEQUENCE: 83
atggtgaccg gtccaaagaa gaagcgtaag gtagactaca aggatgacga tgacaagctc   60
gatggaggat acccatacga tgttccagat tacgctgctc gaggttatca aacaagtttg  120
tacaaaaaag caggctccac catggggcat atgaagctga caatcattcg cctggagaaa  180
ttttccgacc aggatagaat cgaccttcag aagatctggc cgaatattc tcccagtagc  240
ctccaagtag acgacaacca tcgaatctac gccgcgagat ttaatgaacg actgcttgcg  300
```

-continued

```
gcggttaggg taaccctcag cggtacggaa ggtgctctgg actccctgcg ggtccgagga   360
gcaaacgtct atatcaaggc cgacaagcag aagaacggca tcaaggcgaa cttcaagatc   420
cgccacaaca tcgaggacgg cggcgtgcag ctcgcctacc actaccagca gaacacccc    480
atcggcgacg gccccgtgct gctgcccgac aaccactacc tgagcgtgca gtccaaactt   540
tcgaaagacc ccaacgagaa gcgcgatcac atggtcctgc tggagttcgt gaccgccgcc   600
gggatcactc tcggcatgga cgagctgtac aagggcggta ccggagggag catggtgagc   660
aagggcgagg agctgttcac cggggtggtg cccatcctgg tcgagctgga cggcgacgta   720
aacgccaca agttcagcgt gtccggcgag ggtgagggcg atgccaccta cggcaagctg   780
accctgaagt tcatctgcac caccgccaag ctgcccgtgc cctggcccac cctcgtgacc   840
accctgacct acggcgtgca gtgcttcagc cgctacccg accacatgaa gcagcacgac   900
ttcttcaagt ccgccatgcc cgaaggctac atccaggagc gcaccatctt cttcaaggac   960
gacggcaact acaagacccg cgccgaggtg aagttcgagg gcgacaccct ggtgaaccgc  1020
atcgagctga agggcatcga cttcaaggag gacggcaaca tcctgggca caagctggag  1080
tacaacggtg ctgaggtgac aagacggaga ggggtaggac aatatttgct cgaggaggtc  1140
cttagaaata accccggagt aagttgctgg tggatggcgg acgctggagt tgaggatcgc  1200
ggagtcatga cggctttcat gcaggccctt gggttcaccg cacagcaagg gggctgggag  1260
aagtgctaa                                                          1269
```

```
SEQ ID NO: 84          moltype = DNA  length = 876
FEATURE                Location/Qualifiers
source                 1..876
                       mol_type = other DNA
                       organism = synthetic construct
SEQUENCE: 84
atggtgaccg gtccaaagaa gaagcgtaag gtagactaca aggatgacga tgacaagctc   60
gatggaggat acccatacga tgttccagat tacgctgctc tcgaggttat aacaagtttg  120
tacaaaaaag caggctccac catggggcat aacgtctata tcaaggccga caagcagaag  180
aacggcatca aggcgaactt caagatccgc cacaacatcg aggacggcgg cgtgcagctc  240
gcctaccact accagcagaa cacccccatc ggcgacggcc ccgtgctgct gcccgacaac  300
cactacctga gcgtgcagtc caaactttcg aaagacccca acgagaagcg cgatcacatg  360
gtcctgctgg agttcgtgac cgccgccggg atcactctcg gcatggacga gctgtacaag  420
ggcggtaccg gagggagcat ggtgagcaag ggcgaggagc tgttcaccgg ggtggtgccc  480
atcctggtcg agctggacgg cgacgtaaac ggccacaagt tcagcgtgtc cggcgagggt  540
gagggcgatg ccacctacgg caagctgacc ctgaagttca tctgcaccac cggcaagctg  600
cccgtgccct ggcccaccct cgtgaccacc ctgacctacg gcgtgcagtg cttcagccgc  660
taccccgacc acatgaagca gcacgacttc ttcaagtccg ccatgcccga aggctacatc  720
caggagcgca ccatcttctt caaggacgac ggcaactaca gacccgcgc cgaggtgaag  780
ttcgagggcg cacccctggt gaaccgcatc gagctgaagg catcgactt caaggaggac  840
ggcaacatcc tggggcacaa gctggagtac aactaa                            876
```

```
SEQ ID NO: 85          moltype = DNA  length = 1281
FEATURE                Location/Qualifiers
source                 1..1281
                       mol_type = other DNA
                       organism = synthetic construct
SEQUENCE: 85
atggtgaccg gtctgcagaa aaagctggaa gagctggaac tggacgacta caaggatgac   60
gatgacaagc tcgatggagg atacccatac gatgttccag attacgctgc tcgaggttat  120
caaacaagtt tgtacaaaaa agcaggctcc accatggggc atatgaagct gacaatcatt  180
cgcctggaga aattttccga ccaggataga atcgaccttc agaagatctg gcccgaatat  240
tctcccagta gcctccaagt agacgacaac catcgaatct acgccgcgag atttaatgaa  300
cgactgcttg cggcggttag ggtaaccctc agcggtacgg aaggtgctct ggactccctg  360
cgggtccgag gagcaaacgt ctatatcaag gccgacaagc agaagaacgg catcaaggcg  420
aacttcaaga tccgccacaa catcgaggac ggcggcgtgc agctcgccta ccactaccag  480
cagaacaccc ccatcggcga cggccccgtg ctgctgcccg acaaccacta cctgagcgtg  540
cagtccaaac tttcgaaaga ccccaacgag aagcgcgatc acatggtcct gctggagttc  600
gtgaccgccg ccgggatcac tctcggcatg gacgagctgt acaagggcgg taccggaggg  660
agcatggtga gcaagggcga ggagctgttc accggggtgg tgcccatcct ggtcgagctg  720
gacggcgacg taaacggcca caagttcagc gtgtccggcg agggtgaggg cgatgccacc  780
tacggcaagc tgaccctgaa gttcatctgc accaccggca agctgcccgt gccctggccc  840
accctcgtga ccaccctgac ctacggcgtg cagtgcttca gccgctaccc gaccacatg  900
aagcagcacg acttcttcaa gtccgccatg cccgaaggct acatccagga gcgcaccatc  960
ttcttcaagg acgacggcaa ctacaagacc cgcgccgagg tgaagttcga gggcgacacc  1020
ctggtgaacc gcatcgagct gaagggcatc gacttcaagg aggacggcaa catcctgggc  1080
cacaagctgg agtacaacgg tgctgaggtg acaagacgga gaggggtagg acaatatttg  1140
ctcgaggagg tccttagaaa taaccccgga gtaagttgct ggtggatggc ggacgctgga  1200
gttgaggatc gcggagtcat gacggctttc atgcaggccc ttgggttcac cgcacagcaa  1260
gggggctggg agaagtgcta a                                            1281
```

```
SEQ ID NO: 86          moltype = DNA  length = 888
FEATURE                Location/Qualifiers
source                 1..888
                       mol_type = other DNA
                       organism = synthetic construct
SEQUENCE: 86
atggtgaccg gtctgcagaa aaagctggaa gagctggaac tggacgacta caaggatgac   60
gatgacaagc tcgatggagg atacccatac gatgttccag attacgctgc tcgaggttat  120
caaacaagtt tgtacaaaaa agcaggctcc accatggggc ataacgtcta tatcaaggcc  180
gacaagcaga gaacggcat caaggcgaac ttcaagatcg ccacaacat cgaggacggc  240
```

-continued

```
ggcgtgcagc tcgcctacca ctaccagcag aacacccca tcggcgacgg ccccgtgctg   300
ctgcccgaca accactacct gagcgtgcag tccaaacttt cgaaagaccc caacgagaag   360
cgcgatcaca tggtcctgct ggagttcgtg accgccgccg ggatcactct cggcatggac   420
gagctgtaca agggcggtac cggagggagc atggtgagca agggcgagga gctgttcacc   480
ggggtggtgc ccatcctggt cgagctggac ggcgacgtaa acggccacaa gttcagcgtg   540
tccggcgagg gtgagggcga tgccacctac ggcaagctga ccctgaagtt catctgcacc   600
accggcaagc tgcccgtgcc ctggcccacc ctcgtgacca ccctgaccta cggcgtgcag   660
tgcttcagcc gctaccccga ccacatgaag cagcacgact tcttcaagtc cgccatgccc   720
gaaggctaca tccaggagcg caccatcttc ttcaaggacg acggcaacta caagacccgc   780
gccgaggtga agttcgaggg cgacaccctg gtgaaccgca tcgagctgaa gggcatcgac   840
ttcaaggagg acggcaacat cctggggcac aagctggagt acaactaa                888
```

```
SEQ ID NO: 87             moltype = DNA   length = 1317
FEATURE                   Location/Qualifiers
source                    1..1317
                          mol_type = other DNA
                          organism = synthetic construct
SEQUENCE: 87
atggtgctgg ccacccgcgt gttcagcctg gtgggcaagc gcgccatcag caccagcgtg   60
tgcgtgcgcg cccacaccgg tgactacaag gatgacgatg acaagctcga tggaggatac   120
ccatacgatg ttccagatta cgctgctcga ggttatcaaa caagtttgta caaaaaagca   180
ggctccacca tggggcatat gaagctgaca atcattcgcc tggagaaatt ttccgaccag   240
gatagaatcg accttcagaa gatctggccc gaatattctc ccagtagcct ccaagtagac   300
gacaaccatc gaatctacgc cgcgagattt aatgaacgac tgcttgcggc ggttagggta   360
accctcagcg gtacggaagg tgctctggac tccctgcggg tccgaggagc aaacgtctat   420
atcaaggccg acaagcagaa gaacggcatc aaggcgaact tcaagatccg ccacaacatc   480
gaggacgacg gcgtgcagct cgcctaccac taccagcaga acacccccat cggcgacggc   540
cccgtgctgc tgcccgacaa ccactacctg agcgtgcagt ccaaactttc gaaagacccc   600
aacgagaagc gcgatcacat ggtcctgctg gagttcgtga ccgccgccgg gatcactctc   660
ggcatggacg agctgtacaa gggcggtacc ggagggagca tggtgagcaa gggcgaggag   720
ctgttcaccg gggtggtgcc catcctggtc gagctggacg gcgacgtaaa cggccacaag   780
ttcagcgtgt ccggcgaggg tgagggcgat gccacctacg gcaagctgac cctgaagttc   840
atctgcacca ccggcaagct gcccgtgccc tggcccaccc tcgtgaccac cctgacctac   900
ggcgtgcagt gcttcagccg ctaccccgac cacatgaagc agcacgactt cttcaagtcc   960
gccatgcccg aaggctacat ccaggagcgc accatcttct tcaaggacga cggcaactac   1020
aagacccgcg ccgaggtgaa gttcgagggc gacaccctgg tgaaccgcat cgagctgaag   1080
ggcatcgact tcaaggagga cggcaacatc ctggggcaca agctggagta caacggtgct   1140
gaggtgacaa gacggagagg ggtaggacaa tatttgctcg aggaggtcct tagaaataac   1200
cccggagtaa gttgctggtg gatggcggac gctggagttg aggatcgcgg agtcatgacg   1260
gctttcatgc aggcccttgg gttcaccgca cagcaagggg gctgggagaa gtgctaa      1317
```

```
SEQ ID NO: 88             moltype = DNA   length = 924
FEATURE                   Location/Qualifiers
source                    1..924
                          mol_type = other DNA
                          organism = synthetic construct
SEQUENCE: 88
atggtgctgg ccacccgcgt gttcagcctg gtgggcaagc gcgccatcag caccagcgtg   60
tgcgtgcgcg cccacaccgg tgactacaag gatgacgatg acaagctcga tggaggatac   120
ccatacgatg ttccagatta cgctgctcga ggttatcaaa caagtttgta caaaaaagca   180
ggctccacca tggggcataa cgtctatatc aaggccgaca agcaagagaa cggcatcaag   240
gcgaacttca agatccgcca acatcgag gacggcggcg tgcagctcgc ctaccactac   300
cagcagaaca ccccatcgg cgacggcccc gtgctgctgc ccgacaacca ctacctgagc   360
gtgcagtcca actttcgaa agaccccaac gagaagcgcg atcacatggt cctgctggag   420
ttcgtgaccg ccgccgggat cactctcggc atggacgagc tgtacaaggg cggtaccgag   480
gggagcatgg tgagcaaggg cgaggagctg ttcaccgggg tggtgcccat cctggtcgag   540
ctggacggcg acgtaaacgg ccacaagttc agcgtgtccg gcgagggtga gggcgatgcc   600
acctacggca agctgaccct gaagttcatc tgcaccaccg gcaagctgcc cgtgccctgg   660
cccaccctcg tgaccaccct gacctacggc gtgcagtgct tcagccgcta ccccgaccac   720
atgaagcagc acgacttctt caagtccgcc atgcccgaag gctacatcca ggagcgcacc   780
atcttcttca aggacgacgg caactacaag acccgcgccg aggtgaagtt cgagggcgac   840
accctggtga accgcatcga gctgaagggc atcgacttca aggaggacgg caacatcctg   900
gggcacaagc tggagtacaa ctaa                                          924
```

```
SEQ ID NO: 89             moltype = AA   length = 8
FEATURE                   Location/Qualifiers
source                    1..8
                          mol_type = protein
                          organism = synthetic construct
SEQUENCE: 89
DYKDDDDK                                                             8
```

The invention claimed is:

1. A recombinant acetyl-coenzyme A (acetyl-CoA) biosensor polypeptide comprising:

an acetyl-CoA binding protein having an amino acid sequence at least 95% identical to SEQ ID NO: 1, wherein the acetyl-CoA binding protein is divided into:

a first acetyl-CoA binding protein fragment comprising an N-terminal portion of the acetyl-CoA binding protein; and a second acetyl-CoA binding protein fragment comprising a C-terminal portion of the acetyl-CoA binding protein;

wherein the first and second acetyl-CoA binding protein fragments collectively include all of the amino acids of the acetyl-CoA binding protein; and a fluorescent protein inserted between the first and second acetyl-CoA binding protein fragments and attached to a C-terminus of the first acetyl-CoA binding protein fragment and an N-terminus of the second acetyl-CoA binding protein fragment; and wherein:

(i) the C-terminus is an arginine at position 69 of SEQ ID NO: 1 (Arg69) and the N-terminus is a glutamic acid at position 70 of SEQ ID NO: 1 (Glu70);

(ii) the C-terminus is a tryptophan at position 23 of SEQ ID NO: 1 (Trp23) and the N-terminus is a proline at position 24 of SEQ ID NO: 1 (Pro24);

(iii) the C-terminus is a valine at position 71 of SEQ ID NO: 1 (Val71) and the N-terminus is a threonine at position 72 of SEQ ID NO: 1 (Thr72);

(iv) the C-terminus is an aspartic acid at position 99 of SEQ ID NO: 1 (Asp99) and the N-terminus is an alanine at position 100 of SEQ ID NO: 1 (Ala100);

(v) the C-terminus is an aspartic acid at 104 of SEQ ID NO: 1 (Asp104) and the N-terminus is an arginine at position 105 of SEQ ID NO: 1 (Arg105); or (vi) the C-terminus is a glycine at position 116 of SEQ ID NO: 1 (Gly116) and the N-terminus is a phenylalanine at position 117 of SEQ ID NO: 1 (Phe117); and wherein the recombinant acetyl-CoA biosensor polypeptide selectively binds acetyl-CoA, and the binding of acetyl-CoA induces a change in the fluorescence of the fluorescent protein.

2. The recombinant acetyl-CoA biosensor polypeptide of claim 1, wherein the fluorescent protein is a circularly permuted GFP (cpGFP), a circularly permuted yellow fluorescent protein (cpYFP), or a circularly permuted blue fluorescent protein (cpBFP).

3. The recombinant acetyl-CoA biosensor polypeptide of claim 2, wherein the cpGFP comprises an amino acid sequence of SEQ ID NO: 2, the cpYFP comprises an amino acid sequence of SEQ ID NO: 3, and the cpBFP comprises an amino acid sequence of SEQ ID NO: 4.

4. The recombinant acetyl-CoA biosensor polypeptide of claim 1, wherein the acetyl-CoA binding protein comprises an amino acid sequence at least 99% identical to SEQ ID NO: 1.

5. The recombinant acetyl-CoA biosensor polypeptide of claim 1, wherein the acetyl-CoA binding protein comprises the amino acid sequence of SEQ ID NO: 1.

6. The recombinant acetyl-CoA biosensor polypeptide of claim 1, wherein:

the fluorescent protein is either directly attached to the C-terminus of the first acetyl-CoA binding protein fragment or is attached by a first amino acid linker that is from 1 to 3 amino acids in length; and the fluorescent protein is either directly attached to the N-terminus of the second acetyl-CoA binding protein fragment or is attached by a second linker that is from 1 to 3 amino acids in length.

7. The recombinant acetyl-CoA biosensor polypeptide of claim 6, wherein the first and second amino acid linkers are each independently selected from the group consisting of a Gly, Gly-Ala, Ala-Ser, and Gly-Ala-Ser.

8. The recombinant acetyl-CoA biosensor polypeptide of claim 6, wherein:

(i) the first linker is Gly-Ala and the second linker is Gly-Ala;

(ii) the first linker is Ala-Ser and the second linker is Ala-Ser;

(iii) the first linker is Gly-Ala-Ser and the second linker is Gly;

(iv) the C-terminus and N-terminus are directly attached to the fluorescent protein;

(v) the C-terminus is directly attached to the fluorescent protein and the second linker is Gly-Ala-Ser;

(vi) the first linker is Gly-Ala-Ser and the N-terminus is directly attached to the fluorescent protein;

(vii) the first linker is Gly-Ala and the N-terminus is directly attached to the fluorescent protein; or (viii) the first linker is Gly and the second linker is Gly-Ala-Ser.

9. The recombinant acetyl-CoA biosensor polypeptide of claim 1, further comprising one or more of a histidine tag, a TEV cleavage site, a tag having the amino acid sequence of SEQ ID NO: 89, a human influenza hemagglutinin (HA) tag, a nuclear export signal, a nuclear localization signal, a cytoplasmic localization signal, and a mitochondrial localization signal at the N-terminal portion of the acetyl-CoA binding protein.

10. The recombinant acetyl-CoA biosensor polypeptide of claim 1, wherein:

(i) the recombinant acetyl-CoA biosensor polypeptide comprises the amino acid sequence of SEQ ID NO: 5;

(ii) the recombinant acetyl-CoA biosensor polypeptide comprises the amino acid sequence of SEQ ID NO: 6;

(iii) the recombinant acetyl-CoA biosensor polypeptide comprises the amino acid sequence of SEQ ID NO: 7;

(iv) the recombinant acetyl-CoA biosensor polypeptide comprises the amino acid sequence of SEQ ID NO: 8;

(v) the recombinant acetyl-CoA biosensor polypeptide comprises the amino acid sequence of SEQ ID NO: 9;

(vi) the recombinant acetyl-CoA biosensor polypeptide comprises the amino acid sequence of SEQ ID NO: 10;

(vii) the recombinant acetyl-CoA biosensor polypeptide comprises the amino acid sequence of SEQ ID NO: 11;

(viii) the recombinant acetyl-CoA biosensor polypeptide comprises the amino acid sequence of SEQ ID NO: 12;

(ix) the recombinant acetyl-CoA biosensor polypeptide comprises the amino acid sequence of SEQ ID NO: 13;

(x) the recombinant acetyl-CoA biosensor polypeptide comprises the amino acid sequence of SEQ ID NO: 14;

(xi) the recombinant acetyl-CoA biosensor polypeptide comprises the amino acid sequence of SEQ ID NO: 15;

(xii) the recombinant acetyl-CoA biosensor polypeptide comprises the amino acid sequence of SEQ ID NO: 16;

(xiii) the recombinant acetyl-CoA biosensor polypeptide comprises the amino acid sequence of SEQ ID NO: 17;

(xiv) the recombinant acetyl-CoA biosensor polypeptide comprises the amino acid sequence of SEQ ID NO: 18; or (xv) the recombinant acetyl-CoA biosensor polypeptide comprises the amino acid sequence of SEQ ID NO: 19.

11. The recombinant acetyl-CoA biosensor polypeptide of claim 10, wherein the recombinant acetyl-CoA biosensor polypeptide comprises the amino acid of SEQ ID NO: 5.

12. An expression vector comprising:

a nucleic acid that encodes the recombinant acetyl-CoA biosensor polypeptide of claim 1; and a promoter operably linked to the nucleic acid.

13. The expression vector of claim 12, wherein the expression vector is a lentiviral vector, an adeno-associated virus (AAV) vector, or a cytomegalovirus (CMV) vector.

14. A method of detecting acetyl-CoA in a sample comprising:

contacting the sample with the recombinant acetyl-CoA biosensor polypeptide of claim 1;

exciting the recombinant acetyl-CoA biosensor polypeptide in the sample at an excitation wavelength;

measuring a fluorescence intensity of the recombinant acetyl-CoA biosensor polypeptide in the sample at an emission wavelength; and comparing the fluorescence intensity to a standard curve, wherein the fluorescence intensity correlates with a concentration of acetyl-CoA in the sample.

15. The method of claim 14, wherein the excitation wavelength is from about 460 nm to about 490 nm.

16. The method of claim 14, wherein the excitation wavelength is 485 nm.

17. The method of claim 14, wherein the emission wavelength is from about 513 nm to about 540 nm.

18. The method of claim 14, wherein the emission wavelength is 514 nm.

19. The method of claim 14, wherein the pH of the sample is maintained at a pH of 6.5-8.0.

20. A method of monitoring acetyl-CoA activity in a cell, comprising:

providing a cell with the recombinant acetyl-CoA biosensor polypeptide of claim 1;

exciting the recombinant acetyl-CoA biosensor polypeptide in the cell at a first excitation wavelength between about 400 nm and about 430 nm while measuring a first fluorescence intensity at an emission wavelength between about 513 nm and about 540 nm;

exciting the recombinant acetyl-CoA biosensor polypeptide in the cell at a second excitation wavelength between about 460 nm and about 490 nm while measuring a second fluorescence intensity at the emission wavelength; and normalizing the second fluorescence intensity based on the first fluorescence intensity.

21. The method of claim 20, wherein normalizing comprises dividing the second fluorescence intensity by the first fluorescence intensity.

22. The method of claim 20, further comprising treating the cell with an acetyl-CoA precursor or nutrient affecting the function of the cell and comparing the normalized fluorescence intensity of the cell to the normalized fluorescence intensity of a control cell.

23. The method of claim 22, wherein one or more of a nuclear export signal, a nuclear localization signal, a cytoplasmic localization signal, and a mitochondrial localization signal is attached to an N-terminus of the recombinant acetyl-CoA biosensor polypeptide.

24. The method of claim 23, further comprising determining where acetyl-CoA is localized in the cell.

25. The method of claim 20, wherein the first excitation wavelength is 405 nm.

26. The method of claim 20, wherein the second excitation wavelength is 485 nm.

27. The method of claim 20, wherein the emission wavelength is 514 nm.

28. The method of claim 20, wherein the providing step comprises transforming the cell with a plasmid comprising a polynucleotide that encodes the recombinant acetyl-CoA biosensor polypeptide.

* * * * *